(12) United States Patent
Farritor et al.

(10) Patent No.: US 8,968,332 B2
(45) Date of Patent: *Mar. 3, 2015

(54) MAGNETICALLY COUPLEABLE ROBOTIC SURGICAL DEVICES AND RELATED METHODS

(75) Inventors: Shane Farritor, Lincoln, NE (US); Amy Lehman, Seward, NE (US); Nathan A. Wood, Papillion, NE (US); Mark Rentschler, Omaha, NE (US); Jason Dumpert, Omaha, NE (US); Dmitry Oleynikov, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 1322 days.

This patent is subject to a terminal disclaimer.

(21) Appl. No.: 11/766,683

(22) Filed: Jun. 21, 2007

(65) Prior Publication Data

US 2008/0004634 A1 Jan. 3, 2008

Related U.S. Application Data

(60) Provisional application No. 60/815,741, filed on Jun. 22, 2006, provisional application No. 60/845,608, (Continued)

(51) Int. Cl.
*A61B 19/00* (2006.01)
*A61B 5/05* (2006.01)
(Continued)

(52) U.S. Cl.
CPC ............... *A61B 5/05* (2013.01); *A61B 1/00158* (2013.01); *A61B 1/041* (2013.01); *A61B 1/313* (2013.01);
(Continued)

(58) Field of Classification Search
CPC ............... A61B 19/22; A61B 19/2203; A61B 19/5212; A61B 10/06; A61B 1/00156; A61B 1/00158; A61B 1/041; A61B 1/313; A61B 1/00188; A61B 2017/00876; A61B 2017/22082; A61B 2017/00039; A61B 2017/00044; A61B 2017/00221; A61B 2017/00734; A61B 2017/2943; A61B 2019/2215; A61B 2019/2249; A61B 2019/2253; A61B 2019/465; A61B 2019/5206; A61B 5/05; A61B 5/062; A61B 5/073; A61B 5/416; A61M 2205/3523; A61M 2205/3569; A61M 31/00; A61M 5/14276; A61M 5/1452; A61M 5/16827; A61M 5/19; A61M 5/20; A61M 5/2066; B25J 5/00; B25J 7/00; B25J 18/00; Y10S 901/02; Y10S 901/28; Y10S 901/30
USPC .......................................... 606/1; 901/1–15
See application file for complete search history.

(56) References Cited

U.S. PATENT DOCUMENTS 3,870,264 A 3/1975 Robinson
3,989,952 A 11/1976 Timberlake et al.
(Continued)

FOREIGN PATENT DOCUMENTS

EP 2286756 A1 2/2011
JP 2004144533 5/1990
(Continued)

OTHER PUBLICATIONS

Abbou et al., "Laparoscopic Radical Prostatectomy with a Remote Controlled Robot." *The Journal of Urology.* Jun. 2001, 165: 1964-1966.
(Continued)

*Primary Examiner* — Gary Jackson
*Assistant Examiner* — Boniface N Nganga
(74) *Attorney, Agent, or Firm* — Davis, Brown, Koehn, Shors & Roberts, P.C.; Sean D. Solberg

(57) ABSTRACT

The present invention relates to magnetically coupleable robotic surgical devices. More specifically, the present invention relates to robotic surgical devices that can be inserted into a patient's body and can be positioned within the patient's body using an external magnet.

20 Claims, 58 Drawing Sheets

Related U.S. Application Data filed on Sep. 19, 2006, provisional application No. 60/868,030, filed on Nov. 30, 2006, provisional application No. 60/884,792, filed on Jan. 12, 2007, provisional application No. 60/888,182, filed on Feb. 5, 2007.

(51) Int. Cl.

| | | |
|---|---|---|
| *A61B 1/00* | (2006.01) | |
| *A61B 1/04* | (2006.01) | |
| *A61B 1/313* | (2006.01) | |
| *A61B 5/06* | (2006.01) | |
| *A61B 5/07* | (2006.01) | |
| *A61B 5/00* | (2006.01) | |
| *A61M 5/142* | (2006.01) | |
| *A61M 5/145* | (2006.01) | |
| *A61M 31/00* | (2006.01) | |
| *B25J 5/00* | (2006.01) | |
| *B25J 7/00* | (2006.01) | |
| *A61B 10/06* | (2006.01) | |
| *A61B 17/00* | (2006.01) | |
| *A61B 17/22* | (2006.01) | |
| *A61M 5/168* | (2006.01) | |

(52) U.S. Cl.
CPC ............. *A61B 5/062* (2013.01); *A61B 5/073* (2013.01); *A61B 5/416* (2013.01); *A61B 19/22* (2013.01); *A61M 5/14276* (2013.01); *A61M 5/1452* (2013.01); *A61M 31/00* (2013.01); *B25J 5/00* (2013.01); *B25J 7/00* (2013.01); *A61B 10/06* (2013.01); *A61B 19/2203* (2013.01); *A61B 19/5212* (2013.01); *A61B 2017/00398* (2013.01); *A61B 2017/00876* (2013.01); *A61B 2017/22082* (2013.01); *A61B 2019/2215* (2013.01); *A61B 2019/2249* (2013.01); *A61B 2019/2253* (2013.01); *A61B 2019/465* (2013.01); *A61M 5/16827* (2013.01); *A61M 2205/3523* (2013.01); *A61M 2205/3569* (2013.01); *Y10S 901/01* (2013.01); *Y10S 901/15* (2013.01); *Y10S 901/19* (2013.01)
USPC .......... 606/130; 606/1; 901/1; 901/15; 901/19

(56) References Cited

U.S. PATENT DOCUMENTS

| | | |
|---|---|---|
| 4,246,661 A | 1/1981 | Pinson |
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyake |
| 4,623,183 A | 11/1986 | Aomori |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,897,014 A | 1/1990 | Tietze |
| 4,922,755 A | 5/1990 | Oshiro et al. |
| 4,990,050 A | 2/1991 | Tsuge et al. |
| 5,019,968 A | 5/1991 | Wang et al. |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A * | 11/1994 | Schempf et al. ............ 180/9.1 |
| 5,382,885 A | 1/1995 | Salcudean et al. |
| 5,388,528 A | 2/1995 | Pelrine et al. |
| 5,436,542 A | 7/1995 | Petelin et al. |
| 5,441,494 A | 8/1995 | Oritz |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,398 A * | 4/1997 | Smith et al. ............ 604/95.01 |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,674,030 A | 10/1997 | Sigel |
| 5,728,599 A | 3/1998 | Rosteker et al. |
| 5,736,821 A | 4/1998 | Suyaman et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A * | 8/1998 | Cohn et al. ............ 92/88 |
| 5,792,135 A | 8/1998 | Madhani et al. |
| 5,797,900 A | 8/1998 | Madhani et al. |
| 5,807,377 A | 9/1998 | Madhani et al. |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A * | 3/1999 | Mizuno et al. ............ 600/102 |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,911,036 A | 6/1999 | Wright et al. |
| 5,971,976 A | 10/1999 | Wang et al. |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A * | 8/2000 | Smart ............ 324/220 |
| 6,132,368 A | 10/2000 | Cooper |
| 6,132,441 A | 10/2000 | Grace |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |

(56) References Cited

U.S. PATENT DOCUMENTS

| | | |
|---|---|---|
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Okamoto et al. |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Tierney et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 * | 5/2004 | Green ............................ 700/3 |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |

(56) References Cited

U.S. PATENT DOCUMENTS

| | | |
|---|---|---|
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,179,073 B2 | 5/2012 | Farritor et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0026186 A1 | 2/2002 | Woloszka et al. |
| 2002/0038077 A1 | 3/2002 | de la Torre et al. |
| 2002/0065507 A1 | 5/2002 | Azizi |
| 2002/0091374 A1 | 7/2002 | Cooper |
| 2002/0103417 A1 | 8/2002 | Gazdzinski |
| 2002/0111535 A1* | 8/2002 | Kim et al. ............ 600/158 |
| 2002/0120254 A1 | 8/2002 | Julien et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1* | 12/2002 | Schempf et al. ......... 318/568.11 |
| 2003/0020810 A1 | 1/2003 | Takizawa et al. |
| 2003/0032855 A1* | 2/2003 | Shahinpoor ............ 600/16 |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 7/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0001750 A1* | 1/2004 | Kremerman ............ 414/744.1 |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0106916 A1 | 6/2004 | Quaid et al. |
| 2004/0111113 A1 | 6/2004 | Nakamura et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0096502 A1* | 5/2005 | Khalili ............ 600/106 |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1* | 10/2006 | Wilk ............ 606/1 |
| 2006/0241732 A1 | 10/2006 | Denker et al. |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Okeynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1* | 5/2008 | de la Pena ............ 606/130 |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0164079 A1 | 7/2008 | Jacobsen |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2009/0020724 A1 | 1/2009 | Paffrath |
| 2009/0024142 A1 | 1/2009 | Ruiz Morales |

(56) References Cited

U.S. PATENT DOCUMENTS

| | | |
|---|---|---|
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9* | 6/2009 | de la Pena .............. 606/130 |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Scott |
| 2010/0204713 A1 | 8/2010 | Ruiz |
| 2010/0245549 A1 | 9/2010 | Allen et al. |
| 2010/0262162 A1 | 10/2010 | Omori |
| 2010/0318059 A1 | 12/2010 | Farritor et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0077478 A1 | 3/2011 | Freeman et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0270443 A1 | 11/2011 | Kamiya et al. |
| 2012/0035582 A1 | 2/2012 | Nelson et al. |
| 2012/0109150 A1 | 5/2012 | Quaid et al. |
| 2012/0253515 A1 | 10/2012 | Coste-Maniere et al. |
| 2013/0041360 A1 | 2/2013 | Farritor |
| 2013/0131695 A1 | 5/2013 | Scarfogliero et al. |

FOREIGN PATENT DOCUMENTS

| | | |
|---|---|---|
| JP | 5115425 | 5/1993 |
| JP | 200716235 | 6/1993 |
| JP | 2006507809 | 9/1994 |
| JP | 07 136173 | 5/1995 |
| JP | 07306155 | 11/1995 |
| JP | 7306155 | 11/1995 |
| JP | 08-224248 | 9/1996 |
| JP | 2003220065 | 8/2003 |
| JP | 2004322310 | 6/2004 |
| JP | 2004180781 | 7/2004 |
| JP | 2004329292 | 11/2004 |
| JP | 2006508049 | 3/2006 |
| WO | WO 92/21291 | 5/1991 |
| WO | WO 02/082979 | 10/2002 |
| WO | 02100256 | 12/2002 |
| WO | WO 02/100256 | 12/2002 |
| WO | WO 2005/009211 | 2/2005 |
| WO | WO 2006 005075 | 1/2006 |
| WO | WO 2006/079108 | 1/2006 |
| WO | WO 2006/052927 | 5/2006 |
| WO | WO 2007/111571 | 10/2007 |
| WO | 2007149559 | 12/2007 |
| WO | WO 2007/149559 | 12/2007 |
| WO | WO 2009023851 A1 | 2/2009 |
| WO | WO 2009/144729 | 12/2009 |
| WO | WO2010/042611 | 4/2010 |
| WO | WO2010/046823 | 4/2010 |
| WO | WO 2011/118646 A1 | 9/2011 |
| WO | WO 2011/135503 A1 | 11/2011 |
| WO | WO 2013009887 | 1/2013 |

OTHER PUBLICATIONS

Fraulob et al., "Miniature assistance module for robot-assisted heart surgery." *Biomed. Tech.* 2002, 47 Suppl. 1, Pt. 1: 12-5.

Guber et al., "Miniaturized Instrument Systems for Minimally Invasive Diagnosis and Therapy." *Biomedizinische Technik.* 2002, Band 47, Erganmngsband 1: 198-201.

Thomann et al., "The Design of a new type of Micro Robot for the Intestinal Inspection." *Proceedings of the 2002 IEEE/RSJIntl. Conference on Intelligent Robots and Systems EPFL.* Oct. 2002: 1385-1390.

Guo et al., "Fish-like Underwater Microrobot with 3 DOF." *Proceedings of the 2002 IEEE International Conference on Robotics &Automation.* May 2002: 738-743.

Fukuda et al., "Mechanism and Swimming Experiment of Micro Mobile Robot in Water." *Proceedings of the 1994 IEEE International Conference on Robotics and Automation.* 1994: 814-.

Guo et al., "Micro Active Guide Wire Catheter System-Characteristic Evaluation, Electrical Model and Operability Evalu-ation of Micro Active Catheter," *Proceedings of the 1996 IEEE International Conference on Robotics and Automation.* Apr. 1996: 2226-2231.

Yu et al., "Microrobotic Cell Injection." *Proceedings of the 2001 IEEE International Conference on Robotics & Automation.* May 2001: 620-625.

Ruurda et al., "Robot-assisted surgical systems: a new era in laparoscopic surgely."*Ann. R. Coll. Surg. Engl.* 2002, 84: 223-226.

Menciassi et al., "Robotic Solutions and Mechanisms for a Semi-Autonomous Endoscope." *Proceedings of the 2002 IEEEIRU Intl. Conference on Intelligent Robots and Systems EPFL.* Oct. 2002: 1379-1384.

Ishiyama et al., "Spiral-type Micro-machine for Medical Applications." *2000 International Symposium on Micromechatronic and Human Science.* 2000: 65-69s.

Fearing et al., "Wing Transmission for a Micromechanical Flying Insect." *Proceedings of the 2000 IEEE International Conference on Robotics & Automation.* Apr. 2000: 1509-1516.

Mei et al., "Wireless Drive and Control of a Swimming Microrobot." *Proceedings of the 2002 IEEE International Conference on Robotics & Automation.* May 2002: 113 1-1136.

Yu, "M2A™ Capsule Endoscopy a Break-through Diagnostic Tool for Small Intestine Imaging," vol. 25, No. 1, *Gastroenterology Nursing*, pp. 24-27 2001.

Strong et al., "Efficacy of Novel Robotic Camera vs a Standard Laparoscopic Camera," *Surgical Innovation*, vol. 12, No. 4, Dec. 2005, Westminster Publications, Inc., pp. 315-318.

Worn et al., Esprit Project No. 33915: Miniaturized Robot for Micro Manipulation (Miniman), Nov. 1998-Mar. 2002, http:llwww,ipr,lra, uka.de/-microrobot/miniman/.

Meron, "The development of the swallowable video capsule (M2a)," Gastrointestinal Endoscopy 2000, 52, 6; 817-819.

Breda et al., "Future developments and perspectives in Lacroscopy", *Eur. Urology*, 2001, 40, 1: 84-91.

Allendorf et al., "Postoperative Immune Function Varies Inversely with the Degree of Surgical Trauma in a Murine Model," Surgical Endoscopy, 1997; 11:427-430.

Ang, "Active Tremor Compensation in Handheld Instrument for Microsurgery," Doctoral dissertation, tech report CMU-RI-TR-04-28, Robotics Institute, Carnegie Mellon University, May 2004, 150 pp.

Atmel 80C5X2 Core, http://www.atmel.com, 2006.

Bailey et al., "Complications of Laparoscopic Surgery," Quality Medical Publishers, Inc., 1995, 25 pp.

Ballantyne, "Robotic Surgery, Telerobotic Surgery, Telepresence, and Telementoring," Surgical Endoscopy, 2002; 16:1389-1402.

Begos et al., "Laparoscopic Cholecystectomy: From Gimmick to Gold Standard," J Clin Gastroenterol, 1994; 19(4):325-330.

Berg et al., "Surgery with Cooperative Robots," Medicine Meets Virtual Reality, Feb. 2007.

(56) References Cited

OTHER PUBLICATIONS

Breedveld et al., "Locomotion through the Intestine by means of Rolling Stents," Proceedings of the ASME Design Engineering Technical Conferences, 2004.

Calafiore et al., "Multiple Arterial Conduits Without Cardiopulmonary Bypass: Early Angiographic Results," Ann Thorac Surg, 1999; 67:450-456.

Camarillo et al., "Robotic Technology in Surgery: Past, Present, and Future," The American Journal of Surgery, 2004; 188: 2S-15S.

Cavusoğlu et al., "Robotics for Telesurgery: Second Generation Berkeley/UCSF Laparoscopic Telesurgical Workstation and Looking Towards the Future Applications," Industrial Robot: An International Journal, 2003; 30(1):22-29.

Cavusoğlu et al., "Telesurgery and Surgical Simulation: Haptic Interfaces to Real and Virtual Surgical Environments." In McLaughlin, M. L., Hespanha, J. P., and Sukhatme, G., editors. Touch in virtual environments. IMSC Series in Multimedia. 2001, 28 pp.

Choi et al., "Flexure-based Manipulator for Active Handheld Microsurgical Instrument," Proceedings of the 27th Annual International Conference of the IEEE Engineering in Medicine and Biology Society (EMBS), Sep. 2005.

CrystalEyes, http://www.reald.com, 2007 (Stereo3D visualization for CAVEs, theaters and immersive environments), 1 pg.

Cuschieri, "Technology for Minimal Access Surgery," BMJ, 1999, 319:1-6.

Stefanini et al., "Modeling and Experiments on a Legged Microrobot Locomoting in a Tubular, Compliant and Slippery Environment," Int. Journal of Robotics Research, vol. 25, No. 5-6, pp. 551-560, May-Jun. 2006.

Dumpert et al., "Improving In Vivo Robot Vision Quality" in the Proceedings of Medicine Meets Virtual Reality, Long Beach, CA, Jan. 26-29, 2005.

Faraz et al., "Engineering Approaches to Mechanical and Robotic Design for Minimally Invasive Surgery (MIS)," Kluwer Academic Publishers (Boston), 2000, 13 pp.

Franklin et al., "Prospective Comparison of Open vs. Laparoscopic Colon Surgery for Carcinoma: Five-Year Results," Dis Colon Rectum, 1996;39:S35-S46.

Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committee," U.S. Food and Drug Administration, available at http://www.fda.gov, Finalized: Nov. 7, 2003; Updated: Jun. 24, 2005, 11 pp.

Glukhovsky et al., "The development and application of wireless capsule endoscopy," Int. J.. Med. Robot. Comput. Assist. Surgery, 2004; 1 (1): 114-123.

Hanly et al., "Value of the Sages Learning Center in introducing new technology," Surgical Endoscopy, 2004; 19(4): 477-483.

Hanly et al., "Robotic Abdominal Surgery," The American Journal of Surgery, 2004; 188 (Suppl. to Oct. 1994): 19S-26S.

Heikkinen et al., "Comparison of laparoscopic and open Nissen fundoplication 2 Years after operation: A prospective randomized trial," Surgical Endoscopy, 2000; 14:1019-1023.

Horgan et al., "Technical Report: Robots in Laparoscopic Surgery," Journal of Laparoendoscopic & Advanced Surgical Techniques, 2001; 11(6):415-419.

Kim., "Early Experience with Telemanipulative Robot-Assisted Laparoscopic Cholecystectomy Using da Vinci," Surgical Laparoscopy, Endoscopy & Percutaneous Techniques, 2002; 12(1):33-40.

Liem et al., "Comparison of Conventional Anterior Surgery and Laparoscopic Surgery for Inguinal-hernia Repair," New England Journal of Medicine, 1997; 336 (22):1541-1547.

MacFarlane et al., "Force-Feedback Grasper Helps Restore the Sense of Touch in Minimally Invasive Surgery," Journal of Gastrointestinal Surgery, 1999: 3: 278-285.

Mack, "Minimally Invasive and Robotic Surgery," JAMA, Feb. 2001; 285(5):568-572.

Mack et al., "Present Role of Thoracoscopy in the Diagnosis and Treatment of Diseases of the Chest," Ann Thorac Surgery, 1992; 54:403-409.

Menciassi et al., "Locomotion of a Legged Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.

Hissink, "Olympus Medical develops capsule camera technology," Dec. 2004, accessed Aug. 29, 2007. http://www.letsgodigital.org , 3 pp.

Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, 1 pg.

Rentschler et al., "In vivo Robotics during the NEEMO 9 Mission," Medicine Meets Virtual Reality, Feb. 2007, 1 pg.

Rentschler et al., "An In Vivo Mobile Robot for Surgical Vision and Task Assistance," ASME Journal of Medical Devices, vol. 1, pp. 23-29, Mar. 2007.

Rentschler et al., "Mechanical Design of Robotic In Vivo Wheeled Mobility," ASME Journal of Mechanical Design, 2006a, pp. 1-11, Accepted.

Rentschler et al., "Mobile In Vivo Camera Robots Provide Sole Visual Feedback for Abdominal Exploration and Cholecystectomy", Journal of Surgical Endoscopy, 20-1: 135-138, 2006b.

Rentschler et al., "Modeling, Analysis, and Experimental Study of In Vivo Wheeled Robotic Mobility", IEEE Transactions on Robotics, 22 (2): 308-321, 2006c.

Rentschler et al., "Natural Orifice Surgery with an Endoluminal Mobile Robot," The Society of American Gastrointestinal Endoscopic Surgeons, Dallas, TX, Apr. 2006d.

Rentschler et al., "Mobile In Vivo Biopsy and Camera Robot", Studies in Health and Informatics—Medicine Meets Virtual Reality, vol. 119., pp. 449-454, IOS Press, Long Beach, CA, 2006e.

Rentschler et al., "Toward In Vivo Wheeled Mobility," Studies in Health Technology and Informatics—Medicine Meets Virtual Reality, ISO Press, Long Beach, CA, 2005a, 111:397-403.

Rentschler et al., "Mobile In Vivo Robots Can Assist in Abdominal Exploration" in the Proceedings of the Society of American Gastrointestinal Endoscopic Surgeons (SAGES) Scientific Conference, Ft. Lauderdale, FL, Apr. 13-16, 2005b.

Rentschler et al., "In Vivo Robots for Laparoscopic Surgery," Studies in Health Technology and Informatics—Medicine Meets Virtual Reality, ISO Press, Newport Beach, CA, 2004a, 98:316-322.

Rosen et al., "The BlueDRAGON—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.

Rosen et al., "Objective Laparoscopic Skills Assessments of Surgical Residents Using Hidden Markov Models Based on Haptic Information and Tool/Tissue Interactions," Studies in Health Technology and Informatics—Medicine Meets Virtual Reality, Jan. 2001.

Sackier et al., "Robotically assisted laparoscopic surgery," Surgical Endoscopy, 1994; 8:63-6.

Satava, "Surgical Robotics: The Early Chronicles," Surgical Laparoscopy, Endoscopy & Percutaneous Techniques, 2002; 12(1):6-16.

Schurr et al., "Robotics and Telemanipulation Technologies for Endoscopic Surgery," Surgical Endoscopy, 2000; 14:375-381.

Stiff et al., "Long-term Pain: Less Common After Laparoscopic than Open Cholecystectomy," British Journal of Surgery, 1994; 81:1368-1370.

Suzumori et al., "Development of Flexible Microactuator and its Applications to Robotics Mechanisms," Proceedings of the IEEE International Conference on Robotics and Automation, 1991.

Taylor et al., "A Telerobotic Assistant for Laparoscopic Surgery," IEEE Eng Med Biol, 1995; 279-87.

Tendick et al., "Applications of Micromechatronics in Minimally Invasive Surgery," IEEE/ASME Transactions on Mechatronics, 1998; 3(1):34-42.

Way et al. , editors. "Fundamentals of Laparoscopic Surgery," Churchill Livingstone Inc., 1995, 14 pp.

(56) References Cited

OTHER PUBLICATIONS

Oleynikov et al., In Vivo Robotic Laparoscopy, Surgical Innovation, Jun. 2005, 12(2): 177-181.
O'Neill, Surgeon takes new rout to gallbladder,: The Oregonian, Jun. 2007, 2 pp.
Rosen et al., "Force Controlled and Teleoperated Endoscopic, Grasper for Minimally Invasive Surgery—Experimental Performance Evaluation,"IEEE transactions of Biomedical Engineering, Oct. 1999; 46(10): pp. 1212-1221.
Salky, "What is the Penetration of Endoscopic Techniques into Surgical Practice?" Digestive Surgery 2000; 17:422-426.
Dakin et al., "Comparison of laparoscopic skills performance between standard instruments and two surfical robotic systems," Surg Endosc., 2003 17:574-579.
Melvin et al., "Computer-Enhanced vs. Standard Laparoscopic Antireflux Surgery," J Gastointest Surg 2002;6:11-16.
Park et al., "Trocar-less Instrumentation for Laparoscopy: Magnetic Positioning of Intra-abdominal Camera and Retractor," Ann Surg, Mar. 2007;245(3):379-384.
Peters, "Mimimally Invasive Colectomy: Are the Potential Benefits Realized?" Dis Colon Rectom 1993; 36:751-756.
Gong et al., "Wireless endoscopy," Gastrointestinal Endoscopy 2000; 51(6), pp. 725-729.
Bauer et al,. "Case Report: Remote Percutaneous Renal Access Using a New Automated Telesurgical Robotic System," Telemedicine Journal and e-Health 2001; (4), pp. 341-347.
Kang et al., "Robotic Assistants Aid Surgeons During Minimally Invasive Procedures," IEEE Engineering in Medicine and Biology, Jan./Feb. 2001, pp. 94-104.
Strong, "Efficacy of Novel Robotic Camera vs a Standard Laparoscopic Camera," Surgical Innovation, Dec. 2005; 12(4), pp. 315-318.
Schwartz, "In the Lab: Robots that Slink and Squirm," The New York Times, Mar. 27, 20074 pp.
Breedveld et al., "Design of Steerable Endoscopes to Improve the Visual Perception of Depth During Laparoscopic Surgery," ASME , Jan. 2004, vol. 126, p. 1-5.
Fireman et al., "Diagnosing small bowel Crohn's disease with wireless capsule endoscopy," Gut 2003; 52:390-392.
U.S. Appl. No. 12/192,663, filed Aug. 15, 2008.
U.S. Appl. No. 12/324,364, filed Nov. 26, 2008.
Applicant Response to Office Action dated Aug. 21, 2006, in related case U.S. Appl. No. 11/403,756, filed Nov. 21, 2006, 52 pp.
Applicant Response to Office Action dated Aug. 18, 2006, in related case U.S. Appl. No. 11/398,174, filed Nov. 7, 2006, 8 pp.
Examiner Interview Summary dated Nov. 30, 2006, in related case U.S. Appl. No. 11/398,174, 2 pp.
Applicant Response to Office Action dated Oct. 29, 2007, in related case U.S. Appl. No. 11/695,944, filed Jan. 22, 2008, 6 pp.
Applicant Amendment after Notice of Allowance under Rule 312, filed Aug. 25, 2008, in related case U.S. Appl. No. 11/695,944, 6 pp.
International Search Report and Written Opinion issued in PCT/US2008/069822, mailed Aug. 5, 2009, 10 pages.
Piers et al., "A miniature manipulator for integration in a self-propelling endoscope," Sensors and Actuators 92 (1-3): 343-349, Aug. 2001.
International Search Report and Written Opinion of international application No. PCT/US2007/014567, mailed Apr. 28, 2008, 19 pp.
Rosen et al., Objective Evaluation of Laparoscopic Skills Based on Haptic Information and Tool/Tissue Interactions, Computer Aided Surgery, vol. 7, Issue 1, pp. 49-61 Jul. 2002.
Li et al. (2000), "Microvascular Anastomoses Performed in Rats Using a Microsurgical Telemanipulator," Comp. Aid. Surg. 5:326-332.
Southern Surgeons Club (1991), "A prospective analysis of 1518 laparoscopic cholecystectomies," N. Engl. 1. Med. 324 (16): 1073-1078.
Wolfe et al. (1991), Endoscopic Cholecystectomy. An analysis of Complications. Arch. Surg. 126: I 192-1196.
Kazemier et al. (1998), "Vascular Injuries During Laparoscopy," J. Am. Coli. Surg. 186(5):604-5.
Leggett et al. (2002), "Aortic injury during laparoscopic Fundoplication," Surg. Endoscopy 16(2):362.
Munro, (2002), Laparoscopic access: complications, technologies, and techniques, Curro Opin. Obstet. Gynecol. 14 (4):365-74.
Tendick et al., (1993), "Sensing and Manipulation Problems in Endoscopic Surgery: Experiment, Analysis, and Observation," Presence 2(1):66-81.
Chanthasopeephan et al., (2003), "Measuring Forces in Liver Cutting: New Equipment and Experimental Results," Annals of Biomedical Engineering 31: 1372-1382.
Franzino, The Laprotek Surgical System and the Next Generation of Robotics Surg Clin North Am, 2003 83(6): 1317-1320.
Rentschler et al., "Miniature in vivo robotics for remote and harsh environments," 2006, pp. 66-75.
Smart Pill "Fastastic Voyage: Smart Pill to Expand Testing," http://www.smartpilldiagnostics.com, Apr. 13, 2005, 1 pg.
U.S. Appl. No. 11/947,097, filed Nov. 29, 2007, entitled "Robotic Devices With Agent Delivery Components and Related Methods," 55 pp.
U.S. Appl. No. 11/966,741, filed Dec. 28, 2007, entitled "Methods Systems, and Devices for Surgical Visualization and Device Manipulation," 52 pp.
Olympus, http://www.letsgodigital.org/en/news/articles/story_2150.html, 2004.
Patronik et al., "Development of a Tethered Epicardial Crawler for Minimally Invasive Cardiac Therapies," IEEE, pp. 239-240.
Patronik et al., "Crawling on the Heart: A Mobile Robotic Device for Minimally Invasive Cardiac Interventions," MICCAI, 2004, pp. 9-16.
Patronik et al., "Preliminary evaluation of a mobile robotic device for navigation and intervention on the beating heart," Computer Aided Surgery, 10(4): 225-232, Jul. 2005.
Peirs et al., "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al., "Analysis and Development of Locomotion Devices for the Gastrointestinal Tract," IEEE Transaction on Biomedical Engineering, vol. 49, No. 6, Jun. 2002, pp. 613-616.
Phee et al., "Development of Microrobotic Devices for Locomotion in the Human Gastrointestinal Tract," International Conference on Computational Intelligence, Robotics and Autonomous Systems (CIRAS 2001), Nov. 28-30, 2001, Singapore.
Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, I pg.
Preliminary Amendment filed Apr. 11, 2007, in related case U.S. Appl. No. 11/403,756, 7 pp.
Preliminary Amendment filed Jul. 30, 2008, in related case U.S. Appl. No. 12/171,413, 4 pp.
RCE and Amendment filed Jun. 13, 2007, in related case U.S. Appl. No. 11/403,756, 8 pp.
Rentschler et al., "Mobile In Vivo Biopsy and Camera Robot," Studies in Health and Infonnatics Medicine Meets Virtual Reality, vol. 119., pp. 449-454, IOS Press, Long Beach, CA, 2006e.
Rentschler et al., Mobile In Vivo Biopsy Robot, IEEE International Conference on Robotics and Automation, Orlando, Florida, May 2006, pp. 4155-4160.
Rentschler et al., "Miniature in vivo Robots for Remote and Harsh Environments," IEEE Transactions on Information Technology in Biomedicine, Jan. 2006; 12(1): 66-75.
Rentschler et al., "An In Vivo Mobile Robot for Surgical Vision and Task Assistance," Journal of Medical Devices, Mar. 2007, vol. 1: 23-29.
Rentschler et al., "In vivo Mobile Surgical Robotic Task Assistance," 1 pg.
Rentschler et al., "In vivo Robotics during the NEEMO 9 Mission," Medicine Meets Virtual Reality, Feb. 2007, I pg.
Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.

(56) References Cited

OTHER PUBLICATIONS

Rentschler et al., "Mechanical Design of Robotic In Vivo Wheeled Mobility," ASME Journal of Mechanical Design, 2006a, pp. 1-11.
Rentschler et al., "Mobile In Vivo Camera Robots Provide Sole Visual Feedback for Abdominal Exploration and Cholecystectomy," Journal of Surgical Endoscopy, 20-I: 135-138, 2006b.
Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.
Rentschler et al., "Modeling, Analysis, and Experimental Study of In Vivo Wheeled Robotic Mobility," IEEE Transactions on Robotics, 22 (2): 308-321, 2005c.
Rentschler et al., "Natural Orifice Surgery with an Endoluminal Mobile Robot," The Society of American Gastrointestinal Endoscopic Surgeons, Dallas, TX, Apr. 2006d, 14 pp.
Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.
Rentschler et al., "Toward In Vivo Mobility," Studies in Health Technology and Infonnatics—Medicine Meets Virtual Reality, ISO Press, Long Beach, CA, 2005a, III: 397-403.
Response to Rule 312 Amendment in related case U.S. Appl. No. 11/695,944, dated Jan. 12, 2009, 2 pp.
Riviere et al., "Toward Active Tremor Canceling in Handheld Microsurgical Instruments," IEEE Transactions on Robotics and Automation, Oct. 2003, 19(5): 793-800.
Rosen et al., "Force Controlled and Teleoperated Endoscopic, Grasper for Minimally Invasive Surgery—Experimental Performance Evaluation," IEEE Transactions of Biomedical Engineering, Oct. 1999; 46(10): 1212-1221.
Rosen et al., "Objective Laparoscopic Skills Assessments of Surgical Residents Using Hidden Markov Models Based on Haptic Information and Tool/Tissue Interactions," Studies in Health Technology and Informatics—Medicine Meets Virtual Reality, Jan. 2001, 7 pp.
Rosen et al., "Spherical Mechanism Analysis of a Surgical Robot for Minimally Invasive Surgery—Analytical and Experimental Approaches," Studies in Health Technology and Informatics—Medicine Meets Virtual Reality, pp. 442-448, Jan. 2005.
Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.
Rosen et al., "The Blue DRAGON—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.
Ruurda et al., "Robot-Assisted surgical systems: a new era in laparoscopic surgery," Ann R. Coll Surg Engl., 2002; 84: 223-226.
Ruurda et al., "Feasibility of Robot-Assisted Laparoscopic Surgery," Surgical Laparoscopy, Endoscopy & Percutaneous Techniques, 2002; 12(1):41-45.
Sackier et al., "Robotically assisted laparoscopic surgery," Surgical Endoscopy, 1994; 8: 63-66.
Salky, "What is the Penetration of Endoscopic Techniques into Surgical Practice?" Digestive Surgery, 2000; 17:422-426.
Satava, "Surgical Robotics: The Early Chronicles," Surgical Laparoscopy, Endoscopy & Percutaneous Techniques, 2002; 12(1): 6-16.
Schippers et al., (1996) "Requirements and Possibilities of Computer-Assisted Endoscopic Surgery," In: Computer Integrated Surgery: Technology and Clinical Applications, pp. 561-565.
Schurr et al., "Robotics and Telemanipulation Technologies for Endoscopic Surgery," Surgical Endoscopy, 2000; 14: 375-381.
Schwartz, "In the Lab: Robots that Slink and Squirm," The New York Times, Mar. 27, 2007, 4 pp.
Sharp LL-151-3D, http://www.sharp3d.com, 2006, 2 pp.
Slatkin et al., "The Development of a Robotic Endoscope," Proceedings of the 1995 IEEE International Conference on Robotics and Automation, pp. 162-171, 1995.
Smart Pill "Fantastic Voyage: Smart Pill to Expand Testing," http://www.smartpilldiagnostics.com, Apr. 13, 2005, 1 pg.
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al., "Long-term Pain: Less Common After Laparoscopic than Open Cholecystectomy," British Journal of Surgery, 1994; 81: 1368-1370.
Strong, et al., "Efficacy of Novel Robotic Camera vs. a Standard Laproscopic Camera," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-287.
Tendick et al.. (1993), "Sensing and Manipulation Problems in Endoscopic Surgery: Experiment, Analysis, and Observation," Presence 2( 1): 66-81.
International Preliminary Report on Patentability from related case PCT/US2007/014567, mailed Jan. 8, 2009, 11 pp.
International Search report and Written Opinion from international application No. PCT/US2012/41911, mailed Mar. 13, 2013.
International Search Report and Written Opinion from international application No. PCT/US12/46274, mailed Sep. 25, 2012.
International Search Report and Written Opinion from international application No. PCT/US2007/089191, mailed Nov. 10, 2008, 20 pp.
"International Search Report and Written Opinion from international application No. PCT/US07/14567, mailed Apr. 28, 2008, 19 pp."
International Search Report and Written Opinion of international application No. PCT/US2008/069822, mailed Aug. 5, 2009, 12 pp.
International Search Report and Written Opinion of international application No. PCT/US2008/073334, mailed Jan. 12, 2009, 11 pp.
International Search Report and Written Opinion of international application No. PCT/US2008/073369, mailed Nov. 12, 2008, 12 pp.
International Search Report and Written Opinion issued in PCT/US11/46809, mailed Dec. 8, 2011.
Ishiyama et al., "Spiral-type Micro-machine for Medical Applications," 2000 International Symposium on Micromechatronics and Human Science, 2000: 65-69.
Jagannath et al., "Peroral transgastric endoscopic ligation of fallopian tubes with long-term survival in a porcine model," Gastrointestinal Endoscopy, 2005; 61(3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan.-Feb. 2001; pp. 94-104.
Kantsevoy et al., "Endoscopic gastrojejunostomy with survival in a porcine model," Gastrointestinal Endoscopy, 2005; 62(2): 287-292.
Kantsevoy et al., "Transgastric endoscopic splenectomy," Surgical Endoscopy, 2006; 20: 522-525.
Kazemier et al. (1998), "Vascular Injuries During Laparoscopy," J. Am. Coli. Surg. 186(5): 604-5.
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136:180-184.
Leggett et al. (2002), "Aortic injury during laparoscopic fundoplication," Surg. Endoscopy 16(2): 362.

(56) References Cited

OTHER PUBLICATIONS

Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
Macfarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Menciassi et al., "Shape memory alloy clamping devices of a capsule for monitoring tasks in the gastrointestinal tract," J. Micromech. Microeng, 2005, 15: 2045-2055.
Meron, "The development of the swallowable video capsule (M2A)," Gastrointestinal Endoscopy 2000; 52 6: 817-819.
Micron, http://www.micron.com, 2006, ¼-inch VGA NTSC/PAL CMOS Digital Image Sensor, 98 pp.
Midday Jeff et al., "Material Handling System for Robotic natural Orifice Surgery", Proceedings of the 2011 Design of medical Devices Conference, Apr. 12-14, 2011, Minneapolis, MN, 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Office Action dated Apr. 17, 2007, received in related case U.S. Appl. No. 11/552,379, 5 pp.
Office Action dated Apr. 3, 2009, received in related case U.S. Appl. No. 11/932,516, 43 pp.
Office Action dated Aug. 18, 2006, received in related case U.S. Appl. No. 11/398,174, 6 pp.
Office Action dated Aug. 21, 2006, received in related case U.S. Appl. No. 11/403,756, 6 pp.
Office Action dated Oct. 29, 2007, received in related case U.S. Appl. No. 11/695,944, 6 pp.
Office Action dated Oct. 9, 2008, received in related case U.S. Appl. No. 11/932,441, 4 pp.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13(3): 181-184.
Park et al., "Trocar-less Instrumentation for Laparoscopy: Magnetic Positioning of Intra-abdominal Camera and Retractor," Ann Surg, Mar. 2007; 245(3): 379-384.
Park et al., "Experimental studies of transgastric gallbladder surgery: cholecystectomy and cholecystogastric anastomosis (videos)," Gastrointestinal Endoscopy, 2005; 61(4): 601-606.
Tendick et al., "Applications of Micromechatronics in Minimally Invasive Surgery," IEEE/ASME Transactions on Mechatronics, 1998; 3(1): 34-42.
Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Way et al., (editors), "Fundamentals of Laparoscopic Surgery," Churchill Livingstone Inc., 1995, 14 pp.
Wolfe et al., "Endoscopic Cholecystectomy: An analysis of Complications," Arch. Surg. Oct. 1991; 126: 1192-1196.
Worn et al., "Espirit Project No. 33915: Miniaturised Robot for Micro Manipulation (MINIMAN)", Nov. 1998; http://www.ipr.ira.ujka.de/-microbot/miniman.
Yu et al., "Microrobotic Cell Injection," Proceedings of the 2001 IEEE International Conference on Robotics and Automation, May 2001; 620-625.
Yu, BSN, RN, "M2ATM Capsule Endoscopy A Breakthrough Diagnostic Tool for Small Intestine Imagining," vol. 25, No. 1, Gastroenterology Nursing, pp. 24-27.
International Search Report and Written Opinion of international application No. PCT/US2010/061137, mailed Feb. 11, 2011, 10 pp.
Abbou et al., "Laparoscopic Radical Prostatectomy with a Remote Controlled Robot," The Journal of Urology, Jun. 2001, 165: 1964-1966.
Glukhovsky et al.., "The development and application of wireless capsule endoscopy," Int. J. Med. Robot. Comput. Assist. Surgery, 2004; I (1): 114-123.
Gong et al., Wireless endoscopy, Gastrointestinal Endoscopy 2000; 51(6): 725-729.
Hanly et al., "Value of the SAGES Learning Center in introducing new technology," Surgical Endoscopy, 2004; 19 (4): 477-483.
Abbott et al., "Design of an Endoluminal Notes Robotic System," from the Proceedings of the 2007 IEEE/RSJ Int'l Conf. on Intelligent Robot Systems, San Diego, CA, Oct. 29-Nov. 2, 2007, pp. 410-416.
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Applicant Amendment after Notice of Allowance under Rule 312, filed Aug. 25, 2008, in related case U.S. Appl. No. 11/695,944, 6pp.
Applicant Response to Office Action dated Apr. 17, 2007, in related case U.S. Appl. No. 11/552,379, filed Aug. 8, 2007, 7 pp.
Applicant Response to Office Action dated Aug. 18, 2006, in related case U.S. Appl. No. 11/398,174, filed Nov. 7, 2006, 8pp.
Applicant Response to Office Action dated Aug. 21, 2006, in related case U.S. Appl. No. 11/403,756, filed Nov. 21, 2006, 52pp.
Applicant Response to Office Action dated Oct. 29, 2007, in related case U.S. Appl. No. 11/695,944, filed Jan. 22, 2008, 6pp.
Atmel 80C5X2 Core, http://www.atmel.com, 2006, 186pp.

(56) References Cited

OTHER PUBLICATIONS

Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Chanthasopeephan et al., (2003), "Measuring Forces in Liver Cutting: New Equipment and Experimenal Results," Annals of Biomedical Engineering 31: 1372-1382.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Cuschieri, "Technology for Minimal Access Surgery," BMJ, 1999, 319: 1-6.
Dakin et al., "Comparison of laparoscopic skills performance between standard instruments and two surgical robotic systems," Surg Endosc., 2003; 17: 574-579.
Dumpert et al., "Improving in Vivo Robot Visioin Quality," from the Proceedings of Medicine Meets Virtual Realtiy, Long Beach, CA, Jan. 26-29, 2005. 1 pg.
Dumpert et al., "Stereoscopic In Vivo Surgical Robots," IEEE Sensors Special Issue on In Vivo Sensors for Medicine, Jan. 2007, 10 pp.
Examiner Interview Summary dated Aug. 6 and Aug. 12, 2008, in related case U.S. Appl. No. 11/695,944, 1 pg.
Examiner Interview Summary dated May 9, 2008, in related case U.S. Appl. No. 11/695,944, 1 pg.
Examiner Interview Summary dated Nov. 30, 2006, in related case U.S. Appl. No. 11/398,174, 2pp.
Falcone et al., "Robotic Surgery," Clin. Obstet. Gynecol. 2003, 46(1): 37-43.
Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Flynn et al., "Tomorrow's Surgery: micromotors and microbots for minimally invasive procedures," Minimally Invasive Surgery & Allied Technologies.
Franklin et al., "Prospective Comparison of Open vs. Laparoscopic Colon Surgery for Carcinoma: Five-Year Results," Dis Colon Rectum, 1996; 39: S35-S46.
Franzino, "The Laprotek Surgical System and the Next Generation of Robotics," Surg Clin North Am, 2003 83(6).
Fraulob et al., "Miniature assistance module for robot-assisted heart surgery," Biomed. Tech. 2002, 47 Suppl. 1, Pt. 1:12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Grady, "Doctors Try New Surgery for Gallbladder Removal," The New York Times, Apr. 20, 2007, 3 pp.
Guber et al., "Miniaturized Instrumetn Systems for Minimally Invasive Diagnosis and Therapy," Biomedizinishe Technic. 2002, Band 47, Erganmngsband 1.
Palm, William, "Rapid Prototyping Primer" May 1998 (revised Jul. 30, 2002) (http://www.me.psu.edu/lamancusa/rapidpro/primer/chapter2.htm).

\* cited by examiner

MAGNETICALLY COUPLEABLE ROBOTIC SURGICAL DEVICES AND RELATED METHODS

CROSS-REFERENCE TO RELATED APPLICATION(S)

This application claims priority to U.S. Provisional Patent Application Ser. No. 60/815,741, filed Jun. 22, 2006, U.S. Provisional Patent Application Ser. No. 60/845,608, filed Sep. 19, 2006, U.S. Provisional Patent Application Ser. No. 60/868,030, filed Nov. 30, 2006, U.S. Provisional Patent Application Ser. No. 60/884,792, filed Jan. 12, 2007, and U.S. Provisional Patent Application Ser. No. 60/888,182, filed Feb. 5, 2007, all of which are hereby incorporated herein by reference in their entirety.

FIELD OF THE INVENTION

The present invention relates to various embodiments of robotic devices for use in laparoscopic surgery. Specifically, these robotic devices can be inserted into a surgical subject for use in various surgical procedures, providing for performance of various procedures and/or viewing of the area in which a procedure is being performed.

BACKGROUND OF THE INVENTION

Laparoscopy is minimally invasive surgery (MIS) performed in the abdominal cavity. It has become the treatment of choice for several routinely performed interventions.

However, known laparoscopy technologies are limited in scope and complexity due in part to 1) mobility restrictions resulting from using rigid tools inserted through access ports, and 2) limited visual feedback. That is, long rigid laparoscopic tools inserted through small incisions in the abdomen wall limit the surgeon's range of motion and therefore the complexity of the surgical procedures being performed. Similarly, using a 2-D image from a typically rigid laparoscope inserted through a small incision limits the overall understanding of the surgical environment. Further, current technology requires a third port to accommodate a laparoscope (camera), and each new viewpoint requires an additional incision.

Robotic systems such as the da Vinci® Surgical System (available from Intuitive Surgical, Inc., located in Sunnyvale, Calif.) have been developed to address some of these limitations using stereoscopic vision and more maneuverable end effectors. However, da Vinci® is still restricted by the access ports. Further disadvantages include the size and high cost of the da Vinci® system, the fact that the system is not available in most hospitals and the system's limited sensory and mobility capabilities. In addition, most studies suggest that current robotic systems such as the da Vinci® system offer little or no improvement over standard laparoscopic instruments in the performance of basic skills. See Dakin, G. F. and Gagner, M. (2003) "Comparison of Laparoscopic Skills Performance Between Standard Instruments and Two Surgical Robotic Systems," *Surgical Endoscopy* 17: 574-579; Nio, D., Bemelman, W. A., den Boer, K. T., Dunker, M. S., Gouma, D. J., and van Gulik, T. M. (2002) "Efficiency of Manual vs. Robotical (Zeus) Assisted Laparoscopic Surgery in the Performance of Standardized Tasks," *Surgical Endoscopy* 16: 412-415; and Melvin, W. S., Needleman, B. J., Krause, K. R., Schneider, C., and Ellison, E. C. (2002) "Computer-Enhanced vs. Standard Laparascopic Antireflux Surgery," *J. Gastrointest Surg* 6: 11-16. Further, the da Vinci® system and similar systems are implemented from outside the body and will therefore always be constrained to some degree by the limitations of working through small incisions. For example, these small incisions do not allow the surgeon to view or touch the surgical environment directly, and they constrain the motion of the endpoint of the tools and cameras to arcs of a sphere whose center is the insertion point.

There is a need in the art for improved surgical methods, systems, and devices.

BRIEF SUMMARY

One embodiment disclosed herein is a robotic device having a body, a power source, a connection component, at least one operational arm, and an attachment component. The body is configured to be disposed within a patient. Further, the arm has a first link operably coupled with the body via a first joint and further has an operational component operably coupled with the arm. In addition, the operational arm is not positionable within the body.

According to one alternative embodiment, the arm also has a second link operably coupled with the first link via a second joint. In one implementation, the first joint is a shoulder joint and the second joint is an elbow joint. In accordance with one alternative embodiment, the attachment component is a first magnetic component. In addition, one embodiment of the device has a light component, while another embodiment has a sensor. In one aspect, the sensor is disposed within an interior portion and the body is fluidically sealed whereby no exterior fluids can enter the interior portion.

Another embodiment is a robotic device having a body, a power source, a connection component, a first operational arm, a second operational arm, and an attachment component. The body is configured to be disposed within a patient. The first operational arm has a first link operably coupled with a first end of the body via a first joint, and further has a first operational component operably coupled with the arm. The second operational arm has a second link operably coupled with a second end of the body via a second joint, and further has a second operational component operably coupled with the arm. Neither of the first or second arms are positionable within the body.

In accordance with an alternative implementation, the first operational arm further has a third link operably coupled with the first link via a third joint, and the second operational arm further has a fourth link operably coupled with the second link via a fourth joint. In another embodiment, the device has a sensor positioned between the first and second operational arms. In one aspect, the operational arms and sensor are positioned to substantially approximate a relative configuration of standard laparoscopic tools. Alternatively, the first and second operational arms are configured to substantially approximate movements of standard laparoscopic tools. In one embodiment, the first and second operational components can any of a scalpel, a biopsy tool, a cauterizer, a forceps, a dissector, a clippers, a stapler, an ultrasound probe, a suction component, or an irrigation component.

Another embodiment disclosed herein is a method of surgery. The method includes inserting a robotic device through a natural orifice of a patient and into a passage connected to the natural orifice and creating an incision in a wall of the passage. The method further includes inserting the robotic device into a cavity of the patient and performing a procedure using at least the robotic device. The device has a body, a power source, a connection component, at least one operational arm, and an attachment component. The arm has a first link operably coupled with the body via a first joint and further has an operational component operably coupled with the arm.

In one alternative, the natural orifice is the mouth and the wall is the stomach. Alternatively, the natural orifice is the anus and the wall is the intestinal wall. In a further embodiment, the natural orifice is the umbilicus. According to one implementation, the method includes making only a single incision in the patient. Another embodiment of the method includes positioning the robotic device using a detached handle.

While multiple embodiments are disclosed, still other embodiments will become apparent to those skilled in the art from the following detailed description, which shows and describes illustrative embodiments of the invention. As will be realized, the embodiments disclosed herein are capable of modifications in various obvious aspects, all without departing from the spirit and scope of the various inventions. Accordingly, the drawings and detailed description are to be regarded as illustrative in nature and not restrictive.

BRIEF DESCRIPTION OF THE DRAWINGS

FIG. 35A shows the results for the motor for link 1, FIG. 35B shows the results for the motor for link 2, and FIG. 35C shows the results for the motor for link 3.

FIG. 36A shows the results for the motor for link 1, FIG. 36B shows the results for the motor for link 2, and FIG. 36C shows the results for the motor for link 3.

FIG. 38A shows the results for link 1, while

FIG. 39A shows the results for link 1, while FIG. 39B shows the results for link 2, and FIG. 39C shows the results for link 3.

FIG. 41A shows the results for link 1 and FIG. 41B shows the results for link 3.

FIG. 66A depicts the target from the viewpoint from one of the two stereo cameras on the robotic device and FIG. 66B depicts the target from the viewpoint of the other stereo camera.

FIGS. 68A and B depict images from the magnetically coupleable device during the procedure.

FIG. 70A depicts a configuration having three revolute joints, similar to the human arm (two large rotations of the shoulder and one rotation at the elbow).

DETAILED DESCRIPTION

The present invention relates to various embodiments of robotic devices for use in surgical methods and systems. Generally, the robotic devices are configured to be inserted into or positioned in a patient's body, such as a body cavity, for example.

The robotic devices fall into three general categories: mobile devices, stationary or "fixed base" devices, and magnetically coupled devices. A "mobile device" includes any robotic device configured to move from one point to another within a patient's body via motive force created by a motor in the device. For example, certain embodiments of mobile devices are capable of traversing abdominal organs in the abdominal cavity. A "fixed base device" is any robotic device that is positioned by a user, such as a surgeon. A "magnetically coupleable device" is any robotic device that can be positioned, operated, or controlled at least in part via a magnet positioned outside the patient's body.

Mobile Robotic Devices

Figure 1:
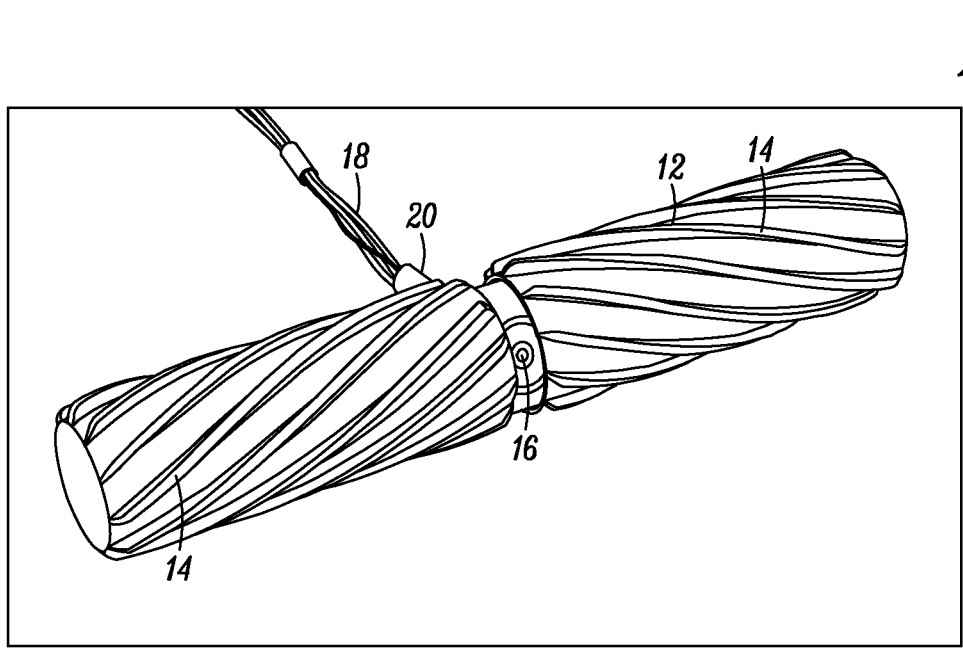
FIG. 1 is a perspective view of a mobile robotic device, according to one embodiment.

FIG. 1 depicts a mobile robotic device 10, according to one embodiment. The device 10 includes a body 12, two wheels 14, a camera 16, and a wired connection component 18 (also referred to herein as a "tether"). Images collected by the camera 16 can be transmitted to a viewing device or other external component via the connection component 18. The device 10 further includes a motor (not shown) configured to provide motive force to rotate the wheels 14, a power supply (not shown) configured to supply power to the motor, and a controller (not shown) operably coupled to the device 10 via the connection component 18. The controller is configured to provide for controlling or operating the device 10 via manipulation of the controller by a user. In one embodiment, the power supply is positioned outside the body and the power is transmitted to the motor via the connection component 18. Alternatively, the power supply is disposed within or on the device 10.

In one alternative embodiment, the device 10 also has a rotation translation component 20 or "tail." The tail 20 can limit counter-rotation and assist the device 10 in translating the rotation of the wheels 14 into movement from one point to another. The "rotation translation component" is any component or element that assists with the translation or conversion of the wheel rotation into movement of the device. In one embodiment, the tail is spring loaded to retract and thus, according to one embodiment, provide for easy insertion of the robotic device 10 through the entry port of a laparoscopic surgical tool.

In another implementation, the device 10 has no tail 20 and the wired connection component 18 or some other component serves to limit counter-rotation.

Alternatively, a mobile robotic device according to another embodiment can also have one or more operational components (also referred to herein as "manipulators") and/or one or more sensor components. In these embodiments, the device may or may not have an imaging component. That is, the device can have any combination of one or more imaging components, one or more operational components, and one or more sensor components.

The operational component might be, for example, biopsy graspers. Further, the one or more sensor components could be chosen from, for example, sensors to measure temperature, blood or other tissue or body fluids, humidity, pressure, and/or pH.

Figure 2:
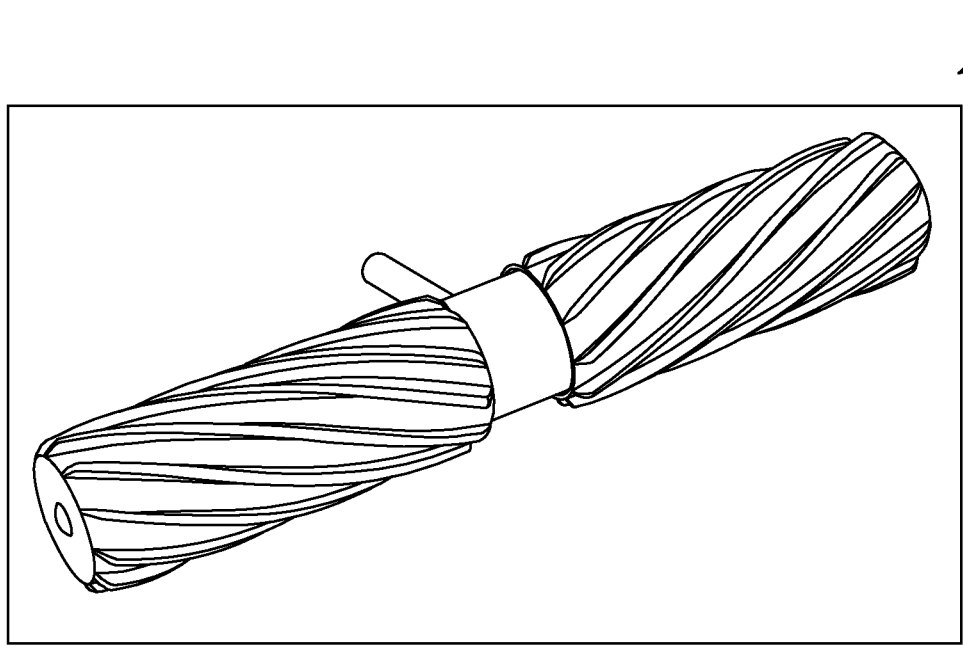
FIG. 2 is a perspective view of a mobile robotic device, according to another embodiment.

In a further alternative, the connection component is a wireless connection component. That is, the controller is wirelessly coupled to, and wirelessly in connection with, the device 10. In such embodiments, the wireless connection component of the device 10 is a transceiver or a transmitter and a receiver to communicate wirelessly with an external component such as a controller. For example, FIG. 2 depicts a wireless mobile robotic device 26, according to one embodiment.

In accordance with one implementation, a mobile robotic device could be used inside the body of a patient to assist with or perform a surgical procedure. In one aspect, the device is sized to fit through standard laparoscopic tools for use during laparoscopic surgery. In another alternative, the device is sized to be inserted through a natural orifice of the patient, such as the esophagus, as will be described in further detail below. In yet another alternative, the device can be sized and configured in any fashion to be used in surgical procedures.

Any of the several embodiments of mobile robotic devices described herein can be used in any number of ways. For example, one implementation of a mobile robotic device could provide visual feedback with a camera system and tissue dissection or biopsy component with a grasper attached to it. Further, such a robot could also be equipped with a sensor suite that could measure pressure, temperature, pH, humidity, etc.

It is understood that a robotic device as described generally above can take on any known configuration and be equipped with any number of sensors, manipulators, imaging devices, or other known components. That is, a robotic device conforming to certain aspects described herein can, in various embodiments, take on many different configurations, such as cylindrical or spherical shapes, or, alternatively, a shape such as that of a small vehicle, and is not limited to the cylindrical robotic devices depicted in FIG. 1, 2, or 3. Further, there are hundreds of different components known in the art of robotics that can be used in the construction of the robotic devices described herein. For example, there are hundreds controllers, motors, power supplies, wheels, bodies, receivers, transmitters, cameras, manipulators, and sensing devices that can be used in various combinations to construct robotic devices as described herein.

Figure 3A:
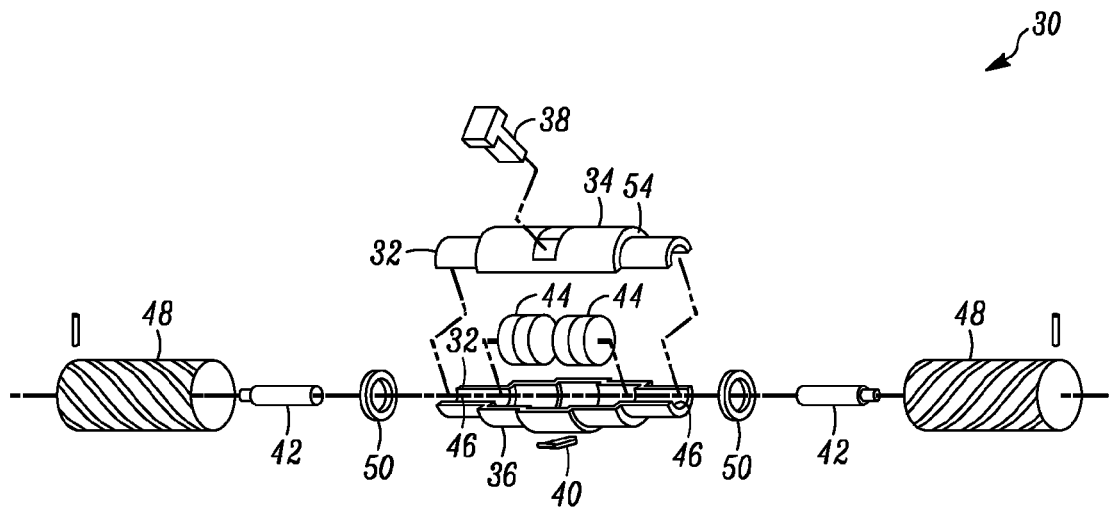
FIG. 3A is an exploded view of a mobile robotic device, according to one embodiment.

FIG. 3A depicts an exploded view of a mobile robotic device 30, according to one embodiment. The device 30 has a body or core component 32 that includes a first portion 34 and a second portion 36. Alternatively, the core component 32 could be a single component. A camera 38 is disposed in the first portion 34, and a tail 40 is attached to the second portion 36. Alternatively, the camera 38 and/or the tail 40 can be attached to either portion 34, 36 or be associated with the device 30 in any other fashion that allows for use of the camera 38 and the tail 40. Further, a motor 42 is disposed in each slot 46 at each end of the body 32 and each motor 42 is operably coupled to one of the wheels 48.

In addition, as shown in FIG. 3A, the device 30 has two wheels 48, each one being rotationally disposed over at least some portion of the body 32. According to one embodiment, two bushings 50 are provided, each disposed between the body 32 and one of the two wheels 48. In one aspect of the invention, the bushing 50 supports the wheel 48 and prevents the wheel 48 from wobbling during rotation. Alternatively, no bushings are provided, or some other type of known support component is provided. In accordance with one implementation, the wheels 48 are coupled to the device 30 via wheel set screws 52.

In one aspect of the invention, the body 32 has a center portion 54 having a radius that is larger than the rest of the body 32. Alternatively, the center portion 54 has the same radius as the rest of the body 32. According to one embodiment, the body 32 can be constructed in any known fashion. For example, according to one embodiment, the body 32 is fabricated via machining or stereolithography.

The device 30 as shown in FIG. 3A also has four batteries 44. According to one embodiment, the batteries 44 are disposed within a cavity of the core component 32. For example, in one embodiment, the batteries 44 are disposed within the center portion 54 of the body 32. Alternatively, the device 30 can have one, two, three, or more than four batteries 44. In one embodiment, each battery 44 is an Energizer™ 309 miniature silver oxide battery. Alternatively, each battery 44 can be any known small battery that can be used within a robotic device. In a further alternative, the power source can be any known power source.

In one implementation, the device 30 also has a wireless connection component (not shown) in the form of transmitter and a receiver (not shown) or a transceiver (not shown) for use in a wireless configuration of the device 30 such that any images collected by the camera 38 can be transmitted to an external component for viewing and/or storage of the image and further such that any control signals can be transmitted from an external controller or other external component to the motor 42 and/or other components of the device 30. Alternatively, the device 30 has a wired connection component (not shown) that is attached to the device 30.

In another implementation, the device 30 can also have a light component (not shown) to illuminate the area to be captured by the imaging component. Alternatively, the device 30 has no light component.

According to one embodiment, a robotic device similar to the device 30 depicted in FIG. 3A can be constructed in the following manner. Any components to be associated with the body 32, such as a camera 38 and a tail 40, are coupled with the body 32. In addition, any components to be disposed within the body 32, such as batteries 44, motors 42, and other electronic components (not shown), are positioned within the body 32. In an embodiment in which the body 32 consists of two portions 34, 36, these components to be associated with or disposed within the body 32 are positioned in or attached to the body 32 prior to the coupling of the two portions 34, 36. According to one embodiment, a bushing 50 is disposed over each end of the body 32. Alternatively, no bushings 50 are provided. Subsequently, the wheels 48 are positioned on the device 30. For example, according to one embodiment, the wheels 48 are positioned on the motor shafts 52.

The device 30 depicted in FIG. 3A, according to one embodiment, is configured to fit through a port in a known laparoscopic surgical tool. For example, in accordance with one implementation, the device 30 is configured to be inserted through a standard 15 mm medical port.

According to another embodiment, the robotic device 30 can be constructed without any sharp edges, thereby reducing damage to the patient during use of the device 30. In a further embodiment, the device 30 is comprised of biocompatible materials and/or materials that are easy to sterilize.

A mobile robotic device conforming to certain characteristics of various embodiments discussed herein has a transport component, which is also referred to herein as a "mobility component." "Transport component" is any component that provides for moving or transporting the device between two points. In one example, the transport component is one or more wheels. For example, the transport components of the mobile robotic devices depicted in FIGS. 1, 2, and 3 are wheels.

Alternatively, a robotic device as described herein can have any known transport component. That is, the transport component is any known component that allows the device to move from one place to another. The present application contemplates use of alternative methods of mobility such as walking components, treads or tracks (such as used in tanks), hybrid components that include combinations of both wheels and legs, inchworm or snake configurations that move by contorting the body of the device, and the like.

According to one embodiment as depicted in FIG. 3A, the robotic device 30 has two wheels 48 independently driven with separate motors 42. According to one embodiment, the motors 42 are direct current motors. In another embodiment, each wheel 48 is attached to the motors 42 through a set of bearings and spur gears. In one implementation, the two separate motors 42 provide forward, reverse and turning capabilities. That is, the two wheels 48 with two separate motors 42 are configured to allow the device 30 to move forward or backward, or to turn. According to one embodiment, the two wheels 48 move the device 30 forward or backward by each wheel 48 rotating at the same speed. In this embodiment, the wheels 48 provide for turning the device 30 by each wheel 48 turning at a different speed or in different directions. That is, the left wheel turns faster than the right wheel when the device 30 turns right, and the right wheel turns faster than the left when the device turns left. In accordance with one implementation, the wheels 48 can also provide for a zero turning radius. That is, one wheel 48 can rotate in one direction while the other wheel 48 rotates in the other direction, thereby allowing the device 30 to turn 180° or 360° while the center portion of device 30 stays in substantially the same location.

Figure 3B:
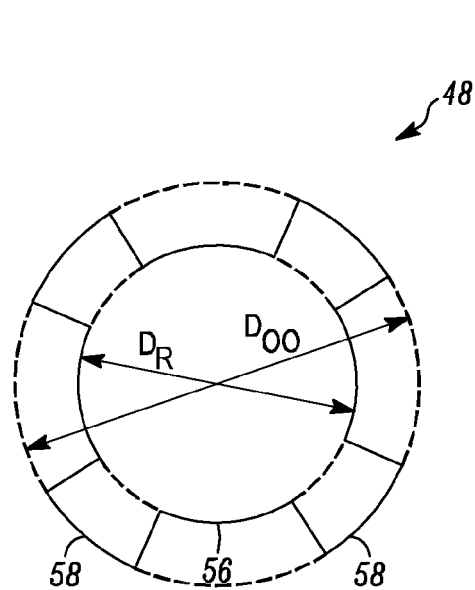
FIG. 3B is a side view of a wheel of a mobile robotic device, according to one embodiment.
Figure 3C:
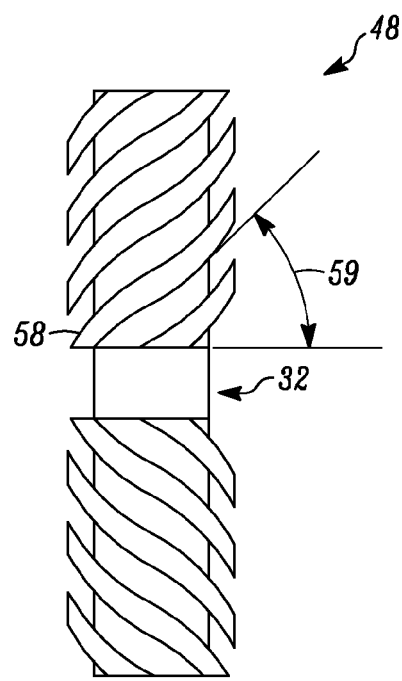
FIG. 3C is a plan view of a wheel of a mobile robotic device, according to one embodiment.

Each wheel 48, according to one implementation, has a surface texture on its exterior surface as shown in FIGS. 3A, 3B, and 3C. According to one embodiment, the surface texture creates traction for the wheel 48 as it moves across a tissue, organ, or other body surface.

FIGS. 3B and 3C depict one embodiment in which the wheels 48 have a surface texture consisting of raised portions 58 (also referred to herein as "grousers") disposed in a particular configuration on the wheels 48. The raised portions 58 are those portions of the wheel 48 that contact the surface that the wheels 48 are traversing.

The raised portion 58, according to one embodiment, defines an outer diameter 58 ($d_{oo}$), while the wheel 48 defines an inner diameter 56 ($d_r$). According to another embodiment, the inner and outer diameters of the wheels in one implementation are 17 mm and 20 mm, respectively. Alternatively, the grouser depth is 1.5 mm, where grouser depth is equal to $(d_{oo}-d_r)/2$. In a further alternative, the diameters and/or the grouser depth are any that would be useful for wheels on the mobile devices disclosed herein.

In another embodiment, the helical profile 59 of the wheels has a pitch of 30° as depicted in FIG. 3C. Alternatively, the helical profile can have a pitch ranging from about 0 degrees to about 90 degrees. In another aspect, the wheels 48 have treads. Alternatively, the surface texture is any surface characteristic that creates traction for the wheel 48.

In accordance with one implementation, the transport component constitutes at least about 80% of the external surface area of the robotic device. Alternatively, the transport component constitutes at least about 90% of the external surface area of the robotic device. In a further alternative, the transport component constitutes from about 80% to about 98% of the external surface area of the robotic device. In yet another alternative, the transport component constitutes any percentage of the external surface area of the robotic device.

The wheels depicted in FIGS. 1, 2, and 3 have a round, tubular-type treaded configuration. Alternatively, virtually any configuration could be employed, such as a round, square, spherical, or triangular configuration.

In addition, the wheels depicted in FIGS. 1, 2, and 3 are comprised of aluminum. Alternatively, the wheels are constructed of rubber or a combination of aluminum and rubber. In a further alternative, virtually any material that allows for traction or mobility can be used to construct the wheel or other transport component. In one embodiment, the material is any material that provides for traction on unusual, slick, hilly, deformable, or irregular surfaces such as any internal tissues, organs such as the liver, stomach, and/or intestines, or other internal surfaces, crevices, and contours of a patient, all of which has different surface properties.

In certain alternative embodiments, the robotic device has one or more sensor components. In various embodiments, such sensor components include, but are not limited to, sensors to measure or monitor temperature, blood, any other bodily fluids, fluid composition, presence of various gases, such as $CO_2$, for example, or other parameters thereof, humidity, electrical potential, heart rate, respiration rate, humidity, pressure, and/or pH. Further, the one or more sensor components can include one or more imaging components, which shall be considered to be a type of sensor component for purposes of this application. The sensors, including imaging devices, can be any such components or devices known in the art that are compatible with the various designs and configurations of the robotic devices disclosed herein.

According to one embodiment, a robotic device having one or more of the sensors described herein assists the user in the performance of a surgical procedure. In accordance with one implementation, the one or more sensors restore some of the natural monitoring or sensing capabilities that are inherently lost when using standard laparoscopic tools. Thus, the one or more sensor components allow the user to perform more complex procedures and/or more accurately monitor the procedure or the patient.

According to one embodiment, the imaging component can be a camera or any other imaging device. The imaging component can help to increase or improve the view of the area of interest (such as, for example, the area where a procedure will be performed) for the user. According to one embodiment, the imaging component provides real-time video to the user.

Current standard laparoscopes use rigid, single view cameras inserted through a small incision. The camera has a limited field of view and its motion is highly constrained. To obtain a new perspective using this prior art technique often requires the removal and reinsertion of the camera through another incision, increasing patient risk. In contrast to such limited imaging, a robotic device having one or more imaging components according to various embodiments described herein eliminates many of the limitations and disadvantages of standard laparoscopy, providing for an expanded and adjustable field of view with almost unlimited motion, thereby improving the user's visual understanding of the procedural area.

As used herein, the terms "imaging component," "camera," and "imaging device" are interchangeable and shall mean the imaging elements and processing circuitry which are used to produce the image signal that travels from the image sensor or collector to a viewing component. According to one embodiment, the image is a moving video image and the viewing component is a standard video viewing component such as a television or video monitor. Alternatively, the image is a still image. In a further alternative, the images are a combination of still and moving video images. The term "image sensor" as used herein means any component that captures images and stores them. In one embodiment, the image sensor is a sensor that stores such images within the structure of each of the pixels in an array of pixels. The terms "signal" or "image signal" as used herein, and unless otherwise more specifically defined, means an image which is found in the form of electrons which have been placed in a specific format or domain. The term "processing circuitry" as used herein refers to the electronic components within the imaging device which receive the image signal from the image sensor and ultimately place the image signal in a usable format. The terms "timing and control circuits" or "circuitry" as used herein refer to the electronic components which control the release of the image signal from the pixel array.

In accordance with one implementation, the imaging component is a small camera. In one exemplary embodiment, the imaging component is a complementary metal oxide semiconductor ("CMOS") digital image sensor such as Model No. MT9V125 from Micron Technology, Inc., located in Boise, Id. Alternatively, the imaging component is a square 7 mm camera. In an alternative example, the camera can be any small camera similar to those currently used in cellular or mobile phones. In another example, the imaging device can be any imaging device currently used in or with endoscopic devices. In one embodiment, the imaging device is any device that provides a sufficient depth of field to observe the entire abdominal cavity.

According to another embodiment, the imaging device can employ any common solid state image sensor including a charged coupled device (CCD), charge injection device (CID), photo diode array (PDA), or any other CMOS, which offers functionality with simplified system interfacing. For example, a suitable CMOS imager including active pixel-type arrays is disclosed in U.S. Pat. No. 5,471,515, which is hereby incorporated herein by reference in its entirety. This CMOS imager can incorporate a number of other different electronic controls that are usually found on multiple circuit boards of much larger size. For example, timing circuits, and special functions such as zoom and anti-jitter controls can be placed on the same circuit board containing the CMOS pixel array without significantly increasing the overall size of the host circuit board. Alternatively, the imaging device is a CCD/CMOS hybrid available from Suni Microsystems, Inc. in Mountain View, Calif.

In accordance with one implementation, the imaging device provides video output in NTSC format. For example, any commercially-available small NTSC video format transmission chips suitable for the devices described herein can be used. Alternatively, any known video output in any known format can be incorporated into any device described herein.

The imaging component, according to one embodiment, has a manual focus adjustment component. Alternatively, the imaging component has a mechanically-actuated adjustable-focus component. A variety of adjustable-focus mechanisms are known in the art and suitable for actuating focusing of many types of known imaging components.

In one embodiment, the imaging component is capable of focusing in range from about 2 mm to infinity. Alternatively, the imaging component can have a focusing range similar to that of any known adjustable focus camera.

Figure 4:
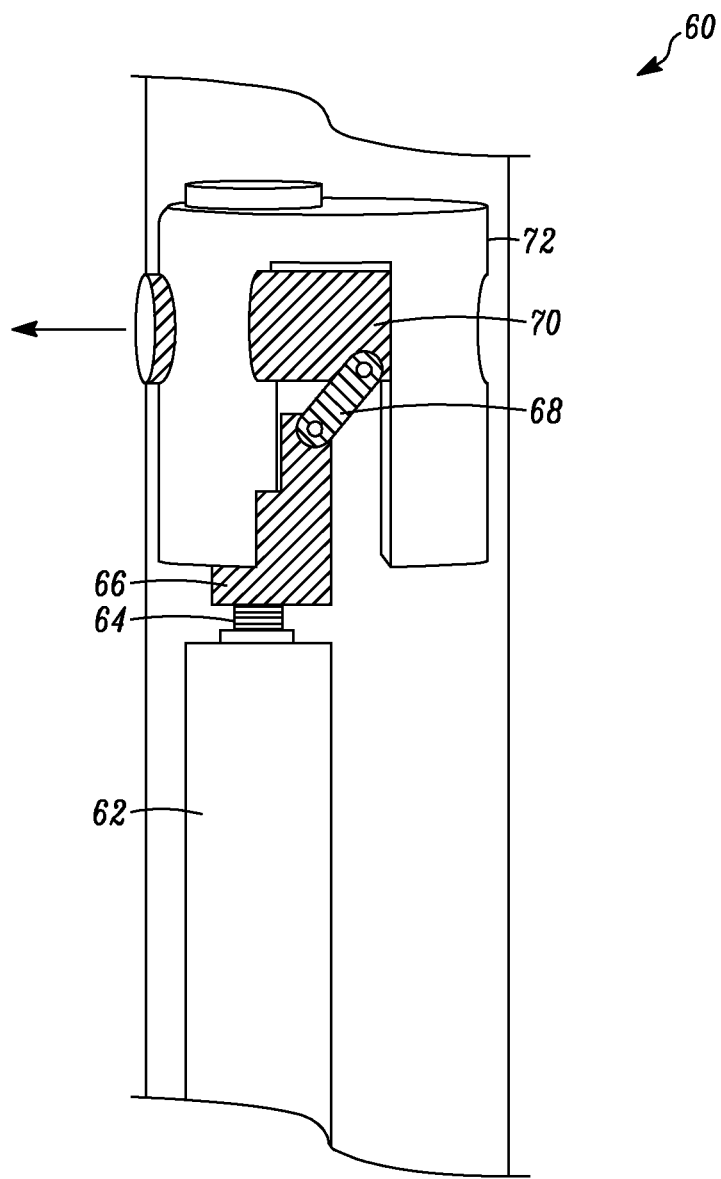
FIG. 4 depicts the adjustable-focus component implemented in a camera robot, according to one embodiment.

Alternatively, the imaging component has an adjustable-focus mechanism 60 as depicted in FIG. 4 that employs a motor 62 that is directly connected to a lead screw 64 which is rotated by motor 62. In this embodiment, as the lead screw 64 rotates, it drives a lead nut 66 up and down. This up-anddown motion is translated by a linkage 68 to a slider 70 that moves left to right. Slider 70 is held in place by a mechanism housing or guide 72. A lens or image sensor mounted to slider 70 can be translated back and forth from left to right to allow adjustable focusing. According to some embodiments, the motor 62 used to power the adjustable-focus mechanism of the imaging component can also be used to power other components of the robotic device, such as, for example, a biopsy component as described in greater detail below.

In accordance with another embodiment, the imaging component can be controlled externally to adjust various characteristics relating to image quality. For example, according to one embodiment, one or more of the following can be adjusted by a user: color, white balance, saturation, and/or any other known adjustable characteristic. According to one embodiment, this adjustment capability can provide quality feedback in poor viewing conditions such as, for example, low lighting.

According to one implementation, any mobile imaging device disclosed herein can have any known lens that can be used with such devices. In one particular embodiment, the lens is model no. DSL756A, a plastic lens available from Sunex, located in Carlsbad, Calif. This embodiment provides only a short depth of field, which requires adjustable-focus capability. To attain this, the lens of this implementation is attached to an actuation mechanism to provide adjustable focus capability. The lens is moved by the actuation mechanism to provide a range of focus from 2 mm to infinity. Alternatively, the lens can be any lens that can be incorporated into any of the imaging devices described herein.

In a further alternative, the imaging component can include an image stabilization component. For example, according to one embodiment, the device could include on-board accelerometer measurements with image motion estimates derived from optical flow to yield base motion estimates, such as are known in the art. Alternatively, the image stabilization component can be any such commercially-available component. Optical flow has been shown to yield reliable estimates of displacements computed across successive image frames. Using these robot base motion estimates, image stabilization algorithm can be used to provide image stabilization. Alternatively, any known image stabilization technology can be incorporated for use with the imaging component.

In certain embodiments, the camera is fixed with respect to the body of the robotic device, such that the position of the robot must be changed in order to change the area to be viewed. Alternatively, the camera position can be changed with respect to the device such that the user can move the camera with respect to the robotic device. According to one embodiment, the user controls the position of the camera using a controller that is operably coupled to the device as described in further detail herein.

The robotic device can also, according to one embodiment, have a lighting component to light the area to be viewed. In one example, the lighting component is an LED light. Alternatively, the lighting component can be any illumination source.

According to one implementation, the camera is disposed on the center portion of the body of the device, as shown in FIG. 3A. Alternatively, the camera can be disposed on any portion of the body. In a further alternative, the camera can be disposed anywhere on the robotic device.

According to one embodiment, the robotic device has one or more operational components. The "operational component," as used herein, is intended to mean any component that performs some action or procedure related to a surgical or exploratory procedure. According to one embodiment, the operational component is also referred to as a "manipulator" and can be a clamp, scalpel, any type of biopsy tool, a grasper, forceps, stapler, cutting device, cauterizing device, ultrasonic burning device, or other similar component, as set forth in further detail herein. In yet another embodiment, the operational component is any device that can perform, or assist in the performance of, any known surgical or exploratory laparoscopic procedure. In one aspect, the one or more operational components assist with procedures requiring high dexterity. In currently known techniques, movement is restricted, as passing the rigid laparoscopic tool through a small incision restricts movement and positioning of the tool tip. In contrast, a robotic device having an operational component inside a cavity is not subject to the same constraints.

In one implementation, the operational component can also include an arm or other positioning component. For example, the operational component can include an arm and a biopsy tool. Alternatively, the operational component can include a positioning component and any operational component as described above.

According to one embodiment, any operational component described or contemplated herein can be an off-the-shelf surgical tool or modified version thereof. Alternatively, any such operational component can be constructed de novo.

Figure 5:
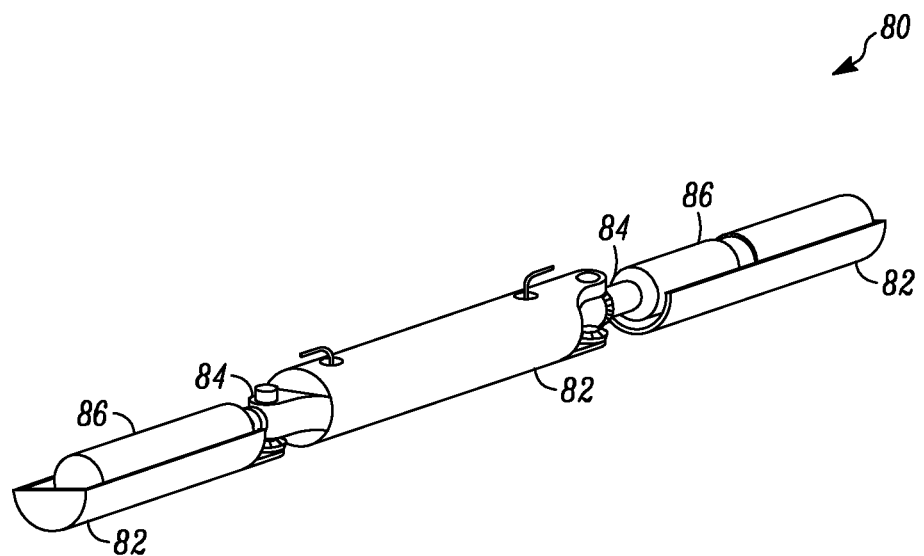
FIG. 5 is a perspective view of a manipulator arm according to one embodiment.
Figure 6:
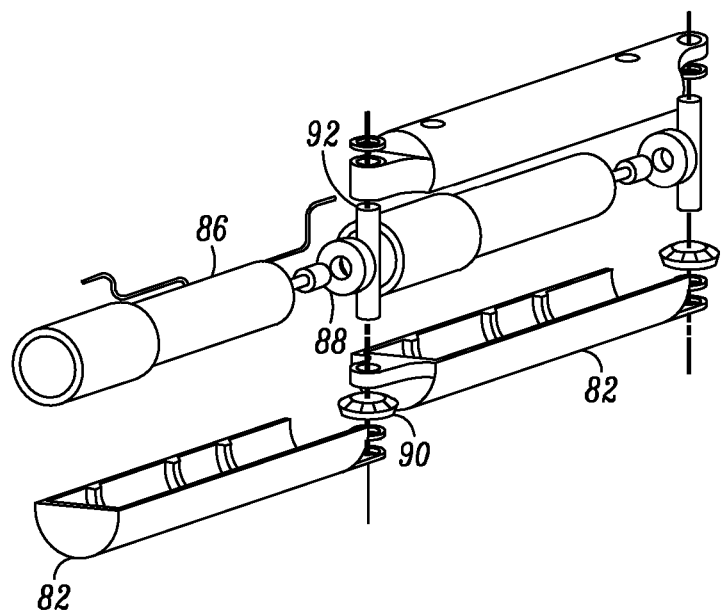
FIG. 6 is an exploded view of a manipulator arm according to one embodiment.

The operational component depicted in FIGS. 5 and 6 is a manipulator arm 80 having three arms or "links" 82, according to one implementation. The arm 80 has two joints 84, each coupled to a motor 86. According to one embodiment, as best depicted in FIG. 6, the links 82 are composed of two halves that attach in only one configuration.

The joints 84 are configured in any known fashion. In one example as depicted in FIGS. 5 and 6, each joint 84 has a gear 88 coupled to the motor, and another gear 90 coupled to a pin 92. In one aspect, the gears are bevel gears. According to one embodiment, the gears are standard miter gears available from Stock Drive Products/Sterling Instruments, located in New Hyde Park, N.Y.

In one implementation, the arm was constructed using stereolithography. According to one embodiment, stereolithography can be used to construct the linkages and the base section out of a cured resin material similar to plastic.

The motor, according to one embodiment, that can be used in the linkages is a DC micromotor with encoders manufactured by MicroMo Electronics, located in Clearwater, Fla. The motor is a 6 V motor having a 15,800 rpm no-load speed, 0.057 oz-in stall torque, and weighed 0.12 oz. The motor has an 8 mm diameter and is 16 mm long. Due to its high no-load speed, a precision planetary gearhead is used. Further description of the motor, gearhead, and an encoder that can be used with the motor are described in Example 2. Alternatively, the arm can use a low voltage motor, such as a 3 V motor.

In one implementation, the arm has an encoder used for the indication and control of both shaft velocity and the direction of rotation, as well as for positioning. In one embodiment, the encoder is a 10 mm magnetic encoder. It is 16.5 mm long, but only adds 11.5 mm to the total length of the assembly.

Figure 7A:
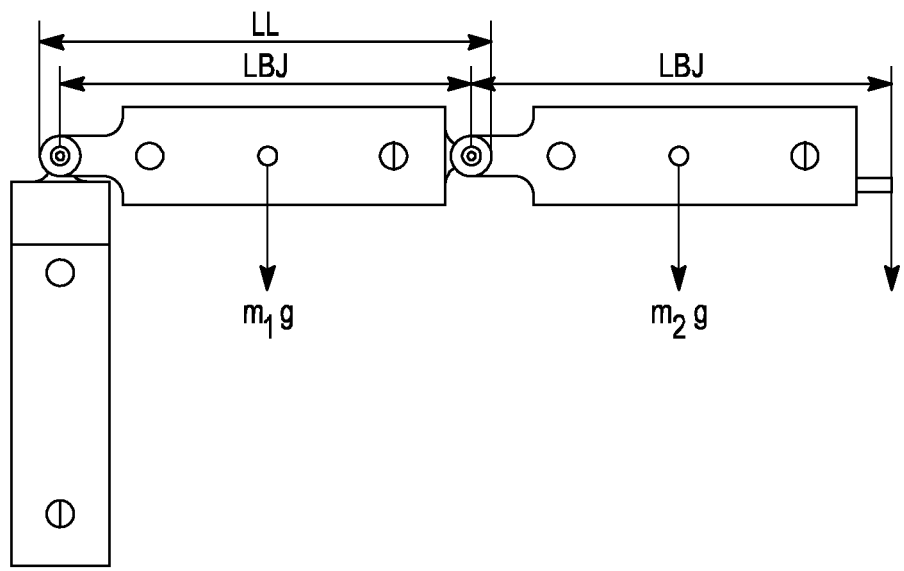
FIG. 7A is a model of one embodiment of a manipulator arm labeled with the parameters used to determine properties of the links.

FIG. 7A shows a schematic of one manipulator embodiment with $L_L$, $L_{BJ}$, $M_1$, $M_2$, $m_1g$, $m_2g$ and $W_p$ labeled. Without being limiting, the schematic was used for calculating various characteristics relating to one manipulator embodiment and is explained in further detail in Example 2 below. Based on the testing, it was determined that for this particular embodiment, a reduction ratio off 64:1 provides sufficient torque while optimizing the design. Alternatively, precision gears with other reduction ratios may be used.

Figure 8:
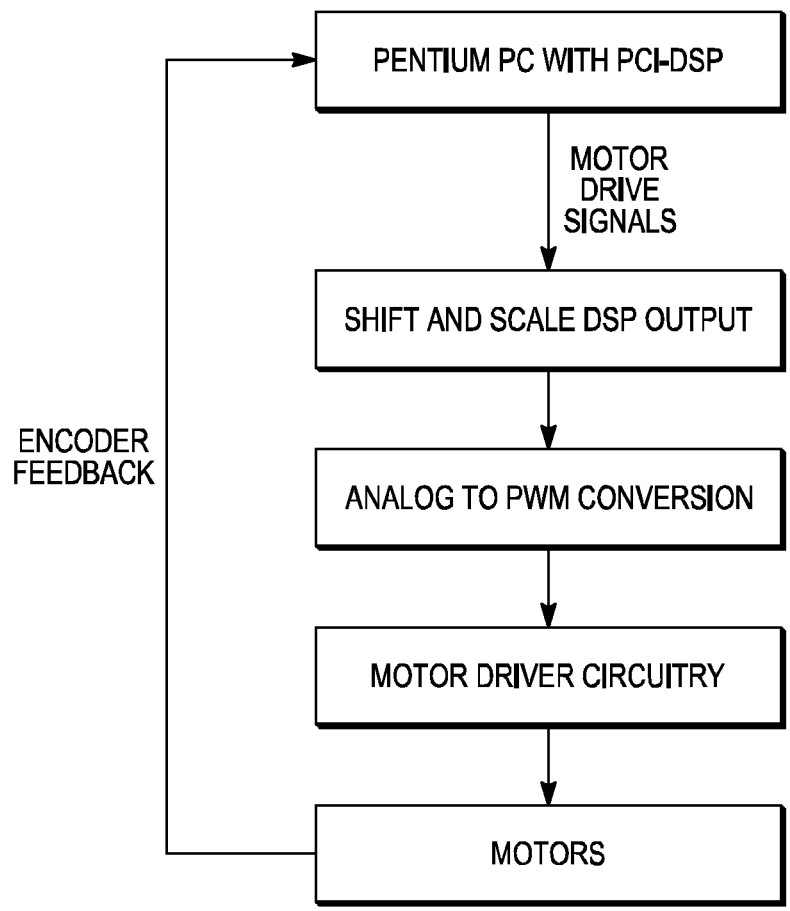
FIG. 8 is a block diagram of the electronics and control system used in one embodiment of a manipulator arm.

In one embodiment as depicted in FIG. 8, the electronics and control for the arm consists of four major sections: PC with a MEI DSP motor driver PCI card, an analog circuit to shift and scale the output voltage from the MEI card, a microcontroller to convert each axis' analog voltage to a PWM signal, and an H-Bridge ICS to drive the motors. This embodiment is described in further detail in Example 2 below.

In one embodiment, the manipulator is a biopsy forceps or grasper. According to one aspect, the manipulator includes a biopsy forceps or graspers at one end of an arm.

In another embodiment, the manipulator of the present invention includes an actuation mechanism that generates forces required for operating the manipulator. For example, according to one embodiment in which the manipulator is a biopsy forceps or graspers, the manipulator also has an actuation mechanism that generates sufficient force to allow the forceps or graspers to cut/obtain a biopsy sample. According to one embodiment, the actuation mechanism generates a drawbar force of magnitude greater than 0.6 N. Alternatively, the actuation mechanism generates any amount of force sufficient to obtain a biopsy sample. In a further alternative, the actuation mechanism generates a sufficient force to operate any type of manipulator, such as a clamp, stapler, cutter, cauterizer, burner, etc.

Figure 9A:
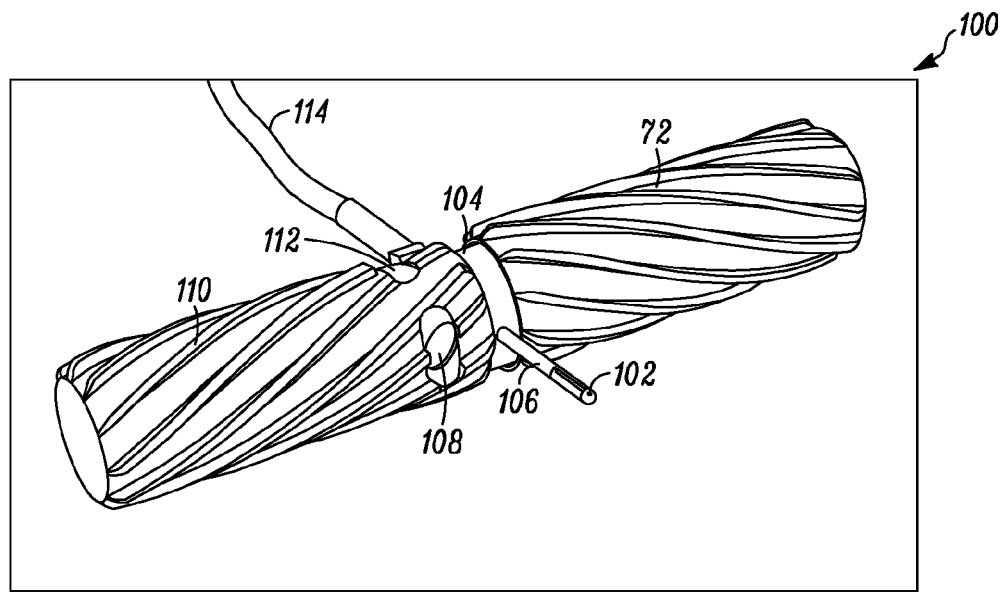
FIG. 9A is a perspective view of a mobile robotic device, according to another embodiment.

FIG. 9A depicts a robotic device 100 having a biopsy tool 102. The cylindrical robotic device 100 has a cylindrical body 104 having an appendage or arm 106 with a biopsy forceps 102 at one end of the arm that is used for sampling tissue. According to one embodiment, the robot's grasper 102 can open to 120 degrees. In a further alternative, the forceps 102 can have any known configuration.

In one embodiment, the body 104 also contains an imaging component (not shown), camera lens 108, motor and video control boards (not shown), and actuation motor (not shown) and a mechanism for camera adjustable-focus (not shown). In this embodiment, the imaging component and lens 108 are offset to the side to allow space for the biopsy grasper 102. The wheel 110 on the camera side has slots 112 machined in it to allow for space for the camera lens 108 to see the abdominal environment and the biopsy grasper 102. Alternatively, the camera and lens 108 are disposed anywhere on the robotic device 100 such that the camera can be used to view the surgical area and/or the biopsy grasper 102 during use. The device 100 a wired connection component 114 that is connected to an external component (not shown).

Figure 9B:
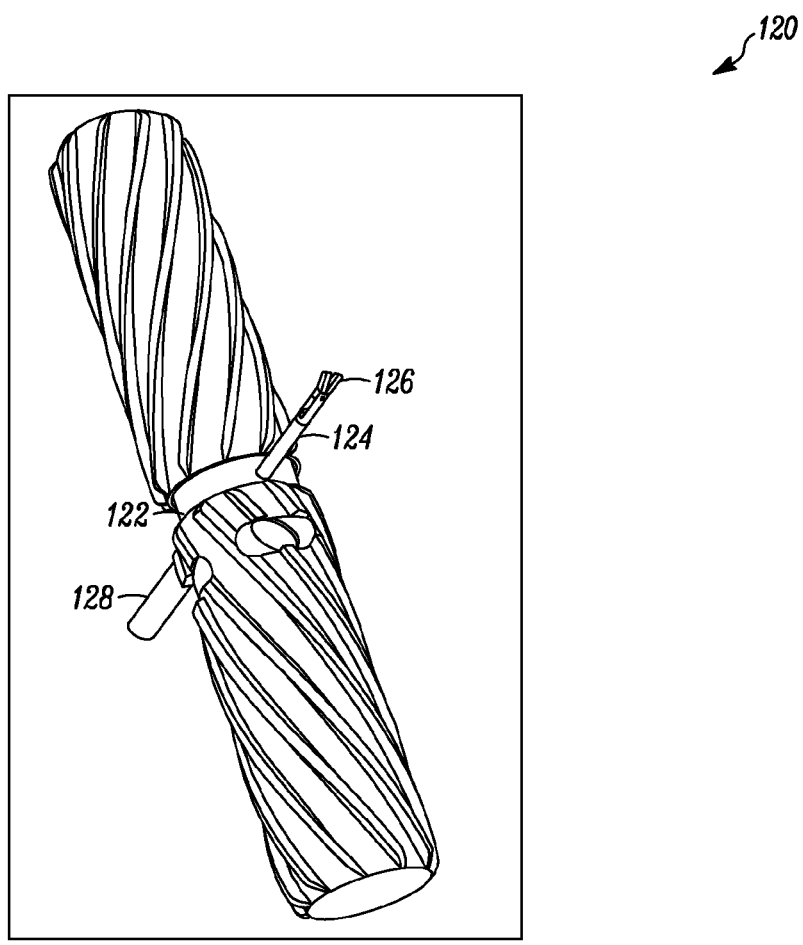
FIG. 9B is a perspective view of a mobile robotic device, according to yet another embodiment.

FIG. 9B depicts a mobile robotic device 120, according to an alternative embodiment. In this embodiment, the device 120 is wireless. That is, the device 120 has no wired connection component physically connecting the device 120 to an external component positioned outside the patient's body. In the configuration of FIG. 9B, the device 120 has a configuration similar to the wired device in FIG. 9A. That is, the device 120 has a cylindrical body 122 and an arm 124 having a biopsy tool 126. Further, the device 120 can also have other components similar to those described above with respect to the embodiment in FIG. 9A. In one alternative implementation, the device 120 also has a "tail" 128, described in further detail above, connected to the body 122.

In use, a robotic device with a camera and a biopsy tool such as the devices depicted in FIGS. 9A and 9B can be used to obtain a biopsy sample. The device can be inserted into the body, such as through a standard trocar or using any of the natural orifice procedures described herein. The user can control the device using visual feedback from the on-board camera. This mobility allows the robot to move to the area of interest to sample specific tissues. The biopsy tool can then be actuated to obtain a tissue sample. In a further embodiment, the biopsy forceps provide a clamp capable of clamping shut a severed artery.

In an alternative embodiment, the manipulator is a drug delivery component. That is, according to one implementation, robotic devices disclosed herein can have a drug delivery component or system that delivers an agent to an animal, including a human. In one embodiment, the agent is a hemostatic agent. Alternatively, the agent can be any deliverable composition for delivery to an animal, including a human.

Figure 10:
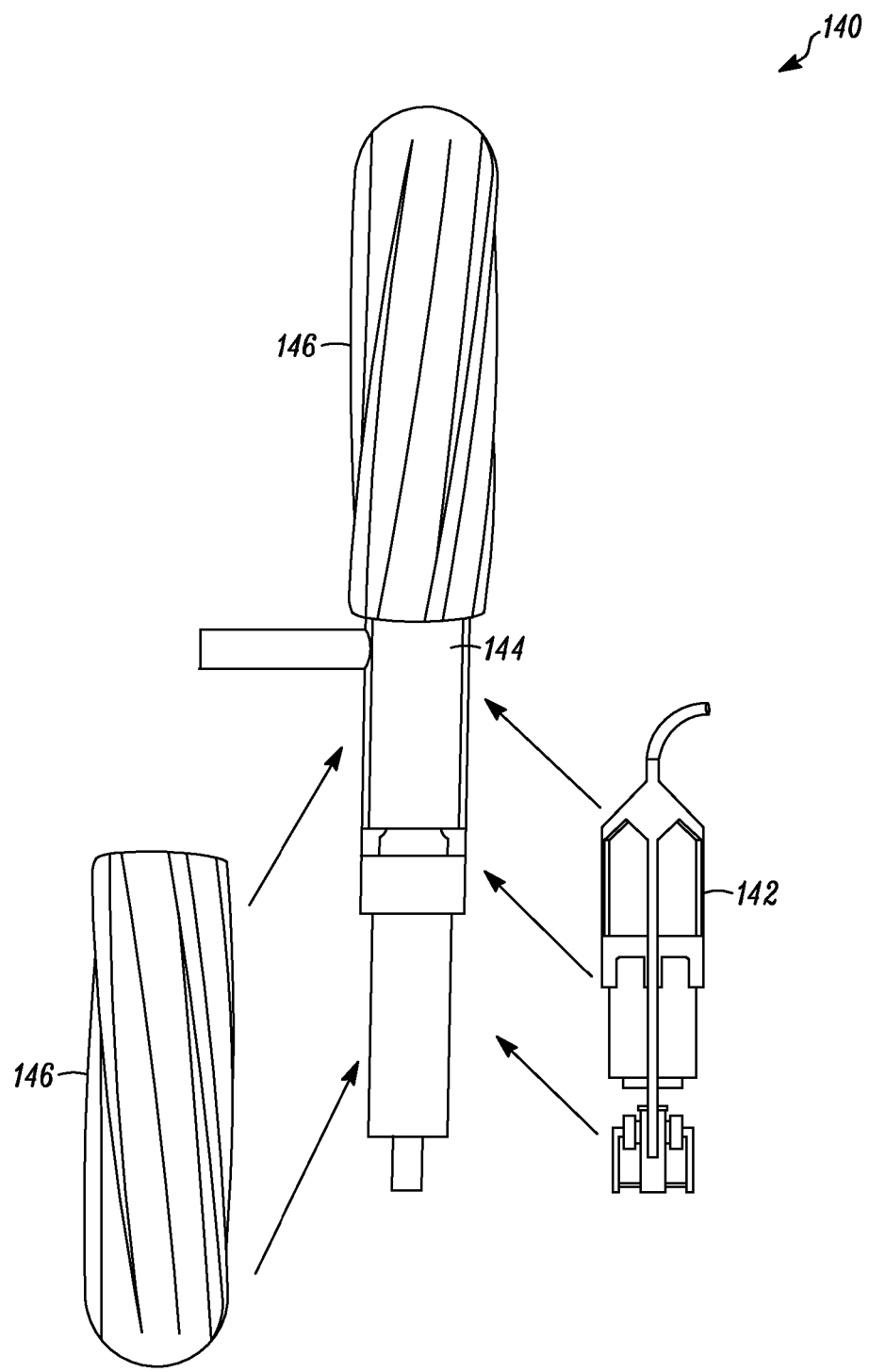
FIG. 10 is a plan view of a mobile robotic device having a drug delivery component, according to another embodiment.

FIG. 10 depicts a robotic device 140 having an agent delivery system 142, according to one embodiment. In this embodiment, the delivery system 142 is disposed within the cylindrical body 144 and two wheels 146 are rotatably disposed over the cylindrical body 144. The device 140 can also have an imaging component (not shown). Alternatively, the device need not have an imaging component.

Figure 11A:
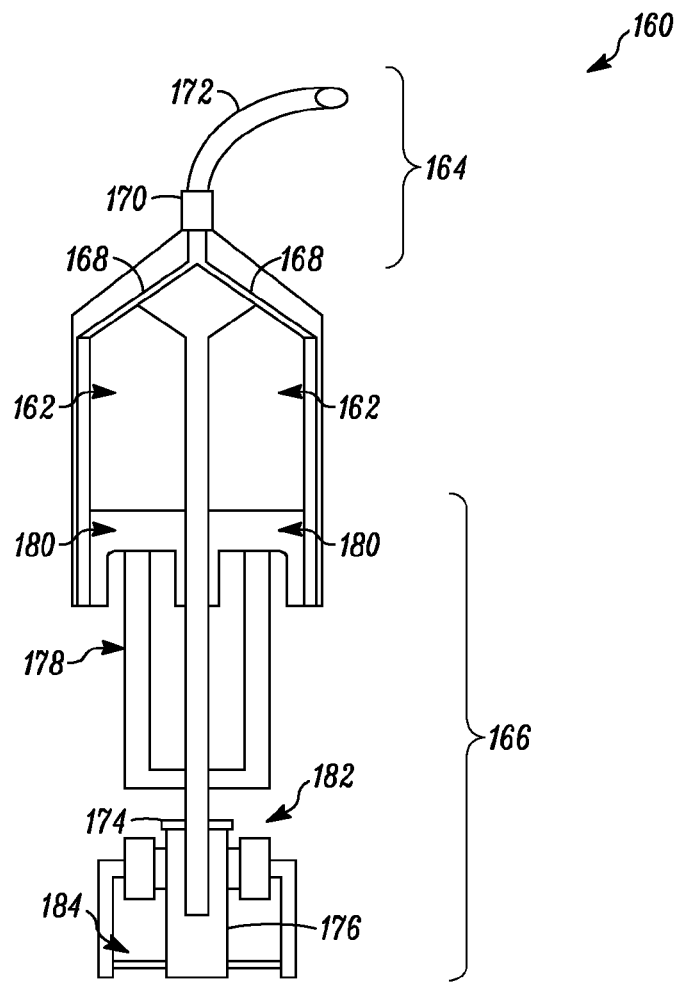
FIGS. 11A and B are schematic depictions of a drug delivery component that can be integrated into a mobile robotic device, according to one embodiment.

FIG. 11A depicts an agent delivery component 160, according to one embodiment. The delivery component 160 in this embodiment is an agent storage and dispensing system. In one embodiment, the agent is a hemostatic agent. The system has dual reservoirs 162 that can contain the agent, a mixing and discharge component 164, and an actuation component 166. According to one embodiment, the mixing and discharge component 164 has two delivery tubes 168, a manifold 170 and a cannula 172. Alternatively, the mixing and discharge component 164 is actually two separate components: a mixing component and a discharge component. In one implementation, the actuation component 166 has a crank wheel 174, a catch lever 176, and a ratcheting linkage 178 coupling the crank wheel 174 to plungers 180 disposed within the reservoirs 162.

In one embodiment, the dual reservoirs 162 of FIG. 11A are configured to store and isolate two agents or agent components. In one implementation, the reservoirs 162 are similar to those used in standard dual syringe injection systems. According to one embodiment, the two components are two separate components of the hemostatic agent. That is, as is understood in the art, many hemostatic agents are comprised of two components that must be preserved separately to prevent premature coagulation prior to application. In this embodiment, the storage and dispensing system has dual reservoirs system configured to store and isolate the two components until they are dispensed. Alternatively, the agent is a single component hemostat that does not need to be combined with another component, and the same agent is placed in both reservoirs. In a further alternative, the system has a single reservoir or container for any agent that need not be combined with another. In yet another alternative, the system can have more than two reservoirs.

Figure 11B:
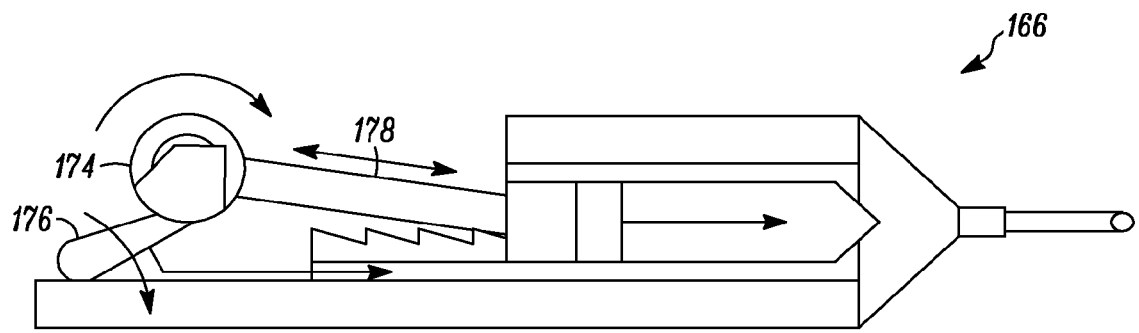

FIG. 11B, along with FIG. 11A, provides an additional perspective relating to the actuation component 166. The actuation component 166 has pre-loaded torsional springs 182 that are pre-wound and rigidly attached to the crank wheel 174. In addition, the lever 176, according to one embodiment, is also attached to torsion springs 184. When the lever 176 is released, the stored mechanical energy in the springs 182 causes the crank wheel 174 to rotate. The off-center attachment point of the ratcheting linkage 178 to the crank wheel 174 converts rotational displacement of the wheel 174 into linear displacement of the plungers 180.

According to one embodiment, the spring-loaded catch lever 176 is a shape memory alloy and is actuated with a SMA wire trigger. SMA wires are made of a nickel-titanium alloy that is easily stretched at room temperature. However, as the wires are heated by passing an electric current through them, they shorten in length and exert a force that is greater than the force required to stretch them. In one embodiment, the wires shorten in length by up to approximately 8% and exert approximately 5 times the force required to stretch them.

Figure 12:
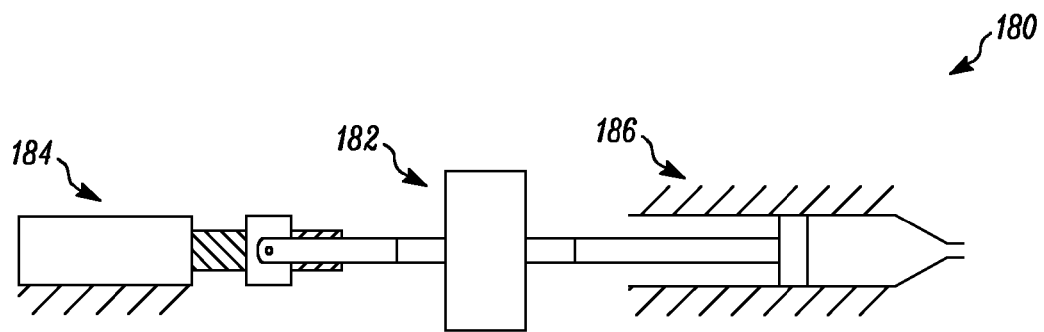
FIG. 12 is a schematic depiction of a test jig for measuring the applied force required to move a plunger in a drug delivery component, according to one embodiment.

A further alternative embodiment of the actuator mechanism is depicted in FIG. 12 and is described in further detail below in Example 6. That mechanism uses a permanent magnet direct current motor as the force actuator.

Alternatively, the actuator mechanism can be any known device for providing for linear displacement of the reservoir plungers 180 that dispense the agent. According to one implementation, the actuator ensures uniform delivery of the agent from the storage reservoir(s).

Figure 13A:
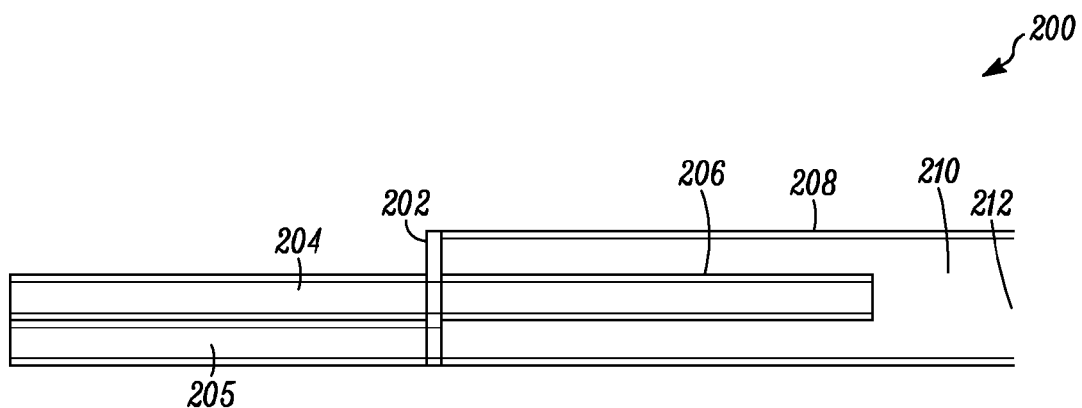
FIGS. 13A and B are schematic depictions of the profile of a drug delivery component, according to one embodiment.

FIG. 13A depicts a mixing component 200, according to one embodiment. The system 200 includes a manifold 202 and two delivery components or tubes 204, 205. Projecting from the end of the manifold 202 is a length of tubing 206 that contains one of the fluid flows and fits inside a larger diameter cannula 208. The system 200 has a mixing site 210 and a discharge site 212. The mixing component is a device for mixing and delivering at least two fluid components simultaneously through a single cannula. In implementations in which the agent is a hemostatic agent requiring two compounds, the mixing component thoroughly mixes the two components as necessary to promote optimal coagulation. In one embodiment, a mixing system ensures that the two components come into contact near the exit port in such a way as to promote efficient mixing and that all reactive material is ejected to prevent clogging of the cannula.

Figure 13B:
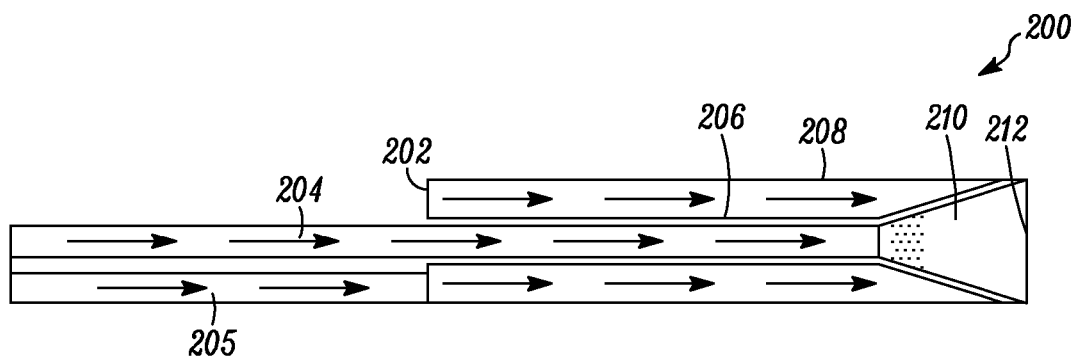

FIG. 13B depicts the flow of agents in the mixing component 200 of FIG. 13A. In this embodiment, the fluids contained in the two storage reservoirs (not shown) are delivered simultaneously to the manifold 202 through the delivery tubes 204, 205. The fluid flow in delivery tube 205 exits the manifold 202 and is forced around the tubing 206 through the length of the cannula 208. The fluids mix in the mixing site 210 near the discharge site 212, and any reactive material is ejected from the larger diameter cannula 208 at the discharge site 212. According to one embodiment, the point at which mixing commences and, hence, the time available prior to delivery, can be adjusted by changing the diameters and lengths of the tubing and cannula. Further, spirals or other features can be incorporated along the inside surface of the cannula 208 to enhance the mixing efficiency of this system.

Alternatively, the mixing component is any known component for mixing two agents, including, but not limited to, hemostatic agents, that can implemented with one or more of the robotic devices described herein.

In accordance with one aspect, the reservoir or reservoirs have at least one externally accessible loading port configured to allow for loading, injecting, or otherwise placing the agent or components into the reservoir. The loading port is a standard rubber stopper and seal commonly used for vaccine vials. Such a rubber stopper and seal facilitates transfer of any agent using a standard syringe. Alternatively, the loading port is any known type of loading port of any known configuration. According to one embodiment, such a loading port is useful for known agents that must be reconstituted shortly before use, such as on-site reconstitution. As such, the loading port or ports accommodate the need for on-site loading of the compounds.

According to one aspect, any robotic device embodiment described herein is connected to an external controller via a connection component. According to one embodiment, the connection component is a wire, cord, or other physical flexible coupling. For purposes of this application, the physical or "wired" connection component is also referred to as "tethered" or "a tether." The flexible connection component can be any component that is coupled at one end to the robotic device and is flexible, pliable, or otherwise capable of being easily formed or manipulated into different shapes or configurations. According to one embodiment, the connection component includes one or more wires or cords or any other type of component operably coupled at the second end to an external unit or device. The component in this embodiment is configured to transmit or convey power and/or data, or anything else necessary or useful for operation of the device between the robotic unit and the external unit or device. In a further alternative, the connection component comprises at least two wires or cords or other such components, each of which are connected to a separate external unit (which, in one example, are a power source and a data transmission and receiver unit as described below).

Alternatively, the connection component is a wireless connection component. That is, the robotic device communicates wirelessly with a controller or any other external component. The wireless coupling is also referred to herein as "untethered." An "untethered device" or "wireless device" is intended for purposes of this application to mean any device that is fully enclosed within the body such that no portion of the device is external to the body for at least a portion of the surgical procedure or, alternatively, any device that operates within the body while the device is not physically connected to any external object for at least a portion of the surgical procedure. In one embodiment, an untethered robotic device transmits and receives data wirelessly, including data required for controlling the device. In this embodiment, the robotic device has an internal power supply, along with a receiver and transmitter for wireless connection.

The receiver and transmitter used with a wireless robotic device as described herein can be any known receiver and transmitter. For example, any known receiver and/or transmitter used in remote vehicle locking devices, remote controls, mobile phones.

In one embodiment, the data or information transmitted to the robotic device could include user command signals for controlling the device, such as signals to move or otherwise operate various components. According to one implementation, the data or information transmitted from the robotic device to an external component/unit could include data from the imaging component or any sensors. Alternatively, the data or information transmitted between the device and any external component/unit can be any data or information that may be useful in the operation of the device.

According to another implementation, any robotic device embodiment described herein is connected via a connection component not only to the external controller, but also to one or more other robotic devices, such devices being either as described herein or otherwise known in the art. That is, according to one embodiment, two or more robotic devices can be operably coupled to each other as well as an external unit or device. According to one embodiment in which there are two robotic devices, the two devices are operably coupled to each other and an external unit or device by a flexible connection component. That is, the two devices are operably coupled to each other by a flexible connection component that is coupled to each device and each device is also operably coupled to an external unit or device by a flexible connection component. In one embodiment, there are three separate flexible connection components: (1) a connection component connecting the two robotic devices, (2) a connection component connecting one of the robotic devices to the external unit, and (3) a connection component connecting the other of the robotic devices to the external unit. Alternatively, one connection component is operably coupled to both devices and the external unit. In a further alternative, any number of connection components can be used in any configuration to provide for connection of two robotic devices to each other and an external unit.

Alternatively, the two or more robotic devices are operably coupled to each other as well as an external unit or device in an untethered fashion. That is, the robotic devices are operably coupled to each other and an external unit or device in a fashion such that they are not physically connected. In one embodiment, the devices and the external unit are operably coupled wirelessly.

In one aspect, any robotic device described herein has a drive component. The "drive component," as defined herein, is any component configured to provide motive force such that the robotic device can move from one place to another or some component or piece of the robotic device can move, including any such component as described herein. The drive component is also referred to herein as an "actuator." In one implementation, the drive component is a motor.

The actuator can be chosen from any number of different actuators. For example, one actuator that can be incorporated into many, if not all, of the robotic devices described herein, is a brushless direct current motor, such as, for example, model no. SBLO4-0829 with gearhead PG04-337 (available from Namiki Precision of California, which is located in Belmont, Calif.). According to one embodiment, this motor requires external connection, which is generally provided by a circuit supplied by the manufacturer. In another implementation, the motor is model no. SBL02-06H1 with gearhead PG02-337, also available from Namiki.

Alternatively, any brushless direct current motor can be used. In a further alternative, another motor that can be used to operate various components of a robotic device, such as a manipulator, is a permanent magnet DC motor made by MicroMo™ Electronics, Inc. (located in Clearwater, Fla.). In yet another alternative, any known permanent magnet DC motors can be used with the robotic devices described herein.

The motor runs on a nominal 3 V and can provide 10.6 [mNm] stall torque at 80 rpm. This motor provides a design factor of 4 for the robot on a 75-degree slope (if frictional force is sufficient to prevent sliding).

In addition, other actuators that can be used with the robotic devices described herein include shape memory alloys, piezoelectric-based actuators, pneumatic motors, hydraulic motors, or the like. Alternatively, the robotic devices described herein can use any type of compatible actuator.

According to one embodiment, the actuator can have a control component, also referred to as a "control board." The control board can have a potentiometer that controls the speed of the motor. relationship between the terminals that created the voltage divider. According to one embodiment, the control board can also control the direction of the motor's rotation.

In accordance with one implementation, any robotic device as described herein can have an external control component, also referred to herein as a "controller." That is, at least some of the devices herein are operated by a controller that is positioned at a location external to the animal or human.

In one embodiment, the external control component transmits and/or receives data. In one example, the unit is a controller unit configured to control the operation of the robotic device by transmitting data such as electronic operational instructions via the connection component, wherein the connection component can be a wired or physical component or a wireless component. The data transmitted or conveyed by the connection component can also include, but is not limited to, electronic data collected by the device such as electronic photographs or biopsy data or any other type of data collected by the device. Alternatively, the external unit is any component, device, or unit that can be used to transmit or receive data.

According to one embodiment, the external component is a joystick controller. In another example, the external component is any component, device, or unit that can be used to control or operate the robotic device, such as a touch screen, a keyboard, a steering wheel, a button or set of buttons, or any other known control device. Further, the external component can also be a controller that is actuated by voice, such as a voice activation component. Further, a controller may be purchased from commercial sources, constructed de novo, or commercially available controllers may be customized to control any robotic device or any robotic device components disclosed herein.

In one example, the controller includes the "thumb sticks" from a Playstation™ Dual-Shock controller. In this example, the Playstation™ controller had two analog thumb sticks, each with two degrees of freedom. This allows the operator to move the thumbsticks a finite amount in an XY coordinate plane such that pushing the stick forward a little yields a different output than pushing the stick forward a great deal. That is, the thumb sticks provide speed control such that movement can be sped up or slowed down based on the amount that the stick is pushed in the corresponding direction.

According to one embodiment, the connections between the controller and the robotic device are configured such that each wheel is controlled by a separate joystick.

In another example, the controller is a directional pad similar to the directional pad on an original Nintendo™ game system. The pad resembles a + sign and has four discrete directions.

In use, the controller can be used to control the movement of the robotic device and further to control the operation of any components of the device such as a sensor component, a manipulator component, or any other such component. For example, one embodiment of the controller controls the wheels, the focus adjustment of the camera, and further controls the biopsy tool.

In accordance with one embodiment, the control component also serves as a power source for the robotic device.

In accordance with one embodiment, a mobile robotic device is coupled to an image display component. Signal from the camera is transmitted in any format (e.g., NTSC, digital, PAL, etc.) to the image display component. According to one embodiment, the signal is a video signal or a still image signal. In one embodiment, the image display component is a video display that can be viewed by the operator. Alternatively, the image display component is a still image display. In a further alternative, the image display component displays video and still images. In one embodiment, the image display component is a standard video monitor. Those of ordinary skill in the art recognize that a signal from a camera can be processed to produce a display signal for many different types of display devices, including televisions configured to display an NTSC signal, televisions configured to display a PAL signal, cathode ray tube based computer monitors, LCD monitors, and plasma displays. In a further embodiment, the image display component is any known image display component capable of displaying the images collected by a camera that can be used with any of the robotic devices described herein.

In one embodiment, the image display component is a component of the controller.

A robotic device as described herein, according to one implementation, has a power source or power supply. According to one embodiment, the power source is integrated into the body of robotic device. In this embodiment, the power source can be one or more batteries. The battery can be an alkaline, lithium, nickel-cadmium, or any other type of battery known in the art.

Alternatively, the power source is positioned in a location external to the body of the patient. In this embodiment, the connection component operably coupled to the power source and the robotic device transmits or conveys power between the power source and the robotic device. For example, the external power source according to one embodiment is an electrical power source such as a battery or any other source of electricity. In this example, the electricity is conveyed from the battery to the robotic device via the connection component, which is any known wire or cord configured to convey electricity, and thereby supplies power to the robotic device, including the motor of the robotic device. In one example, the power source is integrated into the control component or is operably coupled to the control component.

According to one embodiment, the power source can be any battery as described above. Alternatively, the power source can be magnetic induction, piezoelectrics, nuclear, fluid dynamic, solar or any other known power source that can be used to supply power to any robotic device described herein.

Fixed Base Devices

Certain robotic devices disclosed herein relate to fixed base robots. As discussed above, a "fixed base robotic device" is any robotic device that has no propelled transport component or is positioned manually by a user. Such a device is also referred to herein as a "stationary" robotic device. In one embodiment, a fixed base robot has a camera and is positioned manually by the user to provide visual feedback or a visual overview of the target area. A fixed base robotic camera device according to one implementation facilitates the application of laparoscopy and other surgical techniques by providing a remote-control camera robot to provide visual feedback during a surgical procedure, thereby minimizing incisions and patient risk.

Figure 14:
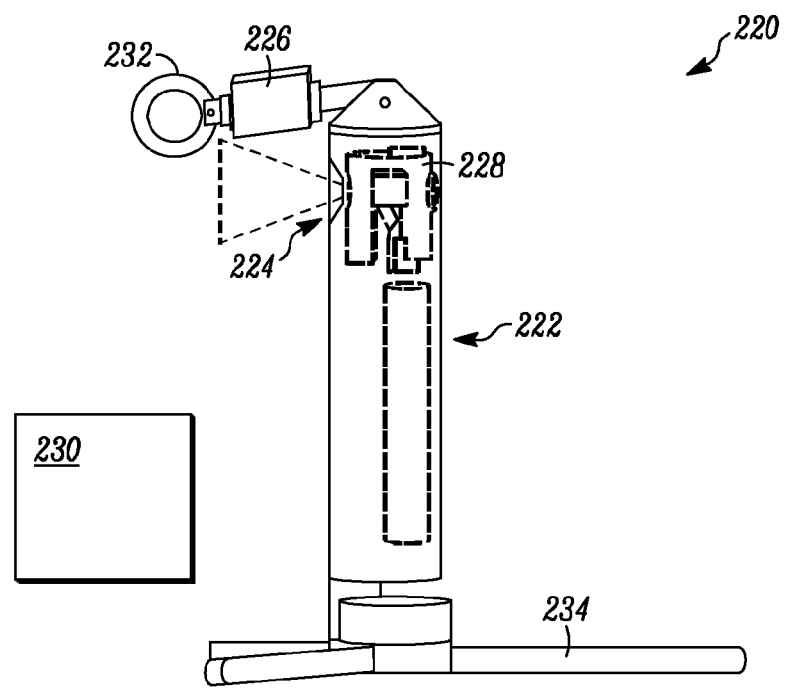
FIG. 14 is a side view of a stationary or fixed base robotic device in the deployed configuration, according to one embodiment.

FIG. 14 depicts a robotic imaging device 220, according to one embodiment. The device 220 has a main body 222 with an imaging component 224 disposed therein, an adjustable-focus component 228, and a support component 234 for supporting the body 222 inside an open space (e.g., a body cavity). In one embodiment, the device 220 further contains a light component 226 for illumination, a handle 232, and a controller 230 for controlling various components of the device 220 such as the panning or tilting components (discussed below) or the adjustable-focus component 228. According to one embodiment, the device 220 is sized for use with standard laparoscopic tools.

In one embodiment, the device 220 is made of a biocompatible material capable of being easily sterilized. According to one embodiment, the materials can include, but are not limited to, sterilizable plastics and/or metals. Alternatively, the device 220 can be made of any material that can be used in surgical procedures.

The body 222 can take on many different configurations, such as cylindrical or spherical shapes so as to be compatible with laparoscopic tools known currently in the art. However, as with the other components, the body 222 configuration is not limited to that exemplified herein. In general, the only constraints on the shape of the body are that the body be able to incorporate at least one of the components described herein.

The handle 232, according to one embodiment as depicted in FIG. 14, is a retractable or otherwise movable handle 232 formed into the shape of a ring or loop. Alternatively, the handle can be rigid or unmovable. In a further alternative, the handle 232 is any component in any configuration that allows for easy repositioning or manipulation of the device 220. In one aspect, the handle 232 is provided to allow for a grasping tool or other type of tool to attach to the device 220 via the handle 232 and thereby reposition or otherwise manipulate the device 220 in the patient. That is, the device 220 can be repositioned using the handle 232 to provide a different field of view for the imaging component 224, thereby providing a new viewpoint for the user. Thus, the movement of the device 220 enables the imaging component 224 to obtain an image of at least a portion of the surgical area from a plurality of different angles without constraint by the entry incision.

The light component 226, according to one embodiment, is configured to light the area to be viewed, also referred to as the "field of view." In one implementation, the light component 226 is proximate to the imaging component to provide constant or variable illumination for the camera. Alternatively, the light component 226 is associated with the handle 232 as depicted in FIG. 14. In such an embodiment, the light source 226 illuminates the field of view as well as the handle 232, thereby facilitating easy capture or grasping of the handle 232 by a tool.

In one example, the lighting component 226 is an LED light. Alternatively, an exemplary light source is two 5 mm LEDs. In a further alternative, the lighting component 226 can be any suitable illumination source.

In one implementation, the imaging component 224 depicted in FIG. 14 can be a camera or any other imaging device. In certain embodiments, the imaging component can be any imaging component as described above with respect to mobile robotic devices. Regardless, the camera can be any known imaging component that can be used with any of the fixed base robotic devices contemplated herein. In one embodiment, the imaging component is a stereo camera that creates a three-dimensional image.

The imaging component can help to increase or improve the view of the area of interest (such as, for example, the area where a procedure will be performed) for the user. According to one embodiment, the imaging component provides real-time video to the user. Alternatively, the imaging component can be any imaging component as described above with respect to the mobile robotic devices.

Figure 15:
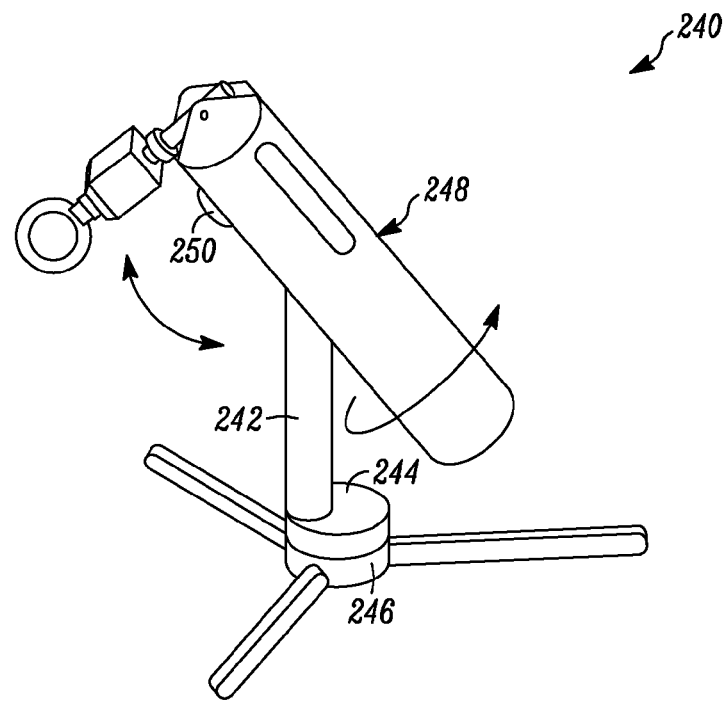
FIG. 15 is a side view of a fixed base robotic device in the deployed configuration, according to one embodiment.

FIG. 15 depicts another embodiment of a fixed base robotic camera device 240. The device 240 has a tilting component 242 and a panning component 244, 246. The panning component 244, 246 has a small ball bearing structure 244 that is attached to a base 246, thereby allowing freedom of rotation. That is, the structure 244 is rotatable with respect to the base 246. In certain embodiments, the panning and tilting components provide rotation about two independent axes, thereby allowing the surgeon more in-depth visualization of the abdominal cavity for surgical planning and procedures.

In accordance with one implementation, the tilting component 242 is pivotally coupled to the body 248 via a pin (not shown). Alternatively, the tilting component can be a standard ratchet mechanism or any other type of suitable component known in the art. According to one embodiment, the tilting component 242 can tilt up to about 45 degrees from vertical (i.e., a range of about 90 degrees). Alternatively, the tilting component 242 can tilt any amount ranging from about 0 degrees to about 360 degrees from vertical, or the tilting component 242 can configured to rotate beyond 360 degrees or can rotate multiple times. In certain embodiments such as the embodiment depicted in FIG. 2, the tilting component 242 is a separate component associated with, but independent of, the body 248. Alternatively, the tilting component is incorporated into the body 248 or into the camera component 250.

The panning component 244, 246, according to one embodiment, has the two components 244, 246 that rotate with respect to each other as described above with respect to FIG. 2. Alternatively, the panning component can be any suitable component known in the art. According to one implementation, the panning component 244, 246 provides for panning the device up to and including or beyond 360 degrees. Alternatively, the panning component 244, 246 provides for panning any amount ranging from about 180 degrees to about 360 degrees. In a further alternative, the panning component 244, 246 provides for panning any amount ranging from about 0 degrees to about 360 degrees. In certain embodiments such as the embodiment depicted in FIG. 2, the panning component 244, 246 is a separate component associated with, but independent of, the body 248. Alternatively, the panning component is incorporated into the body 248 or into the camera component 250.

In one aspect, any fixed base robotic device described herein has a drive component (not shown). In accordance with certain embodiments, the fixed base robotic device can have more than one drive component. For example, in one embodiment, a fixed base robotic device has a motor for actuating the panning component and another motor for actuating the tilting component. Such motors can be housed in the body component and/or the support component. In one example, the actuator or actuators are independent permanent magnet DC motors available from MicroMo™ Electronics, Inc. in Clearwater, Fla. Other suitable actuators include shape memory alloys, piezoelectric-based actuators, pneumatic motors, hydraulic motors, or the like. Alternatively, the drive component can be any drive component as described in detail above with respect to mobile robotic devices. In a further alternative embodiment, the panning and tilting components can be actuated manually.

In one embodiment, the actuator is coupled to a standard rotary-to-translatory coupling such as a lead screw, a gear, or a pulley. In this fashion, the force created by the actuator is translated with the rotary-to translatory coupling.

Moreover, it is also contemplated that the body or camera in certain embodiments could be capable of a side-to-side motion (e.g., yaw).

Various embodiments of fixed base robotic devices have an adjustable-focus component. For example, one embodiment of an adjustable-focus component 60 that can incorporated into various embodiments of the fixed base robotic devices described herein is depicted in FIG. 4 and described in detail above. Alternatively, a variety of adjustable-focus means or mechanisms are known in the art and suitable for active or passive actuation of focusing an imaging component. For example, one design employs the use of a motor and a lead screw. The motor turns a turn-table that is attached to a lead screw. A mating nut is attached to the imager. As the lead screw turns the imager translates toward and away from the lens that is mounted to the body of the robot.

According to one embodiment, the imaging component can have a lens cleaning component. For example, the lens cleaning component can be a wiper blade or sacrificial film compose of multiple layers for maintaining a clear view of the target environment. In a further embodiment, the lens cleaning component can be any known mechanism or component for cleaning a camera lens.

Figure 16:
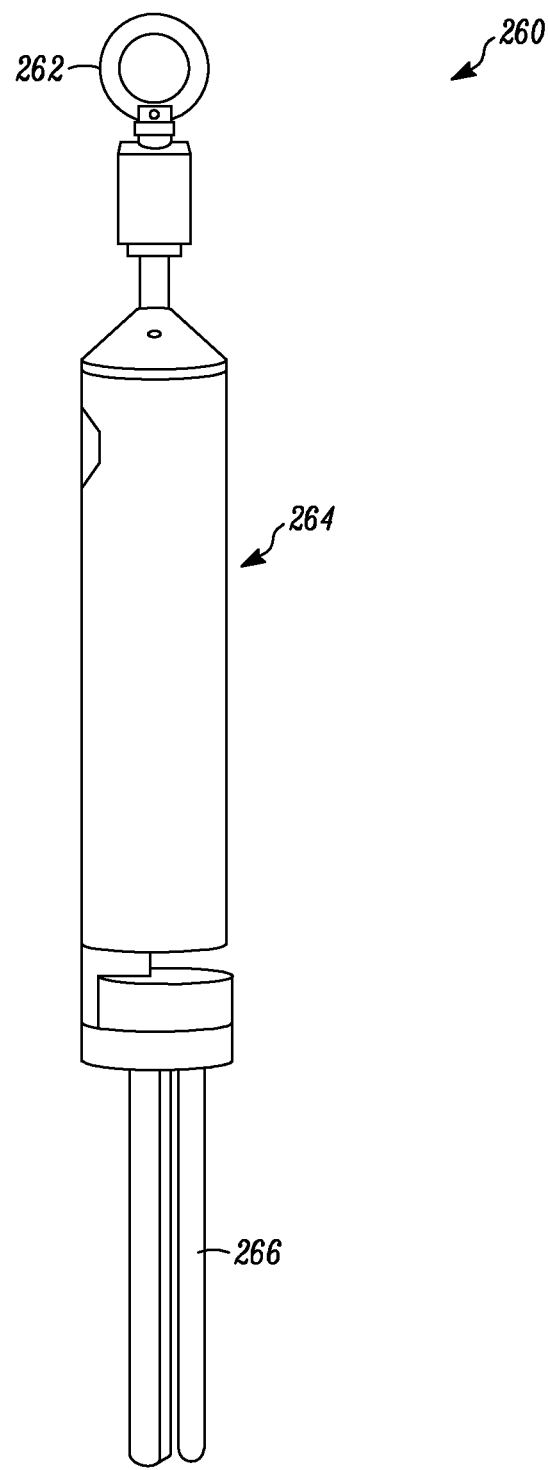
FIG. 16 is a side view of a fixed base robotic device in the collapsed configuration, according to one embodiment.

Certain embodiments of the fixed base robotic devices, such as the embodiment depicted in FIG. 16, are designed to collapse or otherwise be reconfigurable into a smaller profile. For example, according to one embodiment, the device 260 is configurable to fit inside a trocar for insertion into and retraction from an animal's body. In the collapsed position as depicted, handle 262 is coaxial with robot body 264 of device 260. Upon introduction into an open space, handle 262 can be deployed manually, mechanically actuated, or spring loaded as exemplified herein to rotate down 90 degrees to a position similar to that shown in FIGS. 1 and 2. In one embodiment, such passive actuation is achieved with torsion springs (not shown) mounted to the handle at the axis of rotation.

The support component 266, as depicted in FIG. 16, is a set of one or more legs 266 that are moveable between a collapsed and a operational or deployed position. For example, in FIG. 16, the legs in the collapsed position are coaxial with body 264 of the device 260. The support component 266 can be deployed manually, or by mechanical actuation, or as by spring loading as exemplified herein (e.g., with torsion springs) to rotate up 90 degrees to a configuration similar to that shown in the FIGS. 1 and 2. According to one implementation, the support component can be, but is not limited to, legs, feet, skis or wheels, or any other component that can facilitate positioning, weight distribution, and/or stability of a fixed base robotic device of any configuration described herein within a patient's body. Alternatively, the support component can be equipped with magnets such that the device could be suspended within the open space by positioning a magnet external of the open space.

According to one aspect, any fixed base robotic device embodiment described herein is connected to an external controller via a connection component. According to one embodiment, the connection component is any wired or flexible connection component embodiment or configuration as described above with respect to mobile robotic devices. Alternatively, the connection component is a wireless connection component according to any embodiment or configuration as described above with respect to mobile robotic devices. The receiver and transmitter used with a wireless robotic device as described herein can be any known receiver and transmitter, as also described above. According to another implementation described in additional detail above with respect to the mobile devices, any fixed base robotic device embodiment described herein can be connected via a (wired or wireless) connection component not only to the external controller, but also to one or more other robotic devices of any type or configuration, such devices being either as described herein or otherwise known in the art.

In one embodiment, the data or information transmitted to the robotic device could include user command signals for controlling the device, such as signals to move or otherwise operate various components. According to one implementation, the data or information transmitted from the robotic device to an external component/unit could include data from the imaging component or any sensors. Alternatively, the data or information transmitted between the device and any external component/unit can be any data or information that may be useful in the operation of the device.

In accordance with one implementation, any fixed base robotic device as described herein can have an external control component according to any embodiment as described above with respect to the mobile robotic devices. That is, at least some of the fixed base devices herein are operated by a controller that is positioned at a location external to the animal or human. In one embodiment, the external control component transmits and/or receives data. In one example, the unit is a controller unit configured to control the operation of the robotic device by transmitting data such as electronic operational instructions via the connection component, wherein the connection component can be a wired or physical component or a wireless component. Alternatively, the external unit is any component, device, or unit that can be used to transmit or receive data.

In use, the controller can be used to control the movement or operation of any components of the device such as the camera component, a sensor component, or any other component. For example, one embodiment of the controller controls the focus adjustment of the camera, and further controls the panning and/or tilting functions of the device.

According to one embodiment, the control component is configured to control the operation of the image sensor, the panning component, and the tilting component. In one embodiment, the control component transmits signals containing operational instructions relating to controlling each of those components, such as, for example, signals containing operational instructions to the image sensor relating to image quality adjustment, etc.

In accordance with one embodiment, the control component also serves as a power source for the robotic device.

According to one implementation, the fixed base robotic device is coupled to an image display component. The image display component can be any image display component as described above with respect to the mobile robotic devices.

A fixed base robotic device as described herein, according to one implementation, has a power source or power supply. According to one embodiment, the power source is any power source having any configuration as described above with respect to the mobile robotic devices. According to various embodiments, power can be provided by an external tether or an internal power source. When the device is wireless (that is, the connection component is wireless), an internal power supply can be used. Various implementations of the fixed base robotic devices can use alkaline, lithium, nickel-cadmium, or any other type of battery known in the art. Alternatively, the power source can be magnetic induction, piezoelectrics, fluid dynamics, solar power, or any other known power source. In a further alternative, the power source is a power unit positioned within the patient's body. In this embodiment, the power unit can be used to supply power not only to one or more robotic camera devices, but can also to any other surgical robotic devices.

In one embodiment, the fixed base robotic device has one or more sensor components. In various embodiments, such sensor components include any of the sensor components as described above with respect to the mobile robotic devices.

According to one embodiment, any of the components on any fixed base robotic device as described herein can be known, commercially available components.

In use, any of the fixed base robotic devices can be used in various surgical procedures. For example, a fixed base device can be used in combination with a laparoscopic surgical tool, wherein the device is adapted to fit through a port of the laparoscopic surgical tool and used for obtaining an internal image of an animal. In still other embodiments, the whole of the device is introduced into an open space to obtain internal images.

Alternatively, the fixed base robotic devices can be used in oral surgery and general dental procedures to provide an image of particularly difficult-to-access locations. Additionally, it will also be appreciated by those skilled in the art that the devices set forth herein can be applied to other functional disciplines wherein the device can be used to view difficult-to-access locations for industrial equipment and the like. For example, the device could be used to replace many industrial boroscopes.

Magnetically Coupleable Robotic Devices and Systems

Certain robotic devices disclosed herein relate to magnetically coupleable robotic devices and related systems. As discussed above, a "magnetically coupleable device" is any robotic device that can be positioned, operated, or controlled at least in part via a magnet positioned outside the patient's body.

Figure 17A:
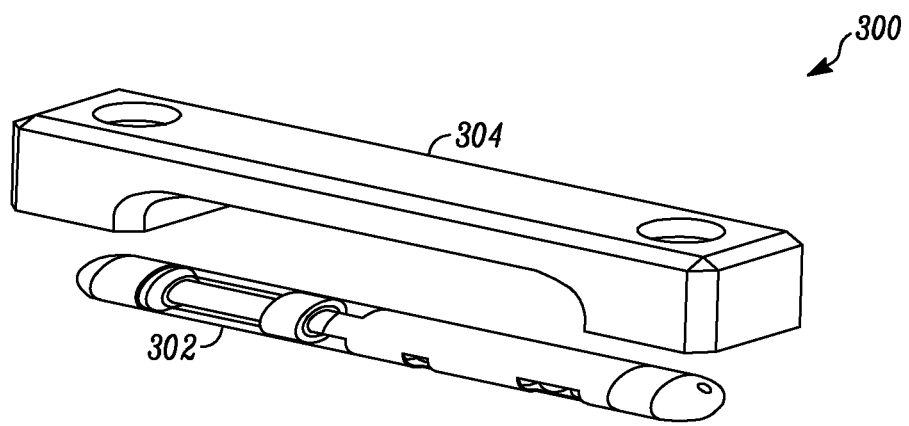
FIGS. 17A and 17B are a schematic depiction of a magnetically coupleable robotic system, according to one embodiment.
Figure 17B:
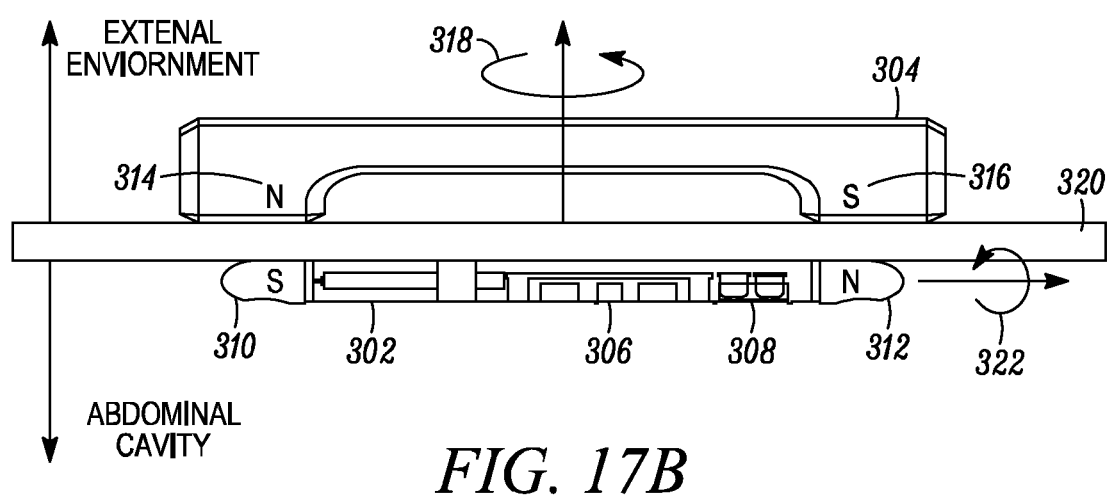

FIGS. 17A and 17B depict a magnetically coupleable robotic system 300, according to one embodiment. The system 300 includes a robotic device 302 and a magnetic handle 304. In one embodiment as best depicted in FIG. 17B, the robotic device 302 is disposed within the abdominal cavity of a patient, and the magnetic handle 304 is disposed at a location external to the patient. The handle 304 operates to hold the device 302 inside the abdominal cavity against the peritoneum (abdominal wall) 320 via magnetic forces.

In one implementation, the robotic device 302 is a cylindrical robotic device 302 having an imaging component 306 and a lighting component 308, along with two magnets 310, 312, each positioned at an end of the device 302. In accordance with one embodiment, the device magnets 310, 312 are magnetically coupled with magnets 314, 316 on the handle 304 such that the device 302 is urged toward and held against the body cavity wall 320. In one embodiment, the magnets 310, 312 are configured to ensure that the imaging component 306 is positioned to provide a view of the body cavity or the target area of interest. Alternatively, the robotic device can be any known robotic device as disclosed herein or otherwise known in the art that can be positioned, operated, or controlled at least in part by an external magnet.

The imaging component 306, according to one embodiment is a single camera. Alternatively, the imaging component 306 can be multiple cameras used to create stereoscopic vision.

It is understood that the magnets 310, 312 can be positioned anywhere in or on the device 302. It is also understood that the device 302 can have two magnets 310, 312, one disposed at each end of the device 302 as shown in FIG. 17B. The two magnets 310, 312 provide two attachment points, thereby providing a considerable contact area with the abdominal wall and hence, stable attachment to the external magnet 304. Alternatively, the robotic device can have one or more magnets.

Similarly, it is understood that the magnets 314, 316 in the handle 304 can be positioned anywhere in or on the handle 304 so long as the magnets can be magnetically coupleable with the magnets in the device. It is also understood that the handle 304 can have two magnets 314, 316 as shown in FIG. 17B, or the handle 304 can have one magnet or more than two magnets.

In accordance with one aspect, the magnetic handle 304, also referred to herein as an "external magnet") is in the shape of a handle. It is understood, however, that "magnetic handle" and/or "external magnet" as used herein is intended to encompass any magnetic component that is magnetically coupleable with any robotic device as described herein such that the magnetic component can be used to position, operate, or control the device.

In one embodiment, the handle 304 can be rotated as shown by arrow 318 to allow a tilting functionality for the imaging component 306. That is, the imaging component 306 can "tilt," which shall mean, for purposes of the present application, moving perpendicular to the axis of the cylinder of the device 302. Further, the device 302 can also provide for a panning functionality via rotation of the imaging component 306 as shown by arrow 322, as described in further detail below. That is, the imaging component 306 can also "pan,"

which shall mean, for purposes of the present application, rotating about the axis of the cylinder.

In use, the handle 304 can be moved across the entire abdomen to a desired position by moving the handle 304 outside the body. Alternatively, the device 302 can be positioned anywhere within an animal body and positioned, operated, or controlled at least in part by the magnetic handle 304 positioned outside the body. According to one implementation, the device 302 can also reattach itself if one end is knocked free. In one embodiment, the magnets 310, 312 provide sufficient magnetic attraction with the external magnet to resist vibration. Use of magnets allows for easy adjustment via the handle 304 outside the abdomen and easy attachment to the wall after insertion. In another embodiment, attachment is achieved by placing the handle 304 against the abdomen near the entry incision and pressing the handle 304 inward. The opposing poles of the magnets cause the device 302 to be lifted to the abdominal wall.

In one embodiment, the device 302 is sized to be inserted into the abdominal cavity and can be positioned on the abdominal wall such that it does not obstruct any surgical operation or procedure being performed. In such an embodiment, the imaging component 306 provides a view of the surgical procedure for the user. In one variation of this embodiment, the device 302 is sized to fit through standard laparoscopic tools.

Figure 18:
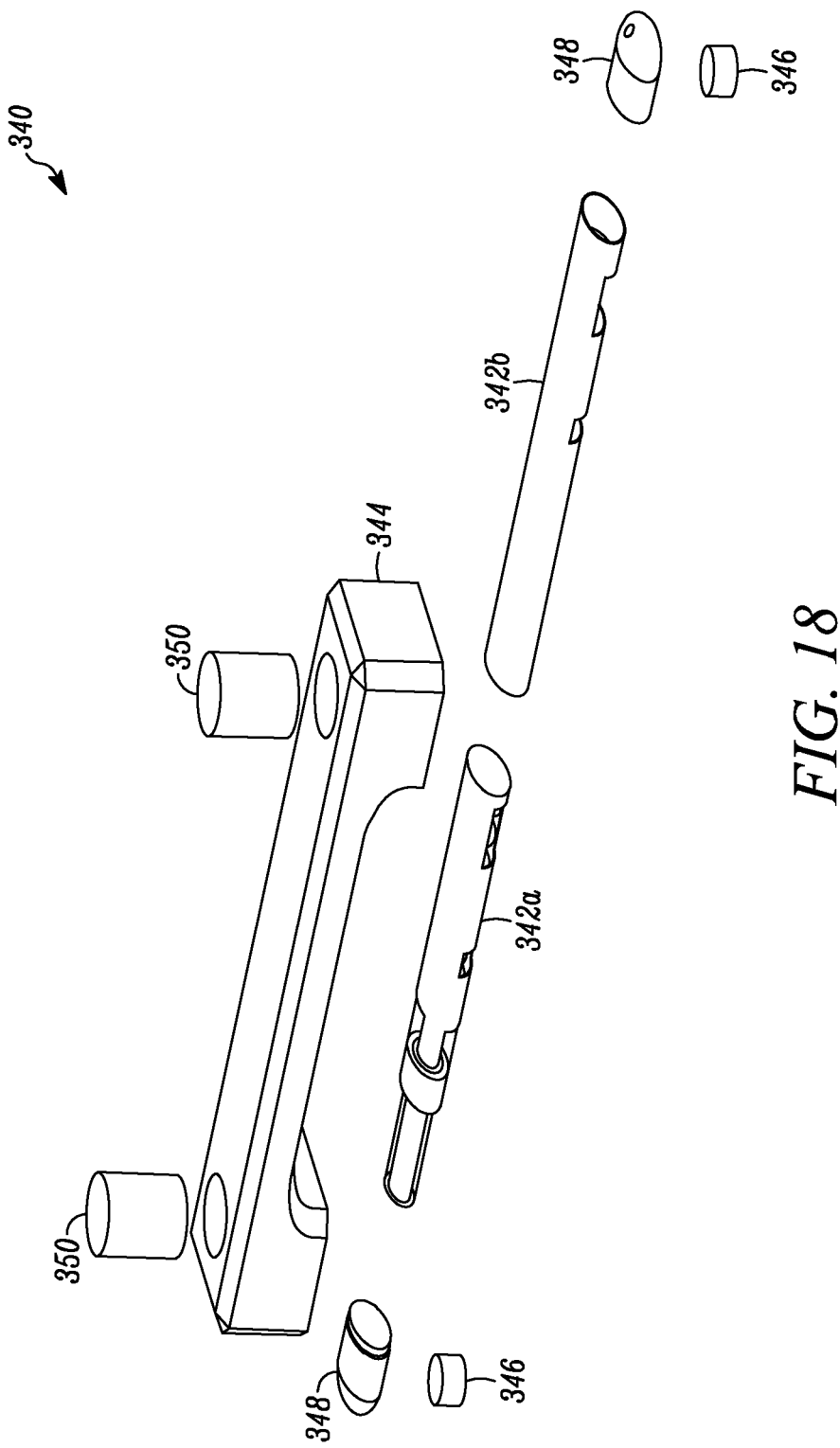
FIG. 18 is an exploded view of a magnetically coupleable robotic system, according to another embodiment.

FIG. 18 depicts an exploded view of a magnetically coupleable robotic system 340, according to one embodiment. The system 340 has a robotic device 342a, 342b and an external magnet 344. The robotic device 342a, 342b as shown in FIG. 18 has two portions: an inner portion 342a and an outer portion 342b. The inner portion 342a, according to one embodiment, is a cylindrically shaped inner body 342a, and the outer portion 342b is an outer sleeve 342b configured to be rotatably disposed over the inner body 342a. The device 342a, 342b also has two magnets 346. In this embodiment, the magnets 346 are disposed in the end portions 348 at each end of the device 342a, 342b. The magnets 346 are configured to be magnetically coupleable with the magnets 350 disposed in each end of the magnetic handle 344, such that the handle 344 can be used from a position external to the patient's body to position, operate, and/or control the device 342a, 342b positioned within the body.

Figure 19A:
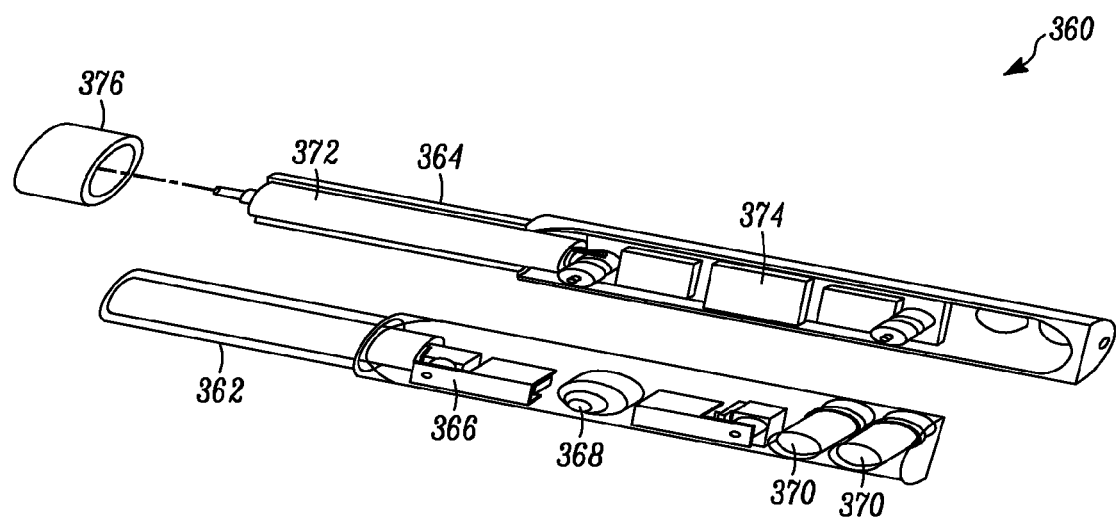
FIGS. 19A and B are perspective views of an inner body 360 of a magnetically coupleable robotic device, according to one embodiment, with FIG. 19A being an exploded view.
Figure 19B:
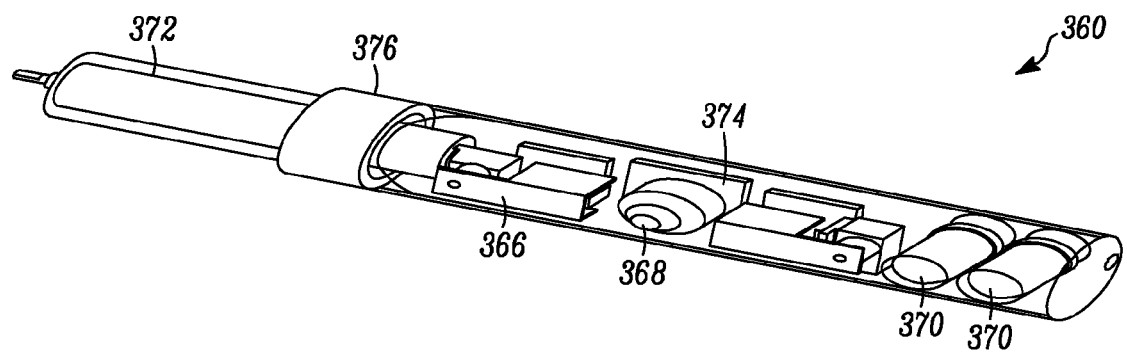

FIGS. 19A and 19B depict one embodiment of an inner body 360 of a magnetically coupleable robotic device. FIG. 19A is a schematic depicting various components of the body 360, including a first portion 362 and a second portion 364, an adjustable focusing component 366, a lens 368, a lighting component 370, an actuation component 372, an imaging component 374, and a bushing 376. In one embodiment, the two portions 362, 364 are connectable halves that are combined during assembly to form the tubular inner body 360.

In accordance with one implementation, an inner body similar to the body 360 depicted in FIG. 19B has an outer sleeve similar to the sleeve 342b depicted in FIG. 18 rotatably disposed over the body 360. In such an embodiment, the imaging component 374 and lens 368 can be panned by rotating the inner body 360 with respect to the sleeve 342b, causing the lens 368 to rotate in a fashion similar to that depicted by the arrow 322 in FIG. 17B. Slots in the sleeve 342b allow the sleeve 342b to be positioned on the body 360 without blocking the lens 368 or the lighting component 370. According to one embodiment, the actuation component 372 is a motor 372 that provides force for rotating the inner body 360 with respect to the outer sleeve 342b. In one embodiment, the motor 372 is a 6 mm brushed motor that turns a planetary gear (not shown), which revolves around a stationary sun gear (not shown), thereby causing the inner body 360 to rotate inside the outer sleeve 342b.

According to one embodiment, the adjustable focusing mechanism 366 includes two coils of wire (not shown) and a magnetic field produced by two additional magnets (not shown) near the lens 368. Current through the coiled wire that is placed in magnetic field creates a force that is used to drive the position of the lens 368. In one embodiment, a restoring force is provided that urges the lens back to its resting position when the force from the coiled wire is removed. According to one implementation, the restoring force is provided by a foam component. Alternatively, any known component for providing a restoring force can be used.

Figure 20:
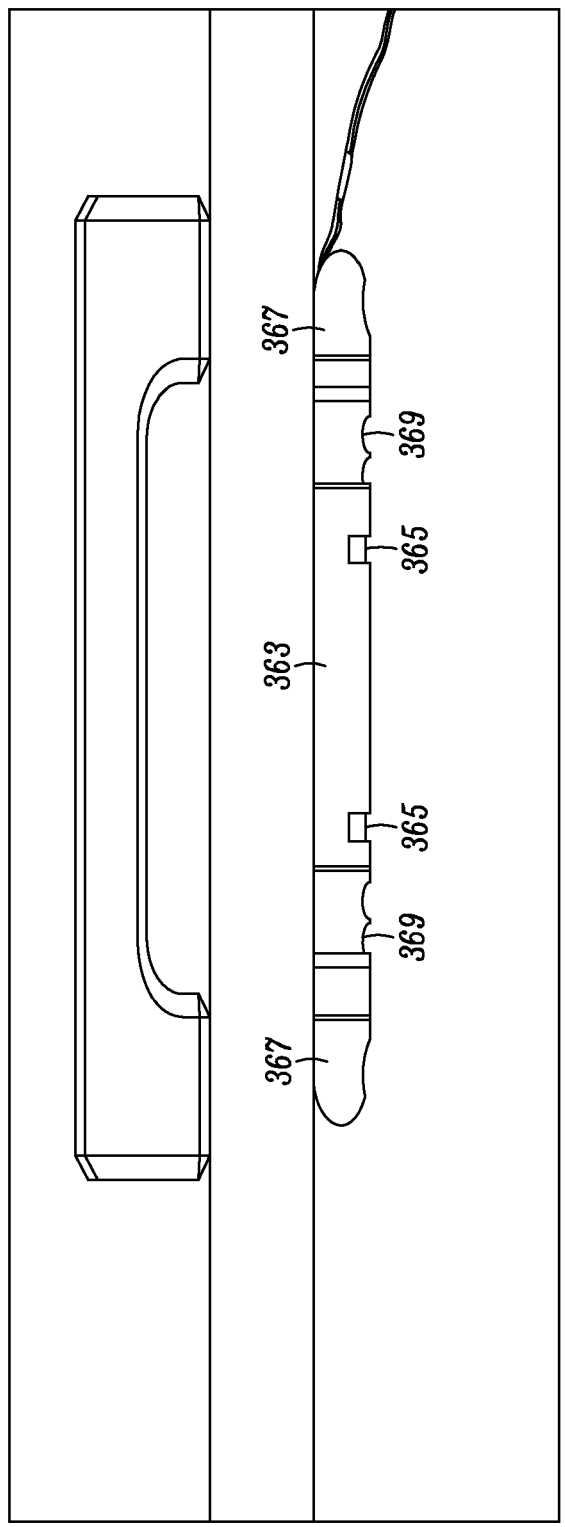
FIG. 20 is a side view of a magnetically coupleable robotic device with stereoscopic imaging, according to an alternative embodiment.

FIG. 20 depicts an alternative embodiment of a magnetically coupleable robotic device 363 with stereoscopic imaging. The device 363 has two imaging components 365, two magnets 367 disposed at each end of the device 363, and two lighting components 369, each disposed between one of the imaging component 365 and an end of the device 363.

Figure 21:
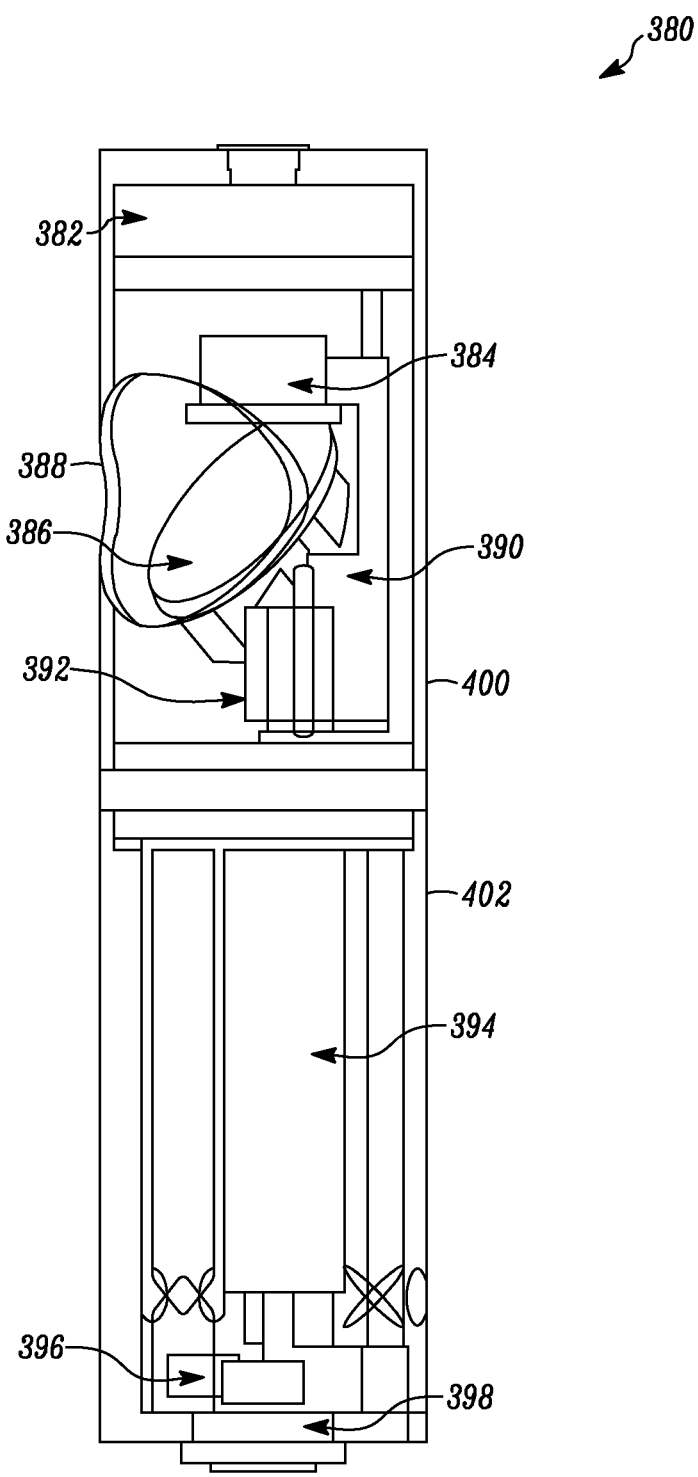
FIG. 21 is a side view of a magnetically coupleable robotic device, according to another alternative embodiment.

FIG. 21 depicts an alternative embodiment of a magnetically coupleable robotic device 380. According to one embodiment, an outer sleeve can be disposed around the device 380. Alternatively, no sleeve is used. In one embodiment, the device 380 has a top portion 400 and a bottom portion 402. The top portion 400 has an imaging component 382, a lens 384, and a mirror 386 positioned in an aperture 388. In one embodiment, the aperture 388 is covered by an transparent cover (not shown). Alternatively, there is no cover. The bottom portion 402, according to one embodiment, contains at least one actuation component 394 operably coupled to a gear 396 and bearing 398 used to rotate the device 380.

The lens 384 is operably coupled to a lens adjustment component 390 and the mirror 386 is operably coupled to a mirror adjustment component 392. Light is allowed through the aperture 388 and reflected off the mirror 386 up to the imaging component 382 through the lens 384. In this embodiment, adjusting the angle of the mirror 386 makes it possible to capture an image from a wide variety of different angles without otherwise tilting the device 380. In this embodiment, the mirror adjustment component 392 includes a 6 mm motor that operates to turn a threaded rod to move a nut up and down in a guide slot. The nut is attached to the mirror causing it to change its tilt angle. Alternatively, any known mechanism for providing adjustment of the disposition of the mirror 386 can be used. In one embodiment, adjustable mirror 386 allows for the capture of images from a wide area around the device 380. That is, the device 380 can remain relatively stationary.

According to one embodiment, the image is focused by moving the lens 384. In this embodiment, lens 384 adjustment is accomplished with the lens adjustment component 390. The component 390 has an actuation component operably coupled to a threaded rod that drives a nut in a guide slot, where the lens is rigidly fixed to the nut. According to an alternative embodiment, focusing is accomplished by any known focusing component.

According to one embodiment, the bottom portion 402 is a solid portion with cavities for the actuation component 394 and, according to another embodiment, the lens adjustment motor and the mirror adjustment motor.

In this embodiment, the device 380 provides for panning the imaging component 382 by rotating the device 380 using the actuation component 394 and further provides for tilting functionality via tilting the mirror 386 as described above.

Alternatively, the magnetically coupleable robotic device can have any known component that provides for panning capabilities and/or any known component that provides for tilting capabilities. In another embodiment, the device has no panning capabilities and/or no tilting capabilities. In a further embodiment, the device has both pan and tilt components.

Figure 22A:
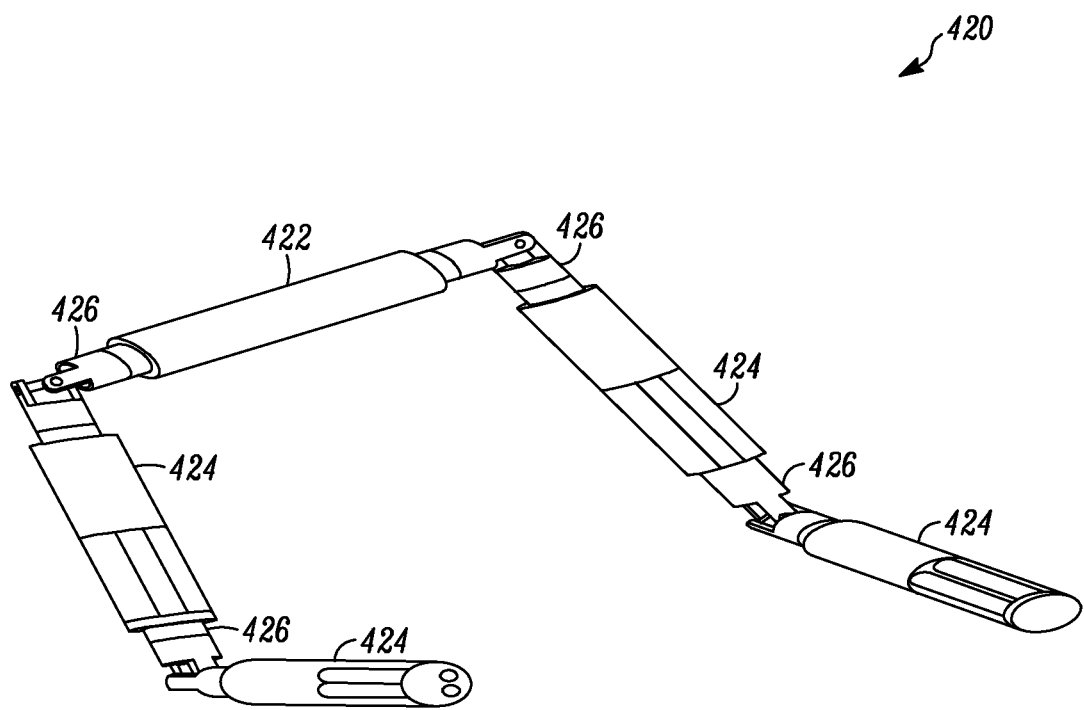
FIGS. 22A and B are perspective views of a magnetically coupleable robotic device, according to a further alternative embodiment.
Figure 22B:
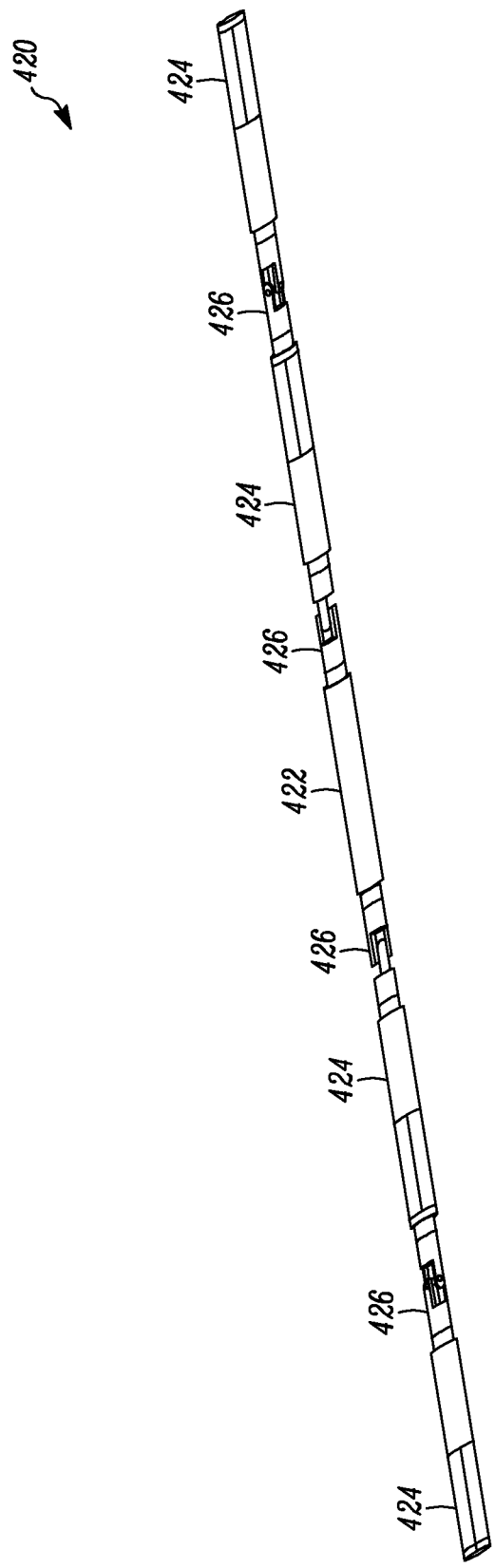

FIGS. 22A and 22B depict another embodiment of a magnetically coupleable robotic device 420. The device 420 has a cylindrical housing 422 that is coupled to arms 424 via joints 426. The device 420 has four arms 424 and four joints 426. Alternatively, the device 420 has one or more arms 424 coupled to the cylindrical housing 422 via one or more joints 426.

In one implementation, the cylindrical housing 422 has an imaging component (not shown). According to one implementation, the imaging component is a camera. Alternatively, the imaging component is a pair of stereoscopic cameras.

The device 420, according to one implementation, has an actuator (not shown) for actuating each of the joints 426. In one embodiment, the device 420 has a separate actuator for each joint 426. Alternatively, the device 420 has one or more actuators. In one embodiment, each actuator is disposed within an arm 424. Alternatively, each actuator is disposed in any portion of the device 420.

FIG. 22B depicts the device 380 in a linear configuration. That is, the components of the device 380 are configured via the joints 426 such that the device 380 is generally in a linear tubular shape that allows for easy insertion into and removal from a patient's body. In one embodiment, the device 420 has a diameter that allows for insertion through a standard laparoscopic surgical port and for use with all standard laparoscopic tools.

The device 420, according to one aspect, has an external controller (not shown) coupled to the device 420. The controller can be coupled to the device 420 via a wired connection component or it can be coupled wirelessly. In certain embodiments, the controller can be any controller as described above with respect to other embodiments of robotic devices. In another embodiment, the controller is a controller similar to those used in industrial robots in which each joint is controlled or activated separately using a switch or button or other type of input component (certain versions of such a controller also being referred to in the art as a "teach pendant"). Alternatively, the controller is a joystick controller similar to those described above.

In a further alternative, the controller is a "closed loop" controller system commonly used in robotic technologies. As is understood, a "closed loop" controller system is a system that provides for a controller that allows the user to provide specific instructions regarding a specific movement or action and further provides for a feedback sensor that ensures the device completes the specific movement or action. This system allows for very specific instructions or commands and very precise actions. For example, in the embodiment in FIG. 22A, the user may input instructions into the controller that the device 420 should position the right arm 424 at a 30° angle with respect to the body 422, and the right arm 424 then moves until the sensor senses that the arm 424 is positioned at the desired angle. The feedback sensor can be a joint sensor, a visual sensor, or any other known feedback sensor. A controller system thus allows for utilizing very specific and precise control of a device, including very precise device positioning, trajectory control, and force control. In one embodiment, the device could then be precisely operated in joint space or Cartesian space. Further, it is understood that any known robotic controller technologies can be incorporated into any of the robotic devices disclosed herein.

In yet another alternative, the controller is a component having a configuration similar to the device component itself. For example, in the embodiment depicted in FIG. 23A, the controller could have a kinematic configuration similar to that of the arms 444, such that the controller would have arms with "shoulder joints" and "elbow joints" that could be moved to activate the arms 444 of the device 420 in a similar fashion.

The controller is used to activate the components of the device 420. That is, the controller can be operated by a user to operate the device 420. The controller is coupled to the actuators (not shown) of the device 420 to operate the arms 424 and joints 426, any imaging component, and any operational components operably coupled to the device 420. Alternatively, two or more controllers (not shown) can be coupled to the device 420 to operate different components of the device 420.

In use, the robotic device 420 is a retractor device 420, according to one embodiment. The device 420 can be inserted into a patient's body while in the linear configuration of FIG. 22B and positioned entirely inside the body. In one embodiment, the device 420 is inserted into the body through a standard laparoscopic port. Alternatively, the device 420 can be inserted through a natural orifice as described in further detail elsewhere herein.

In one embodiment, the device is controlled by an operator to provide gross tissue manipulation, stereoscopic vision and visual feedback via the imaging component, and/or task assistance capabilities for any type of procedure within a patient's body. That is, once the device 420 has been positioned inside the body, the user can operate an external controller to activate the actuators to configure the arms 424 into an appropriate configuration. In one embodiment, the device 420 is used for gross manipulation of tissue and organs, retracting those that physically or visually obstruct the surgeon. In this embodiment, the arms 424 of the device 420 can be used to hold back tissue and organs to allow the surgeon physical and visual access to the necessary surgical field.

According to one embodiment, the positioning or configuration of the arms 424 can be maintained following initial positioning by the user such that the user does not need to rely on clamping or manual holding. In addition, the configuration of the arms 424 can be remotely adjusted throughout the procedure by the user.

Figure 23A:
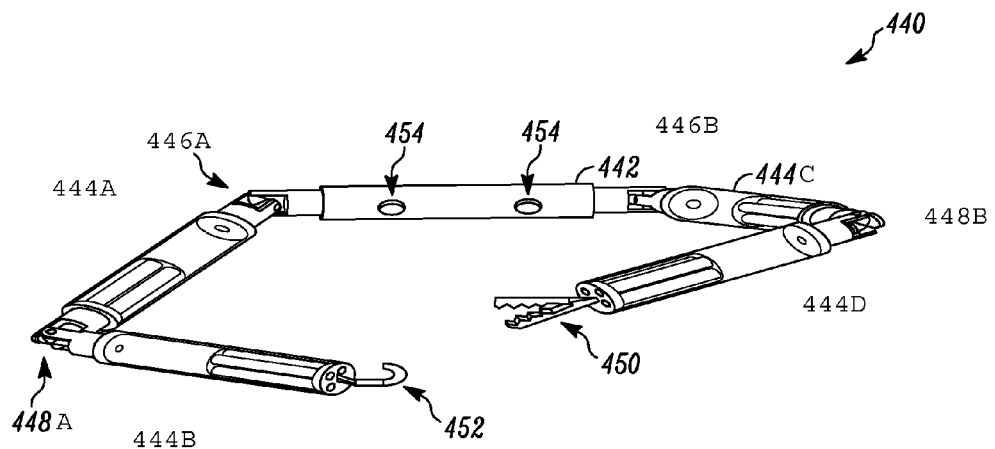
FIGS. 23A and B are perspective views of a magnetically coupleable robotic device, according to yet another alternative embodiment.
Figure 23B:
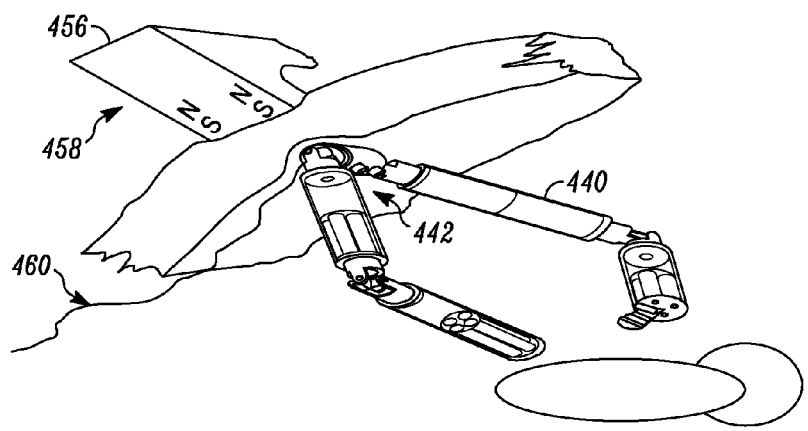
Figure 23C:
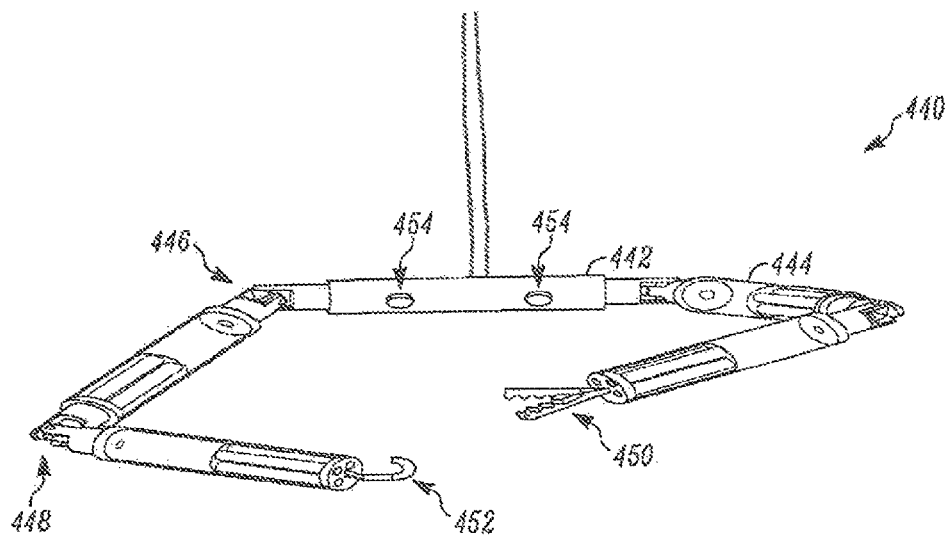
Figure 23D:
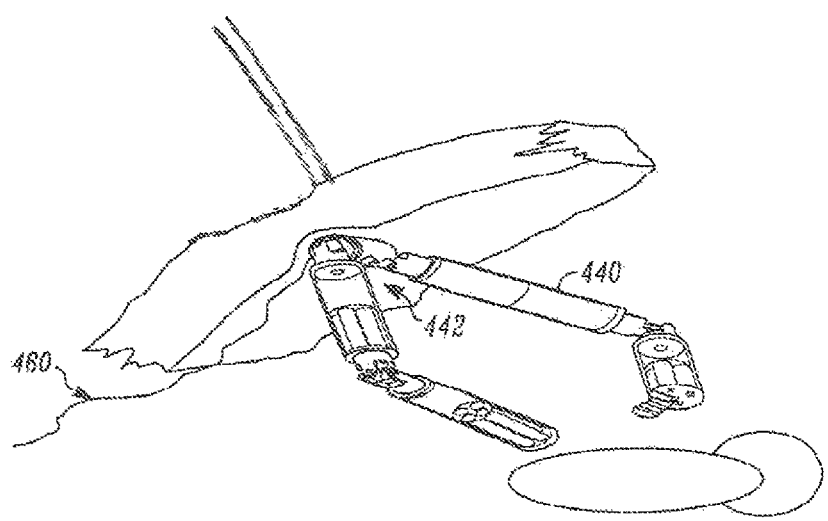

In an alternative embodiment, a magnetically coupleable device can have additional components and be used for additional procedures. That is, the device can have at least one operational component attached to an arm or the cylindrical housing. FIGS. 23A and 23B depict an alternative embodiment of a magnetically coupleable robotic device 440 having two operational components 450, 452. The device 440 has a cylindrical housing 442 that is coupled to four arm segments 444A, 444B, 444C, 444D via four joints 446A, 446B, 448A, 448B. More specifically, as shown in FIGS. 23A and 23B, the first inner arm segment 444A (also referred to as an "upper arm") is coupled to the housing 442 at the joint 446A, and the first outer arm segment 444B (also referred to as a "forearm") is coupled to the first inner segment 444A at the joint 448A. Further, the second inner arm segment or upper arm 444C is coupled to the housing 442 at the joint 446B, and the second outer arm segment or forearm 444D is coupled to the second inner segment 444C at the joint 448B. In addition, the cylindrical housing 442 has an imaging component 454, which, in this example, is a pair of stereoscopic cameras 454. The device 440 also has two operational components 450, 452 coupled to the first and second outer segments 444B, 444D of the device 440. In this embodiment, the operational components are a forceps 450 and a cautery 452.

Figure 25:
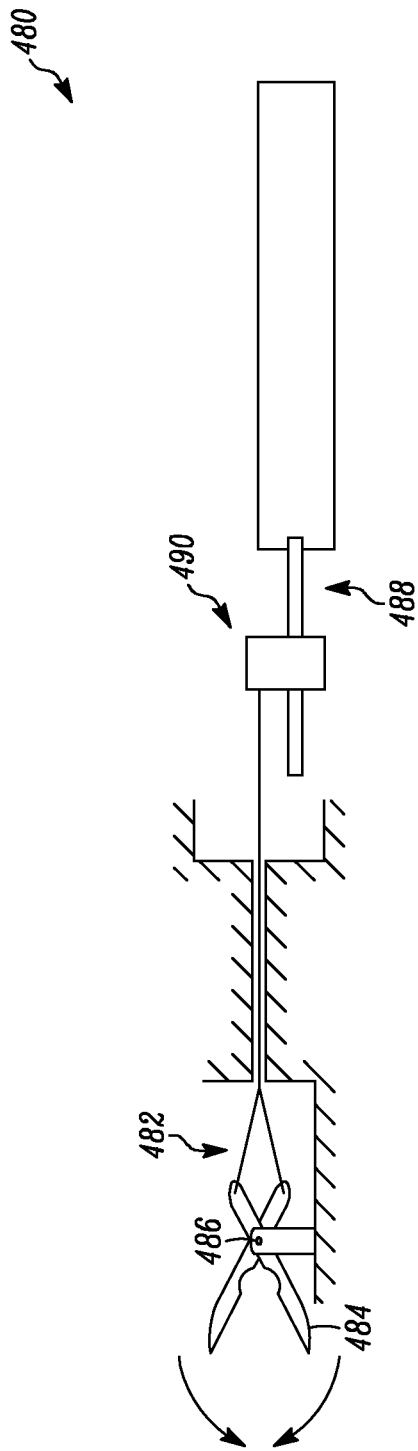
FIG. 25 is a schematic depiction of a biopsy tool, according to one embodiment.

In one embodiment, the forceps 450 are similar to standard hand-held laparoscopic forceps, similar to the forceps tool 480 depicted in FIG. 25. The tool 480 generally operates using a simple lever in which an inner shaft 482 (or cable) is pulled within an outer sheath. The inner shaft 482 then actuates both of the opposing "jaws" 484, which pivot about a common pin 486. In one embodiment, the tool 480 can have a permanent magnet direct current motor with a lead screw 488 mounted on the motor shaft. The lead screw 488 would move a lead nut 490 in and out to move the inner shaft and actuate the opposing jaws 484. Alternatively, the motor can be any actuation component. Further, in another embodiment, the forceps can be any known forceps tool that can be incorporated into a magnetically coupleable robotic device according to any embodiment described herein.

In one implementation, the cautery 452 can be a commercially-available handheld single use cautery tools such as those made by ACMI Corporation, Medtronic, or several other manufacturers. Such devices consist of a specialized tip and often use two standard AA batteries as a power source. The devices generally operate at 3 volts and pass approximately 2 amps through the tip to reach temperatures around 1200° C. (2200° F.). The tips of these devices can be removed and installed as detachable operational components. In one embodiment, the cautery tool also has a Darlington transistor pair that is controlled by a microprocessor, and through which electrical current can be passed. Alternatively, the cautery component 452 can be any known component that can be used with a magnetically coupleable robotic device of any embodiment described herein.

Alternatively, the operational component according can be a grasper or a scalpel. In a further embodiment, the operational component can be any operational component as described above with respect to the mobile robotic device embodiments that could be used with the present magnetically coupleable robotic device. For example, the operational component can be a dissector, a clippers, a stapler, an ultrasound probe, a suction component, an irrigation component, or any component that may be useful in a medical procedure of any kind. As such, a magnetically coupleable device as described herein with the operational component could be used in such procedures as tissue dissection, suturing, or any other medical procedure that could be performed with an operational component coupled to a magnetically coupleable device as described herein.

In one embodiment, the joints 446A, 446B depicted in FIG. 23A positioned on each end of the cylindrical body 442 can be referred to as "shoulder" joints 446A, 446B and the joints 448A, 448B between the inner arm segments (or upper arms) 444A, 444C attached to the shoulder joints 446A, 446B and the outer arms segments (or forearms) 444B, 444D are "elbow" joints 448A, 448B. According to one embodiment, the shoulder joints 446A, 446B and the elbow joints 448A, 448B have different degrees of freedom. For example, according to one embodiment, the shoulder joints 446A, 446B have two degrees of freedom and the elbow joints 448A, 448B have one degree of freedom. Alternatively, each of the shoulder joints 446A, 446B and the elbow joints 448A, 448B can have the same degrees of freedom. The degrees of freedom for each joint 446A, 446B, 448A, 448B can vary from about 0 degrees of freedom to about 360 degrees of freedom, or, alternatively, the joint can be configured to rotate beyond 360 degrees or can rotate multiple times.

As shown in FIG. 23B, an exterior magnetic handle 456 is positioned outside the patient's body in such a fashion that the magnets 458 in the handle interact with the magnets (not shown) in the device 440, thereby causing the device 440 to be urged toward the handle 456 and thus urged against a portion of the abdominal wall between the device 440 and the handle 456. In one embodiment, the magnet or magnets in the device 440 are disposed in the cylindrical body 442. Alternatively, the magnets are disposed anywhere in or on the device 440 such that the magnets can interact with the handle magnets 458. The handle 456 can be moved across the exterior of the body to position the robot. This will allow for gross positioning of the robot, while, according to one embodiment, more precise movements can be accomplished using the device's arms 444. In one implementation, the force of the magnetic attachment is sufficient to support reaction forces created by interaction between any operational components of the device 440 and the surgical target.

In one embodiment, the imaging component 454 includes a CMOS sensor available from by Micron Technology, Inc., located in Boise, Id. The sensor consists of an array of 640×480 pixels with an active image area of 3.63 mm×2.78 mm, and has on-board signal processing circuitry that outputs an analog color NTSC composite video signal. The sensor also has several settings that can be used to optimize image quality. These are programmable via a standard serial connection, and include color saturation, brightness, hue, white balance, exposure, and gain. The entire sensor is 9 mm×9 mm×1.3 mm in size, requires only a single-ended 2.5 Volt power supply, and draws approximately 40 mA (100 mW). Alternatively, any known imaging component can be used. According to another embodiment, any one of a number of compound lenses matched to these types of sensors are widely available. In addition, the device 440 can also have a variable focus mechanism based on a voice coil design. Alternatively, any known variable focus component can be used.

In accordance with one implementation, the imaging component can provide visual feedback relating to the operation of the device 420. For example, the imaging component can be used to determine the location of the arms 424 and/or provide visual feedback to the user with respect to any surgical procedure being performed. That is, the user could utilize the visual feedback from the imaging component to aid in positioning of tissues for inspection or in the performance of any procedure that might be accomplished with an operational component, such as dissection or suturing. All of this type of information can be utilized for the adjustment of the arms 424 to attain any desired configuration for providing tissue retraction or procedural assistance.

In one aspect, the device 440 as configured in FIGS. 23A and 23B approximates the "look and feel" of a laparoscopic procedure using standard, known laparoscopic tools. During a standard procedure using known tools, the surgeon typically creates an incision for a camera device, wherein the camera device incision is positioned between the incisions through which the standard tools are inserted for performing the procedure. This positioning provides the camera with best field of view for allowing the user or surgeon to easily view the image(s) captured by the camera. Similarly, the device 440 provides for an imaging component 454 (which can be two stereoscopic cameras as depicted in FIG. 23A) that is positioned between the arms 444, thereby providing a field of view similar to that provided during standard laparoscopic procedures and thus approximating the configuration and "look and feel" of the standard procedures using the standard tools in which the imaging laparoscope is placed between two standard tools.

In one embodiment, each actuator has two 6 mm brushed motors and two springs disposed in a cylindrical arm 424. The actuator articulates a joint 426 primarily in two planes. In this embodiment, the rotational motion of the motor is transformed to linear motion using a lead screw and nut in a guide. Each nut is attached via a swing or cable to one side of the joint 426. The motor pulls this segment of the joint 426 causing the joint 426 to rotate. A spring attached to the other side of the joint 426 provides the restoring force for articulation of the joint 426 in one plane. Alternatively, the actuator can be any known actuation component that can be used with this device 420.

Figure 24:
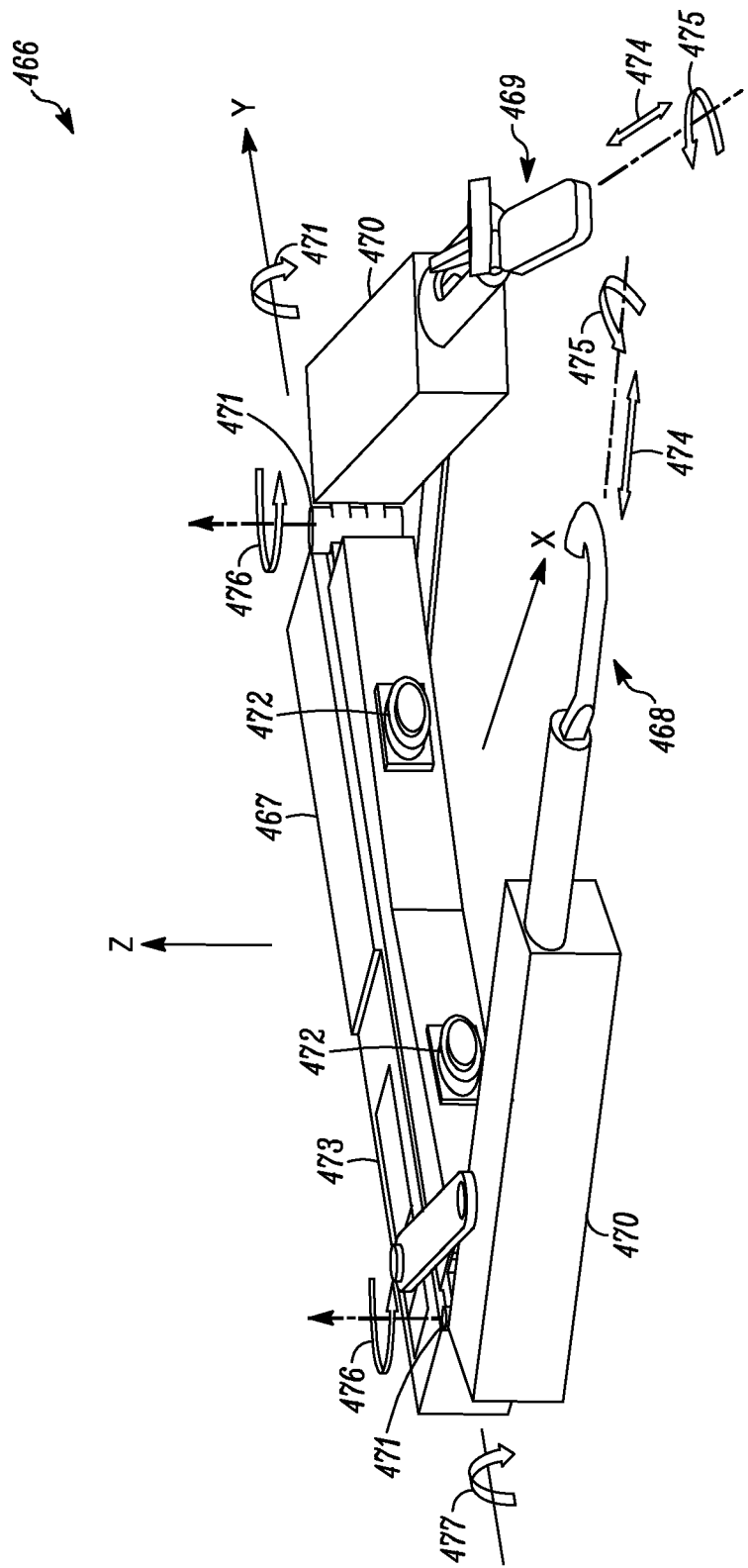
FIG. 24 is a perspective view of a magnetically coupleable robotic device, according to another alternative.

FIG. 24 depicts another embodiment of a magnetically coupleable robotic device 466 having two operational components 468, 469. The device 466 has a housing 467 that is coupled to two arms 470 via two joints 471. In addition, the housing 467 has an imaging component 472, which, in this example, is a pair of stereoscopic cameras 472, and further has at least one magnetic component 473 embedded or incorporated into the housing 467.

The arms 470 are movably coupled to the housing 467 to allow for movement of the arms 470. More specifically, in the embodiment depicted in FIG. 24, the arms 470 are coupled to the housing 467 via hinges 471 that allow for pivoting around an axis as depicted by arrow 476. In addition, the device also allows for pivoting or rotating the arms around the axis that runs along the length of the housing 467 as depicted by arrow 471. Further, it is understood that any known hinge, joint, rotatable component, or any other coupling component can be used to couple the arms 470 to the housing 467 such that the arms 470 can move in relation to the housing 467.

The two operational components 468, 469 are each coupled to an arm 470 such that each operational component 468, 469 can move in relation to the respective arm 470. More specifically, in this embodiment, both operational components 468, 469 are movably coupled to the arms 470 such that each of the components 468, 469 can extend and retract laterally along the axis of the arms 470 as depicted by the arrow 474. Further, the component 468, 469 can also rotate around that axis as indicated by the arrow 475. It is understood that any known joint, rotatable component, or any other coupling component can be used to couple the components 468, 469 to the arms 470 such that the arms components 468, 469 can move in relation to the arms 470. In addition, according to an alternative embodiment, the components 468, 469 are coupled to a second set of arms (not shown) that are movably coupled to the arms 470 such that the second set of arms can be moved laterally (arrow 474) and/or rotationally (arrow 475). In further embodiments, the second set of arms can each have a single motion or multi-motion joint on its distal end that is operably coupled to the operational component whereby the operational component can be move in relation to the second set of arms.

The device 466, according to one aspect, has a flat surface (not shown) along the side of the housing 467 opposite the imaging component 472. When the device 466 is magnetically coupled via the magnet component 473 to an exterior magnet and thus positioned against an interior surface of the cavity as described in previous embodiments, the flat surface inhibits rotation of the housing 467 along the y axis as shown in FIG. 24.

In accordance with one implementation, the device 466 as configured in FIG. 24 approximates both the "look and feel" of known laparoscopic tools and the movement of those tools. As discussed above with respect to FIGS. 23A and 23B, the device 466 approximates the "look and feel" of the known tools by the configuration of the imaging component 472 between the two arms 470. Further, the device 466 approximates the movement of the known tools via the movement capabilities of the operational components 468, 469 in relation to the arms 470. That is, the extension and retraction of the components 468, 469 as depicted by arrow 474 and the rotation of the components 468, 469 as depicted by arrow 475 approximate the movement of the known tools, thereby providing familiar movement capabilities for a user.

Figure 26A:
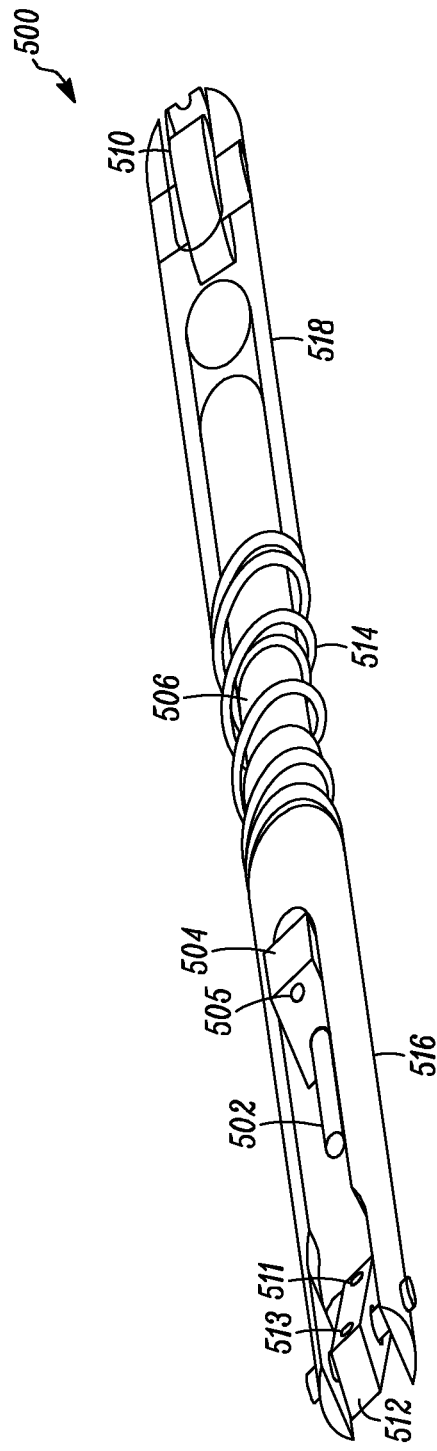
FIG. 26A is a perspective view of a joint that can be implemented into a robotic device, according to one embodiment.
Figure 26B:
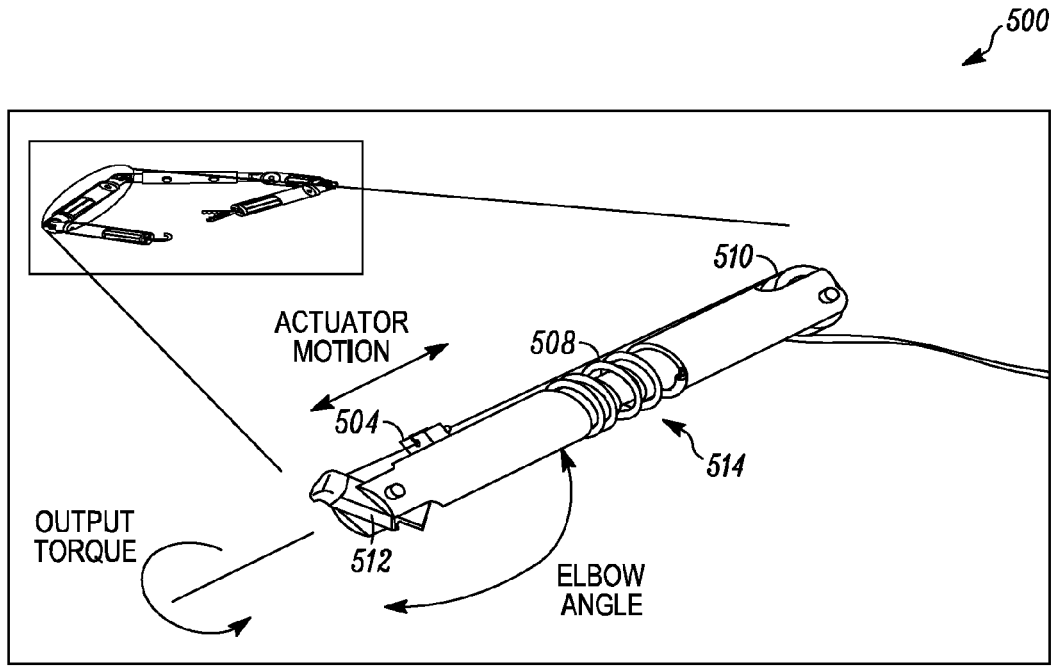
FIG. 26B is a perspective view of a joint that can be implemented into a robotic device, according to another embodiment.

An alternative arm or link 500, according to another embodiment, is depicted in FIGS. 26A & B. As best depicted in FIG. 26A, the link 500 has a lead screw 502 operably coupled to the motor 506 and also to a nut 504. As best depicted in FIG. 26B in combination with FIG. 26A, a string or cable 508 is provided that is attached to the nut 504 through hole 505, passes around a pulley 510 at one end, and is attached at one end of the string 508 to hole 511 in one end of the rotatable joint component 512 and is further attached at the other end of the string 508 to hole 513 in the other end of the rotatable joint component 512.

The lead screw 502 and nut 504 in this embodiment provide linear translation. More specifically, the motor 506 operates to turn the lead screw 502, which causes the nut 504 to move in a linear fashion. The string 508 attached to the nut 504 moves as a result, and this causes the joint component 512 to rotate, resulting in movement of the link 500 with respect to the link (not shown) connected at the joint component 512 (thereby changing the elbow angle at the joint).

The link 500 also has a compression or tension spring 514 positioned between the two cover components 516, 518 positioned to at least partially cover the motor 506. The spring 514 operates to maintain string 508 tension by urging the two components 516, 518 outward away from each other. Further, during the use, the spring 514 provides some passive compliance by allowing for relaxing the tension on the string 508 as the link 500 and other links of the operational component of the device are bent or twisted, such as during insertion into the patient's body. The relaxing of the tension allows for the links to move with respect to each other, thereby allowing for some bending and twisting of the device and thus making insertion somewhat easier.

In accordance with one embodiment, a magnetically coupleable robotic device system can include an insertion component that is used to insert the robotic device into the patient's stomach during a natural orifice procedure as described in further detail below. In one aspect, the insertion component is a sterile tubular component (also referred to herein as an "insertion overtube"). In one embodiment, in which the device is inserted into the body using a standard upper endoscope, the overtube is sized for both the robotic device and the endoscope.

Any of the magnetically coupleable robotic device embodiments described above can have a light component. For example, the light component in one embodiment is a light component 370 similar to that depicted in FIGS. 19A and 19B. In another embodiment, the lighting component is an array of high intensity, low power light emitting diodes (LEDs). For example, in one embodiment, the lighting component is a pair of 10,000 milli-candle LED's. The light component, according to one embodiment, is configured to light the field of view. In one implementation, the light component is proximate to the imaging component to provide constant or variable illumination for the camera. Alternatively, the light component can be positioned anywhere on the robotic device to provide appropriate illumination. In one example, the lighting component is an LED light. Alternatively, an exemplary light source is two 5 mm LEDs. In a further alternative, the lighting component can be any suitable illumination source.

The imaging component used with any magnetically coupleable robotic device can be a camera or any other imaging device. In certain embodiments, the imaging component can be any imaging component as described above with respect to mobile robotic devices or the fixed base robotic devices.

Regardless, the camera can be any known imaging component that can be used with any of the magnetically coupleable robotic devices contemplated herein. In one embodiment, the imaging component is a stereo camera that creates a three-dimensional image.

The imaging component can help to increase or improve the view of the area of interest (such as, for example, the area where a procedure will be performed) for the user. According to one embodiment, the imaging component provides real-time video to the user. Alternatively, the imaging component can be any imaging component as described above with respect to the mobile robotic devices or the fixed base robotic devices.

In one aspect, the at least one actuation component described herein with respect to the magnetically coupleable robotic devices can be permanent magnet DC motors, shape memory alloys, piezoelectric-based actuators, pneumatic motors, hydraulic motors, or the like. Alternatively, the drive component can be any drive component as described in detail above with respect to mobile robotic devices or fixed base robotic devices.

Various embodiments of the magnetically coupleable robotic devices have an adjustable-focus component, some of which are described above. A variety of adjustable-focus components or mechanisms are known in the art and suitable for active or passive actuation of focusing an imaging component. Alternatively, the adjustable focus component can be any such focus component as described in detail above with respect to mobile robotic devices or fixed base robotic devices.

According to one aspect, any magnetically coupleable robotic device embodiment described herein is connected to an external controller via a connection component. In one embodiment, the connection component is a wired connection component that is a seven conductor cable that is configured to carry two video signals, electrical power, and operational signals from the controller. In this embodiment, the device can also have a microprocessor to decode any incoming operational signals and provide commands the device components. For example, the microprocessor can be an 8-bit embedded microprocessor (such as, for example, an 80C5X2 Core, available from Atmel Corporation located in San Jose, Calif.) with a full speed on-board USB interface. The interface receives input commands from the controller and the processor has 34 digital I/O pins to interact with component circuitry, such as motor drivers, focus mechanism, camera settings, etc. Alternatively, the microprocessor can be any known microprocessor that can be used for any robotic device as described herein.

Alternatively, the connection component is any wired or flexible connection component embodiment or configuration as described above with respect to mobile or fixed base robotic devices. In a further alternative, the connection component is a wireless connection component according to any embodiment or configuration as described above with respect to mobile or fixed base robotic devices. The receiver and transmitter used with a wireless robotic device as described herein can be any known receiver and transmitter, as also described above. According to another implementation described in additional detail above with respect to the mobile and fixed base devices, any magnetically coupleable robotic device embodiment described herein can be connected via a (wired or wireless) connection component not only to the external controller, but also to one or more other robotic devices of any type or configuration, such devices being either as described herein or otherwise known in the art.

In one embodiment, the data or information transmitted to the magnetically coupleable robotic device could include user command signals for controlling the device, such as signals to move or otherwise operate various components. According to one implementation, the data or information transmitted from the robotic device to an external component/unit could include data from the imaging component or any sensors. Alternatively, the data or information transmitted between the device and any external component/unit can be any data or information that may be useful in the operation of the device.

In accordance with one implementation, any magnetically coupleable robotic device as described herein can have an external control component according to any embodiment as described above with respect to the mobile or fixed base robotic devices. That is, at least some of the magnetically coupleable devices herein are operated not only by an external magnet, but also by a controller that is positioned at a location external to the animal or human. In one embodiment, the external control component transmits and/or receives data. In one example, the unit is a controller unit configured to control the operation of the robotic device by transmitting data such as electronic operational instructions via the connection component, wherein the connection component can be a wired or physical component or a wireless component. Alternatively, the external unit is any component, device, or unit that can be used to transmit or receive data.

In one embodiment, in which the magnetically coupleable robotic device has arms and joints similar to those embodiments depicted in FIGS. 22A, 23A, 25, and 26, the controller is a master controller that has the same or similar kinematic configuration as the robotic device such that the user will move the arms and joints on the master and signals will be transmitted to the robotic device such that the device mirrors the new configuration of the master controller. The controller also has a visual display such that the user can view the configuration of the device and utilize that information to determine the proper configuration and operation of the device.

In use, the controller can be used to control the movement or operation of any components of the device such as the camera component, a sensor component, or any other component. For example, one embodiment of the controller controls the focus adjustment of the camera, and further controls the panning and/or tilting functions of the device.

According to one embodiment, the control component is configured to control the operation of the imaging component, the panning component, and the tilting component of a robotic device such as the device 380 depicted in FIG. 19. In one embodiment, the control component transmits signals containing operational instructions relating to controlling each of those components, such as, for example, signals containing operational instructions to the imaging component relating to image quality adjustment, etc.

In accordance with one embodiment, the control component also serves as a power source for the robotic device.

According to one implementation, the magnetically coupleable robotic device is coupled to an image display component. In one embodiment, the image display component is a component of the controller. In one embodiment, the image display component is a commercially-available stereoscopic 3-D image display system. Such systems use images from two video sensors and display the images in such a way as to create a 3-D effect. For example, the image display component can be a Sharp LL-151-3D computer monitor. Alternatively, the image display component is special wireless eyewear that rapidly switches between images from the two sensors, such as, for example, the CrystalEyes 3™, which is available from Real D, located in Beverly Hills, Calif. Alternatively, the image display component can be any image display component as described above with respect to the mobile or fixed base robotic devices.

A magnetically coupleable robotic device as described herein, according to one implementation, has a power source or power supply. According to one embodiment, the power source is any power source having any configuration as described above with respect to the mobile or fixed base robotic devices. According to various embodiments, power can be provided by an external tether or an internal power source. When the device is wireless (that is, the connection component is wireless), an internal power supply can be used. Various implementations of the magnetically coupleable robotic devices can use alkaline, lithium, nickel-cadmium, or any other type of battery known in the art. Alternatively, the power source can be magnetic induction, piezoelectrics, fluid dynamics, solar power, or any other known power source. In a further alternative, the power source is a power unit positioned within the patient's body. In this embodiment, the power unit can be used to supply power not only to one or more robotic camera devices, but can also to any other surgical robotic devices.

In one embodiment, the magnetically coupleable robotic device has one or more sensor components. In various embodiments, such sensor components include any of the sensor components as described above with respect to the mobile or fixed base robotic devices.

According to one embodiment, any of the components on any magnetically coupleable robotic device as described herein can be known, commercially available components.

Although the above embodiments have included magnetic coupling components, it is understood that other attachment components or devices can be used to removably attach any of the device embodiments disclosed above or throughout the specification to an interior portion of a patient. For example, the attachment component could be a clip, a pin, a clamp, or any other component that provides for attachment or positioning along an interior surface of a patient.

Further, It is understood that any of the components disclosed herein with respect to any particular embodiment of a robotic device are also intended to be capable of being incorporated into any other robotic device embodiment disclosed herein. For example, any component disclosed with respect to a magnetically coupleable robotic device embodiment can also be incorporated into any embodiment of a mobile or fixed base robotic device as described herein.

Methods of Using Robotic Devices

Any of the robotic devices described herein can be used in various different surgical methods or procedures in which the device is used inside the patient's body. That is, the robotic devices can be used inside the patient's body to perform a surgical task or procedure and/or provide visual feedback to the user.

According to one embodiment, any of the mobile devices described above can be inserted entirely into the patient, wherein the patient can be any animal, including a human. In known laparoscopic procedures, the use of small incisions reduces patient trauma, but also limits the surgeon's ability to view and touch directly the surgical environment, resulting in poor sensory feedback, limited imaging, and limited mobility and dexterity. In contrast, the methods described herein using the various robotic devices inside the body can provide vision and surgical assistance and/or perform surgical procedures while the robotic device is not constrained by the entry incision.

In one embodiment, any of the above devices can be used inside an abdominal cavity in minimally invasive surgery, such as laparoscopy. Certain of the devices are sized and configured to fit through standard laparoscopic tools. According to one embodiment, the use of a robotic device inserted through one standard laparoscopy port eliminates the need for the second port required in standard laparoscopic procedures.

According to one embodiment, robotic devices as described herein having a camera can allow for planning of trocar insertion and tool placement, as well as for providing additional visual cues that will help the operator to explore and understand the surgical environment more easily and completely. Known laparoscopes use rigid, single view cameras with limited fields of view inserted through a small incision. To obtain a new perspective using this prior art device often requires the removal and reinsertion of the camera through another incision, thereby increasing patient risk. In contrast, the robotic devices with cameras as described herein provide one or more robots inside an abdominal cavity to deliver additional cavity images and easy adjustment of the field of view that improve the surgeon's geometric understanding of the surgical area. The ability to reposition a camera rapidly to arbitrary locations will help the surgeon maintain optimal orientation with respect to other tools.

In accordance with one implementation, any of the mobile robotic devices described herein can be used not only in traditional surgical environments such as hospitals, but also in forward environments such as battlefield situations.

According to another embodiment, any of the robotic devices described herein can be used in a natural orifice procedure. "Natural orifice surgery," as used herein, is any procedure in which the target portion of the body is accessed through a natural orifice such as the mouth, anus, vagina, urethra, ear, or nostril, or any other natural orifice, for surgical or exploratory purposes.

For purposes of this application, the umbilicus is deemed to be a natural orifice. More specifically, the umbilicus is a natural orifice that can be reopened for use in a surgical or exploratory procedure and then subsequently allowed to heal closed again.

Natural orifice surgery, according to one embodiment, can be performed by inserting an appropriate medical device into the body through the mouth and penetrating into the abdominal cavity via an incision in the stomach wall, which is also referred to as "transgastric" surgery. In one embodiment, the gastrotomy (a hole in the stomach wall) is formed using a standard endoscopic tool. Alternatively, the gastrotomy is formed using one of the robotic devices.

One advantage of such surgery is the elimination of skin incisions and a reduction in post-operative pain and/or discomfort. Another advantage of natural orifice surgery through the gastric cavity is the substantially antiseptic state of the stomach, thereby reducing the risk of infection. Another advantage is the rapid healing characteristics of the stomach. That is, gastric incisions heal more quickly than incisions made in the abdominal wall. Natural orifice surgery eliminates skin incisions and reduces post-operative pain and discomfort. Such an approach provides a distinct benefit compared to conventional laparoscopy where multiple entry incisions are required for tools and a camera. Thus, access through a natural orifice eliminates the need for external incisions, thereby avoiding possible wound infections while reducing pain, improving cosmetics, speeding recovery, and reducing adhesions and ileus. Further, natural orifice procedures can also for the first time allow minimally invasive techniques to be used on obese patients for whom the thickness of the abdominal wall makes laparoscopy impossible.

Figure 27:
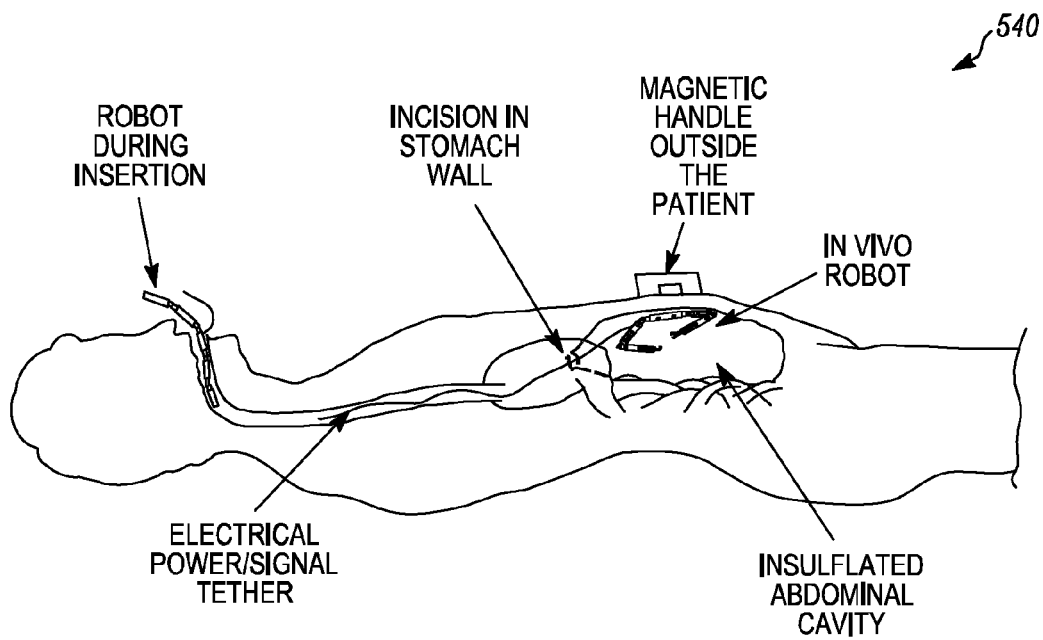
FIG. 27 is a schematic depiction of a natural orifice surgical procedure using a magnetically coupleable robotic device, according to one embodiment.

FIG. 27, according to one embodiment, depicts a natural orifice surgical method 540. The robotic device is inserted through the mouth of the human patient and through an incision in the stomach wall and into the insufflated abdominal cavity. In this embodiment, a wired connection component is coupled to the device. Alternatively, the device is wireless.

In accordance with one aspect, the method of performing natural orifice surgery includes performing the procedure with an untethered robotic device. Alternatively, the method relates to a method of performing natural orifice surgery with a robotic device that is tethered with a flexible connection component. The device can be any of the robotic devices disclosed herein. Alternatively, the device can be any robotic device that can be inserted into a natural orifice of the body for surgical or exploratory purposes. In a further alternative, the device can have any known form or structure so long as the device is a robotic device that can be inserted into a natural orifice for surgical or exploratory purposes.

According to another embodiment, any one of the robotic devices disclosed herein can be used with one or more other robotic devices, including any of the devices disclosed herein. That is, the robotic devices disclosed herein constitute a family of robotic devices that can be utilized together and/or in combination with other known robotic devices to perform surgical procedures. That is, any combination of the robotic devices can be positioned inside the patient's body to cooperatively perform a surgical procedure.

In one implementation, the two or more robotic devices, whether coupled in an untethered fashion or via a wired connection component, can be operated in cooperative or sequential fashion or any other fashion during a procedure in which more than one robotic device provides an advantage. In another embodiment, multiple mobile, fixed-base, and/or magnetically coupleable devices with a variety of sensors and manipulators are used cooperatively as a low-cost robotic surgical "team" that are inserted into the patient's body through a single incision. This family can perform an entire procedure while being remotely controlled by the user.

Figure 28:
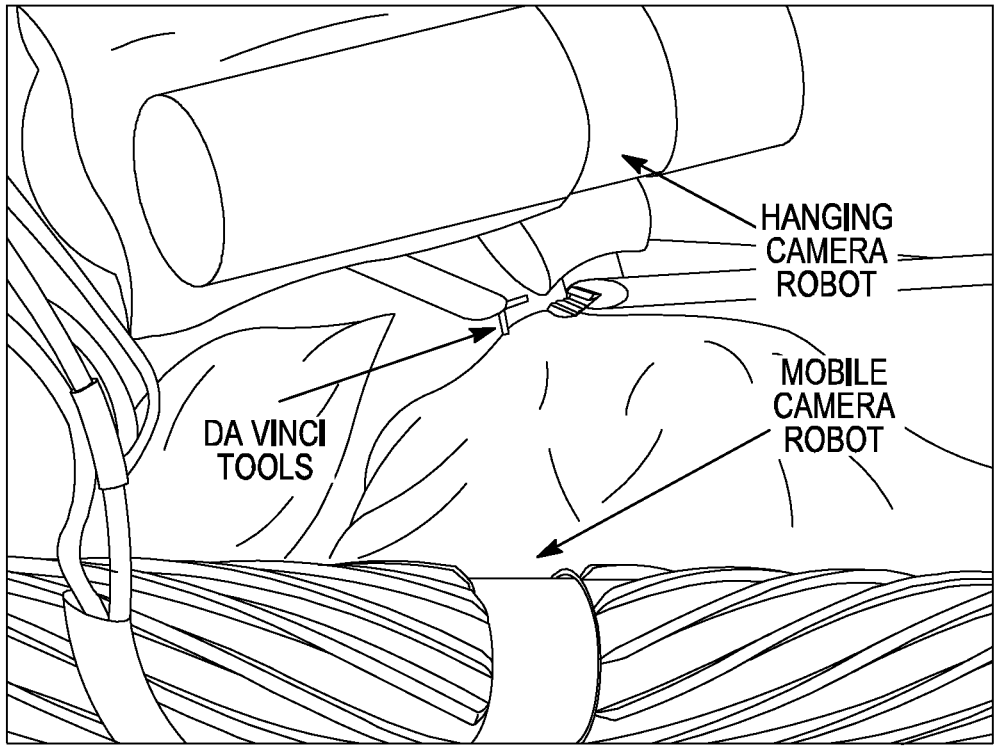
FIG. 28 is a visual image taken of a mobile robotic device according to one embodiment and a magnetically coupleable robotic camera device according to another embodiment being used in cooperation with the da Vinci™ system.

One example of more than one robotic device being used cooperatively, according to one embodiment, is depicted in FIG. 28, which shows a mobile robotic device similar to those described above and a magnetically coupleable robotic camera device similar to those described above being used in cooperation with the da Vinci™ system. The robotic camera device positioned against the upper peritoneal wall can be used to capture images of the procedures being performed by the mobile robotic device and the da Vinci™ tools.

Further, it is contemplated that multiple robotic camera devices can be used simultaneously to provide the operator with improved visual feedback from more than one viewing angle. Likewise, the one or more robotic camera devices can be used in conjunction with one or more surgical robots.

In a further embodiment, a process can be implemented during surgical procedures so that the number and location of all wireless robots can be documented throughout a procedure.

In accordance with one implementation, the cooperative method can be combined with the natural orifice method. That is, multiple robots, each with various different functions, could be inserted into the patient's body through a natural orifice. This method allows multiple robots to be independently inserted through the orifice, thereby providing a surgical "team" inside the patient's body during a surgical procedure. In one embodiment, the current method allows sufficient room in the esophagus to remove discarded tissue (such as a gall bladder) and for insertion of specialized tools (cauterizing, etc).

Another embodiment relates to methods, systems and devices for cooperative use of a robotic device with (1) standard laparoscopic tools, (2) the da Vinci® system, and/or (2) at least one other robotic device, including any of the devices discussed or referenced above, or any combination thereof.

In one embodiment, a robotic camera device can be used in conjunction with a standard laparoscope to give the surgeon an auxiliary viewpoint, such as, for example, a rear viewpoint of an abdominal feature. In another embodiment, the robotic camera device can be used by itself to reduce patient trauma by inserting it through a tool port. In another embodiment, the robotic camera device is used as the camera or cameras for a minimally invasive abdominal surgery where the camera or cameras can be moved to any position inside the cavity, eliminating the need for the laparoscope. This requires only two incisions in the abdominal wall instead of three, reducing patient trauma and risk of complications.

According to one embodiment, robotic devices disclosed herein cooperate with da Vinci® tools, thereby complimenting the da Vinci® system with auxiliary viewpoints and thus improving visual feedback to the surgeon. One or more of the robotic devices are placed entirely within the abdominal cavity and are therefore not constrained by the entry incisions.

In one example, two robotic devices can be used in cooperation with the da Vinci® system during a surgical procedure. The first device is a magnetically coupleable pan-and-tilt robotic camera device that is attached to the abdominal wall using magnets. The second is a wheeled mobile robotic device with a camera. The pan-and-tilt device provides a view from above the surgical target while the mobile device provides a view from a low perspective. The point-of-view of both these devices is easily changeable throughout the procedure. In one embodiment, the video from these devices is sent directly to the da Vinci® console and can, by the surgeon's choice, be displayed as one image in the stereo-vision system. In another embodiment, both devices are repositioned throughout the surgery to give perspectives that would otherwise require a new incision and a time consuming repositioning of da Vinci® tools. In one embodiment, the robotic devices are controlled by the surgeon via a separate joystick.

In one embodiment, the da Vinci® system is positioned as per normal procedure. Three small incisions are made in the abdominal wall for the two tool ports and the laparoscope. A special, slightly larger, trocar is used for insertion of the robotic devices that allows for the devices' electrical wire tethers. Alternatively, the robotic devices are wireless. The remaining trocars are then placed and the abdomen is insufflated. The da Vinci® tools and laparoscope are then inserted and readied for the surgery. The robotic devices are then powered and the pan/tilt device is lifted from the organs to the upper surface of the abdominal wall using a magnet holder outside the abdomen. The robotic devices can be positioned using their cameras, the da Vinci® tools, or the laparoscope. Once the robotic devices are properly positioned, the da Vinci® video input is switched from the standard laparoscope to the hanging device. The robotic devices' functions are then checked to establish proper operation and lighting. The operating surgeon then begins the procedure. In one embodiment, the robotic devices can be repositioned and the pan/tilt features can be actuated to track tool movements during the procedure. The procedure can then be performed using the da Vinci® system tools but with primary video feedback coming from the devices. After the procedure, the robotic devices are moved back to the special trocar, the abdomen is deflated, and the robotic devices are retracted.

Those skilled in the art will understand that the process described represents merely one embodiment and that the order described could be varied and various steps could be inserted or removed from the process described.

The process described above and similar procedures show the benefits of using robotic devices to assist surgeons by cooperative use of more than one cooperative device, including in certain embodiments using at least one robotic device cooperatively with the da Vinci® system. In this embodiment, the robotic devices provide complimentary visual feedback to the surgeon during a procedure. The multiple viewpoints improve the understanding of the surgical environment, thus demonstrating how at least one robotic device can cooperate with each other or with the da Vinci® system to improve surgical care.

In one embodiment, unobstructed access to the surgical site is achieved by a device designed to allow for mobility and flexibility in placement while being configured for use in the already limited space of the abdominal cavity. In the present embodiment, a cooperative surgical environment is achieved by suspending a robotic device from the abdominal wall in a fashion that allows for mobility in placement within the abdominal cavity. Functionality through useful video feedback of the appropriate surgical site is also provided. In another embodiment, the device can pan and tilt the camera as well as focus on objects at differing distances within the abdominal cavity.

In another embodiment, a hanging pan/tilt robotic device is used cooperatively with the da Vinci® system to perform a surgical procedure. The hanging device provides the primary (non-stereo) visual feedback to the da Vinci® console. It is repositioned and actuated throughout the procedure to optimize the feedback available to the surgeon.

In another embodiment, video feedback to the da Vinci® console from the robotic device is provided to only one of the console's two eyepieces. The surgeon controls the pan/tilt device functions from the console via a separate joystick. The multiple viewpoints available through the use of the cooperative robotic device improves understanding of the surgical environment.

In another embodiment, a da Vinci® procedure utilizing device visual feedback demonstrates the implementation of cooperative devices in minimally invasive surgery. The additional feedback is invaluable and allows the surgeon to scan the surgical site from varying angles. The pan/tilt device suspension system also allows for repositioning of the device throughout the procedure without necessitating multiple incisions for the laparoscopic arm.

In one embodiment, a natural orifice procedure can include an insertion component that is used to insert the robotic device into the patient's stomach. In one aspect, the insertion component is a sterile tubular component (also referred to herein as an "insertion overtube"). In one embodiment, in which the device is inserted into the body using a standard upper endoscope, the overtube is sized for both the robotic device and the endoscope.

One method of natural orifice procedure, according to one embodiment, includes advancing a sterile overtube into the patient's stomach with a standard upper endoscope and irrigating the stomach with antibiotic solution. The robotic device is then inserted into the gastric cavity through the overtube. The robot is then inserted into the abdominal cavity through a transgastric incision created with an endoscopic needle-knife. The incision can be approximately the same diameter as the robot. Finally, the device is retracted into the gastric cavity. Subsequently, endoscopic closure of the transgastric incision can be accomplished using two endoclips and one endoloop. Further, the robotic device is grasped with an endoloop and retracted back through the esophagus.

Although the present invention has been described with reference to preferred embodiments, persons skilled in the art will recognize that changes may be made in form and detail without departing from the spirit and scope of the invention.

EXAMPLE 1

Motor Torque

One factor to consider in the development of the mobile robotic devices was the amount of torque needed to move the device.

Figure 29:
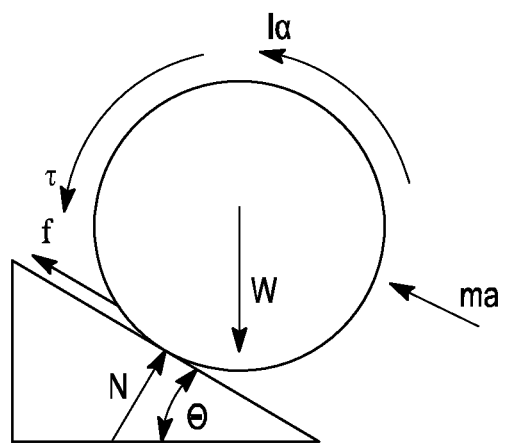
FIG. 29 is a free body diagram of a mobile robotic device sitting motionless on a slope.

To calculate the needed torque, a free-body diagram of the robot sitting motionless on a slope was used to calculate the torque required to keep the robot stationary on the slope. This calculation would be the stall torque that the motor would need (provided that the friction of the surface was enough to prevent the wheels from slipping). The free-body diagram is shown below in FIG. 29.

From this free-body diagram the following equations were written:

$$(W \sin \theta)r = (ma) + I\alpha + \tau$$

$$W \sin \theta - f = ma$$

$$W \cos \theta = N$$

This results in the following:

$$\tau = (W \sin \theta)r$$

where
W is the weight of the cylinder,
θ is the angle of the slope,
r is the radius of the cylinder,
m is the mass of the cylinder,
a is the acceleration of the cylinder,
I is the moment of inertia of the cylinder,
α is the angular acceleration of the cylinder,
τ is the torque of the motor,
f is the friction between the cylinder and slope,
N is the normal force.

The robot was modeled as a solid aluminum cylinder 15 mm in diameter and 76 mm long. A solid aluminum cylinder of this size would have a mass of 36.4 g and a moment of inertia of 1.02 [kg-m²]. The resulting calculations show that for the robot to hold its position on a slope of θ degrees a torque, τ, is needed (Table 1).

TABLE 1

| Slope Angle and Required Torque | |
|---|---|
| θ | τ |
| 0 | 0.00 mN-m |
| 15 | 0.69 mN-m |
| 30 | 1.34 mN-m |
| 45 | 1.89 mN-m |
| 60 | 2.32 mN-m |
| 75 | 2.58 mN-m |

After determining what torque was required to move the robot, a motor and a gearhead were selected that would reduce the speed and increase the torque output from the motor. Two motors were tested to determine if they met the torque requirements. The first motor was a standard, commercially-available 6 mm diameter pager motor and the second was a 6 mm blue motor taken from a toy ZipZap™ remote-controlled car, which is available from Radio Shack.

Tests determined the stall torque of each motor per volt input. For the test, a bar was placed on the motor shaft and a voltage was applied to the motor. The angle at which the bar stalled was then measured for each applied voltage. The torque that was present on the motor shaft was calculated and plotted versus the voltage, and a linear fit was used to determine the stall torque/volt of the motor. The results of the test are shown in Table 2.

TABLE 2

Motor Torques

| 6 mm Pager Motor | | | | ZipZap ™ Motor (Blue) | | | |
| --- | --- | --- | --- | --- | --- | --- | --- |
| Voltage [V] | Angle [Degrees] | Torque [mNm] | [mNm]/[V] | Voltage [V] | Angle [Degrees] | Torque [mNm] | [mNm]/[V] |
| 0.5 | 5.0 | 0.02 | 0.043 | — | — | — | — |
| 1.0 | 8.5 | 0.04 | 0.037 | 1.0 | 3.5 | 0.02 | 0.015 |
| 1.5 | 12.0 | 0.05 | 0.035 | 1.5 | 6.0 | 0.03 | 0.017 |
| 2.0 | 16.0 | 0.07 | 0.034 | 2.0 | 8.5 | 0.04 | 0.018 |
| 2.5 | 18.5 | 0.08 | 0.032 | 2.5 | 10.5 | 0.05 | 0.018 |
| 3.0 | 21.5 | 0.09 | 0.030 | 3.0 | 12.0 | 0.05 | 0.017 |
| | | Linear Fit | 0.028 | | | Linear Fit | 0.019 |

The results of this test show that neither motor supply enough torque to hold the mobile robot on more than a minimal slope. The ZipZap™ motor can provide 0.057 [mNm] at 3 V and the pager motor can supply 0.084 [mNm] at 3 V. Both motors could only hold the robot stationary on a 15 degree slope.

Another motor tested was model SBLO4-0829 with gearhead PG04-337, available from Namiki. The motor runs on 3 V and testing determined that it can provide 10.6 [mNm] stall torque at 80 rpm. This motor provides a design factor of 4 for the robot on a 75-degree slope (if frictional force is sufficient to prevent sliding).

Wheel Friction

The friction characteristics of two wheels were tested.

The device tested was a robot having a weight ("W") of 1.0 oz. The radius of the two wheels was 7.5 mm, and they were made of aluminum.

Experiments were conducted on top of four types of objects: a tabletop, a mouse pad, particleboard and sliced beef liver. The robot was placed on top of each of these objects and the maximum friction force, F, was measured. The force was measured using an Ohaus Spring Scale with one-quarter ounce divisions. The force was approximated to the nearest 0.05 ounces.

The coefficient of friction was determined by the formula $\mu = F/W$. Table 3 shows the four coefficients of friction measured by experiments.

TABLE 3

Friction Coefficients on Various Surfaces

| | Maximum Friction Force (oz.) | Coefficient of Friction |
| --- | --- | --- |
| Table | 0.05 | 0.050 |
| Mouse pad | 0.65 | 0.65 |
| Particle board | 0.2 | 0.2 |
| Beef liver | 0.1 | 0.1 |

Additional force analysis was also applied to the two-wheeled device described above. That is, the amount of required frictional force was determined in the following manner.

Figure 30:
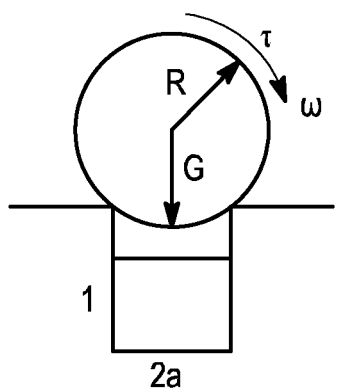
FIG. 30 is an elastic body model used in friction analysis of one embodiment of a mobile robotic device.

The force analysis was based on an elastic foundation, i.e., where the mobile robot was assumed to roll on an elastic surface (see FIG. 30). In this model, friction resistance to rolling is largely due to the hysteresis from deformation of the foundation. In the contact portion, the elastic force $\delta(x)$ was assumed to be the normal distribution function of x. Here x range was from −a to a. The following equation was derived:

$$\frac{G}{2aL} = \int_{-a}^{a} \delta(x) dx$$

Then from the equation above, $$\delta(x) = \frac{2G}{\pi a}\left[1 - \left(\frac{x}{d}\right)^2\right]^{\frac{1}{2}}$$

Thus, the sum of partial differential friction force:

$$\Sigma f = \delta(\theta)\cos(\theta) + \tau(\theta)\sin(I)$$

By the integral calculation, one can get the friction force:

$$f = \frac{4}{3}\left(\frac{W}{\pi}\right)^{3/2} \frac{1}{\sqrt{R}} \sqrt{\frac{1-v^2}{\Sigma}}$$

here $\Sigma$ is the Young's modulus and R is the Poisson's ratio.

From the force analysis, it was determined that the frictional force was proportional to the weight and inversely proportional to the radius of the wheel. Therefore, either of the following two methods could be used to influence frictional force. First, the mass of the robot could be increased. One good way to do so would be to change the material of the wheels. Second, the radius of the wheels might be reduced. Another solution is to add treads to the wheels. Alternatively, the tips of the treads may have a smaller radius without reducing the diameter of the wheel itself.

EXAMPLE 2

In this example, a velocity analysis was performed on a manipulator arm for a mobile robot, according to one embodiment discussed above.

When performing such an analysis, it was helpful to define a matrix quantity called the Jacobian. The Jacobian specifies a mapping from velocities in joint space to velocities in Cartesian space. The Jacobian can be found for any frame and it can be used to find the joint torques, discussed infra.

Figure 7B:
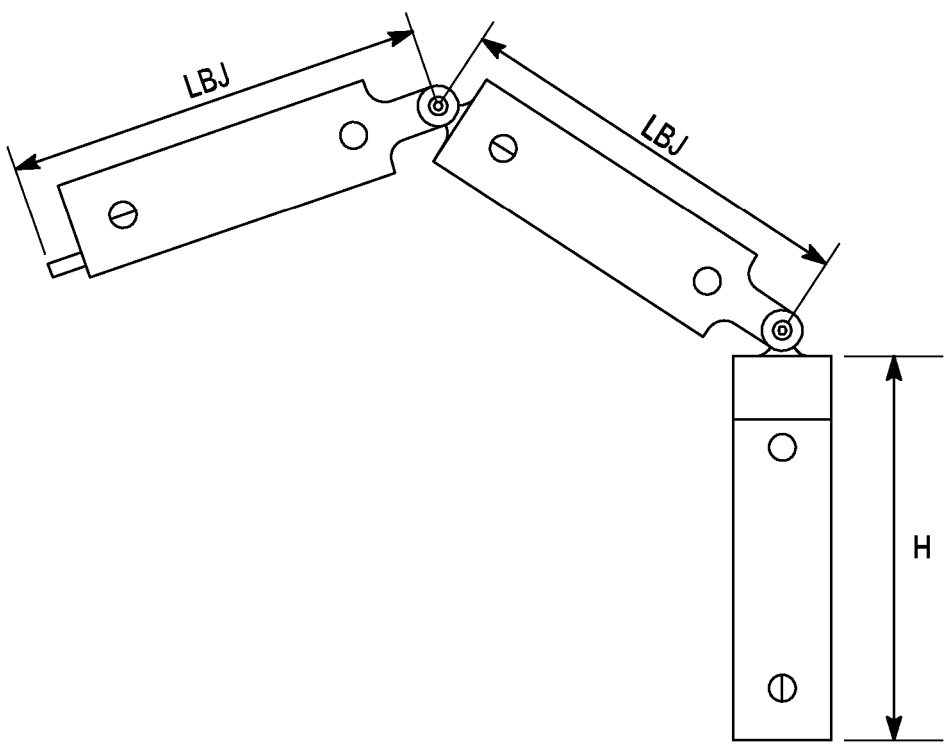
FIG. 7B is a schematic of the manipulator arm used to determine the Jacobian.

FIG. 7B depicts a schematic of the manipulator used to find the Jacobian in this example. For additional information on the Jacobian, see "Introduction to Robotics" by John J. Craig.

The fundamental equations used in finding the Jacobian are:

$$^{i+1}V_{i+1} = {}^{i+1}_{i}R \cdot ({}^{i}V_i + {}^{i}\omega_i \times {}^{i}P_{i+1})$$

$$^{i+1}\omega_{i+1} = {}^{i+1}_{i}R \cdot {}^{i}\omega_i + \dot\theta_{i+1} \cdot {}^{i+1}Z_{i+1}$$

$$^{i}V = {}^{i}J(\theta)\dot\theta$$

$$^{0}_{1}R = \begin{bmatrix} c\theta_1 & -s\theta_2 & 0 \\ s\theta_1 & c\theta_1 & 0 \\ 0 & 0 & 1 \end{bmatrix} \Rightarrow {}^{1}_{0}R = \begin{bmatrix} c\theta_1 & s\theta_1 & 0 \\ -s\theta_1 & c\theta_1 & 0 \\ 0 & 0 & 1 \end{bmatrix}$$

$$^{1}_{2}R = \begin{bmatrix} 0 & -1 & 0 \\ 0 & 0 & -1 \\ 1 & 0 & 0 \end{bmatrix} \cdot \begin{bmatrix} c\theta_2 & -s\theta_2 & 0 \\ s\theta_2 & c\theta_2 & 0 \\ 0 & 0 & 1 \end{bmatrix}$$

$$= \begin{bmatrix} -s\theta_2 & -c\theta_2 & 0 \\ 0 & 0 & -1 \\ c\theta_2 & -s\theta_2 & 0 \end{bmatrix} \Rightarrow {}^{2}_{1}R$$

$$= \begin{bmatrix} -s\theta_2 & 0 & c\theta_2 \\ -c\theta_2 & 0 & -s\theta_2 \\ 0 & -1 & 0 \end{bmatrix}$$

-continued $$^{2}_{3}R = \begin{bmatrix} c\theta_3 & -s\theta_3 & 0 \\ s\theta_3 & c\theta_3 & 0 \\ 0 & 0 & 1 \end{bmatrix} \Rightarrow {}^{3}_{2}R = \begin{bmatrix} c\theta_3 & s\theta_3 & 0 \\ -s\theta_3 & c\theta_3 & 0 \\ 0 & 0 & 1 \end{bmatrix}$$

For link 1, $$i = 0 \quad {}^{1}V_1 = {}^{1}_{0}R \cdot ({}^{0}V_0 + {}^{0}\omega_0 \times {}^{0}P_1) = 0$$

$$^{1}\omega_1 = {}^{1}_{0}R \cdot {}^{0}\omega_0 + \dot\theta_1 \cdot {}^{1}z_1 = \begin{bmatrix} 0 \\ 0 \\ \dot\theta_1 \end{bmatrix}$$

For link 2, $$i = 1 \quad {}^{2}V_2 = {}^{2}_{1}R \cdot ({}^{1}V_1 + {}^{1}\omega_1 \times {}^{1}P_2) = 0$$

$$^{2}\omega_2 = {}^{2}_{1}R \cdot {}^{1}\omega_1 + \dot\theta_2 \cdot {}^{2}z_2 = \begin{bmatrix} \dot\theta_1 \cdot c\theta_2 \\ -\dot\theta_1 \cdot s\theta_2 \\ \dot\theta_2 \end{bmatrix}$$

For link 3, i=2

$$^{3}V_2 = {}^{3}_{2}R \cdot ({}^{2}V_2 + {}^{2}\omega_2 \times {}^{2}P_3) = \begin{bmatrix} L_1 \cdot \dot\theta_2 \cdot s\theta_3 \\ L_1 \cdot \dot\theta_2 \cdot c\theta_3 \\ L_1 \cdot \dot\theta_1 \cdot s\theta_2 \end{bmatrix}$$

$$^{3}\omega_3 = {}^{3}_{2}R \cdot {}^{2}\omega_2 + \dot\theta_3 \cdot {}^{3}z_3 = \begin{bmatrix} \dot\theta_1 \cdot c\theta_2 \cdot c\theta_3 - \dot\theta_1 \cdot s\theta_2 \cdot s\theta_3 \\ -\dot\theta_1 \cdot c\theta_2 \cdot s\theta_3 - \dot\theta_1 \cdot s\theta_2 \cdot c\theta_3 \\ \dot\theta_2 + \dot\theta_3 \end{bmatrix}$$

For link 4, i=3

$$^{4}V_4 = {}^{4}_{3}R \cdot ({}^{3}V_3 + {}^{3}\omega_3 \times {}^{3}P_4) = L \begin{bmatrix} \dot\theta_2 \cdot s\theta_3 \\ \dot\theta_2 \cdot (c\theta_3 + 1) \cdot s\theta_3 + \dot\theta_3 \\ \dot\theta(c\theta_2 s\theta_3 + s\theta_2 c\theta_3 + s\theta_2) \end{bmatrix}$$

$$^{0}V_4 = {}^{0}_{4}R \cdot {}^{4}V_4 = {}^{0}_{1}R \cdot {}^{1}_{2}R \cdot {}^{2}_{3}R \cdot {}^{3}_{4}R \cdot {}^{4}V_4$$

$$^{0}_{4}R = \begin{bmatrix} -c\theta_1 \cdot c\theta_2 \cdot s\theta_3 - c\theta_1 \cdot s\theta_2 \cdot c\theta_3 & -c\theta_1 \cdot c\theta_2 \cdot c\theta_3 + c\theta_1 \cdot s\theta_2 \cdot s\theta_3 & s\theta_1 \\ -s\theta_1 \cdot c_2 \cdot s\theta_3 - s\theta_1 \cdot s\theta_2 \cdot c\theta_3 & -s\theta_1 \cdot c\theta_2 \cdot c\theta_3 + s\theta_1 \cdot s\theta_2 \cdot s\theta_3 & -c\theta_1 \\ 0 & -c\theta_2 \cdot s\theta_3 - s\theta_2 \cdot c\theta_3 & 0 \end{bmatrix}$$

$$^{0}V_4 = L \cdot \begin{bmatrix} s_1 \cdot (c_2 \cdot s_3 + s_2 \cdot c_3 + s_2) & c_1 \cdot (s_2 \cdot s_3 - c_2 \cdot c_3 - c_2) & c_1 \cdot (s_2 \cdot s_3 - c_2 \cdot c_3) \\ -c_1 \cdot (c_2 \cdot s_3 + s_2 \cdot c_3 + s_2) & s_1 \cdot (s_2 \cdot s_3 - c_2 \cdot c_3 - c_2) & s_1 \cdot (s_2 \cdot s_3 - c_2 \cdot c_3) \\ 0 & -s_2 \cdot c_3 - c_2 \cdot s_3 - s_2 & -c_2 \cdot s_3 - s_2 \cdot c_3 \end{bmatrix} \cdot \begin{bmatrix} \dot\theta_1 \\ \dot\theta_2 \\ \dot\theta_3 \end{bmatrix}$$

$$^{0}J(\theta) = L \cdot \begin{bmatrix} (s_2 + s_{23})s_1 & -(c_2 + c_{23})c_1 & -c_{23}c_1 \\ -(s_2 + s_{23})c_1 & -(c_2 + c_{23})s_1 & -c_{23}s_1 \\ 0 & -s_2 - s_{23} & -s_{23} \end{bmatrix}$$

where $S_n \sin\theta_n c_n = \cos\theta_n$, $s_{nm} = \sin(\theta_n + \theta_m)$, $c_{nm} = \cos(\theta_n + \theta_m)$.

Figure 7C:
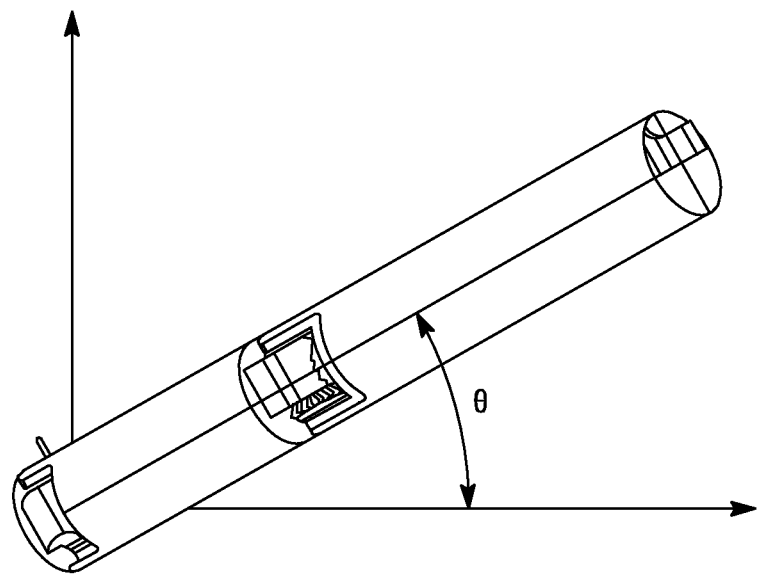
FIG. 7C is a top view of one embodiment of a manipulator arm.

The second method provides the results seen in FIG. 7C. The x, y and z equations are for the tip of link 3.

$$z = L_1 + L_2 \cdot \cos\theta_2 + L_3 \cdot \cos(\theta_2 + \theta_3)$$

$$x = -[L_2 \cdot \sin\theta_2 + L_3 \cdot \sin(\theta_2 + \theta_3)] \cdot \cos\theta_1$$

$$y = -[L_2 \cdot \sin\theta_2 + L_3 \cdot \sin(\theta_2 + \theta_3)] \cdot \sin\theta_1$$

-continued $$^0J(\theta) = \begin{bmatrix} \frac{\partial x}{\partial \theta_1} & \frac{\partial x}{\partial \theta_2} & \frac{\partial x}{\partial \theta_3} \\ \frac{\partial y}{\partial \theta_1} & \frac{\partial y}{\partial \theta_2} & \frac{\partial y}{\partial \theta_3} \\ \frac{\partial z}{\partial \theta_1} & \frac{\partial z}{\partial \theta_2} & \frac{\partial z}{\partial \theta_3} \end{bmatrix}$$

$$^0J(\theta) = \begin{bmatrix} (L_2s_2 + L_3s_{23})s_1 & -(L_2c_2 + L_3s_{23})c_1 & -L_3c_{23}c_1 \\ -(L_2s_2 + L_3s_{23})c_1 & -(L_2c_2 + L_3s_{23})s_1 & -L_3c_{23}s_1 \\ 0 & -L_2s_2 + L_3s_{23} & -L_3s_{23} \end{bmatrix}$$

where $s_n = \sin\theta_n, c_n = \cos_n, S_{nm} = \sin(\theta_n + \theta_m), C_{nm} = \cos(\theta_n + \theta_m)$ since $L_1 = L_2 = L$ $$^0J(\theta) = L \cdot \begin{bmatrix} (s_2 + s_{23})s_1 & -(c_2 + c_{23})c_1 & -c_{23}c_1 \\ -(s_2 + s_{23})c_1 & -(c_2 + c_{23})s_1 & -c_{23}s_1 \\ 0 & -s_2 - s_{23} & -s_{123} \end{bmatrix}$$

The motor selected for the manipulator in this example was a 6 V DC Micromotor manufactured by Faulhaber Company. The 6 V motor had a 15,800 rpm no-load speed, 0.057 oz-in stall torque, and weighed 0.12 oz. The motor had an 8 mm diameter and it was 16 mm long.

Due to its high no-load speed, a precision gearhead was used. The precision gearhead used was a planetary gearhead. For the preliminary analysis, a gearhead with a reduction ratio of 256:1 was selected. It had an 8 mm diameter, is 17.7 mm long, and weighs 0.19 oz.

A 10 mm magnetic encoder was chosen for this particular examination. It was 16.5 mm long, but it only added 11.5 mm to the total length of the assembly. The weight of the encoder was assumed to be 0.1 oz. The encoder provided two channels (A and B) with a 90° phase shift, which are provided by solid-state Hall sensors and a low inertia magnetic disc. Table 4 shows a summary of motor, planetary gearhead, and encoder properties.

TABLE 4

Summary of motor properties

| | Mass (m) | Length (L) |
|---|---|---|
| Motor (M) Series 0816 006 S | 0.12 oz | 16 mm |
| Planetary Gearhead (G) Series 08/1 Ratio 256:1 | 0.19 oz | 17.7 mm |
| Encoder (E) Type HEM 0816 | ≈0.1 oz | 11.5 mm |
| Total | 0.41 oz | 45.2 mm |

$L_T = L_M + L_{PG} + L_E = 45.2$ $m_T = m_M + m_{PG} + M_E = 0.41$ oz $m_T = 0.41 \text{ oz} \times 28.3495 \frac{\text{g}}{\text{oz}} = 11.623 \text{ g}$ FIG. 7A shows a schematic drawing of the manipulator used in this example with $L_L$, $L_{BJ}$, $M_1$, $M_2$, $m_1g$, $m_2g$ and $W_p$ labeled.

TABLE 5

Summary of Link Properties
Link Properties

| | |
|---|---|
| Length, $L_L$ (=$L_2$ = $L_3$) | 60 mm |
| Length between joints, $L_{BJ}$ | 59.5 mm |
| Outside diameter, $D_o$ | 12 mm |
| Inside diameter, $d_i$ | 8 mm |
| Wall thickness, t | 2 mm |
| Density, ρ | 1.18 g/cm³ |

Figure 7D:
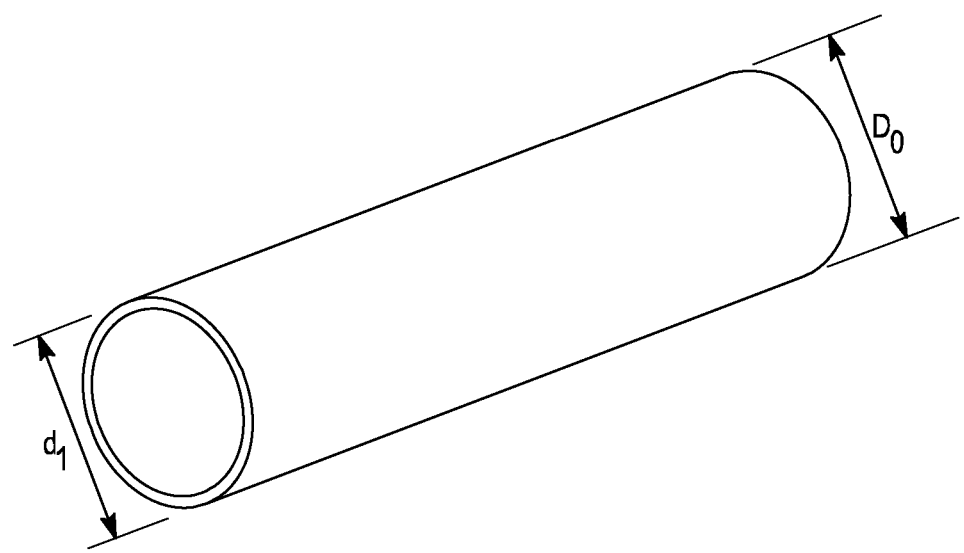
FIG. 7D is a schematic of the link shape assumed to calculate moment.

For purposes of the following calculations, it was assumed that the links were cylindrical tubes, as shown in FIG. 7D.

Link Volume:

$$V_L = \frac{D_o^2}{4} \cdot L_L - \frac{d_i^2}{4} \cdot (L_1 - 2t)$$

$$V_L = \frac{(12 \text{ mm})^2}{4} \times 60 \text{ mm} - \frac{(8 \text{ mm})^2}{4} \times (60 - 2 \times 2) \text{ mm}$$

$$= 2160 \text{ mm}^3 - 896 \text{ mm}^3$$

$$= 1264 \text{ mm}^3$$

Link Mass:

$$m_L = \rho \cdot V_L$$

$$m_L = 1.18 \frac{\text{g}}{\text{cm}^3} \times \frac{\text{cm}^3}{(10 \text{ mm})^3} \times 1264 \text{ mm}^3 = 1.49152 \text{ g}$$

Total Weight of Motor and Link:

$$m = m_\tau + m_L$$

$$m = 11.6233 \text{ g} + 1.49152 \text{ g} = 13.1148 \text{ g}$$

$$m_1 = m_2 = m$$

Payload Mass:

$m_p = 5$ g

Moment Calculations (Refer to FIG. 7A):

$$M_1 = m_1 \cdot g \cdot \frac{L_1}{2} + m_2 \cdot g \cdot \left(L_1 + \frac{L_2}{2}\right) + m_3 \cdot g \cdot (L_1 + L_2)$$

Since $L_1 = L_2 = L$ $$M_1 = \left(\frac{m_1}{2} + \frac{3 \cdot m_2}{2} + 2 \cdot m_3\right) \cdot g \cdot L_{BJ}$$

$$M_1 = \left(\frac{13.1148}{2} \text{ g} + \frac{3 \cdot 13.1148}{2} \text{ g} + 2 \cdot 5 \text{ g}\right) \cdot 9.81$$

$$\frac{\text{m}}{\text{s}^2} \cdot 59.5 \text{ mm} \cdot \frac{1 \text{ m}}{1000 \text{ mm}} \cdot \frac{1 \text{ kg}}{1000 \text{ g}}$$

$$M_1 = 0.021147 \text{ kg} \cdot \frac{\text{m}}{\text{s}^2} \cdot \text{m} = 0.021147 N \cdot \text{m} = \underline{21.147 mN \cdot \text{m}}$$

$$M_2 = m_2 \cdot g \cdot \frac{L_2}{2} + m_3 \cdot g \cdot L_2$$

-continued $$M_2 = \left(\frac{M_2}{2} + m_3\right) \cdot g \cdot L_{BJ}$$

$$M_2 = \left(\frac{13.1148}{2} g + 5 g\right) \cdot 9.81 \frac{m}{s^2} \cdot 59.5 \text{ mm} \cdot \frac{1 \text{ m}}{1000 \text{ mm}} \cdot \frac{1 \text{ kg}}{1000 \text{ g}}$$

$$M_2 = 0.006746 \text{ kg} \cdot \frac{m}{s^2} \cdot m = 0.006746 N \cdot m = \underline{6.746 mN \cdot m}$$

It was calculated based on the above equations that the maximum torque allowed by the motor for a continuous operation is 8.5 oz-in, which is 0.41 mNm. Using the reduction ratio of 256:1, the maximum torque allowed is 104.86 mNm (256×0.41 mNm).

As discussed above, precision gears with other reduction ratios may also be used, according to various embodiments. Tables with calculations for lower reduction ratios are provided below. These calculations are exemplary and are not intended to be limiting in any fashion.

TABLE 6

Gear Reduction Ratios

|  | Weight (oz) | Weight (g) | Length (mm) |
|---|---|---|---|
| Link 1 | | | |
| Motor | 0.12 | 3.40194 | 16 |
| Planetary gears | 0.16 | 4.53592 | 15 |
| Encoder | 0.1 | 2.83495 | 11.5 |
| Total | 0.38 | 10.77281 | 42.5 |
| Link length (mm) = Length + 15 = | 57.5 | | |
| Length between joints (mm) = Link length − 0.5 = | 57 | | |
| Outside diameter, $D_o$ (mm) = | 12 | | |
| Inside diameter, $d_i$ (mm) = | 8 | | |
| Wall thickness, t (mm) = | 2 | | |
| Density of resin, ro (g/cm³) = | 1.18 | | |
| Volume of link, V (mm³) = | 1214 | | |
| Weight of link, m (g) = | 1.43252 | | |
| Weight of motor and link, m_tot (g) = | 12.20533 | | |
| Link 2 | | | |
| Motor | 0.12 | 3.40194 | 16 |
| Planetary gears | 0.16 | 4.53592 | 15 |
| Encoder | 0.1 | 2.83495 | 11.5 |
| Total | 0.38 | 10.77281 | 42.5 |
| Link length (mm) = Length + 15 = | 57.5 | | |
| Length between joints (mm) = Link length − 0.5 = | 57 | | |
| Outside diameter, $D_o$ (mm) = | 12 | | |
| Inside diameter, $d_i$ (mm) = | 8 | | |
| Wall thickness, t (mm) = | 2 | | |
| Density of resin, ro (g/cm³) = | 1.18 | | |
| Volume of link, V (mm³) = | 1214 | | |
| Weight of link, m (g) = | 1.43252 | | |
| Weight of motor and link, m_tot (g) = | 12.20533 | | |
| Weight of camera or tool, m_c (g) = | 5 | | |
| Moment around joint 2, M1 (mNm) = | 19.24140875 | | |
| Moment around joint 3, M2 (mNm) = | 6.2082771 | | |
| Link length, L1 (mm) = | 57.5 | | |
| Link length, L2 (mm) = | 57.5 | | |
| Maximum moment, M_max (mNm) = | 19.24 | | |
| Maximum torque allowed, M_max_all (oz-in) = | 8.5 | =60.027 MNm | |
| is M_max > M_max_all? | NO | | |
| Maximum torque possible, M_max_pos (mNm) = | Gear Ratio | * Motor Torque = 26.214144 | |
| Is M_max_pos > M_max? | YES | | |
| This motor can be used to move the links. | | | |

TABLE 7

Gear Reduction Ratios

|  | Weight (oz) | Weight (g) | Length (mm) |
|---|---|---|---|
| Link 1 | | | |
| Motor | 0.12 | 3.40194 | 16 |
| Planetary gears | 0.19 | 5.386405 | 17.7 |
| Encoder | 0.1 | 2.83495 | 11.5 |
| Total | 0.41 | 11.623295 | 45.2 |
| Link length (mm) = Length + 15 = | 60.2 | | |

TABLE 7-continued

Gear Reduction Ratios

| | Weight (oz) | Weight (g) | Length (mm) |
|---|---|---|---|
| Length between joints (mm) = Link length – 0.5 = | 59.7 | | |
| Outside diameter, $D_o$ (mm) = | 12 | | |
| Inside diameter, $d_i$ (mm) = | 8 | | |
| Wall thickness, t (mm) = | 2 | | |
| Density of resin, ro (g/cm³) = | 1.18 | | |
| Volume of link, V (mm³) = | 1268 | | |
| Weight of link, m (g) = | 1.49624 | | |
| Weight of motor and link, m_tot (g) = | 13.119535 | | |
| Link 2 | | | |
| Motor | 0.12 | 3.40194 | 16 |
| Planetary gears | 0.19 | 5.386405 | 17.7 |
| Encoder | 0.1 | 2.83495 | 11.5 |
| Total | 0.41 | 11.623295 | 45.2 |
| Link length (mm) = Length + 15 = | 60.2 | | |
| Length between joints (mm) = Link length – 0.5 = | 59.7 | | |
| Outside diameter, $D_o$ (mm) = | 12 | | |
| Inside diameter, $d_i$ (mm) = | 8 | | |
| Wall thickness, t (mm) = | 2 | | |
| Density of resin, ro (g/cm³) = | 1.18 | | |
| Volume of link, V (mm³) = | 1268 | | |
| Weight of link, m (g) = | 1.49624 | | |
| Weight of motor and link, m_tot (g) = | 13.119535 | | |
| Weight of camera or tool, m_c (g) = | 5 | | |
| Moment around joint 2, M1 (mNm) = | 21.2236650 | | |
| Moment around joint 3, M2 (mNm) = | 6.77005875 | | |
| Link length, L1 (mm) = | 60.2 | | |
| Link length, L2 (mm) = | 60.2 | | |
| Maximum moment, M_max (mNm) = | 21.22 | | |
| Maximum torque allowed, M_max_all (oz-in) = | 8.5 | =60.027 MNm | |
| is M_max > M_max_all? | NO | | |
| Maximum torque possible, M_max_pos (mNm) = | Gear Ratio | * Motor Torque = 104.85658 | |
| Is M_max_pos > M_max? | YES | | |
| This motor can be used to move the links. | | | |

By using the Jacobian that was previously developed and is shown below, it is possible to calculate the torques provided by the force exerted to the tip of the manipulator used in this example. However, it should be noted that this method does not take into account the weights of links and motors.

$$^0J(\theta) = L \cdot \begin{bmatrix} (s_2 + s_{23})s_1 & -(c_2 + c_{23})c_1 & -c_{23}c_1 \\ -(s_2 + s_{23})c_1 & -(c_2 + c_{23})s_1 & -c_{23}s_1 \\ 0 & -s_2 - s_{23} & -s_{23} \end{bmatrix}$$

$$f = \begin{bmatrix} 0 \\ 0 \\ -f_z \end{bmatrix}$$

where $$f_z = 0.005 \text{ kg} \times 9.81 \frac{m}{s^2} = 0.04905 N$$

and L=59.5 mm $$^0\tau_j = {}^0J(\theta)^T \cdot f$$

$$^0\tau_j = L \cdot \begin{bmatrix} (s_2 + s_{23})s_1 & -(c_2 + c_{23})c_1 & -c_{23}c_1 \\ -(s_2 + s_{23})c_1 & -(c_2 + c_{23})s_1 & -c_{23}s_1 \\ 0 & -s_2 - s_{23} & -s_{23} \end{bmatrix} \cdot \begin{bmatrix} 0 \\ 0 \\ -f_z \end{bmatrix}$$

$$^0\tau_j = 59.5 \text{ mm} \cdot \begin{bmatrix} (s_2 + s_{23})s_1 & -(c_2 + c_{23})c_1 & -c_{23}c_1 \\ -(s_2 + s_{23})c_1 & -(c_2 + c_{23})s_1 & -c_{23}s_1 \\ 0 & -s_2 - s_{23} & -s_{23} \end{bmatrix} \cdot \begin{bmatrix} 0 \\ 0 \\ -0.4905N \end{bmatrix}$$

$$= \begin{bmatrix} 0 \\ 2.918 \cdot (s_2 + s_{23}) \\ 2.918 \cdot s_{23} \end{bmatrix}$$

Using $\theta_1 = 0°$, $\theta_2 = 90°$, $\theta_3 = 0°$ $$^0\tau_j = \begin{bmatrix} 0 \\ 5.836 \\ 2.918 \end{bmatrix} mN \cdot m$$

Thus the torque for the base motor is 0 mNm: for link 1 it is 5.836 mNm, and for link 2 it is 2.918 mNm. This result makes sense because the largest torque will be exerted on the joint farthest away from the tip of the manipulator. Also, since the distance is two times the distance to middle joint, the result is two times bigger.

Accounting for the link and motor masses, $$^0\tau_{LM}\begin{bmatrix}0\\W_{LM}\cdot\left(\dfrac{L_1}{2}+\dfrac{3\cdot L_2}{2}\right)\\W_{LM}\cdot\dfrac{L_2}{2}\end{bmatrix}=m\cdot g\cdot L\cdot\begin{bmatrix}0\\2\\1\\\dfrac{1}{2}\end{bmatrix}$$

$$^0\tau_{LM}=13.1148\text{ g}\times 9.81\dfrac{m}{s^2}\times 59.5\text{ mm}\times\begin{bmatrix}0\\2\\1\\\dfrac{1}{2}\end{bmatrix}\times\dfrac{1\text{ m}}{1000\text{ mm}}\times\dfrac{1\text{ kg}}{1000\text{ g}}$$

$$=\begin{bmatrix}0\\15.31\\3.828\end{bmatrix}mN\cdot m$$

The total torque is, $$^0\tau={^0\tau_j}+{^0\tau_{LM}}=\begin{bmatrix}0\\5.836\\2.918\end{bmatrix}+\begin{bmatrix}0\\15.31\\3.828\end{bmatrix}=\begin{bmatrix}0\\21.146\\6.746\end{bmatrix}mN\cdot m$$

As shown, both methods provide the same result.

In the embodiment of the manipulator arm robot used in this example, the electronics and control consisted of four major sections described above in the detailed description and depicted in block diagram form in FIG. 8. Each hardware section will be described in detail, followed by the PC software controlling the PCI-DSP card and the software running on the microcontroller.

The first section of the hardware in this embodiment was a PC with Motion Engineering, Inc. PCI/DSP motion controller card. This card used an Analog Devices DSP chip running at 20 MHz to provide closed-loop PID control of up to four axes simultaneously. It had encoder inputs for positional feedback. The servo analog outputs were controlled by a 16-bit DAC, which allowed very precise output control. The card also featured several dedicated digital I/O functions, including amplifier enable output, amplifier fault input, home input, positive limit input, and negative limit input. However, only the basic functions were used in this application: servo analog output and digital encoder inputs. The PCI/DSP came with a full-featured C programming library to aid in programming different motion functions. Also provided was a Windows-based program, Motion Control, to configure and tune the controller, as well as to capture data from simple one-axis motion profiles.

Figure 31A:
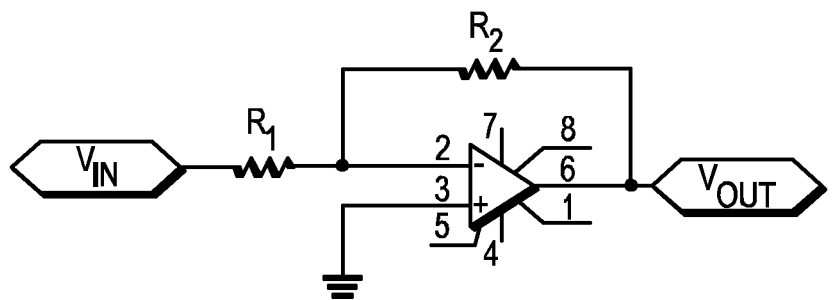
FIG. 31A is an inverting amplifier circuit used in one embodiment of a manipulator arm.

The output from the PCI/DSP was an analog signal with a range of ±10V. In order to interface with the microcontroller, this signal was converted to a 0.5V range. Two simple op-amp circuits performed this function. Both op-amp circuits used the LM318 op-amp from National Semiconductor. The first section was a standard inverting circuit with a gain of −0.25. This converts the ±10V input into a ±2.5V output. This circuit is shown in FIG. 31A. The second section is a summing amplifier circuit with a transfer function given by:

$$V_0=(V_z-V_1)\dfrac{R_z}{R_1}$$

Figure 31B:
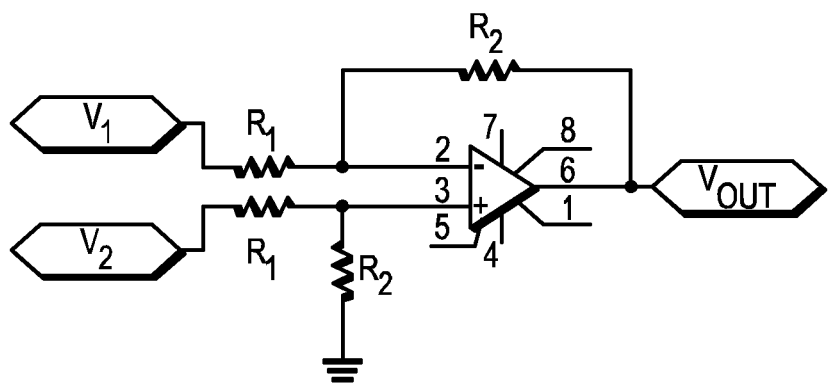
FIG. 31B is a summer amplifier circuit used in one embodiment of a manipulator arm.

With V2 a constant 2.5V, an output voltage of 0-5V results. This circuit is shown in FIG. 31B.

Capacitors were placed at the output of each op-amp to filter out high frequency noise. This two-amplifier circuit is duplicated exactly for each axis. The 2.5V reference is supplied by a 10 K potentiometer.

After the analog voltages were scaled and shifted, each was sampled by the PsoC (Programmable System on a Chip) microcontroller and converted to a PWM output signal and a direction signal. The PsoC also provides direction output based on the input voltage. The PsoC is made by Cypress Semiconductor, and is an 8-bit microcontroller with several generic digital and analog "blocks" that can be configured using the PsoC Designer software package to perform many different functions. These functions include, but are not limited to: ADCs, DACs, PWM generators, timers, UARTS, LCD drivers, filters, and programmable amplifiers. PsoC Designer also provides an API accessible from C and assembly to interface with these on-board components. For the embodiment described here, a single ADC, an analog multiplexer, and three PWM generators were used. The duty cycle of the PWM outputs are directly proportional to the analog input signals. Table 8 summarizes the function of the microcontroller.

TABLE 8

| | Microcontroller Function | |
|---|---|---|
| Analog Input | PWM Positive Duty Cycle | Direction Output |
| Vin = 2.5 V | 0% | X |
| 0 < Vin < 2.5 | 50% < Dc < 0% | Low |
| 2.5 < Vin < 5 | 0% < Dc < 50% | High |

The outputs of the microcontroller circuit were fed to the inputs of the FAN8200. These were H-Bridge Driver circuits, in a 20-pin surface mount package. Each driver had an enable and direction input. For this embodiment, the PWM signal was fed to the enable input, and the direction output of the microcontroller was fed to the direction input of the motor driver. The motors on the robot were connected directly to the PCI/DSP card, with no signal conditioning required. As mentioned previously, the PsoC microcontroller sampled each of the three analog outputs, and updated the corresponding PWM duty cycle and direction output accordingly.

Figure 32:
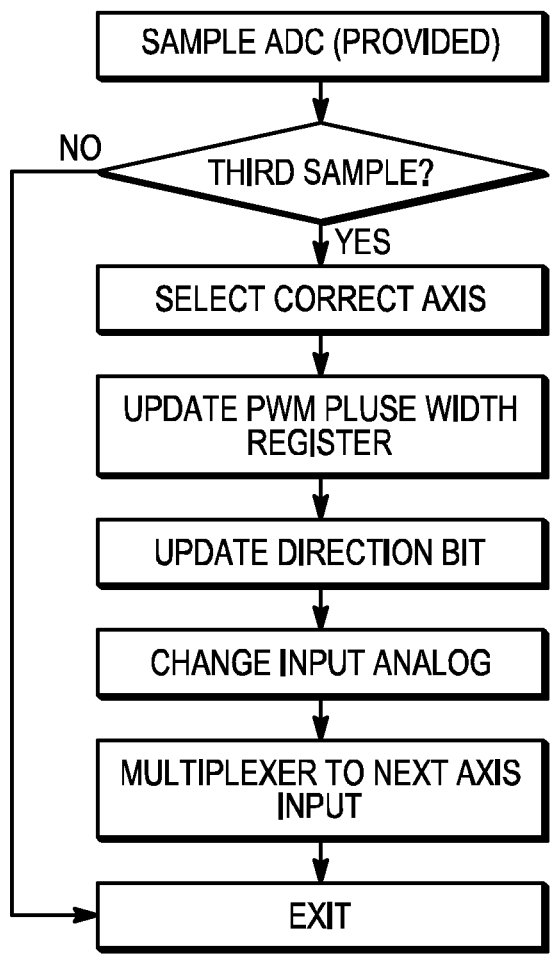
FIG. 32 is a flowchart for an interrupt service routine used in one embodiment of a manipulator arm.

The majority of the code was executed in the ADC interrupt service routine. A flowchart of the ISR is shown in FIG. 32. After initialization, the PsoC main program entered an endless loop. The ADC was set up to generate a periodic interrupt. After the data was sampled, a check was performed to see if the last two samples hade been ignored. Since three different input signals were sampled, a limitation of the hardware required skipping two samples before getting a valid value. If the last two samples were skipped, the appropriate PWM pulse width register and direction bit were set. Next, the input of the analog multiplexer was switched to the next axis input. This cycle was then repeated when the next interrupt occurred.

The other software element in the system was the PC program that was used for testing the robot. This was a console-based Windows program that used the Motion Engineering library to send commands to the PCI/DSP. This program can move each axis individually, or move all three simultaneously using the DSP's coordinated motion functions, allowing the user to enter a desired position, in encoder counts, for each axis. The DSP card then creates an appropriate motion profile, and moves each motor to the correct position. This program also was used to generate impulse responses for each motor for analysis.

Figure 33:
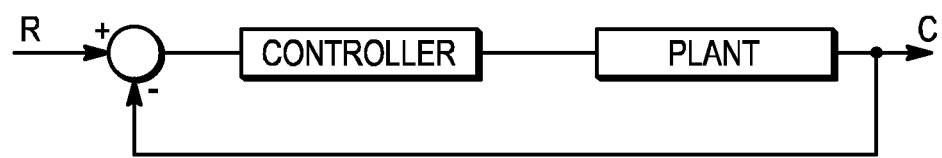
FIG. 33 is a block diagram of a controller and plant for a modern control system for control design of a three-link manipulator arm according to one embodiment.

There are several techniques available for designing system controls; here, modern control theory was used for control design of a three link robotic arm. A typical modern control system contains a plant and a controller in the feed forward. This design theory is shown in FIG. 33 as a block diagram. Modern control theory is an effective and commonly used theory for control design.

In this case, modern control theory was used to design three separate controllers. Three controllers were required in order to control the three motors used to manipulate the arm. In order to do this, it was assumed that three separate systems exist. Each system was designed assuming that only one motor, the motor being controlled in the system, was active. This was acceptable based on the method for determining the reaction of a system to a disturbance.

Figure 34:
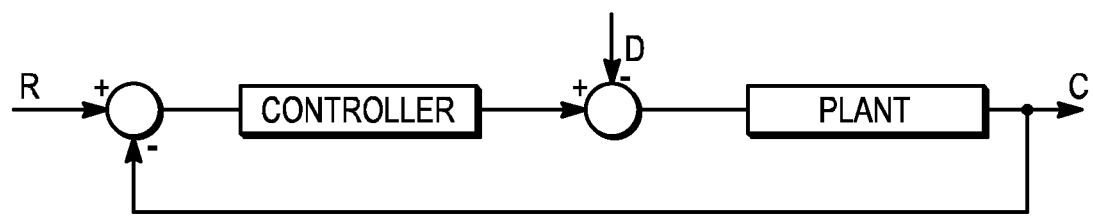
FIG. 34 is a block diagram of a controller and plant for a modern control system, with a disturbance included, for a three-link manipulator arm according to one embodiment.

Shown in FIG. 34 is a block diagram of a system that includes a disturbance. In order to determine how the output, C, responds to the input, R, the disturbance, D, is set to zero. Using this method, the uncontrolled motors are considered equivalent to the disturbance and are set to zero. With this, a controller was then designed based on a single output containing a single input. However, three separate systems are still required, since there are three separate outputs. These outputs are motor positions, in encoder counts, of axes 1, 2 and 3.

Figure 35A:
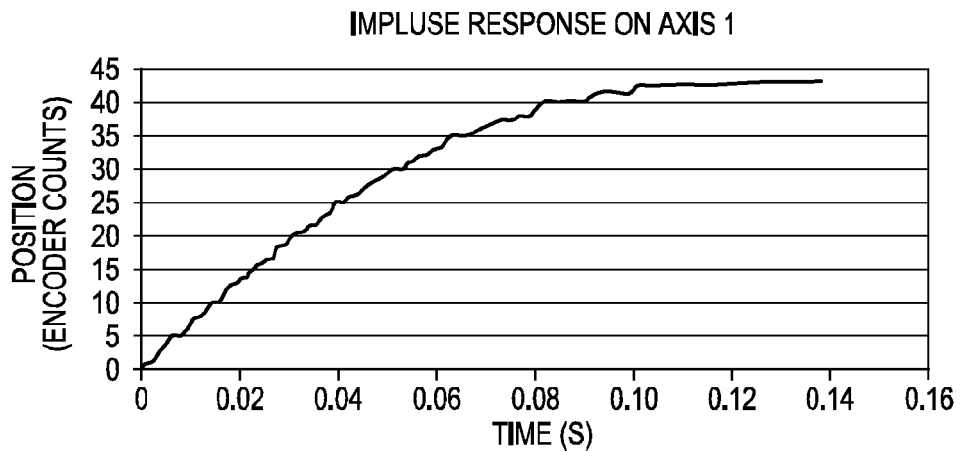
FIGS. 35A-C are plots of motor position, based on encoder counts versus time in seconds, for the three motors used in the linkages of a three-link manipulator arm according to one embodiment.
Figure 35B:
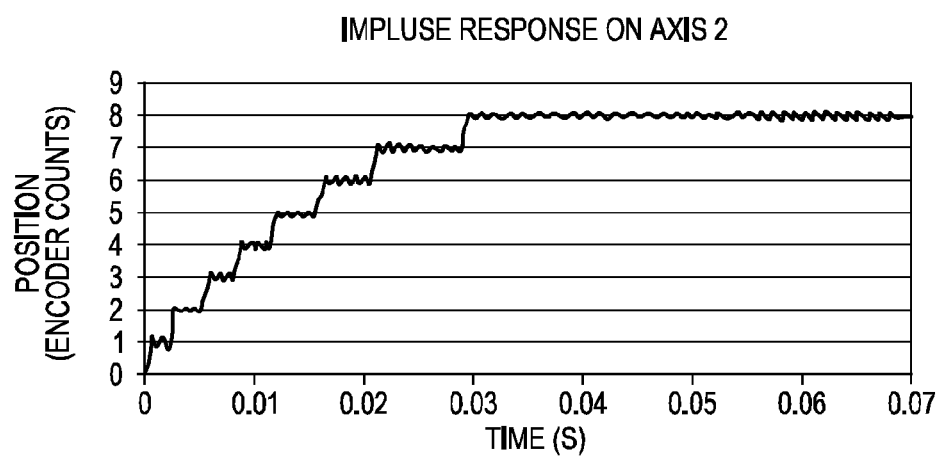
Figure 35C:
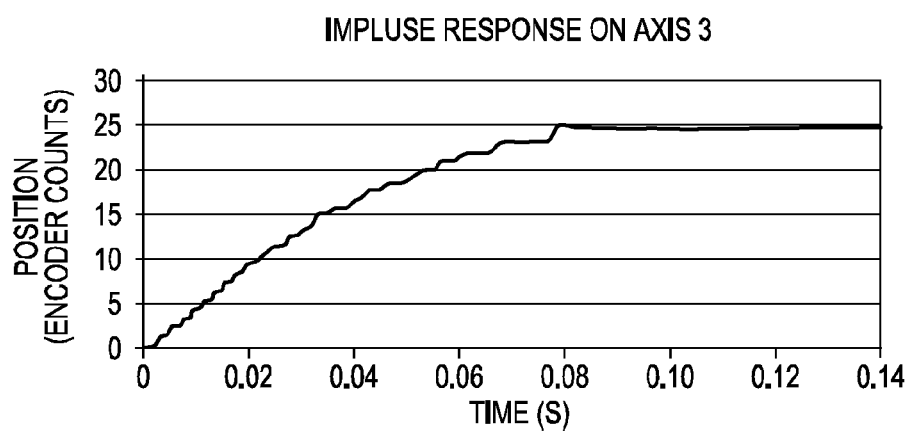

In one embodiment, there are several methods a designer can use to design a plant. Most methods used are analytical. In this case an experimental approximation of the plant was created. This was an effective and verifiable method for approximating the system. To collect the experimental data, a computer program was used to send a voltage impulse to the motor. The program simultaneously recorded the position of the motor, using the encoder. This procedure was performed three separate times, once for each motor. The data was then used to construct plots of motor position (based on encoder counts) versus time in seconds. Plots from the data are shown in FIGS. 35A, 35B and 35C. In these plots, axis 1 represents the motor for link 1, axis 2 represents the motor for link 2, and axis 3 represents motor for link 3.

From analyzing the data in FIGS. 35A, 35B and 35C, an approximation of the time response to an impulse input was developed. Experience helped determine that this system most likely contained two more poles than zeros. To determine if this was correct, approximations of the digital systems were made using a continuous time domain. An algorithm for the plant in the continuous time domain was developed for FORTRAN using Maple V. This algorithm was then integrated into an error subroutine. A simplex search program to determine the values of up to 9 variables utilized the error subroutine. The program ran until it could no longer reduce the sum of the square of the error developed by the approximate plant, compared to the experimental plant.

Multiple configurations of the plant were used to find the approximation to the experimental plant. This included the use of complex poles, as well as changing the number of poles and zeros in the transfer function. From these configurations, it was determined that the plant, G(s), can be modeled using the transfer function in the continuous time domain shown the following in equation. In this equation, the poles are 0, −b and −c, and the zero is −α.

$$G(s) = \frac{s+\alpha}{s(s+b)(s+c)}$$

Using the simplex search program, along with the error subroutine, the following system plant values were determined:

System for axis 1:
a=427251.2
b=465.3229
c=18.28435
sum of square of error=16.3779

System for axis 2:
$a=22.219726*10^9$
$b=4.142605*10^{16}$
c=56.9335
sum of square of error=2.86986

System for axis 3:
a=282220.0
b=414.5029
c=24.2966
sum of square of error=9.7724

Since all motors were identical, they should have similar system poles and zeros, even though they are located in different positions on the robot. This was shown to be true for the systems for axis 1 and 3. However, the system for axis 2 did not conform to the other two systems very closely. This was most likely due to poor data. A larger impulse on the motor for axis 2 would have helped to obtain more realistic data.

Figure 36A:
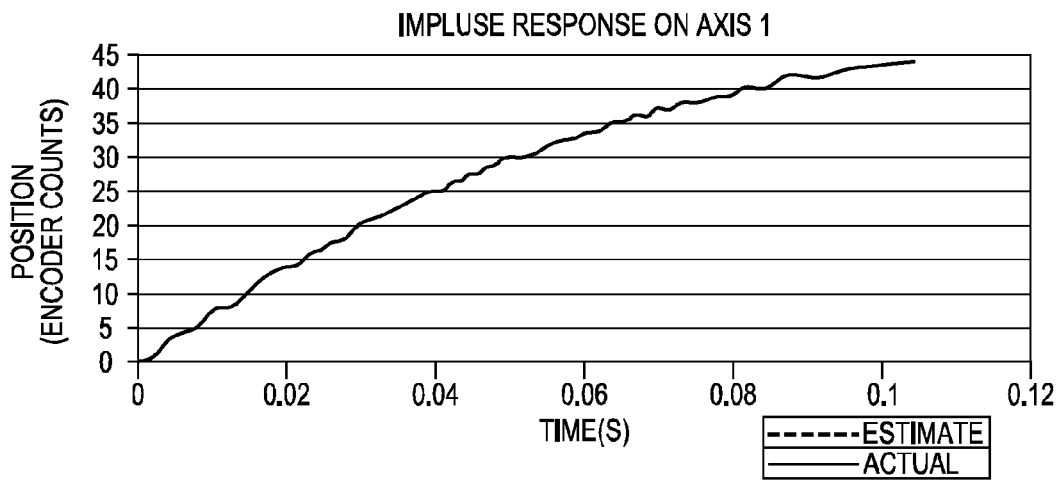
FIGS. 36A-C are plots of motor position, based on encoder counts versus time in seconds, for the three motors used in the linkages of a three-link manipulator arm, according to one embodiment.
Figure 36B:
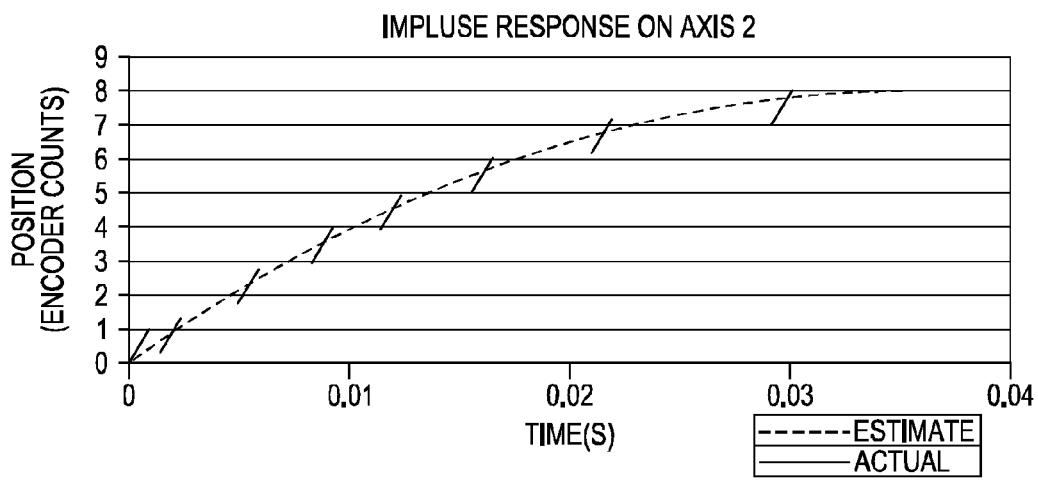
Figure 36C:
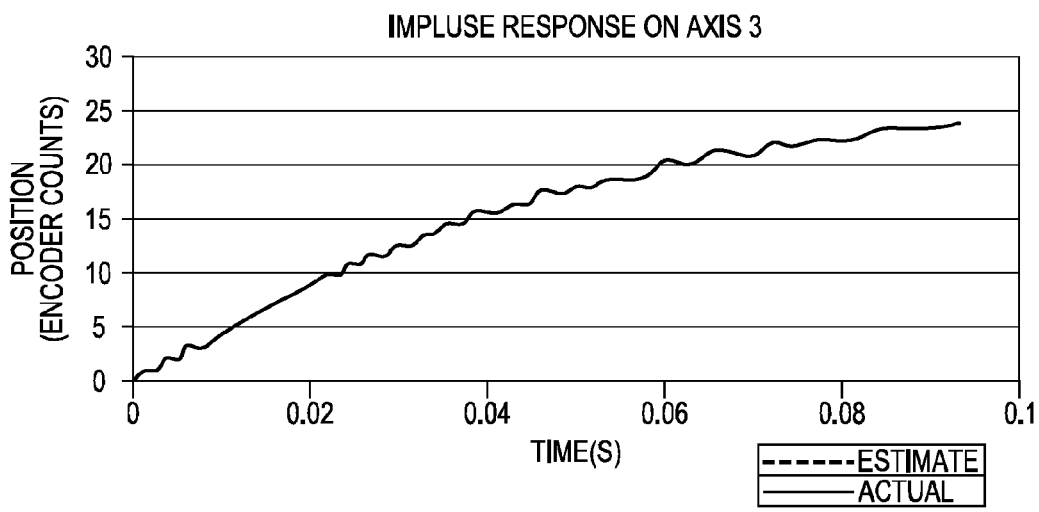

To see how well the system in the continuous time domain reflected the data taken from the digital system, the error subroutine was used once again. This time the error subroutine was compiled as a program rather than as a subroutine. By substituting the above values for a, b and c into the error program, the continuous fit was mapped to the actual digital data. The results were plotted once again as motor position (based on encoder counts) versus time in seconds. These plots are shown in FIGS. 36A, 36B and 36C. As shown in each of these figures, the approximation developed was a good fit to the actual data.

To control the motor positions on the robot, a PID controller was used. When using a PID controller, the controller from FIGS. 31A and 31B takes the form of the following equation.

$$D(s) = K_P + K_D s + \frac{K_I}{s}$$

Where $K_p$ is the proportional constant, $K_D$ is the derivative constant, and $K_I$ is the integral constant. With the PID controller, the system becomes a type 2 system. This means that the error in the response to a step and ramp input is zero. However, the error for the response to a parabolic input is $1/K_a$. Where $K_a$ is the acceleration constant and is defined as:

$$K_a = \lim_{s \to 0} [s^2 D(s) G(s)] = \frac{K_I \alpha}{bc}$$

Since the input can be defined, a parabolic input is not used.

Computing the values for $K_p$, $K_D$ and $K_I$ was done using Routh Analysis along with Ziegler-Nichols tuning. Routh Analysis uses the characteristic equation of the system transfer function. In this case, though, $D(s)=K_p$, only. The transfer function of this system with gain only, using G(s) as defined above, is shown in the following equation.

$$TF = \frac{K_p(s+\alpha)}{S^3 + (b+c)s^2 + (bc+K_p)s + \alpha K_p}$$

Note that Routh Analysis only can be used if the system for D(s)=1 is stable. This is true if the characteristic equation of the system when D(s)=1 has stable roots. Stable system poles, or roots of the characteristic equation, are roots that have negative real values or are located at the origin. The following equation is the characteristic equation for the system when D(s)=1.

$$CE = s(s+b)(s+c)+(s+a)$$

The following poles or roots of CE are:
System for axis 1:
−467.3563980,
−8.125425989−29.12326516*I,
−8.125425989+29.12326516*I
System for axis 2:
−4142605000e17,
−56.93350000,
−1811514786e−12
System for axis 3:
−417.1080124,
−10.84574379−30.11125593*I,
−10.84574379+30.11125593I Since all poles have negative real parts, the uncontrolled system was stable and Routh Analysis can be used.

Using the characteristic equation, or the denominator from the equation, solving for TF, above, Routh Analysis is performed as follows:

$$\begin{array}{c|cc} s^3 & a_0 & a_2 \\ s^2 & a_1 & a_3 \\ s^1 & b_1 & \\ s^0 & c_1 & \end{array}$$

where:

$a_0 = 1$ $a_1 = (b+c)$ $a_2 = (bc + K_p)$ $a_3 = \alpha K_p$ $b_1 = \dfrac{a_1 a_2 - a_0 a_3}{a_1}$ $c_1 = \dfrac{b_1 a_3 - a_1 * 0}{b_1} = a_3$ Using Maple V, the term ($b_1$*s) is set equal to zero and then solved for $K_p = K_{p(max)}$. The results are as follows:
System for axis 1:
$K_{p(max)} = 9.641293894$
System for axis 2:
$K_{p(max)} = 0.4409880606*10^{16}$
System for axis 3:
$K_{p(max)} = 15.68292936$ These results were all obtained using Maple V.

In order to use Ziegler-Nichols tuning with Routh Analysis, the system period was also needed. The system period was found by setting s=jω, $K_p = K_{p(max)}$, and solving for w (system frequency in rad/s) from the following equation.

$$a_1(j\omega)^2 + a_3 = 0$$

Since, $$\omega = 2\pi f$$

Then the system period in seconds was:

$$T = \frac{1}{f} = \frac{2\pi}{\omega}$$

The resulting system periods were as follows:
System for axis 1:
T=0.06807959499 sec
System for axis 2:
T=0.4087460141*10$^{-8}$ sec
System for axis 3:
T=0.06256709734 sec With the Ziegler-Nichols tuning equations for $K_p$, $K_I$, and $K_D$, the controller, D(s), as defined above, was designed. The Ziegler-Nichols tuning equations for PID control are shown below.

$$K_p = 0.6 K_{p(max)}$$

$$K_I \leq \frac{2K_p}{T}$$

$$K_D \geq \frac{K_p T}{8}$$

The resulting values for $K_p$, $K_I$, and $K_D$ are as follows:
System for axis 1:
$K_p$=5.784776336
$K_D$=0.04922815376
$K_I$=169.9
System for axis 2:
$K_p$=0.2645928364e16
$K_D$=1351890.840
$K_I$=0.1 294656473e25
System for axis 3:
$K_p$=9.408
$K_D$=0.07357890648
$K_I$=300.7331456

Figure 37:
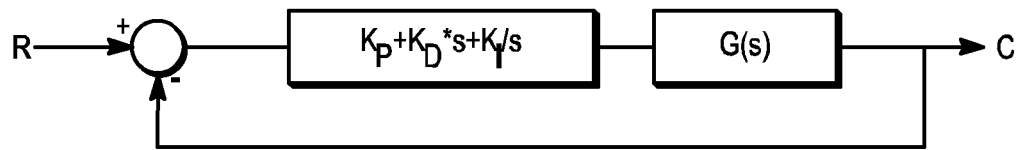
FIG. 37 is a system block diagram for a controller based on Ziegler-Nichols tuning, according to one embodiment.

The resulting system with PID control for all systems is shown in FIG. 37, where G(s), $K_p$, $K_D$, and $K_I$ are previously defined constants and functions, C is the motor position in encoder counts and R is the input position, in encoder counts.

Figure 38A:
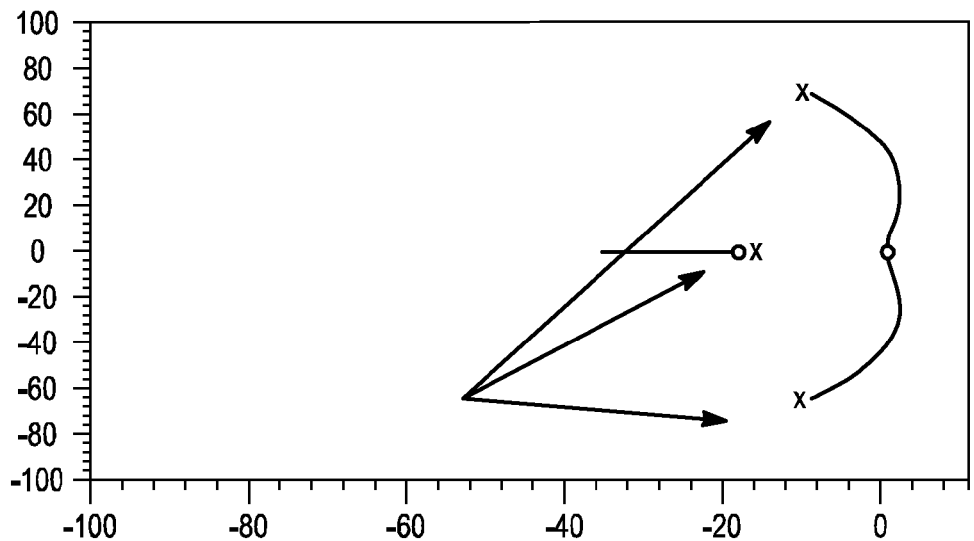
FIGS. 38A and B show plots of the root locus for links 1 and 3, according to one embodiment.
Figure 38B:
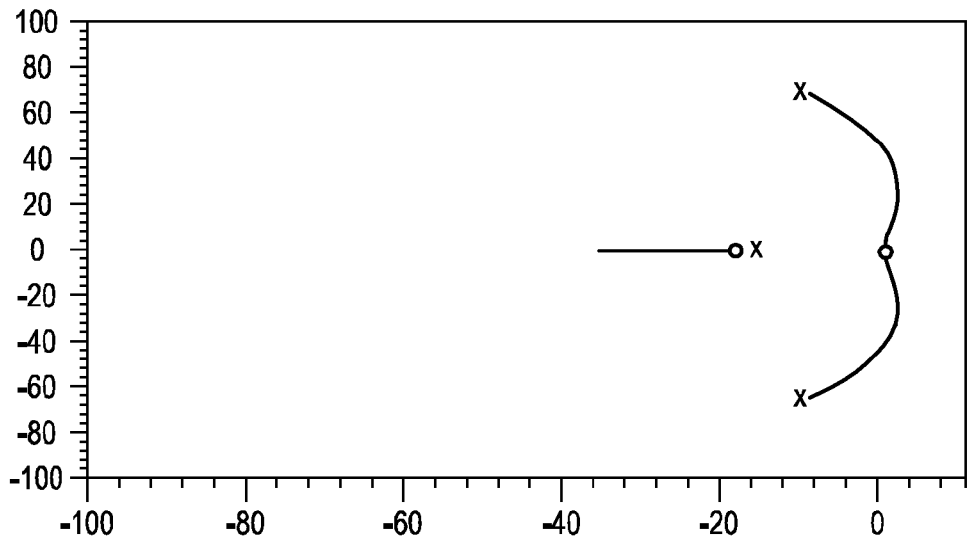
FIG. 38B shows the results for link 3.

One way to decide if these PID values were reasonable was to do a root locus plot of the open loop transfer function, D(s)*G(s). System stability also could be found from the root locus plot. That is, the poles or roots of the characteristic equation on the root locus should be located in the negative real plane. These plots, shown in FIGS. 38A and 38B are made using a Maple V program. Note that the root locus for axis 2 is not shown. From viewing the previous results for determining the PID control values, it was obvious that the data for axis 2 does not follow the data for axes 1 and 3 as would be expected.

Figure 39A:
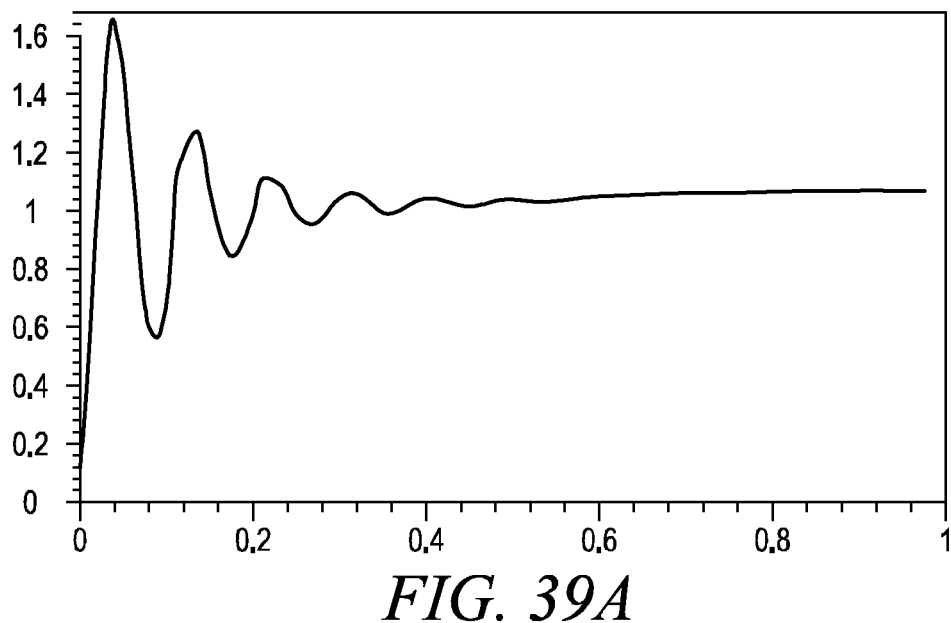
FIGS. 39A-C show plots of time response to unit input of a three-link manipulator arm according to one embodiment.
Figure 39B:
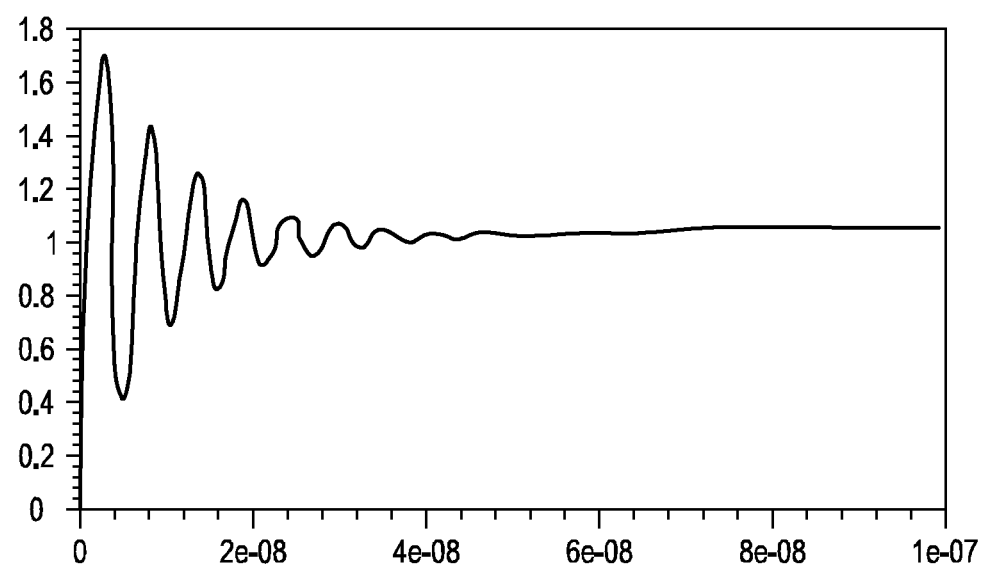

As shown in FIGS. 39A and 39B, both systems for axes 1 and 3 were stable, as was the system for axis 2. When looking at FIGS. 38A and 38B, complete optimization of the system would align the three poles. Since all systems were stable, a time response to a unit input into the system was analyzed.

Figure 39C:
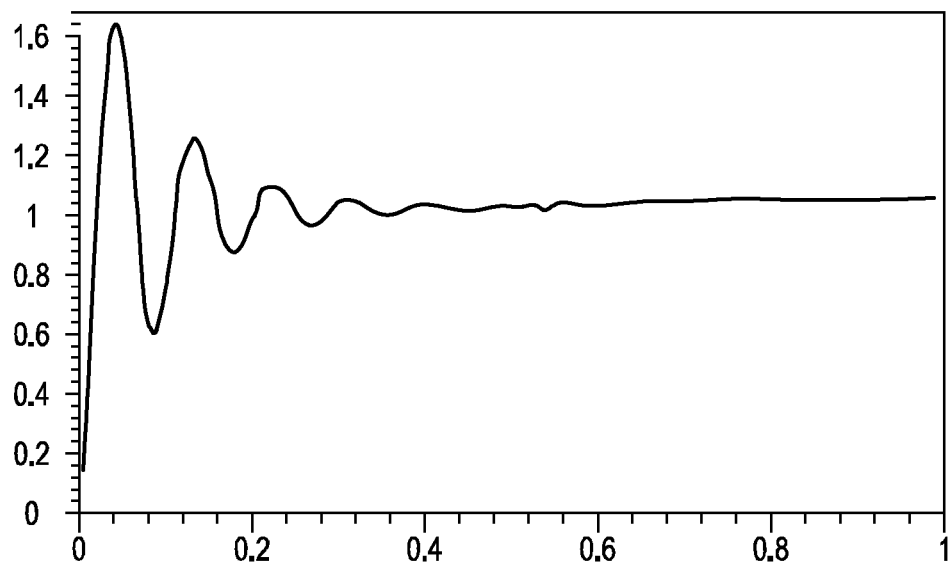

Once again, the Maple V program was used to determine the responses shown in FIGS. 39A, 39B, and 39C. In FIGS. 39A, 39B, and 39C, the abscissa is time in seconds, and the ordinate is motor position in encoder counts.

All responses shown in FIGS. 39A, 39B, and 39C were stable responses. However, in each case, there was over 66 percent overshoot, and such overshoot is undesirable for control of the robotic arm. By using a lead-lag compensator, the overshoot was greatly reduced.

Adjusting the phase margin of a system through the use of a lead or a lead-lag compensator is a technique that generally reduces the percent overshoot of a system. The phase margin is the angle between the negative abscissa and the point on the Nyquist diagram of the system, where the magnitude is 1. In most cases, a phase margin of about 60 degrees is optimal for reducing percent overshoot.

From using a Nyquist plot program, the following data was obtained.

System for axis 1:
Phase Margin=180−162.9633=17.84 degrees
$\omega_c$=71.999 rad/s
$G(j\omega)$=1.0007~1.0
$\phi_{(added)}$=60−17.84=42.96 degrees
To compensate for phase loss due to the lag compensator:
$\phi_{(added)}$=45.0 degrees
System for axis 3:
Phase Margin=180−161.90512=18.095 degrees
$\omega_c$=71.999 rad/s
$G(j\omega)$=1.0007~1.0
$\phi_{(added)}$=60−18.095=41.905 degrees
To compensate for phase loss due to the lag compensator:
$\phi_{(added)}$=48.0 degrees There are a few things to note. Once again, the data for axis 2 resulted in compensator design for axes 1 and 3 only. Also, $\omega_c$ may be changed to any desired frequency. $G(j\omega)$, and $\phi_{(added)}$ would subsequently change depending on the phase and magnitude at the selected $\omega_c$. However, the phase margin would remain the same.

The following equations were used to define a lead and lag compensator, respectively.

$$\frac{1}{k} = \left[\tan\left(\frac{\phi_{added}+90}{2}\right)\right]^2$$

$$\sqrt{kl} = \omega_c$$

$$\text{lead} = \frac{1}{k}\frac{(s+k)}{(s+l)}$$

$$\frac{n}{m} = \frac{1}{G(j\omega)\sqrt{\frac{1}{k}}}$$

$$M = \frac{\omega_c}{5}$$

$$\text{Lag} = \frac{n}{m}\frac{(s+m)}{(s+n)}$$

The resulting compensators from equations 11 and 12 for systems for axes 1 and 3 were as follows:

Compensator for axis 1:

$$\text{lead} = \frac{173.82096}{29.82296}\frac{(s+29.82296)}{(s+173.82096)}$$

$$\text{lag} = \frac{5.96459}{14.3998}\frac{(s+14.3998)}{(s+5.96459)}$$

Compensator for axis 3:

$$\text{lead} = \frac{203.9772}{30.0563}\frac{(s+30.0563)}{(s+203.9772)}$$

$$\text{lag} = \frac{6.0071}{15.65988}\frac{(s+15.65988)}{(s+6.0071)}$$

Figure 40:
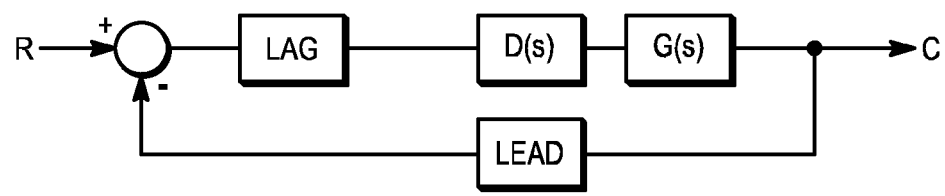
FIG. 40 is a system block diagram for a controller with lead and lag compensators integrated into the design, according to one embodiment.

The lead and lag compensators are integrated into the design as shown in FIG. 40.

Since zeros placed closer to the origin than poles create overshoot, the lead compensator was placed in the feedback. This is because if placed in the feed forward, a zero would be located between the origin and a pole in the root locus plot. For this same reason, the lag compensator was placed in the feed forward.

The effect of these compensators on the system was analyzed. First, the Nyquist plot program, was used once again. This was done to see what effect the compensators had on the phase margin. Finally, a plot of the response of the systems to a unit step input was made using the Maple V program 1.

Figure 41A:
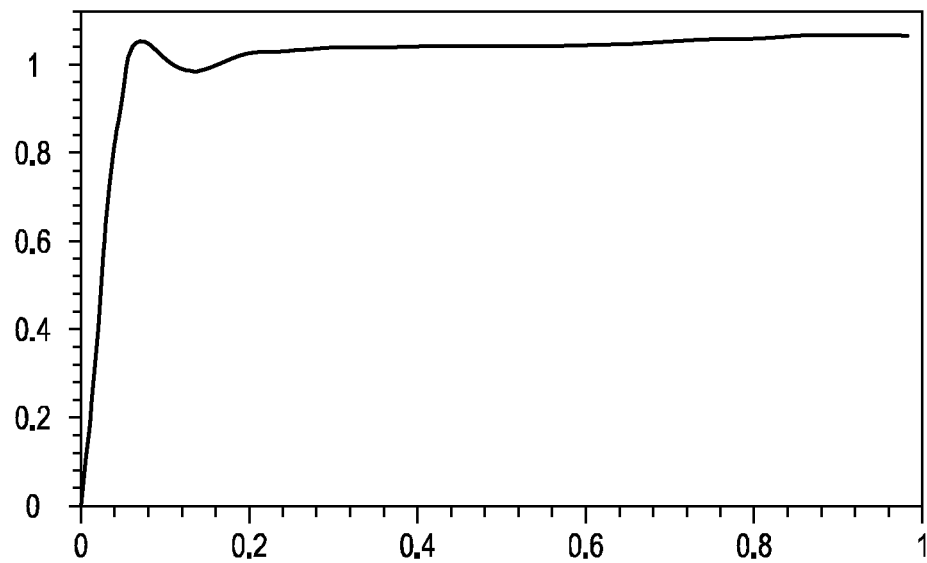
FIGS. 41A and B show the response of the systems for links 1 and 3 with compensators, according to one embodiment.
Figure 41B:
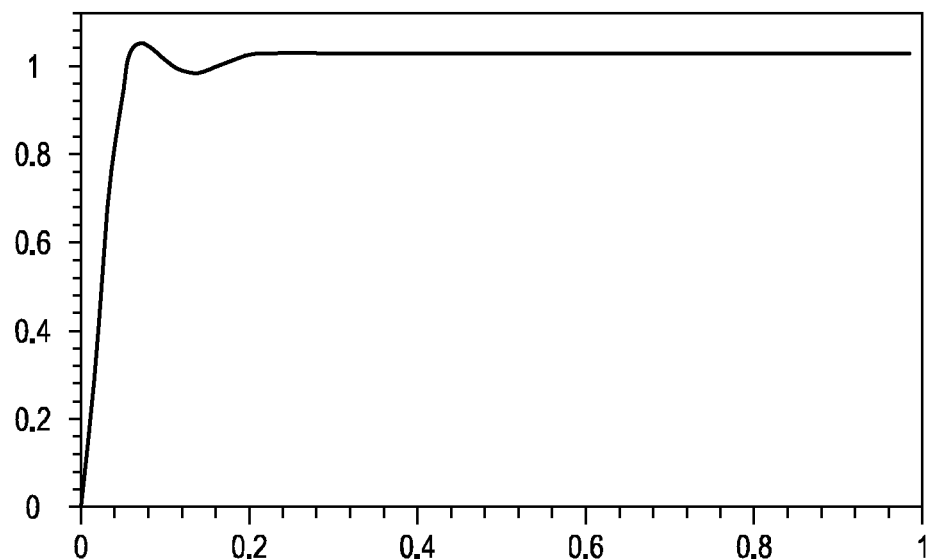

Resulting data from the Nyquist plot program:

System for axis 1:
Phase Margin=180−123.88=56.12 degrees@$\omega$=73.199 rad/s System for axis 3:
Phase Margin=180−120.238=59.76 degrees@$\omega$=79.599 rad/s This was proof that the compensator design was successful in adjusting the phase margin to the desired 60 degrees of phase. Shown in FIGS. 41A and 41B are the responses of the systems for axes 1 and 3 after the addition of the compensators. These plots were made using the Maple V program. Again, the abscissa is time in seconds and the ordinate is motor position in encoder counts.

As shown in FIGS. 41A and 41B, the compensators greatly reduced the percent overshoot. The percent overshoot was reduced to a mere only about 4 percent, a great improvement over the 66 percent figure.

Once the controller design was complete in the continuous time domain, it could be converted to the discrete time domain. This is required in order to control a digital system. However, it was only necessary to convert the compensators and controller to the discrete time domain. When this was done, a control algorithm was introduced to the computer program.

To convert the compensators and controllers to the discrete time domain or z-domain, Tustin's method was used. Tustin's method is only good for linear systems and introduces the relationship shown in the following equation.

$$s = \frac{2}{T}\frac{(z-1)}{(z+1)}$$

where T represents the sampling period of the controller. Substituting this equation into the controller, lead compensator, and lag compensator yields the following equations.

$$D(z) = K_p + \frac{2K_D(z-1)}{T(z+1)} + \frac{K_I T(z+1)}{2(z-1)}$$

$$\text{Lead} = \frac{(2z-2+kTz+kT)l}{(2z-2+lTz+lT)k}$$

$$\text{Lag} = \frac{(2z-2+mTz+mT)n}{(2z-2+nTz+nT)m}$$

Figure 42:
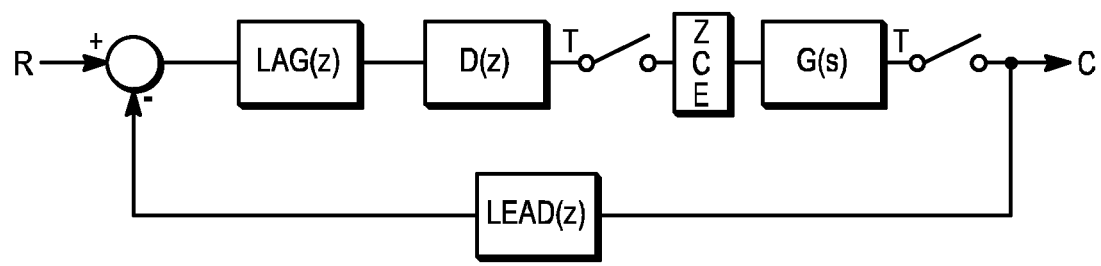
FIG. 42 is a system block diagram for a final design of a controller of a three-link manipulator arm according to one embodiment.

The final system block diagram of this embodiment is shown in FIG. 42.

In FIG. 42, the zero order hold of G(s) yields G(z). The conversion of G(s) to G(z) is only made if a model of TF(z)=C(z)/R(z) is made.

Figure 43:
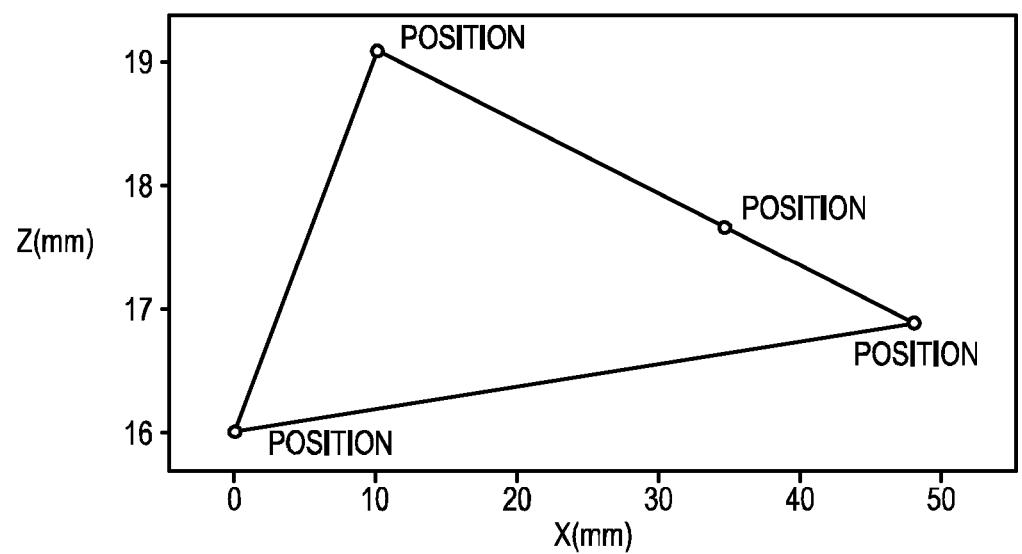
FIG. 43 is the actual movement in the x-z plane of the tip of a three-link manipulator arm according to one embodiment of the present invention.

After the designed components were assembled, a test was performed to verify the controllability and accuracy of the manipulator used in this example. The tip of the manipulator, which was attached to a camera, is supposed to move through four points along the sides of the triangle shown FIG. 43, where position 1 is the starting point and ending point, and distance 1,2 is 39 mm, distance 2,3 is 24 mm, distance 3,4 is 67 mm and distance 4,5 is 29 mm.

To test the accuracy of the movement of the tip, the assumed motor rotation angles were input into the controlling program. These input angles controlled the tip movement along the edges of the triangle. Table 9 shows the motor rotation angles, in encoder counts, for four different points. The ratio of encoder counts per degree was 28.9.

TABLE 9

Position of tip in encoder counts

| Axis | Position 1 | Position 2 | Position 3 | Position 4 | Position 5 |
|---|---|---|---|---|---|
| 1 | −2250 | −1500 | −1250 | −2600 | −2250 |
| 2 | 360 | 200 | 375 | −75 | 360 |
| 3 | 610 | 1400 | 1450 | 2000 | 610 |

The next step was to use the Jacobian to transfer the encoder counts to the xyz coordinates:

$$z = L_1 + L_2 \cdot \cos\left(\frac{2 \cdot \pi \cdot t_1}{28.9 \cdot 360°}\right) + L_3 \cdot \cos\left(\frac{2 \cdot \pi \cdot t_2}{28.9 \cdot 360°} + \frac{2 \cdot \pi \cdot t_3}{28.9 \cdot 360°}\right)$$

$$x = -\left[L_2 \cdot \sin\left(\frac{2 \cdot \pi \cdot t_2}{28.9 \cdot 360°}\right) + L_3 \cdot \sin\left(\frac{2 \cdot \pi \cdot t_2}{28.9 \cdot 360°} + \frac{2 \cdot \pi \cdot t_3}{28.9 \cdot 360°}\right)\right] \cdot \cos\left(\frac{2 \cdot \pi \cdot t_1}{28.9 \cdot 360°}\right)$$

$$z = -\left[L_2 \cdot \sin\left(\frac{2 \cdot \pi \cdot t_2}{28.9 \cdot 360°}\right) + L_3 \cdot \sin\left(\frac{2 \cdot \pi \cdot t_2}{28.9 \cdot 360°} + \frac{2 \cdot \pi \cdot t_3}{28.9 \cdot 360°}\right)\right] \cdot \sin\left(\frac{2 \cdot \pi \cdot t_1}{28.9 \cdot 360°}\right)$$

$L_1$=83 mm, $L_2$=$L_3$=59.5 mm, and $t_1$, $t_2$, $t_3$ represent the motor angles in encoder counts of axes 1, 2 and 3.

Shown below in Table 10 are the results of x, y and z coordinates for the four different points.

TABLE 10

Position of tip in x, y coordinates

| | Position 1 | Position 2 | Position 3 | Position 4 | Position 1 |
|---|---|---|---|---|---|
| X | 9.62 | 34.6 | 48.4 | 0.03 | 9.62 |
| Y | 44.7 | 44.16 | 45.52 | 51.916 | 44.7 |
| Z | 190.67 | 175.9 | 167.8 | 166.1 | 190.67 |

The distance between the four points was then calculated by using the equation shown:

$$\text{Dist} = \sqrt{(x_1-x_2)^2 + (y_1-y_2)^2 + (z_1-z_2)^2}$$

Figure 44:
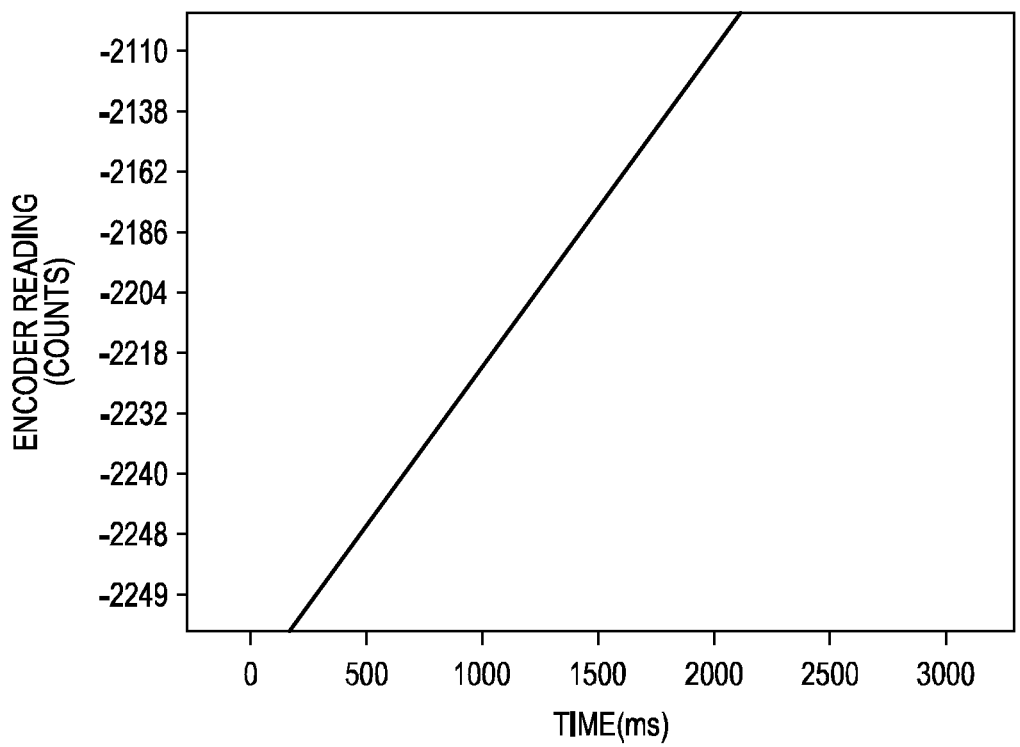
FIG. 44 is a plot of encoder counts versus time showing that movement of a manipulator, according to one embodiment, is linear with time and that the velocity of the tip is constant.

The actual encoder reading was found to describe the movement of the manipulator tip. Shown below in Table 11 are the distances between the four points. FIG. 44 shows that the movement of the manipulator is linear according to time, meaning the velocity of the tip is constant.

TABLE 11

| | Distance between points | | | |
|---|---|---|---|---|
| | pos 1-pos 2 | pos 2-pos 3 | pos 3-pos 4 | pos 4-pos 5 |
| Measured displacement | 39 mm | 24 mm | 67 mm | 29 mm |
| Calculated Displacement | 29 mm | 16 mm | 48 mm | 27.4 mm |
| Error | 25.64% | 33.3% | 28.36% | 5.5% |

The difference between the measured displacement and calculated displacement indicates there is a big error between the two. This was due to several error sources, in the measurement of link lengths $L_1$, $L_2$ and $L_3$, and due to the estimated ratio of the encoder counts to degrees. A source of mechanical error is backlash at the gear mesh.

EXAMPLE 3

Methods and Materials

The goal of the current study is to demonstrate the capability of introducing a mobile robot into the abdominal cavity through the esophageal opening.

Figure 45:
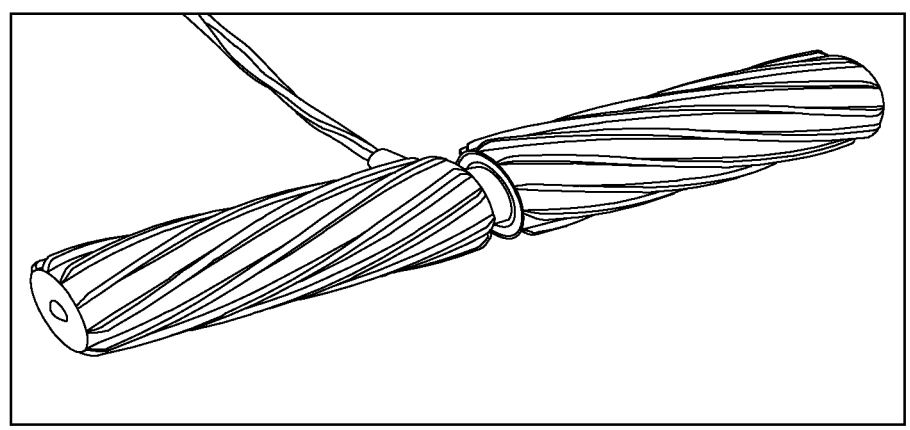
FIG. 45 is a perspective view of a mobile robotic device, according to one embodiment.

In this study we used the mobile robotic device depicted in FIG. 45, which was capable of transgastric exploration under esophagogastroduodenoscopic (EGD) control. The robot was 12 mm in diameter and 35 mm long. The helical wheel profile provided sufficient traction for mobility without causing tissue damage. Two independent motors controlled the wheels, thereby providing forward, backward, and turning capability. The robot tail prevented the counter-rotation of the robot's body when the wheels were turning. The entire length of the robot was 75 mm. This robot was tethered for power during the porcine surgery.

An anesthetized pig was used as the animal model. The 60 lb. pig was fed Gatorade and water for 36 hours prior to the procedure. A sterile overtube was advanced into the pig's stomach with a standard upper endoscope. The stomach was irrigated with antibiotic solution.

Figure 46:
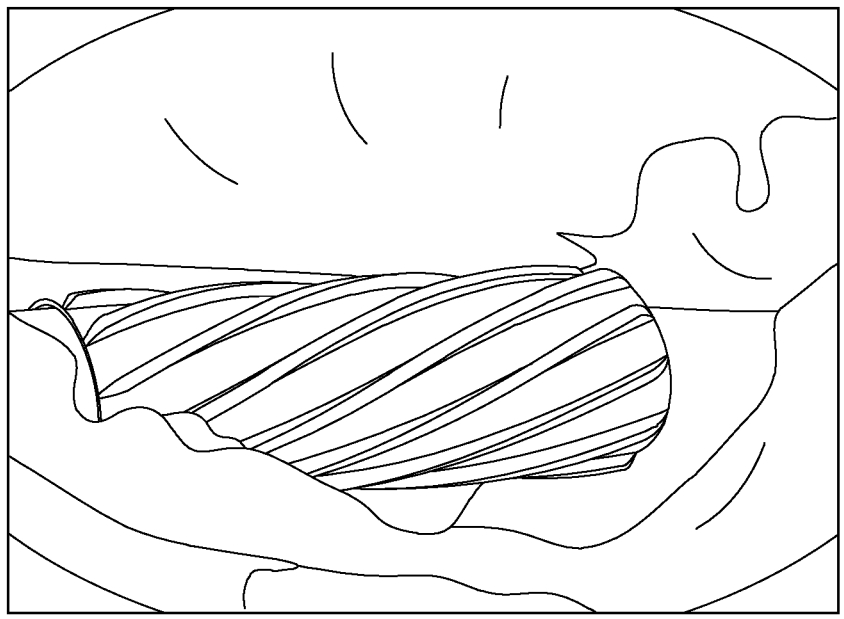
FIG. 46 depicts a mobile robotic device being used in a natural orifice surgical procedure, according to one embodiment.
Figure 47:
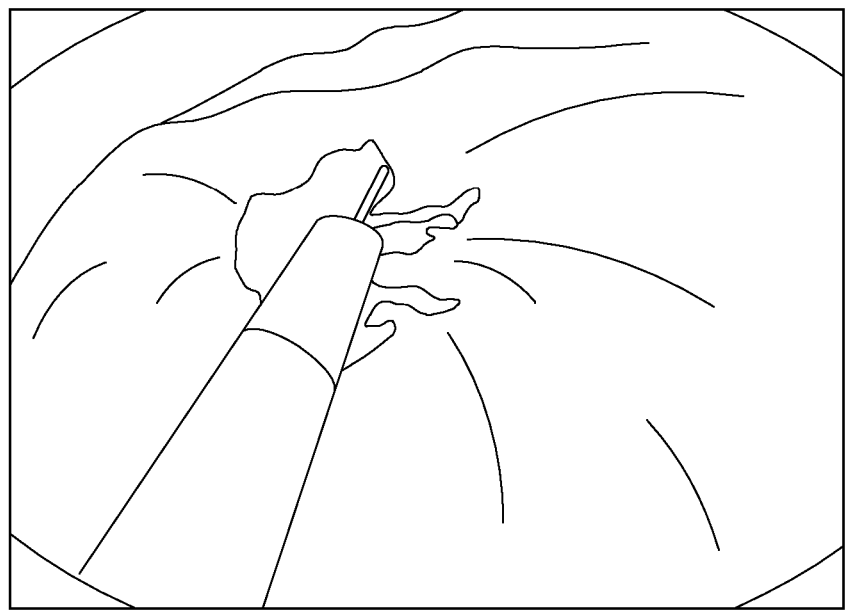
FIG. 47 depicts a mobile robotic device being used in one step of a natural orifice surgical procedure, according to one embodiment.
Figure 48:
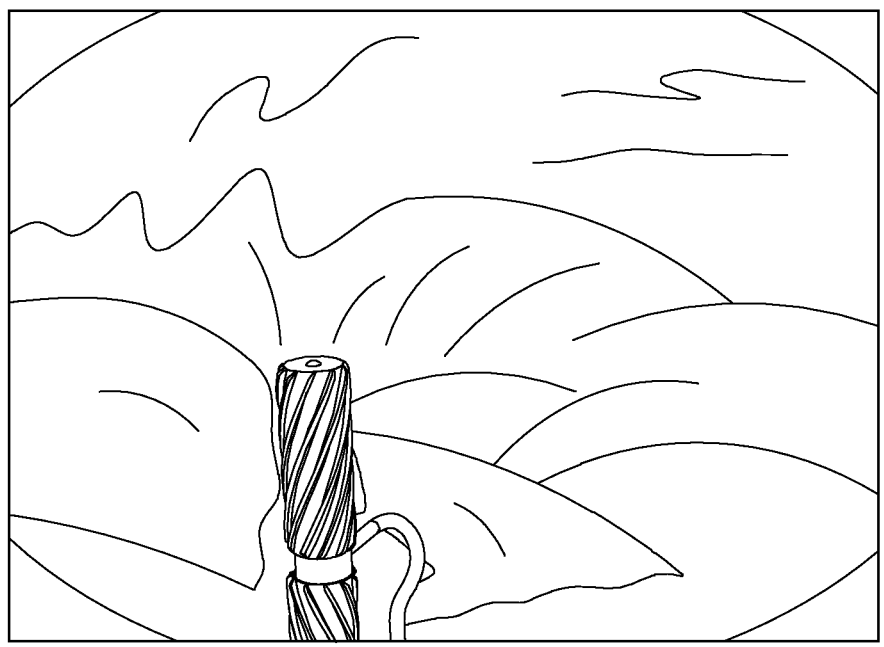
FIG. 48 depicts another step of a natural orifice surgical procedure, according to one embodiment.
Figure 49:
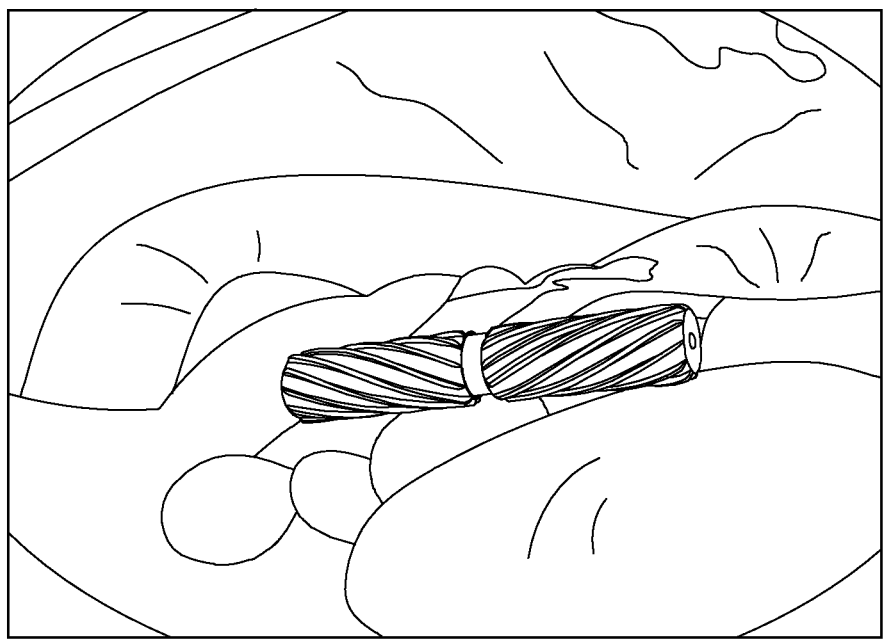
FIG. 49 depicts another step of a natural orifice surgical procedure, according to one embodiment.
Figure 50:
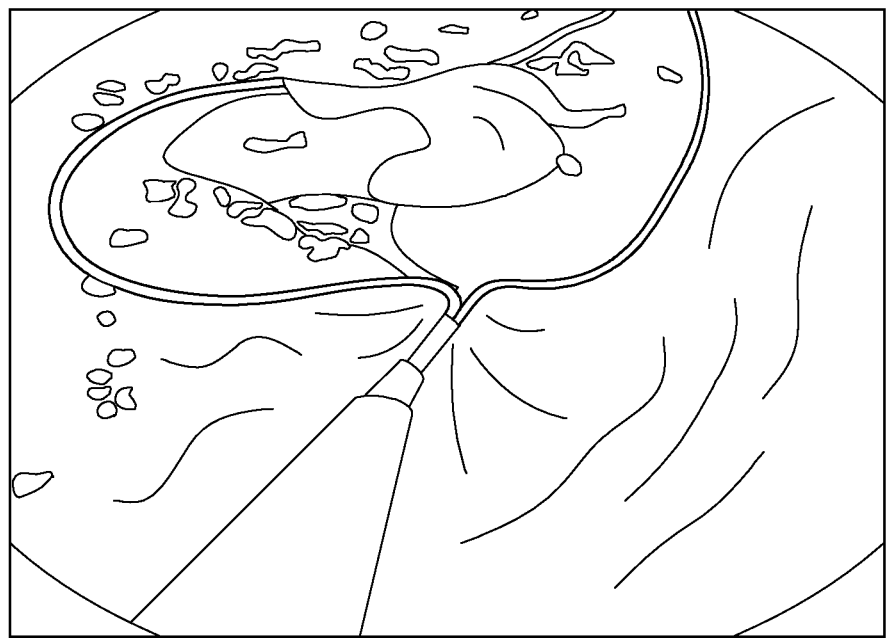
FIG. 50 depicts another step of a natural orifice surgical procedure, according to one embodiment.
Figure 51:
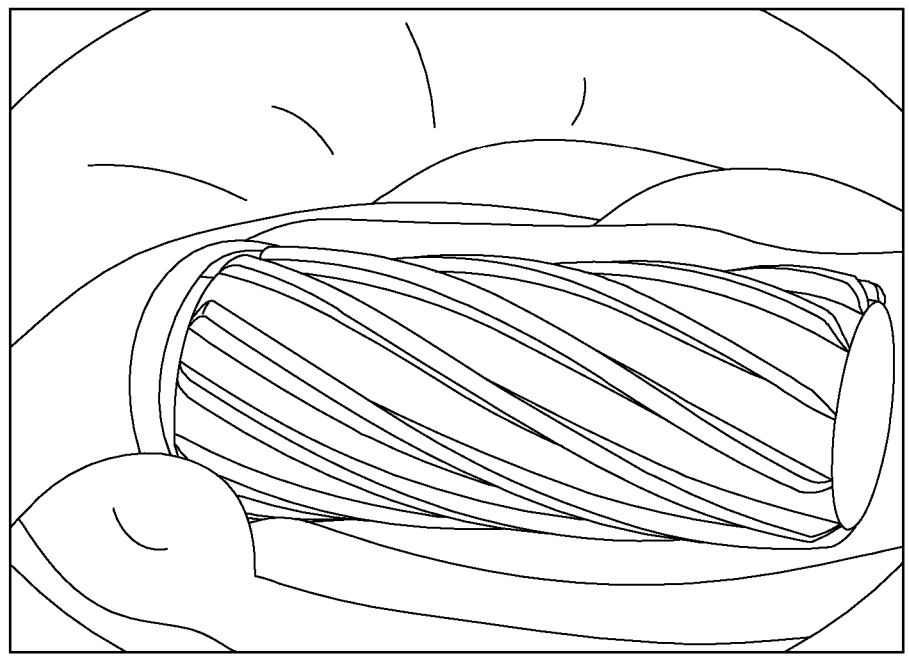
FIG. 51 depicts another step of a natural orifice surgical procedure, according to one embodiment.

The robot was inserted into the gastric cavity through the overtube. The robot explored the gastric cavity as shown in FIG. 46 and was then inserted into the abdominal cavity through a transgastric incision. The gastric incision was performed with an endoscopic needle-knife as shown in FIG. 47. The incision was just large enough to allow the 12 mm diameter robot to pass through. After the robot entered the abdominal cavity, the endoscope was also advanced to view the mobile robot as it explored the abdominal environment. After exploration of the abdominal cavity as shown in FIGS. 48 and 49, the robot was retracted into the gastric cavity. Endoscopic closure of the transgastric incision was successful using two endoclips and one Endoloop, as shown in FIG. 50. The robot was then retracted back through the esophagus, as shown in FIG. 51.

Results

After insertion into the gastric cavity, the mobile robot successfully maneuvered throughout the cavity under EGD control (using visual feedback from the endoscope) (see FIG. 46). The robot's size did not hinder its motion and the wheel design provided sufficient traction to traverse throughout the cavity. After gastric exploration, the miniature robot was deployed into the abdominal cavity and maneuvered by remote control, where the surgical team controlled the robot to successfully clear the gastric cavity.

The mobile robot was capable of traversing the entire abdominal cavity, including the liver (see FIG. 48) and the small bowel (see FIG. 49). This exploration was monitored by the endoscope.

After successfully exploring the abdominal cavity, the mobile robot was retracted into the gastric cavity. Closing the gastrotomy was successfully accomplished using endoclips and one endoloop. Retrieval of the miniature robot was accomplished without difficulty with an Endoscopic snare.

The ability to perform abdominal surgery without skin incisions can reduce patient trauma. However, the difficulties lie in performing these procedures using only EGD video feedback, and introducing sufficiently capable tools into the abdominal cavity. The ability to provide transgastric robotic assistance inside the abdominal cavity may help solve some of these problems. As the robot is not restricted by the length or the angle of the endoscope insertion it will by definition have a greater number of degrees of freedom. The working channel of the endoscope also limits the size and type of instrumentation available to the surgeon. Thus, a miniature robot could perform various surgical procedures and/or be used in conjunction with an endoscope or other surgical devices to achieve better visualization and greater mobility in the peritoneal cavity. According to one embodiment, the endoluminal robots of the present invention can be equipped with cameras and manipulators. The robots can provide surgical assistance. Further, a family of robots can working together inside the gastric and abdominal cavities after insertion through the esophagus. Such technology will help reduce patient trauma while providing surgical flexibility.

EXAMPLE 4

In the instant example, the effectiveness of using mobile camera robots to provide sole visual feedback for abdominal exploration and cholecystectomy was examined.

Methods and Materials

A mobile robotic camera device similar to the device depicted in FIG. 1 was used in the instant example. The device was 20 mm in diameter, and incorporated an on-board adjustable-focus video camera system. Two DC motors independently controlled each wheel, providing the robot with forward, reverse and turning capabilities. The 50 gram device was 100 mm in length with a helical wheel profile and a stabilizing tail. The design of the tail allowed it to be lifted and flipped when reversing the direction of travel. This allowed the device to tilt its camera 15 degrees without changing the position of the wheels. The device was tethered for power.

The device was inserted through a fabricated trocar into an anesthetized pig, and the abdominal cavity was then insufflated with carbon dioxide. The trocar was designed to accommodate the 20 mm diameter of the device. According to an alternative embodiment, the device will use standard 15 mm laparoscopic trocars. Next, a standard trocar was inserted to provide an additional tool port. A third port was also created to accommodate a standard laparoscope. The laparoscope was used to provide lighting for the camera of the mobile robotic device, but the surgeon did not use visual feedback from the laparoscope during the procedure.

Results

Figure 52:
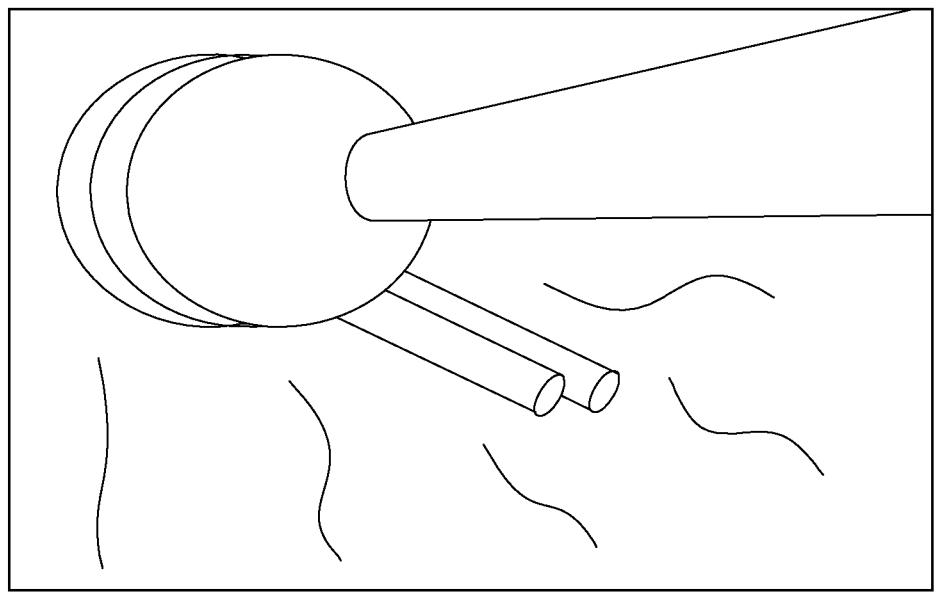
FIG. 52 depicts an image from a mobile robotic device depicting other surgical tools during a surgical procedure, according to one embodiment.

The surgical team used the device to help plan and view the additional trocar insertions and laparoscopic tool placements, as shown in FIG. 52. The multiple achievable views from the camera of the device allowed the surgeon to plan and place trocars safely and appropriately in the abdominal wall of the animal.

Figure 53:
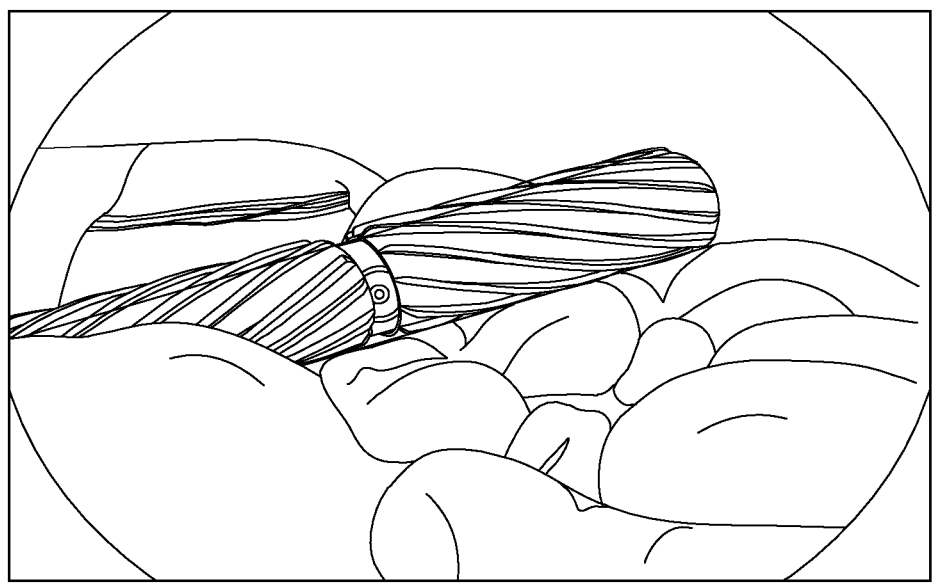
FIG. 53 depicts a mobile robotic device being used during a surgical procedure, according to one embodiment.

The device was also used to explore the abdominal cavity, as shown in FIG. 53. The wheeled mobility allowed the surgeon to explore various regions within the abdominal cavity, while the adjustable-focus camera allowed the surgeon to focus on a specific portion of the region of interest. These video cues allowed the surgeon to navigate the abdominal environment safely and effectively. The ability to maneuver within the abdominal cavity provided additional frames of reference and perspectives that are not available with a standard laparoscope.

Figure 54:
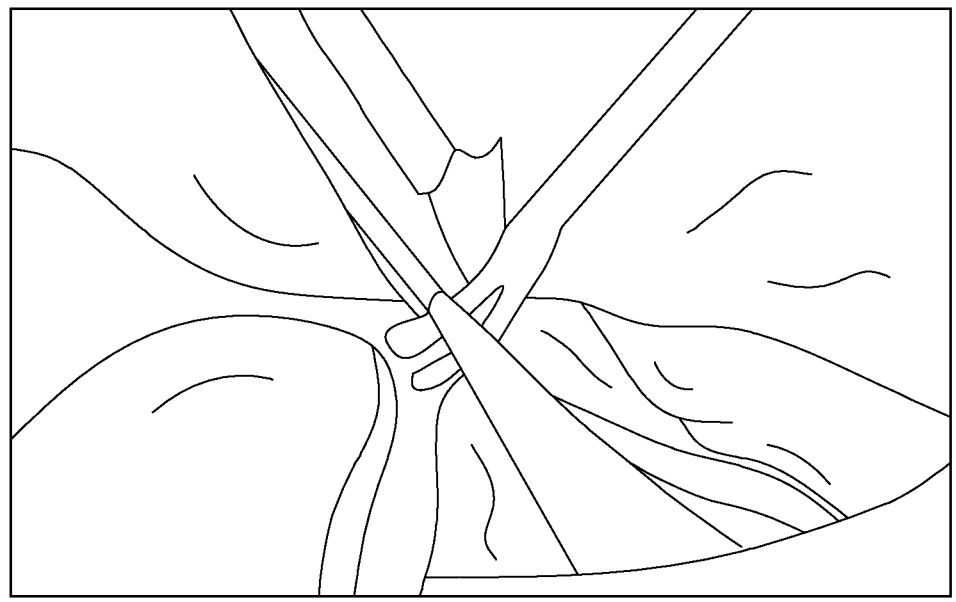
FIG. 54 depicts an image from a mobile robotic device depicting other surgical tools during a cholecystectomy, according to one embodiment.

Finally, a cholecystectomy was performed with the device providing the only visual feedback available to the surgeon (i.e. the video from the laparoscope was not viewed by the surgeon), as shown in FIG. 54. The ability of the device to tilt the adjustable-focus camera 15 degrees without changing the position of the wheels proved extremely useful while retracting the liver. The adjustable-focus capability of the camera system allowed the surgeon to have a better understanding of depth.

Discussion

This successful experiment demonstrated that it is possible to perform a common laparoscopic procedure using an in vivo camera system as the sole source of visual feedback. This has the potential to reduce patient trauma by eliminating the need for a camera port and instead inserting mobile in vivo camera robots, such as the device used in this example, through one of the tool ports.

EXAMPLE 5

This example is an examination biopsy tool design for a mobile robotic device. The device should produce sufficient clamping and drawbar forces to biopsy porcine tissue.

To examine clamping and drawbar forces used during a biopsy, experimental biopsies were conducted. A biopsy forceps device that is commonly used for tissue sampling during esophago-gastroduodenoscopy (EGD) and colonoscopies was modified to measure cutting forces during tissue biopsy. These forceps 560, shown schematically in FIG. 55A, were composed of a grasper 562 on the distal end with a handle/lever system 564 on the proximal end. A flexible tube 566 was affixed to one side of the handle 564 and the other end was attached to the fulcrum point 568 of the biopsy grasper 562. A wire 570 enclosed in plastic (Teflon®) inside tube 566 was used to actuate the grasper 562. This wire 570 was affixed to the free end of the handle lever 564 and at the other end to the end of the grasper lever arm 572. Actuation of the handle lever 564 caused wire 570 to translate relative to the tube 566 and actuate the biopsy graspers 562. The tip of the forceps was equipped with a small spike 574 that penetrated the tissue during sampling.

Figure 55A:
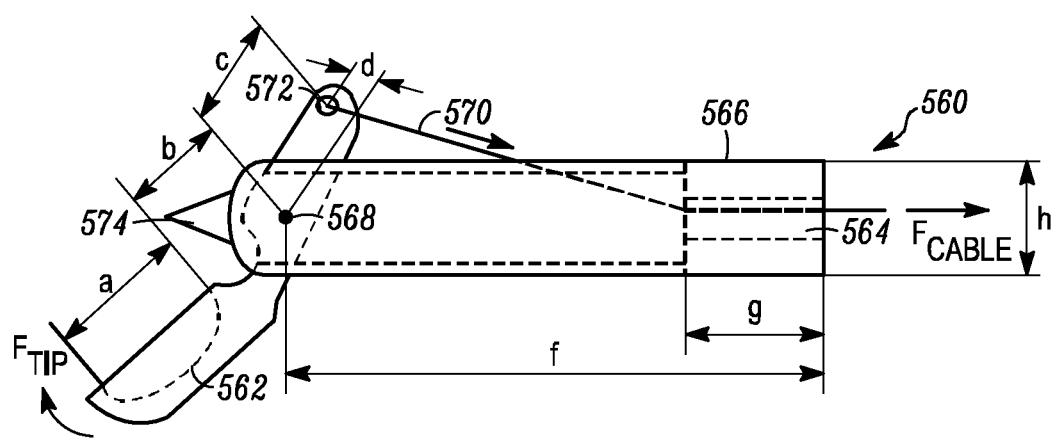
FIG. 55A is a schematic depiction of a forceps tool, according to one embodiment.

The diameter of the forceps (h) depicted in FIG. 55A was 2.4 mm. The dimensions of c, g and f were 2.1 mm, 2.0 mm, and 6.7 mm, respectively. The force at the tip of the grasper when the forceps were nearly closed was a function of the geometric design of the forceps.

$$F_{tip} = F_{cable}\left(\frac{d}{a+b}\right)$$

For a cable force of 10 N, the force at the tip was approximately 1.4 N for this design where a was 2.9 mm, b was 1.7 mm, and d was 0.65 mm. The maximum area of the forceps in contact with tissue during a biopsy was 0.3756 mm².

$$P_{contact} = \frac{F_{tip}}{A_{contact}}$$

Assuming an even distribution of force, the applied pressure was approximately 3.75 MPa. However, by taking a smaller "bite", the contact area was reduced and the pressure can be drastically increased and the required force was decreased.

Figure 55B:
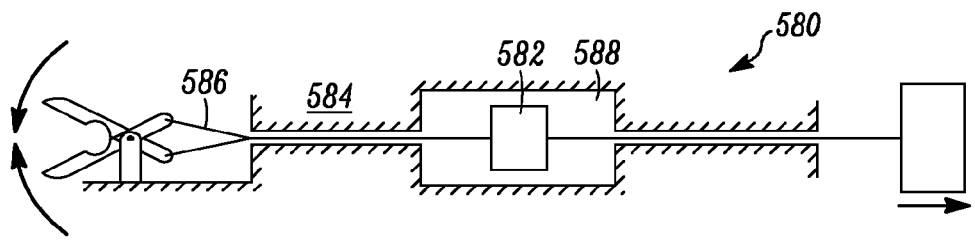
FIG. 55B is a schematic depiction of a biopsy tool modified to contain a load cell, according to one embodiment.

A normal biopsy device was modified to contain a load cell 582 to measure clamping forces indirectly, as shown in FIG. 55B. The modifications made to this tool included cutting the tube 584 and wires 586 to place a load cell 582 in series with the wires 586 to measure tensile force when the wires 586 were actuated as shown in FIG. 55B. A plastic case 588 was built to connect the two free ends of the tube to retain the structure of the system, while the wires 586 were affixed to the free ends of the load cell 582. Using this design, the force in the cable was measured. Along with the above model, the force at the tip of the grasper was estimated while sampling sets of in vivo tissue using a porcine model.

Figure 56A:
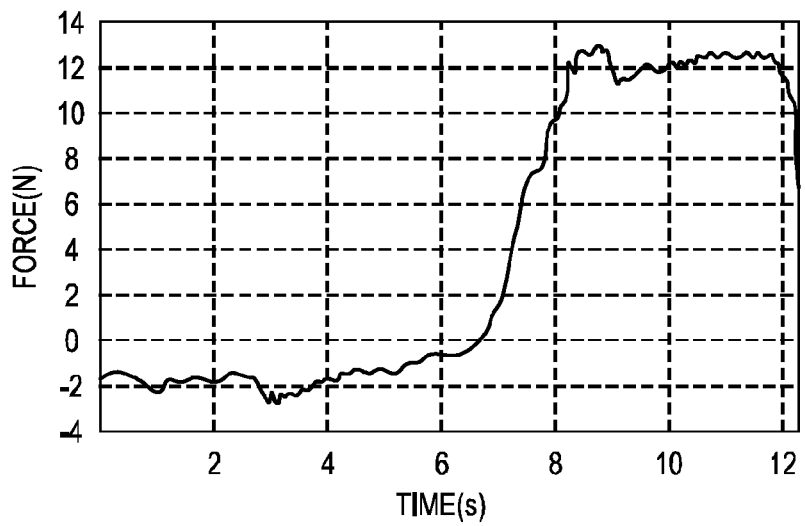
FIG. 56A shows measured cable force to biopsy in vivo porcine hepatic tissue, according to one embodiment.

Measurements of cable force were made while sampling liver, omentum, small bowel and the abdominal wall of an anesthetized pig. Representative results for a liver biopsy are shown in FIGS. 56A and 55C. In one test, with results depicted in FIG. 56A, the initial negative offset was due to the slight compression in the cable to push the grasper jaws open before biopsy. The average maximum measured force to biopsy porcine liver for three samples was 12.0±0.4 N. In another test, with results depicted in FIG. 56C, the average maximum measured force to biopsy porcine liver for three samples was 9.0±0.3 N. These results are consistent in magnitude with other published results (Chanthasopeephan, et al. (2003) *Annals of Biomedical Engineering* 31:1372-1382) concerning forces sufficient to cut porcine liver.

Generally, biopsy forceps do not completely sever the tissue. When this is the case, the forceps are gently pulled to free the sample. This extraction force also needs to be produced by a biopsy robot. The magnitude of the extraction force needed to be determined so that a robot could be designed to provide sufficient drawbar force to free the sample.

A laboratory test jig was built to measure the force needed to free a biopsy sample of bovine liver. After clamping the sample with the biopsy forceps, a load cell attached to the handle of the device was gently pulled to free the sample while the tensile force was recorded. Representative results shown in FIG. 56B indicate that approximately 0.6 N of force is needed to extract bovine liver tissue with the use of the biopsy forceps.

Figure 56B:
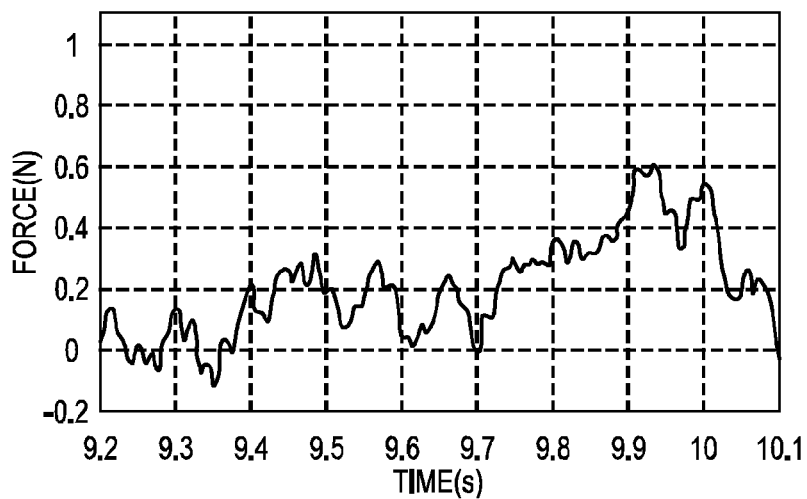
FIG. 56B shows measured extraction force to biopsy ex vivo bovine liver, according to one embodiment.
Figure 56C:
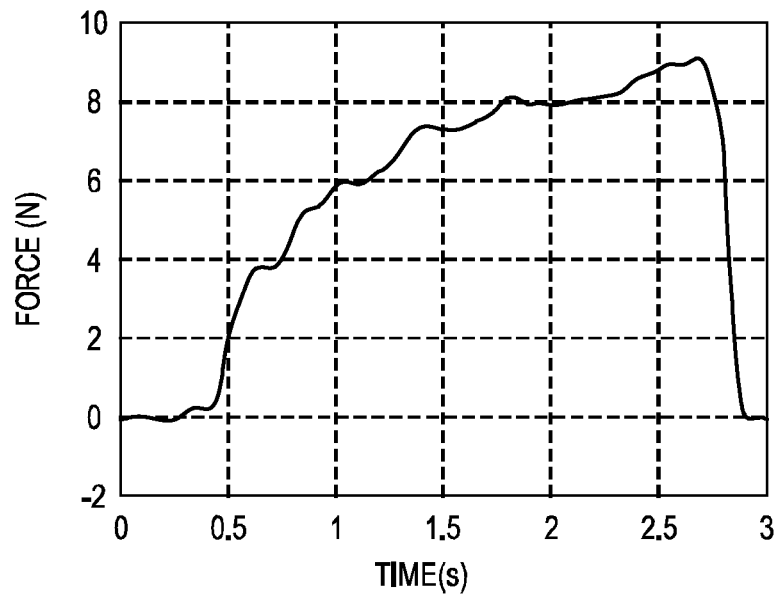
FIG. 56C shows measured extraction force to biopsy porcine liver, according to one embodiment.
Figure 57:
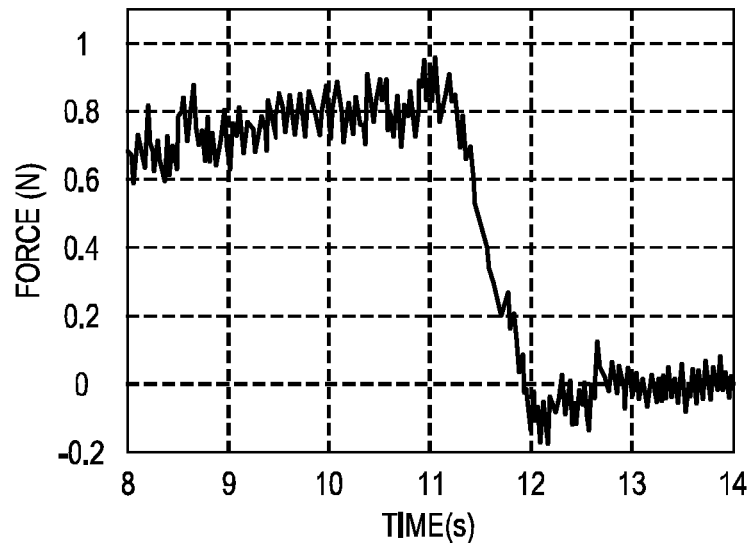
FIG. 57 shows drawbar force production from a robotic biopsy device where maximum drawbar force is produced at 11 seconds, as shown, before slowing down, according to one embodiment.

As indicated, a complete cut of the tissue is rarely achieved and some tearing of the sample is needed to extract the sample. To obtain a biopsy sample, the in vivo robot embodiment of the present example should produce enough drawbar force to pull the sample free. A biopsy robot similar to the devices shown in FIGS. 9A and 9B was tested in vivo and with excised bovine liver to measure drawbar forces. The biopsy grasper (tail of the robot) was attached to a stationary load cell. In the first test, for which results are depicted in FIG. 57, the robot speed was slowly increased as the drawbar force was recorded. After maximum drawbar force was achieved, around 11 seconds, the robot wheel motion was stopped. Results demonstrated that the robot was capable of producing approximately 0.9 N of drawbar force. This amount of force is 50% greater than the target of 0.6 N in the laboratory measurements, as shown in FIG. 56B. This drawbar force is therefore sufficient for sample extraction.

Figure 58:
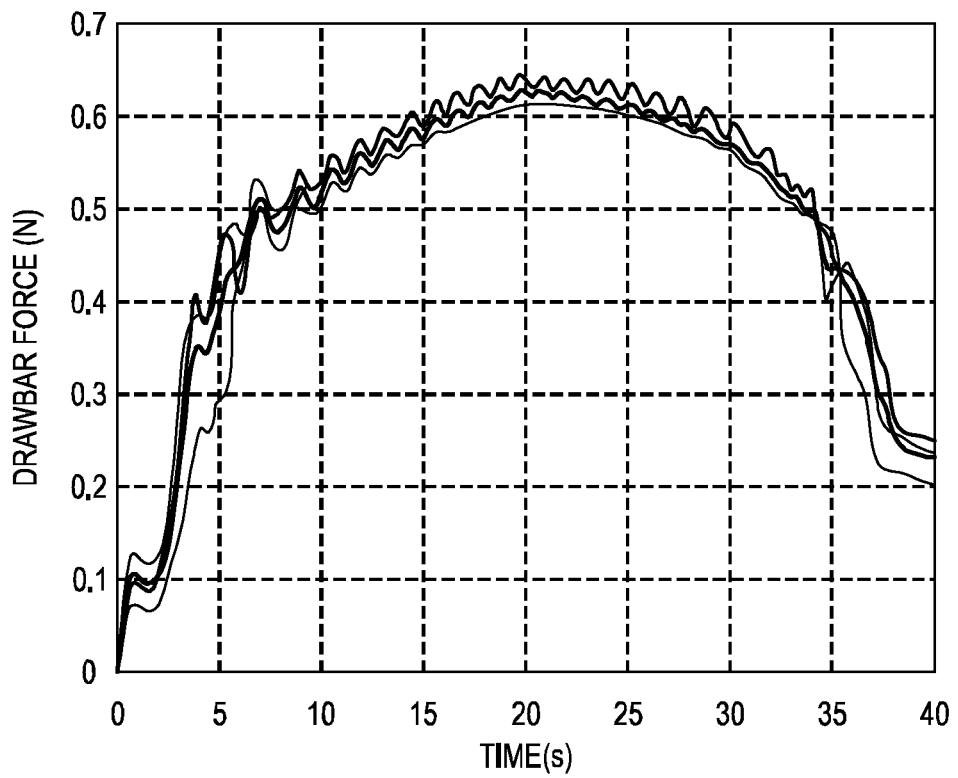
FIG. 58 shows drawbar force production from a robotic biopsy device in which the device speed was first slowly increased and then decreased, according to one embodiment.

In the second test, for which results are depicted in FIG. 58, the robot speed was first slowly increased and then decreased as the drawbar force was recorded. A pulse width modulated voltage signal to the wheel motors was linearly ramped from 0% to 100% during the first 20 seconds and then back to 0% during the second 20 seconds. This test was completed five times. The dark line is the average of all five tests. Results of this test demonstrate that the robot tested is capable of producing approximately 0.65 N of drawbar force. This amount of force is roughly 10% greater than the target of 0.6 N in the laboratory measurements.

Figure 59:
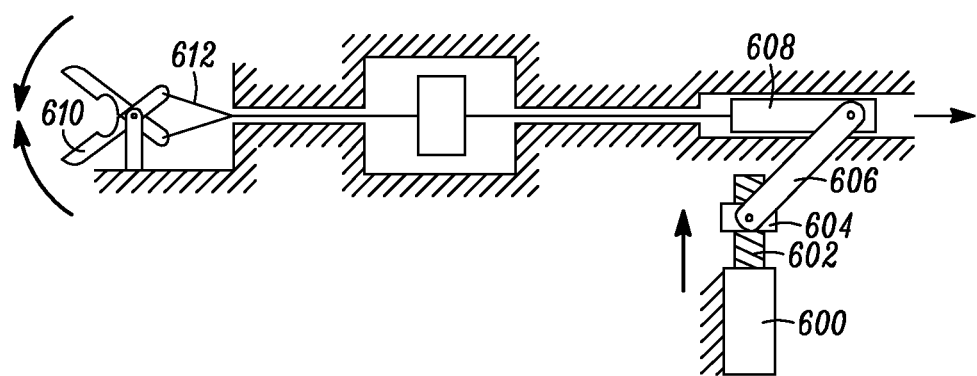
FIG. 59 depicts an actuation mechanism implemented on a biopsy robot for force production measurements, according to one embodiment.

As depicted in FIG. 59, an actuation mechanism was also developed to drive the biopsy grasper and the camera of the embodiment discussed in this example. The lead screw 602 was extended through the slider 608. The lead nut 604 was then allowed to translate far enough so that at the point of grasper 610 closure the linkage 606 approaches a mechanism singularity where output force is very large (i.e., at or approaching 0°). The slider 608 is a nearly hollow cylinder and the lead nut 604 and linkage 606 are inside the slider 608 when the linkage is near its singularity. The grasper wires 612 are attached to slider 608 as is either the camera lens or image sensor. This provides the camera an adjustable-focus feature necessary in the in vivo environment.

A direct current motor 600 drives the lead screw 602 vertically as the linkage 606 transforms the vertical motion of the lead nut 604 to the horizontal translation of the slider 608. This allows for a large mechanical advantage at the point when the graspers are nearly closed.

Figure 60:
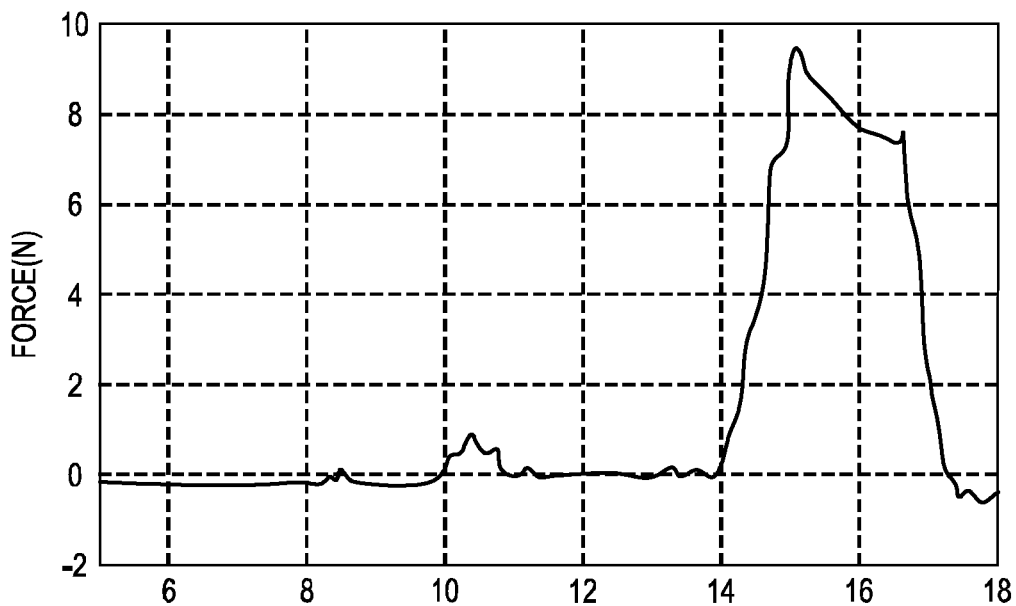
FIG. 60 shows force production measured from the robot biopsy mechanism depicted in FIG. 59, according to one embodiment.

Force measurements were made in the laboratory to determine the maximum amount of force that could be produced using the biopsy robot embodiment of this example. Representative results from these tests are shown in FIG. 60. The average maximum force produced for three samples was 9.6±0.1 N. This force was about 16% smaller than the 12 N measured during one in vivo test as described herein, and about 7% larger than the 9 N measured during the second in vivo test as described herein. However, the 12 N merely represents the force that was applied. It does not represent the minimum force required to biopsy the tissue. Without being limited by theory, it is probable that the surgeon performed the biopsy and continued to increase the force and merely "squeezed" the sample. The surgeon applied what was known to be a sufficient force rather than a minimum force. The required force could also be largely reduced by simply taking a smaller biopsy sample. Reducing the contact area by 16% would produce the same applied stress.

Figure 61:
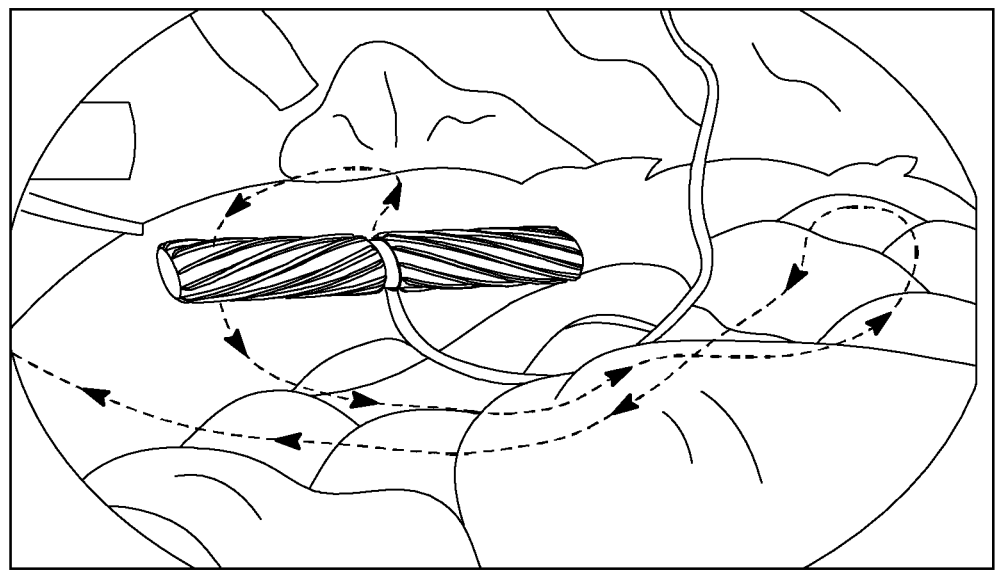
FIG. 61 depicts the path traversed by a mobile robot during an in vivo test, according to one embodiment.

In vivo mobility testing with the embodiment discussed herein indicated that the wheel design of the instant embodiment produces sufficient drawbar forces to maneuver within the abdominal environment, allowing the robot to traverse all of the abdominal organs (liver, spleen, small and large bowel), as well as climb organs two to three times its height. These tests were performed without causing any visible tissue damage. Video recorded during one of the tests was used to reconstruct the path traversed by the robot, a portion of which is illustrated in FIG. 61. The length of travel shown is approximately 0.5 m, while the total distance traveled during the test without assistance was approximately 1 m.

After exploring the abdominal environment, the biopsy mechanism described in this example was used to acquire three samples of hepatic tissue from the liver of the animal. The robot camera was used to find a suitable sample site. The biopsy graspers were opened and the sample site was penetrated with the biopsy forceps' spike. Then the graspers were actuated. This cut nearly all of tissue sample free. The robot was then driven slowly away from the sample site thereby pulling free the tissue sample. This tissue sample was then retrieved after robot extraction through the entry incision. This demonstrated the success of a one-port biopsy and successful tissue manipulation by an in vivo robot, according to one embodiment.

EXAMPLE 6

Figure 62:
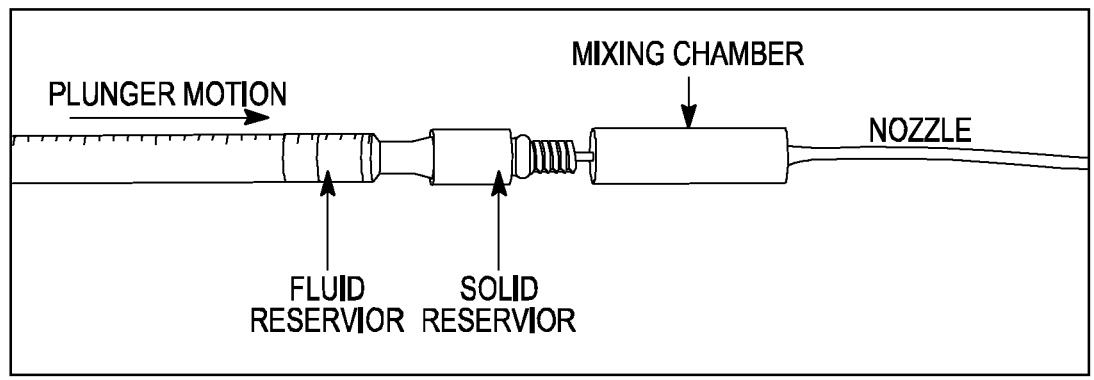
FIG. 62 depicts a laboratory two-component drug delivery system, according to one embodiment.

A laboratory two-component drug delivery system is shown in FIG. 62 that incorporates two drug storage reservoirs. The fluid reservoir, adapted from a standard syringe, is used to hold a drug component in liquid form. The solid reservoir stores a second drug component in powdered form. As force is applied to the plunger, the liquid component flows through the reservoir holding the solid component. A partially mixed solution then flows into a chamber where the mixing process is completed. The activated compound then flows through the delivery nozzle to the targeted site.

Figure 63:
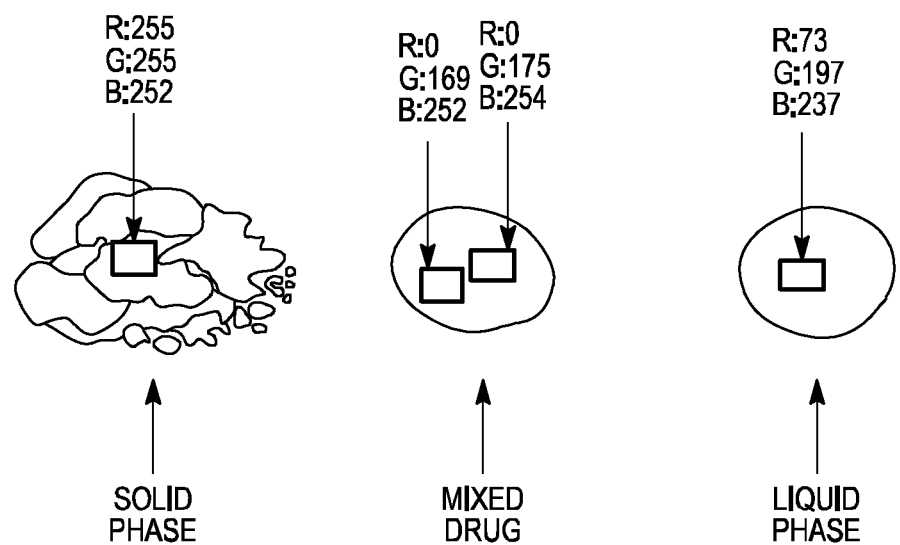
FIG. 63 depict representative results of mixing two drug components, one solid and one liquid, according to one embodiment.

The ability of this system to adequately mix liquid and solid components of a drug was evaluated in a series of bench top experiments. The liquid and solid drug components were simulated using commonly available materials (e.g., corn starch, dyed saline solution, etc). One visual metric of mixing efficiency is the color uniformity of the mixture as determined by measuring the RGB color components of the mixture using image processing software. Representative results are shown in FIG. 63. The images on the left and right show the RGB values for the solid and liquid components prior to mixing, respectively. The image in the center shows the resulting mixture. The similarity of the RGB color values for two representative areas of the mixture is indicative of uniform mixing of the two components.

Bench top tests were also conducted to determine the force that could be applied by an actuation mechanism that could be incorporated into this type of drug delivery tool. One type of mechanism might use a permanent magnet direct current motor (MicroMo, 2005) with a lead screw mounted on the motor shaft. Rotation of the lead screw would move a lead nut attached to the fluid reservoir plunger in and out to dispense the two drug components. This concept was implemented in a test jig 180, illustrated in FIG. 12, that includes a load cell 182 for measuring the applied force created by the motor 184 to move the plunger 186. Force measurements were made in the lab to determine the maximum force that could be produced using this type of actuator design. Representative results from these tests indicate that the average maximum force produced is approximately 10.0 N.

Nagelschmidt (1999) found that the maximum force required to mix and dispense fibrin-based hemostatic agents through 1 mm diameter catheters 27 cm long was less than 5 N. These results strongly suggest that the actuation mechanism described above will generate sufficient forces to deliver dual component fibrin-based hemostatic agents.

EXAMPLE 7

This example presents a quantitative comparison of image quality between a robotic camera device according to one embodiment and a standard laparoscopic camera. Image analyses are presented for both the in vivo robot and a standard laparoscope, including an examination of the Modulation Transfer Function (MTF), color reproduction, and image distortion. Then the stereoscopic three dimensional reconstruction is analyzed in ex vivo experiments. Finally, the use of the in vivo stereoscopic robot is demonstrated during a cholecystectomy in an animal model. These results suggest that these in vivo devices can provide visualization of laparoscopic procedures that is comparable to standard laparoscopes and sufficient for laparoscopy.

Figure 64A:
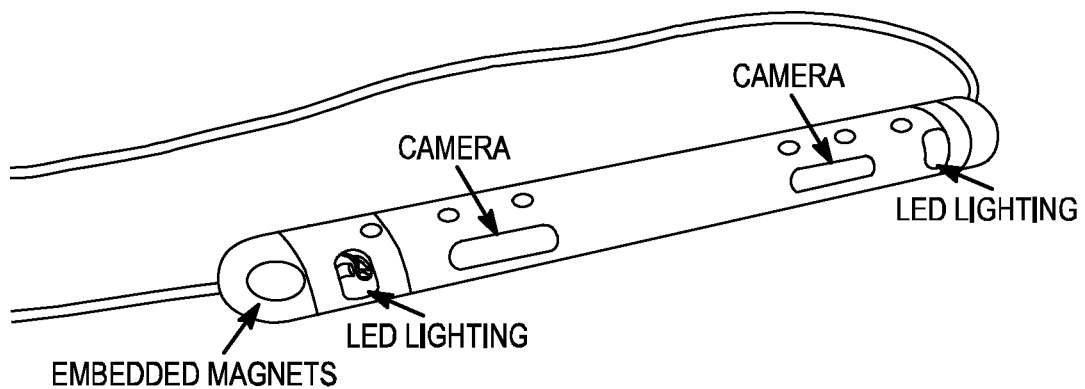
FIG. 64A depicts a robotic camera device, according to one embodiment.

The device tested in this example is depicted in FIG. 64A. This device has a stereoscopic camera pair that can be used with a stereoscopic display to provide the operator with a three dimensional image of the in vivo operating environment.

Single Camera Comparison

In this examination, the imaging device was a color digital CMOS image sensor from Micron. Further, the laparoscope used is a device with a Tricam™ SL NTSC control unit and a Xenon 175 light source, all manufactured by Karl Storz GmbH & Co. KG, located in Tuttlingen, Germany.

Visual metrics are often used to quantify quality differences between the large numbers of commonly available digital imaging devices. One such metric is the well established Modulation Transfer Function (MTF) used as a metric both for optical systems and digital imaging systems. This transfer function measures the amount of detail a given imaging system can display using a frequency domain measurement. The metric is usually expressed in units of spatial frequency, such as line pairs per mm (lp/mm) or cycles per pixel (c/p). The vision target used for MTF testing is an ISO 12233 Resolution chart printed on Kodak photo paper, measuring 196 mm×120 mm (7.75"×4.75").

Color accuracy is another important image quality metric. One measurement of color accuracy is the use of a Macbeth color chart. The chart has 24 zones, 18 color and 6 grayscales. The target chart used for color error measurements is a Mini ColorChecker™. The ColorChecker™ is a standard Macbeth™ color chart, measuring 82 mm×57 mm (3.25"×2.25").

Both these metrics as well as standard measures of distortion are used to quantify and compare the performance of the in vivo imaging robot. For distortion tests, a square grid was generated from the Imatest™ application, and printed using a laser printer. Imatest™ is a software package that can be used to evaluate different types of imaging systems.

All imaging tests (MTF, color error, distortion) were conducted with the same experimental setup. The setup held the imaging targets at a fixed distance and orientation with respect to the imager (in vivo camera and laparoscope). Distances and orientations were chosen to represent the surgical application (e.g. cholecystectomy). The experiments were conducted inside a surgical mannequin with no ambient light. Each imaging device used its own respective light source— external xenon fiber optic light source for the laparoscope and 2 ten candle white LEDs for the robotic camera. The video output from both systems is analog NTSC (National Television Systems Committee) composite. A Sensoray Model 2250 USB 2.0 frame grabber, connected to a laptop PC, was used to capture frames of video for later analysis.

MTF Testing

The modulation transfer function (MTF) is a widely used metric for performing quality evaluation of imaging systems. MTF is a measure of spatial resolution of an imaging system. MTF was used with the ISO 12233 Resolution chart to evaluate image quality. This chart was imaged with both the in vivo camera and laparoscope. The chart was parallel to the image sensor at a distance of 150 mm. Several still images were captured and analyzed. The Modulation Transfer Function is defined as:

$$MTF(v) = \frac{M_i}{M_o} \quad (1)$$

where $M_i$ and $M_o$ are the modulation of the image and the modulation of the object, respectively. The modulation is defined as:

$$M = \frac{Y_{max} - Y_{min}}{Y_{max} + Y_{min}} \quad (2)$$

where $Y_{max}$ is the maximum and $Y_{min}$ is the minimum values of luminance. A plot of the MTF over all spatial frequencies defines the MTF of the system. MTF is calculated by computing the Fourier transform of the impulse response of the system. The impulse response is the response to a narrow line, which is the derivative of an edge response.

Figure 64B:
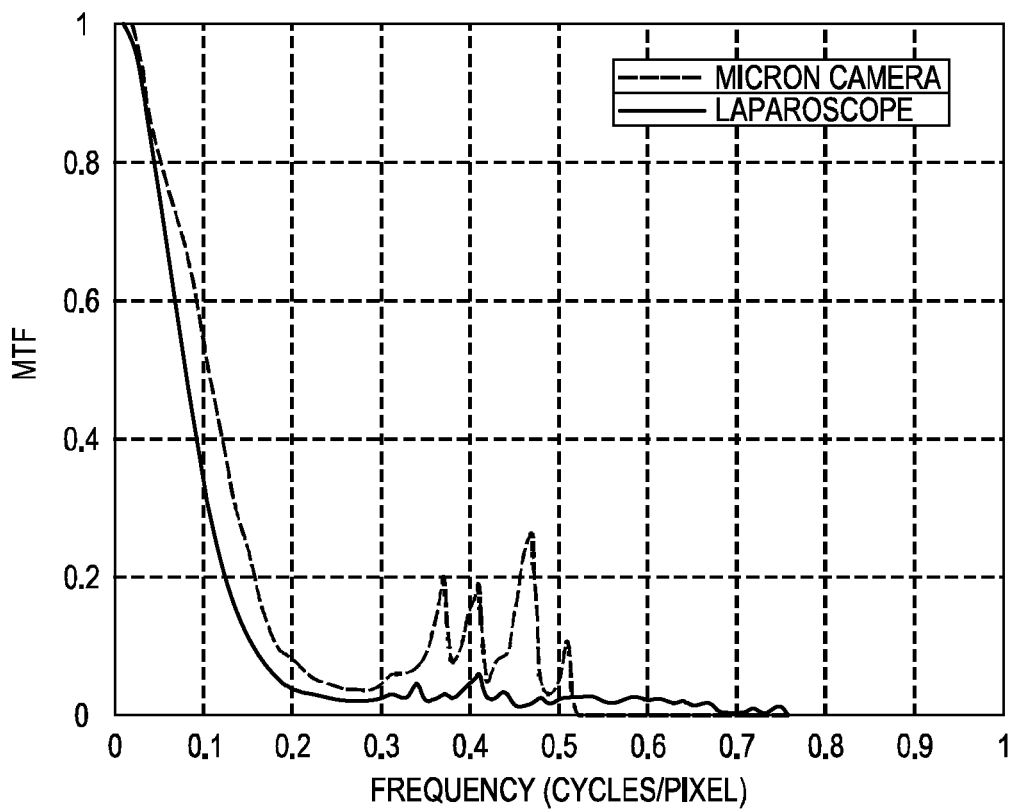
FIG. 64B is a graph depicting the spatial resolution of two imaging systems, according to one embodiment.

These MTF curves are plotted in FIG. 64B. Here, higher MTF values indicate better performance. As shown in FIG. 64A, the laparoscope provides a slightly better response at most frequencies.

Color Accuracy

Color accuracy of the two systems was measured using a Macbeth ColorChecker™. The ColorChecker™ was placed in uniform illumination, and several still images were captured and the results were averaged over several still images. The test images were then converted to CIELAB color space by the Imatest™ application. The CIELAB space is based on human color perception. It is a three-dimensional space, where L* shows lightness, and (a*, b*) show color information. The CIELAB space was laid out to allow specification of color differences, in a linear manner. The Imatest program compares each test image color value to the known color value for each color patch in the target chart. The difference formula is given as:

$$\Delta E_{ab}^* = \sqrt{(\Delta L^*)^2 + (\Delta a^*)^2 + (\Delta b^*)^2} \quad (3)$$

TABLE 12

| Color Error | | |
|---|---|---|
| | Mean Error | RMS Error |
| In vivo Camera | 9.76 | 11.5 |
| Laparoscope | 17.5 | 19.4 |

Figure 64C:
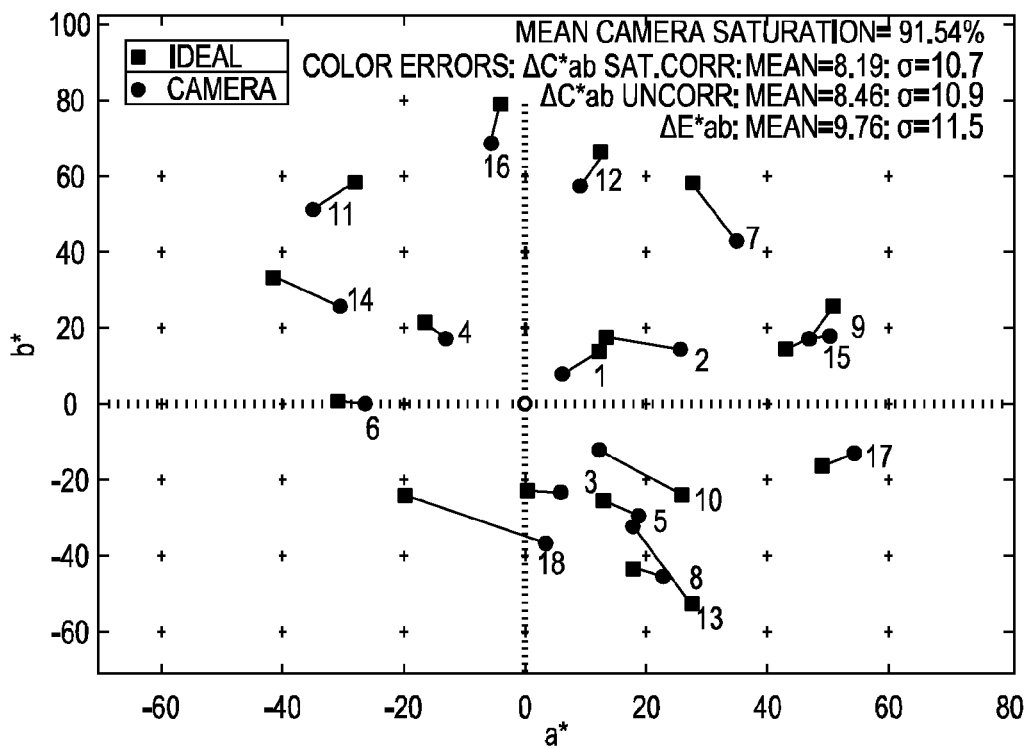
FIGS. 64C and D are graphs depicting the color differences between two imaging systems, according to one embodiment.
Figure 64D:
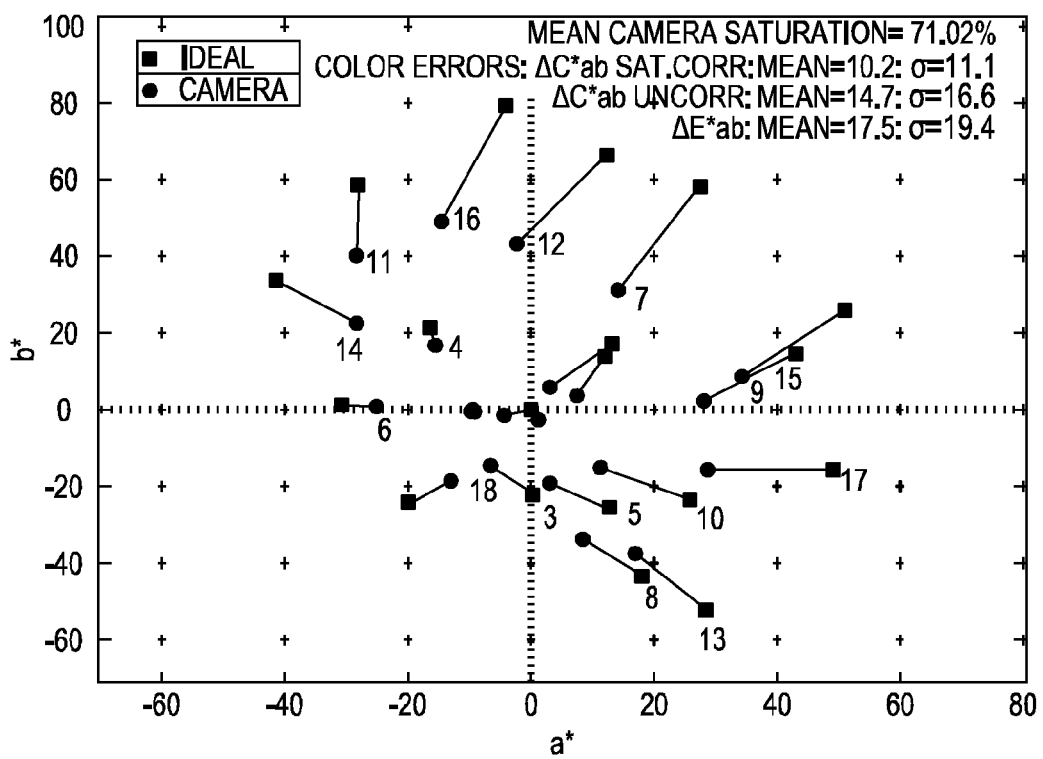
FIG. 64E is a graph depicting the color error for each of two imaging systems, according to one embodiment.
FIGS. 64F and G are graphs depicting lens distortion for each of two imaging systems, according to one embodiment.
FIG. 64H depicts the experimental setup for benchtop tests to test resolution, color accuracy, and distortion of camera systems, according to one embodiment.
FIG. 64I is a graph depicting the geometry of two stereoscopic cameras, according to one embodiment.
Figure 64E:
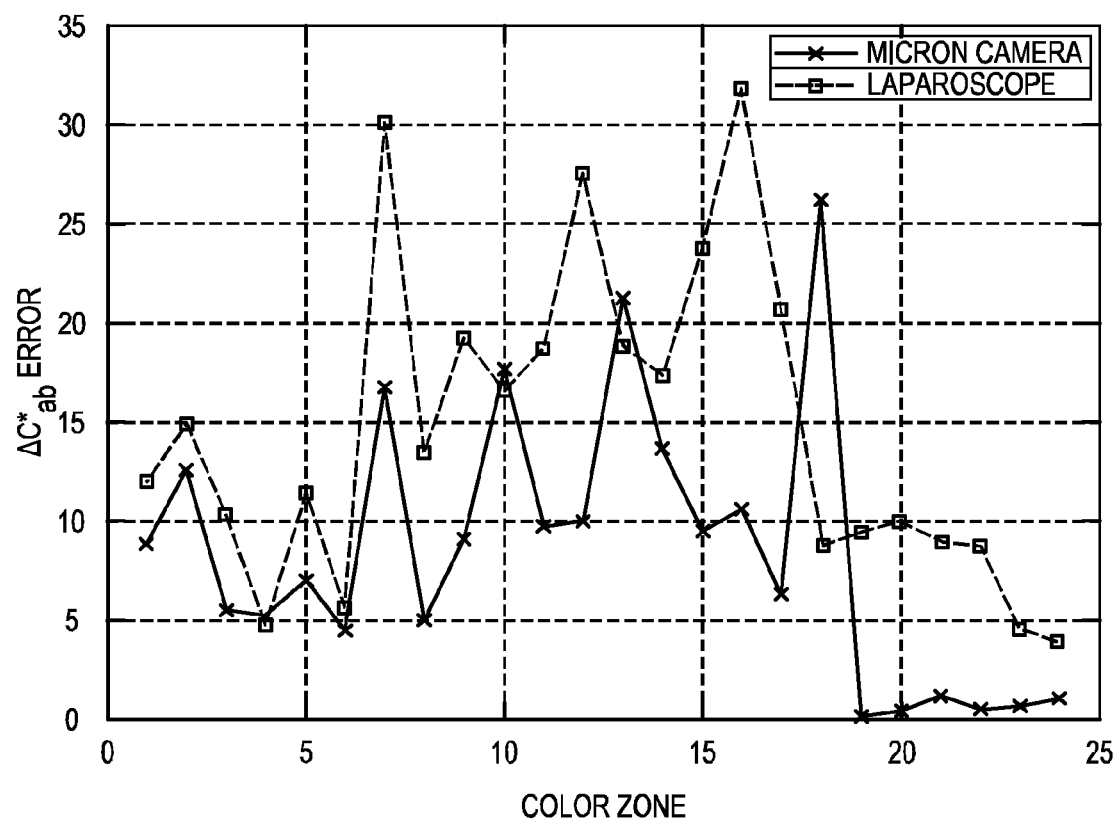

Plots of these color differences are shown in FIG. 64C (in vivo camera) and 64D (Laparoscope). These plots show the ideal color value and the actual color value, plotted in CIELAB color space. Mean and RMS color errors are also shown. These results are summarized in Table 12. Color error for each system, plotted against color zone number, is shown in FIG. 64E. The data presented in Table 12 and FIG. 64E shows that the robotic camera device had significantly less color error than the laparoscope.

Distortion

Distortion is an effect that causes straight lines to appear curved. Infinite series can be used to model lens distortion, which is a combination of radial and tangential components. However, usually only radial distortion needs to be considered, which can be modeled with one term. This can be modeled as:

$$r_u = r_d(1 + \kappa_1 r_d^2) \quad (4)$$

This equation relates the undistorted radius $r_u$ and the distorted radius $r_d$. This one term model of distortion is referred to as barrel or pincushion distortion, depending on the sign of the parameter $\kappa_1$. For these tests, the lower the value of $\kappa_1$ the less distortion of the camera system.

Figure 64F:
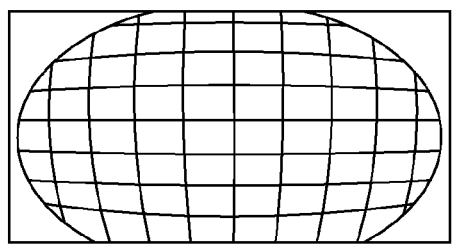
Figure 64G:
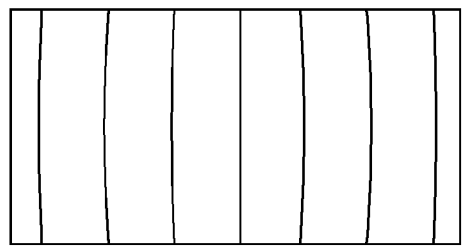

An example of lens distortion for the laparoscope and in vivo camera is shown in FIGS. 64F (laparoscope) and 64G (robotic camera device). The test target used is a square grid pattern. As is evident from the images, the laparoscope has significant radial distortion. The robotic camera device has very little distortion. The numerical results confirm this quantitatively, and are shown in Table 13.

TABLE 13

| Radial Distortion | |
|---|---|
| | $\kappa_1$ |
| In vivo Camera | 0.06 |
| Laparoscope | 0.35 |

Discussion of Single Camera Comparison

In the MTF tests, the laparoscope had better results than the in vivo system. This is most likely caused by the limitation of lower quality optics in the in vivo system, since the MTF of the system is defined to be the product of the MTFs for each component of the system (lens, imager, etc). In the design of these devices, optics quality must be sacrificed for space, given the small physical size of the in vivo system. The laparoscope system is able to have higher quality optics, since the optics are not located in vivo and fiber optics instead lead from the laparoscope tip back to a high-precision optical instrument. This, however, does not mean that the laparoscope is superior to the in vivo robotic devices. The differences in spatial resolution may not be great enough to cause a subjective difference in the two systems. The in vivo robots described here significantly outperform conventional laparoscopes in distortion tests. The high amount of distortion in the laparoscope causes difficulty in quantitative area determinations during procedures. The in vivo robots do not suffer from these problems.

Ex Vivo Stereo Imaging Analysis

Stereoscopic display allows for the perception of depth and this can be extremely valuable in laparoscopic surgery. The robotic camera device shown in FIG. 64A contains two of the Micron™ image sensors described above. This section describes the results of a bench top laboratory study to quantify the stereoscopic performance.

Figure 64H:
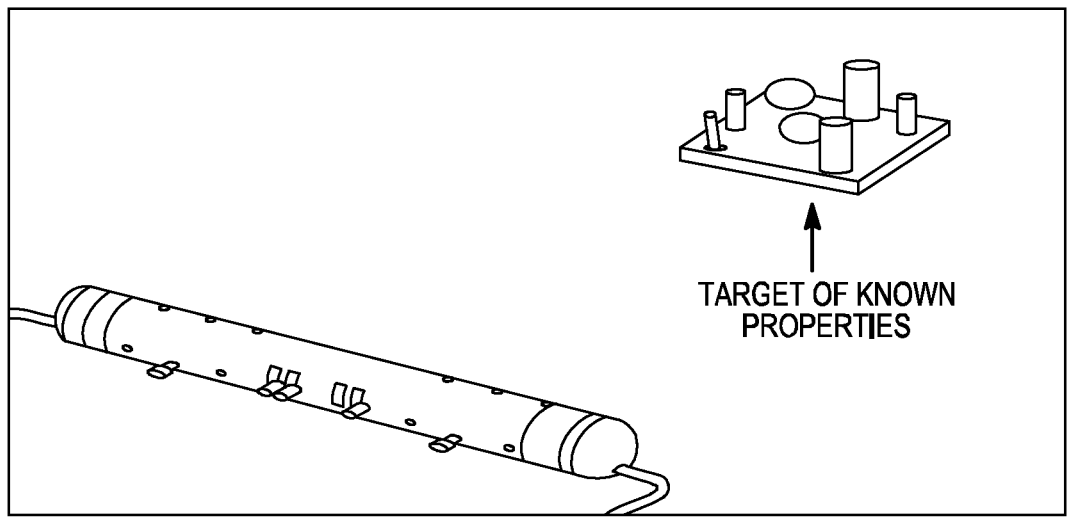

The ex vivo stereo imaging experimental setup can be seen in FIG. 64H. The target is a machined aluminum base with several cylinders and spheres of known and precise dimension. The robotic camera device is the same device as that shown in FIG. 64A.

Figure 64I:
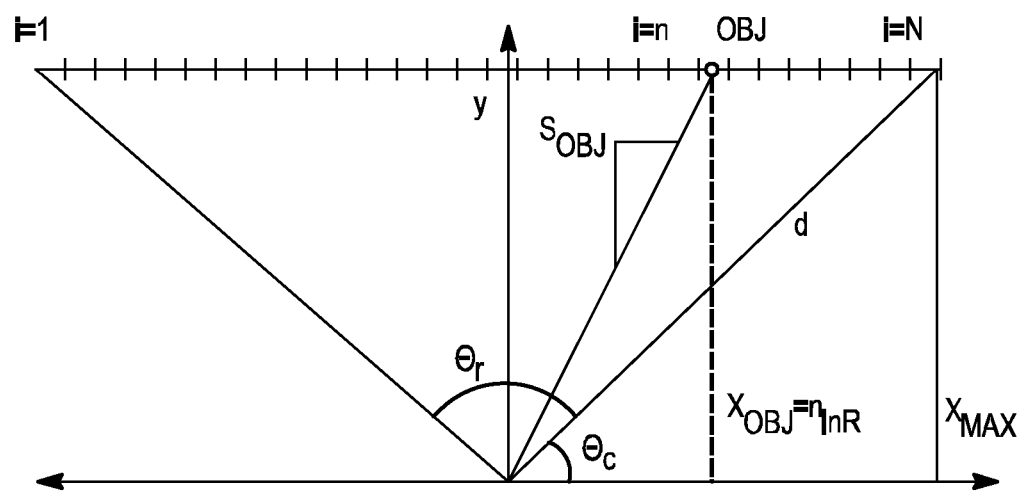

The geometry of the cameras is detailed in FIG. 64I. Using this known geometry, the three-dimensional spatial coordinates of objects in the field of view of both cameras can be determined. FIG. 64I shows the geometry of a point object, labeled obj, that is visible by the camera with a field of view of $\theta_f$. The camera has N pixels and each of these pixels can be projected into a horizontal row i=1 . . . N at the same distance, $y_{obj}$, from the camera as the point object. The point object is indicated in pixel i=n. Here, pixel i=1 and i=N show the widest points (at $-x_{max}$ and $x_{max}$) that are visible at that distance.

The y coordinate of obj (and all points on the imaginary projection) given by $y_{obj}$ can be represented with the field of view angle $\theta_f$ and the length of the line segment d.

$$y_{obj} = d\cos\left(\frac{\theta_f}{2}\right) \quad (5)$$

Similarly, the value $x_{max}$ is represented as $$x_{max} = d\sin\left(\frac{\theta_f}{2}\right) \quad (6)$$

The x coordinate of the object is found using $x_{max}$ and pixel n, the horizontal pixel position of obj.

$$x_{obj} = \left(\frac{2n}{N} - 1\right)x_{max} = \left(\frac{2n}{N} - 1\right)d\sin\left(\frac{\theta_f}{2}\right) \quad (7)$$

The values of $x_{obj}$ and $y_{obj}$ can be used to find the object angle $\theta_{obj}$. This substitution eliminates the unknown variable d.

$$\theta_{obj} = \tan\left(\frac{y_{obj}}{x_{obj}}\right) \quad (8)$$

$$= \tan\left(\frac{d\cos\left(\frac{\theta_f}{2}\right)}{\left(\frac{2n}{N}-1\right)d\sin\left(\frac{\theta_f}{2}\right)}\right)$$

$$= \tan\left(\frac{\tan\left(\frac{\theta_f}{2}\right)}{\left(\frac{2n}{N}-1\right)}\right)$$

Finally, the "slope" to the object, $S_{obj}$, is simply the arctangent of $\theta_{obj}$.

$$S_{obj} = \tan^{-1}(\theta_{obj}) = \frac{\tan\left(\frac{\theta_f}{2}\right)}{\left(\frac{2n}{N} - 1\right)} \quad (9)$$

Figure 65:
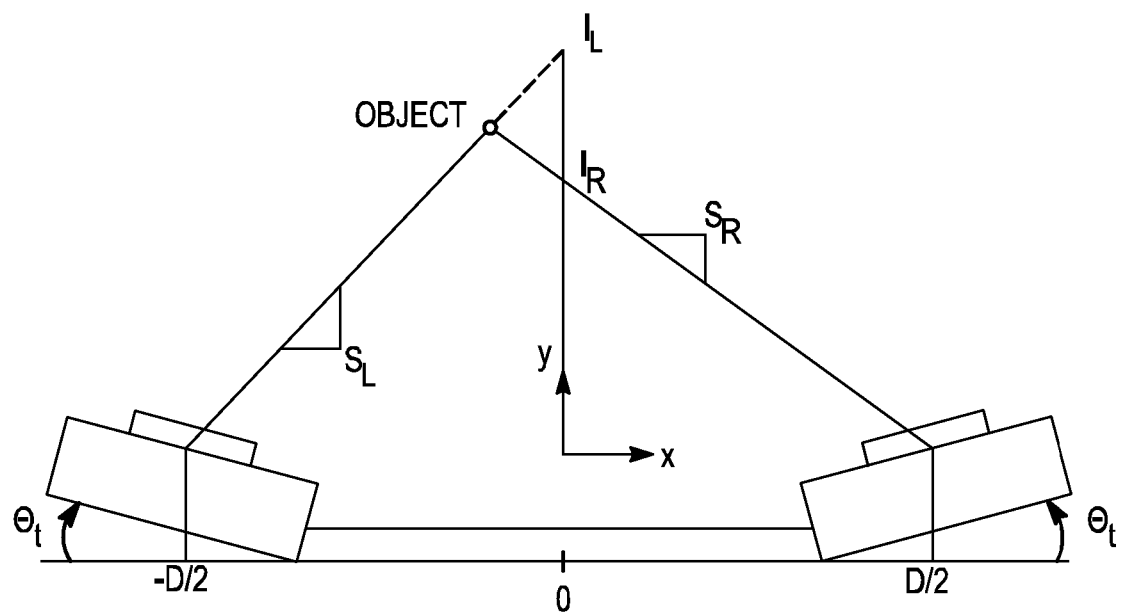
FIG. 65 depicts the light sources used in the experimental setup of FIG. 64H, according to one embodiment.

Once the slope, $S_{obj}$, is found for the object in both of the stereoscopic cameras, the x and y position of the object can be determined. FIG. 65 shows the geometry of the two camera configuration, with baseline (separation) D, and tilt angle $\theta_t$.

The coordinate system for the object distance values, x and y, is centered at a point directly between the two cameras. This sets the x coordinate of the left and right cameras at $-D/2$ and $D/2$, respectfully. The line y=0 is the imaging plane of both cameras. Using the last equation, the "slope" to the object can be found for both the left and right cameras, $S_L$ and $S_R$. $I_L$ and $I_R$ are the left and right y-intercepts where the camera "slopes" cross the system's y-axis.

$$y = S_L x + I_L \quad (10)$$

$$y = S_R x + I_R \quad (11)$$

Setting y=0 in each equation and using the known x coordinate ($-D/2$ and $D/2$) in each equation, $I_L$ and $I_R$ can be found:

$$I_L = S_L\left(\frac{D}{2}\right) \quad (12)$$

$$I_R = S_R\left(\frac{-D}{2}\right) \quad (13)$$

The slope of each line is found from (9).

$$S_R = \frac{\tan\left(\frac{\theta_f}{2}\right)}{2\frac{n_R}{N} - 1}, \quad S_L = \frac{\tan\left(\frac{\theta_f}{2}\right)}{2\frac{n_L}{N} - 1} \quad (14)$$

Setting $x=x_{obj}$ and $y=y_{obj}$ in (10) and (11) and solving for $x_{obj}$ leads to (15).

$$x_{obj} = \frac{I_L - I_R}{S_R - S_L} \quad (15)$$

Similarly solving for $y_{obj}$ leads to (16).

$$y_{obj} = S_L x_{obj} + I_L = S_R x_{obj} + I_R \quad (16)$$

If the cameras are rotated, as they are in the in vivo imaging robot to provide a better view of the object, three new variables are introduced: $\theta_t$, (the rotation angle of camera) and $\Delta x$ and $\Delta y$ (the shifts of the camera due to the rotation). Here, the rotation angle is assumed to be equal for both cameras. The new positions can be found using rotation matrices where $$\begin{bmatrix} 1 \\ S_R \end{bmatrix} \text{ and } \begin{bmatrix} 1 \\ S_L \end{bmatrix}$$

are vectors with the original slope.

$$\begin{bmatrix} x_{R,Rot} \\ y_{R,Rot} \end{bmatrix} = \begin{bmatrix} \cos(\theta_t) & -\sin(\theta_t) \\ \sin(\theta_t) & \cos(\theta_t) \end{bmatrix}\begin{bmatrix} 1 \\ S_R \end{bmatrix} \quad (17)$$

$$\begin{bmatrix} x_{L,Rot} \\ y_{L,Rot} \end{bmatrix} = \begin{bmatrix} \cos(\theta_t) & \sin(\theta_t) \\ -\sin(\theta_t) & \cos(\theta_t) \end{bmatrix}\begin{bmatrix} 1 \\ S_L \end{bmatrix} \quad (18)$$

The slopes in the rotated frame can then be determined from these rotated positions as shown in (19) and (20).

$$S_{R,Rot} = \frac{y_{R,Rot}}{x_{R,Rot}} \quad (19)$$

$$S_{L,Rot} = \frac{y_{L,Rot}}{x_{L,Rot}} \quad (20)$$

Using the shifts $\Delta x$ and $\Delta y$, the new intercepts are found from (10) and (11):

$$I_{L,Rot} = \left[S_{L,Rot}\left(\frac{D - \Delta x_L}{2}\right)\right] + \Delta y_L \quad (21)$$

-continued $$I_{R,Rot} = -\left[S_{R,Rot}\left(\frac{D+\Delta x_R}{2}\right)\right] + \Delta y_R \quad (22)$$

Finally, the x and y coordinates are found by substituting the new slopes and intercepts into (15) and (16). To extend these results into three dimensions, the distance in the z direction is needed. The vertical slope can be determined using the following:

$$S_V = \left(\frac{\tan\left(\frac{\theta_{f,vert}}{2}\right)}{2\frac{m}{M} - 1}\right)^{-1} \quad (23)$$

where $\theta_f$ is the vertical field of view, m is the vertical pixel position, and M is the total number of vertical pixels. The derivation of this is similar to the calculation of $\theta_{obj}$ in (5)-(9). The z component is found using the vertical slope $S_v$, and the distance to the object.

$$z_{real} = S_v \cdot \sqrt{x_{obj}^2 + y_{obj}^2} \quad (24)$$

The x coordinate remains the same (25).

$$x_{real} = x_{obj} \quad (25)$$

The y coordinate must be scaled by the cosine of the vertical angle (26).

$$y_{real} = y_{obj} \cdot \cos(\tan^{-1}(S_v)) \quad (26)$$

This mathematical analysis was implemented in the following section in an off-line Matlab program. Using recorded images, the object's positions were computed and plotted in space. Images are taken of objects of known dimensions to determine the accuracy of the stereo vision from the in vivo camera robot.

Testing of the Robotic Stereoscopic Camera Device

Figure 66A:
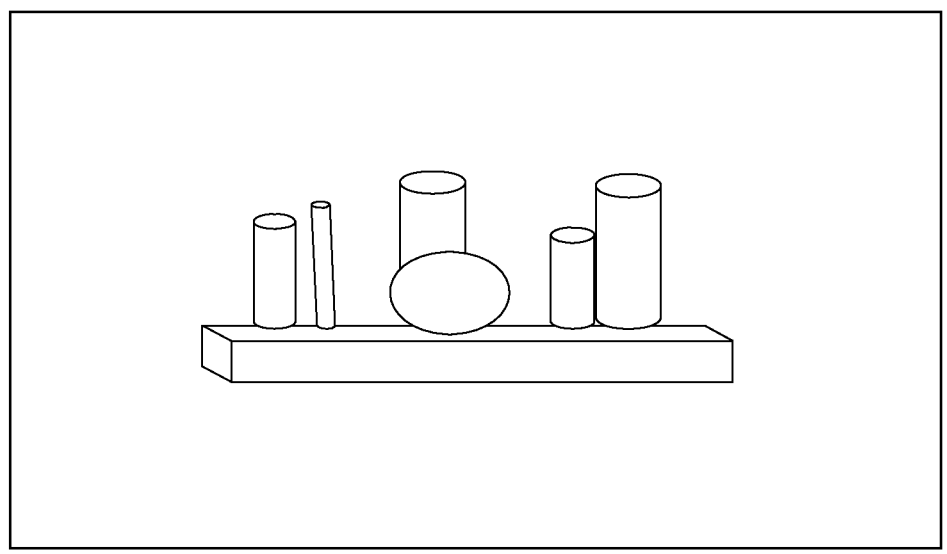
FIGS. 66A and B depict an image of the vision target of FIG. 64H, according to one embodiment.
Figure 66B:
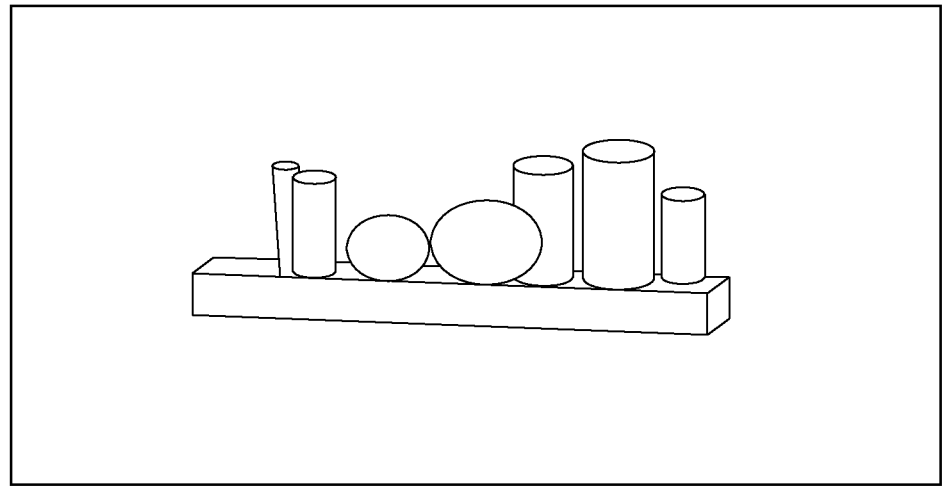

Using the experimental setup in FIG. 64H, several image pairs were captured and analyzed using the above calculations. An example left and right image pair is shown in FIGS. 66A and 66B.

Figure 67A:
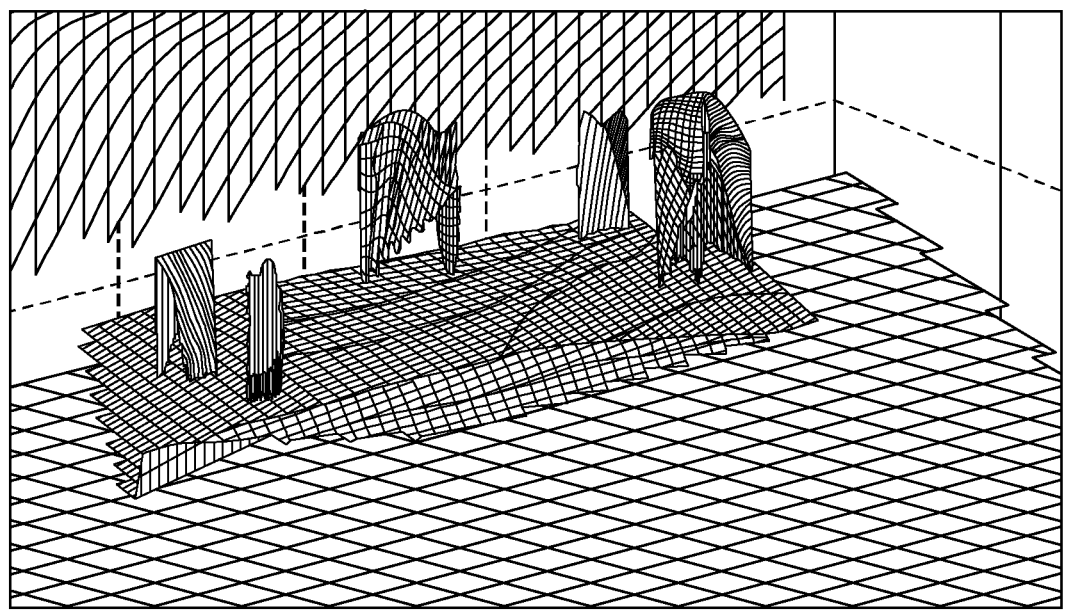
FIG. 67A depicts a depth map of the target area of FIG. 64H, according to one embodiment.
Figure 67B:
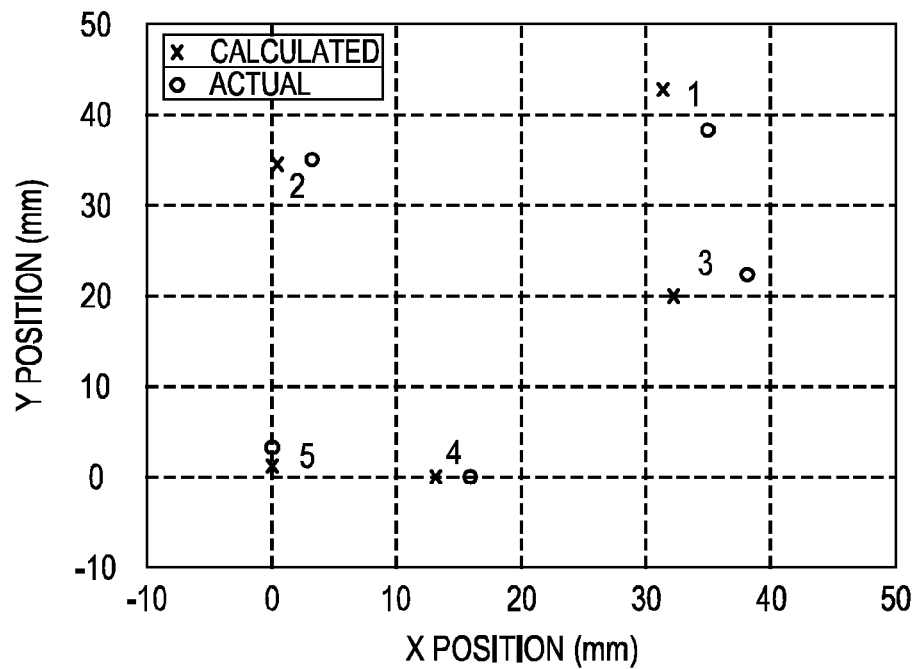
FIG. 67B is a graph depicting the center of the cylinders identified from the point cloud in the map of FIG. 67A, according to one embodiment.
Figure 67C:
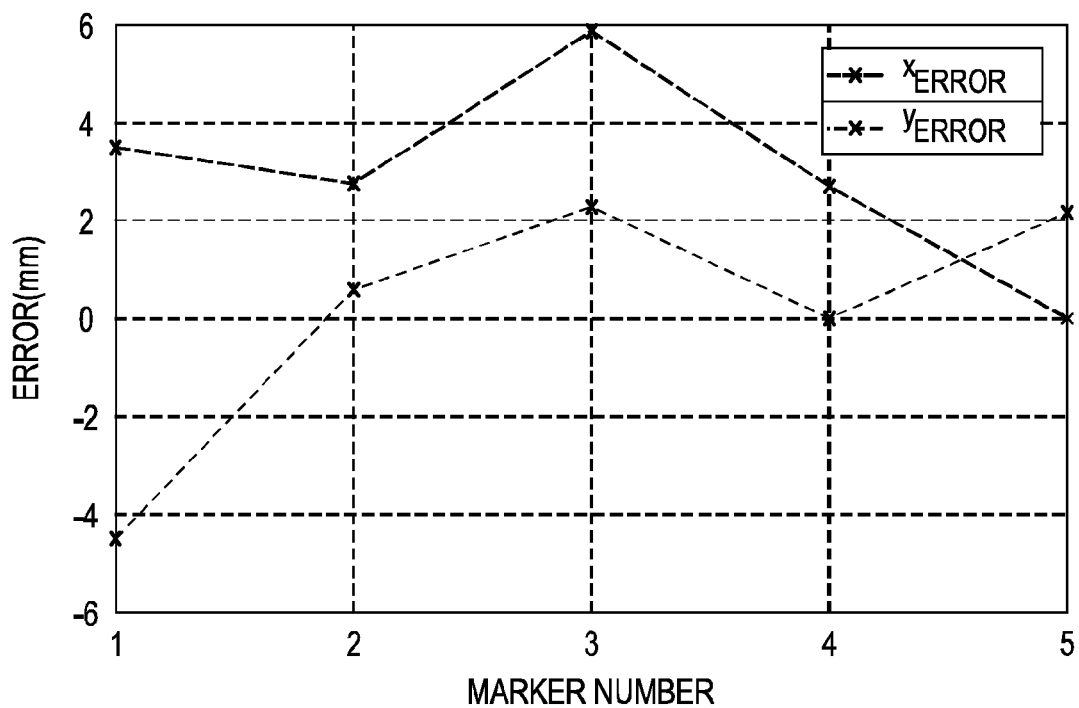
FIG. 67C is a graph depicting the x and y error for all five cylinder objects shown in FIG. 64H.

Pairs of corresponding points from the image pairs were analyzed and plotted. The shapes of the cylinders in the image can be reproduced in a depth map as shown in FIG. 67A. This three dimensional information can be very useful in surgery. FIG. 67B shows the center of the cylinders identified from the point cloud in the depth map. If this data is compared to the known dimensions of the target it can be seen that the error in the y direction (depth) is 1.8 mm and the error in the x direction (transverse) is 2.9 mm. FIG. 67C shows the x and y error for all five cylinder objects. The accuracy could allow precise depth feedback for a surgeon.

Figure 68A:
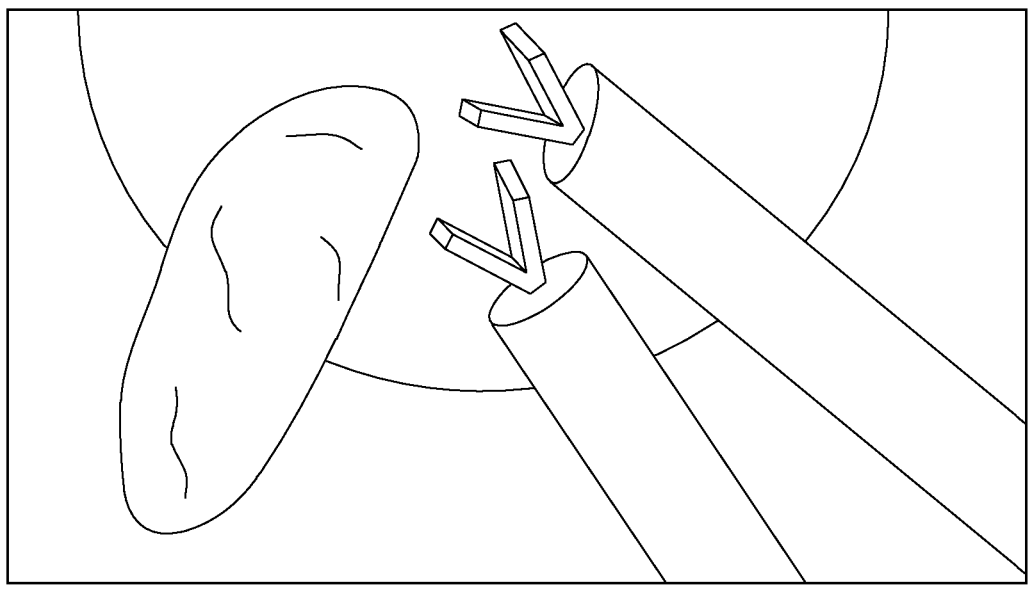
FIGS. 68A-B depict a porcine cholecystectomy in which a magnetically coupleable robotic device is used in cooperation with da VinCi™ tools, according to one embodiment.
Figure 68B:
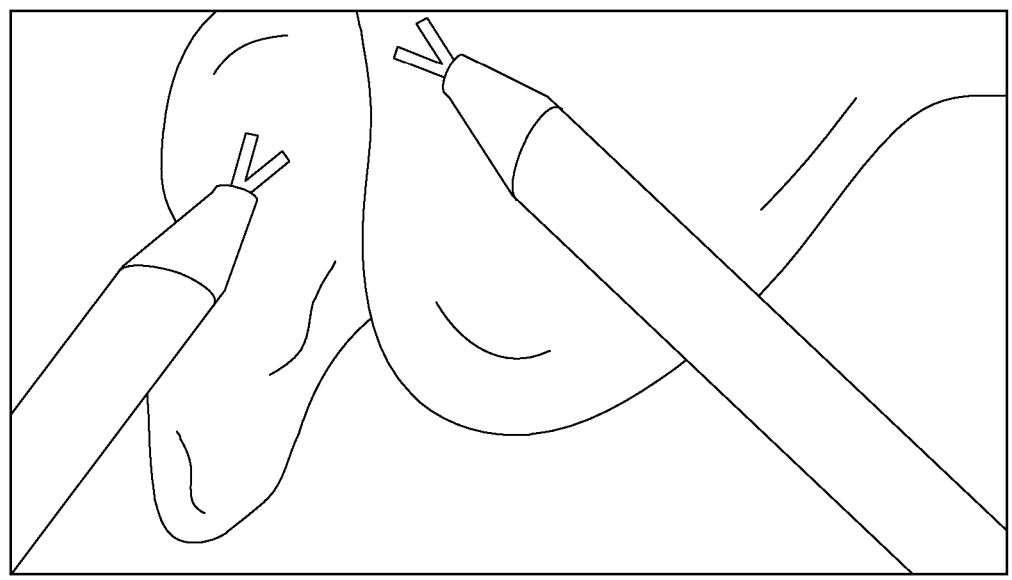

Performing a Porcine Cholecystectomy with the Robotic Stereoscopic Camera Device The in vivo camera robot was used to perform a porcine cholecystectomy (gall bladder removal). The surgeon used the video from the stereoscopic camera robot to perform the procedure. The three dimensional information was viewed by the surgeon using a stereoscopic display. Sample images are shown in FIGS. 68A and 68B. Three surgical tools are visible manipulating tissue in these views.

Figure 68C:
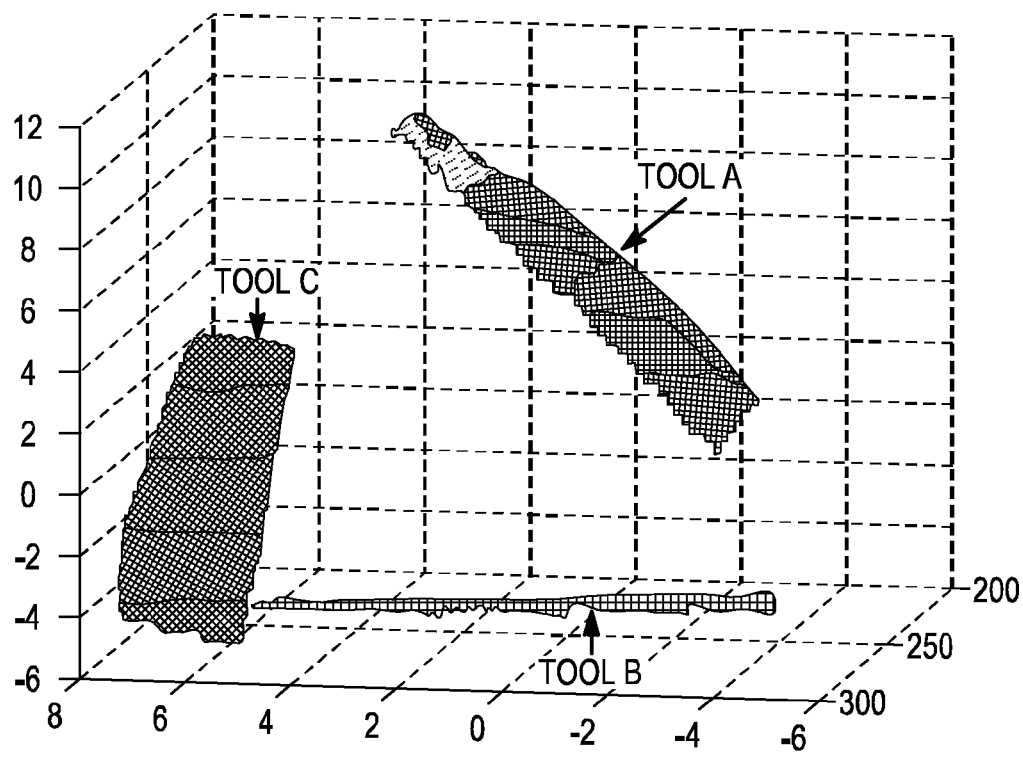
FIG. 68C is a depth map of the images shown in FIGS. 68A and B.

The surgeon performed the surgery in real time using the stereoscopic display. In addition, some captured images were post-processed to demonstrate the depth perception available to the surgeon. The resulting depth map for the images shown in FIGS. 68A and B is shown in FIG. 68C. All three tools and their relative position are clearly visible in the depth map.

Figure 68D:
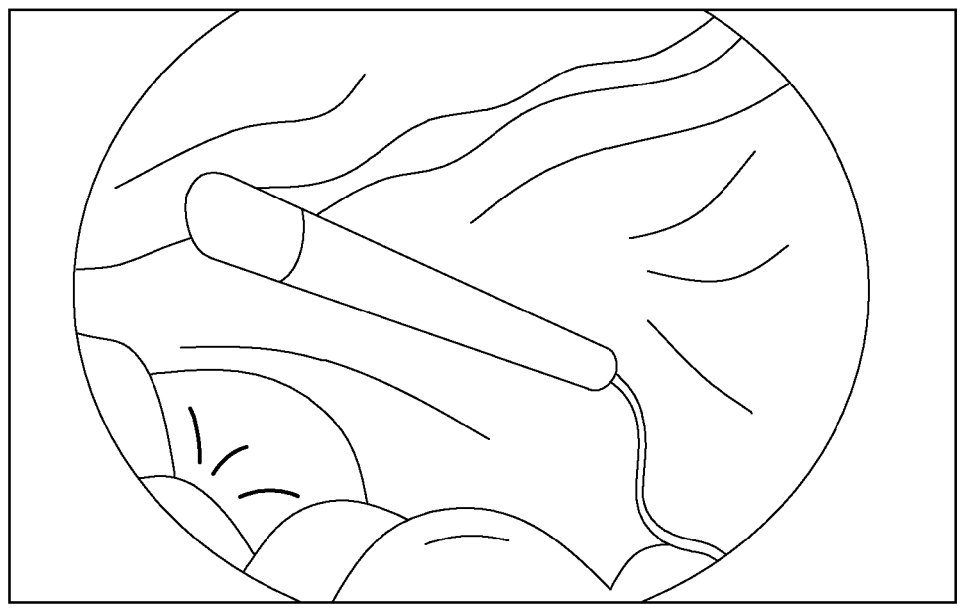
FIG. 68D depicts the magnetically coupleable robotic device positioned against the abdominal wall.

During the cholecystectomy, the animal was prepared as per normal procedure. Three small incisions were made in the pig's abdominal wall for the two tool ports and the laparoscope. The laparoscope was used to observe the procedure, but the surgeon used visual feed back from the in vivo stereoscopic camera. The in vivo stereoscopic robot was first inserted using a special trocar that allowed for the robot's electrical wire tethers. The remaining trocars were then placed and the abdomen was insufflated with carbon dioxide. Then the laparoscopic tools and laparoscope were inserted. A surgical assistant then lifted the in vivo robot into position on the abdominal wall using the magnetic holder and a laparoscopic tool as shown in FIG. 68D. The assistant then held the camera in position and re-positioned it as needed throughout the procedure.

The operating surgeon then began the cholecystectomy, using the stereoscopic video feedback as with a standard laparoscopic surgical procedure. The cholecystectomy was performed using standard tools but with primary video feedback coming from the in vivo robot. After the cholecystectomy the in vivo robot was retracted by the tether.

EXAMPLE 8

Figure 69:
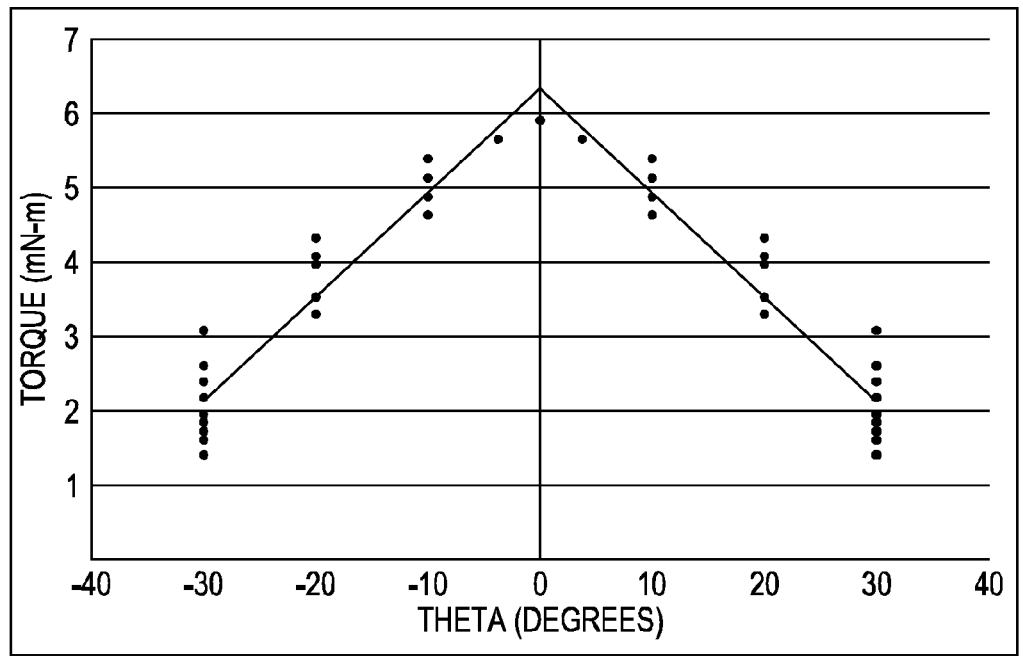
FIG. 69 is a graph depicting the stall torque created with a robotic device disclosed herein, according to one embodiment.

Bench top tests were conducted to determine the torque that could be created with a robotic device similar to that device as depicted in FIGS. 23A and 23B. The test applied static loads to the joint and a stall torque was determined. The results are shown in FIG. 69. The joint torque output (ordinate) changes with the elbow angle (abscissa). The tests show that significant torque can be produced. In a nominal configuration (elbow fully extended) the robot is capable of producing 6 mN-m. The torque is reduced as the elbow is flexed and extended (human elbows don't extend past straight). Ten tests were conducted and a least squares fit is shown. It is believed that additional torque can be obtained with changes in the mechanical amplification inherent in the design (i.e. gear ratio, pivot location, etc.). Kinematic details of "sufficient" torque are given in Section D2 of the Experimental Design section.

Figure 70A:
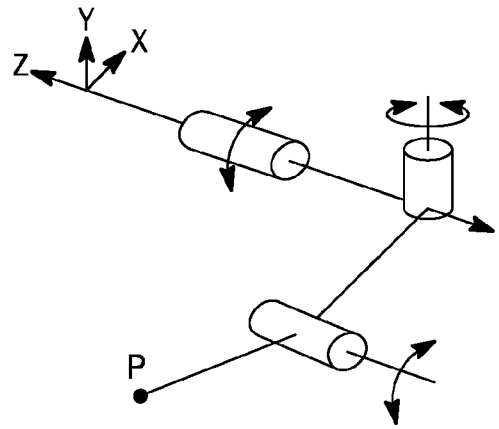
FIGS. 70A and B depict two kinematic configurations of robotic device designs, according to one embodiment.
Figure 70B:
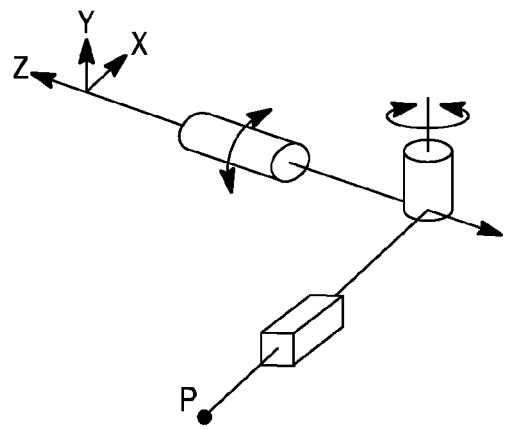
FIG. 70B depicts a configuration having two revolute joints (shoulder) follow by a prismatic (linear) distal joint.

The second set of tests related to an examination of the kinematic configuration (i.e. joint motions) for the robot design, according to one embodiment. The robot is to manipulate tissue by applying forces with its end-effectors. This has to be done at a reasonable velocity. The endpoint forces and velocities that can be generated by a robot are highly dependent on the robot kinematics. Two possible, non-limiting configurations are shown in FIGS. 70A and 70B. The first (FIG. 70A) has three revolute joints, similar to the human arm (two large rotations of the shoulder and one rotation at the elbow). The second (FIG. 70B) has two revolute joints (shoulder) follow by a prismatic (linear) distal joint.

Figure 71:
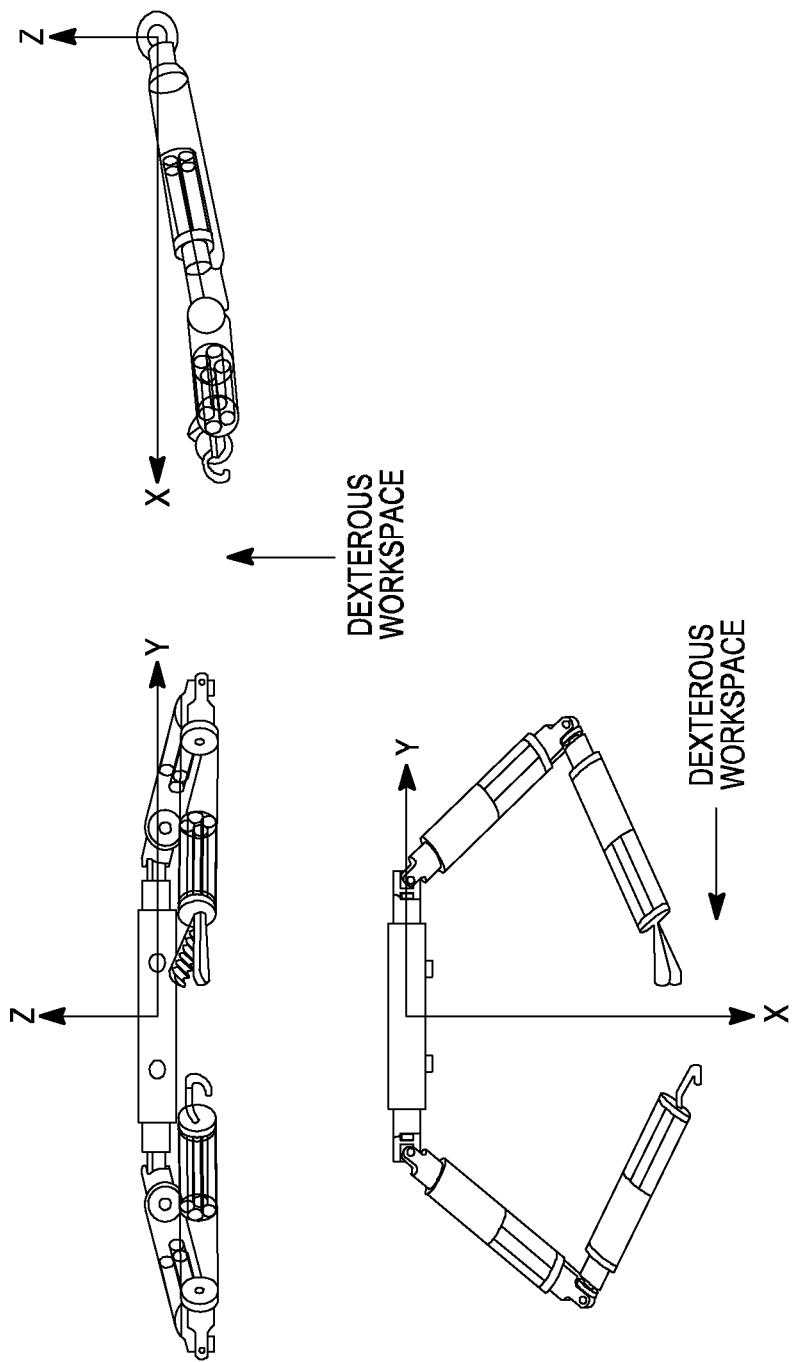
FIG. 71 is a schematic depiction of a kinematic model of a manipulator of a magnetically coupleable device having three revolute joints based on the size of the dexterous workspace, according to one embodiment.

One design, according to one embodiment, is shown schematically in FIG. 71 and has three revolute joints. To develop a kinematic model of the manipulator, a minimum of three parameters must be specified. The first parameter is the size of the "dexterous workspace," defined here as the volume of space that is reachable by the robot. The target workspace will allow the robot to manipulate tissue in a 5 cm cube in front of the robot (2.5 cm<x<7.5 cm; -2.5<y<2.5; -2.5<z<2.5). This workspace i many laparoscopic procedures and is also reasonable to permit the two "hands" of the robot to work cooperatively. Workspace size/shape depends on joint limits and configurations, and various tradeoffs related to these design decisions will be investigated.

The two additional parameters required are the nominal speed that the robot can move its end-effectors, and the maximum endpoint force that can be applied by the end-effectors. In this example, the target endpoint force will be 3 N in all directions (x, y, and z) at every point in the workspace. The target endpoint velocity in this example will be 0.5 cm/second. Both of these parameters will vary throughout the robot's workspace. For example, the robot will be able to apply larger forces in the x direction when its "elbows" are straight. These parameters can be represented mathematically through the robot's Jacobian:

$$\delta \underline{x} = \underline{J} \delta \underline{\theta}.$$

Here, the endpoint velocities, $\underline{\dot{x}}$, are determined by the motors and actuators. They are the product of the joint velocities, $\underline{\dot{\theta}}$, and the Jacobian matrix, $\underline{J}$. The Jacobian contains the design parameters for joint lengths ($a_i$) and joint configuration ($\theta_i$).

For the proposed configuration, the Jacobian is given by:

$$\begin{bmatrix} \dot{x} \\ \dot{y} \\ \dot{z} \end{bmatrix} = \begin{bmatrix} (-s_1 c_2 c_3 + c_1 s_3)a_4 - s_1 c_2 a_3 & -c_1 s_2 c_3 a_4 - c_1 s_2 a_3 & (-c_1 c_2 s_3 + s_1 c_3)a_4 \\ 0 & -c_2 c_3 a_4 - c_2 a_3 & s_2 s_3 a_4 \\ (c_1 c_2 c_3 + s_1 s_3)a_4 + c_1 c_2 a_3 & -s_1 s_2 c_3 a_4 - s_1 s_2 a_3 & (-s_1 c_2 s_3 - c_1 c_3)a_4 \end{bmatrix} \begin{bmatrix} \dot{\theta}_1 \\ \dot{\theta}_2 \\ \dot{\theta}_3 \end{bmatrix},$$

where $s_i = \sin(\theta_i)$ and $c_i = \cos(\theta_i)$. This equation will be used as part of the detailed design of each joint and link in the robot.

What is claimed is:

1. A robotic device, comprising:
   (a) a device body configured to be disposed within a patient;
   (b) an attachment component operably coupled with the device body;
   (c) a connection component operably coupled with the device body, wherein the connection component comprises a tether;
   (d) an external power source operably coupled to the tether;
   (e) a first operational arm comprising:
      (i) a first inner arm segment operably coupled with the device body via a first shoulder joint;
      (ii) a first outer arm segment operably coupled with the first inner arm segment via a first elbow joint; and
      (iii) a first operational component operably coupled with the first outer arm segment;
   (f) a second operational arm comprising:
      (i) a second inner arm segment operably coupled with the device body via a second shoulder joint;
      (ii) a second outer arm segment operably coupled with the second inner arm segment via a second elbow joint; and
      (iii) a second operational component operably coupled with the second outer arm segment, wherein the first and second operational arms are configured such that the first and second operational arms are not positionable within an enclosure of the robotic device;
   (g) at least one actuator disposed within each arm, the at least one actuator operably coupled to the tether and the arm, wherein the actuator is configured to actuate movement of the arm; and
   (h) at least one imaging component operably coupled with the device body, wherein the at least one imaging component is positioned between the first and second operational arms such that the first and second operational arms are viewable by a user via the at least one imaging component during operation of the first and second operational arms.

2. The robotic device of claim 1, wherein each of the first and second operational arms has at least four degrees of freedom.

3. The robotic device of claim 1, further comprising an external controller operably coupled to the tether, the external controller comprising:
   (a) an image display component operably coupled to the at least one imaging component via the tether, the image display component configured to display images acquired by the at least one imaging component; and
   (b) at least one joystick operably coupled to at least one of the first and second operational arms via the tether, the at least one joystick configured to control the at least one of the first and second operational arms.

4. The robotic device of claim 1, wherein each of the first and second operational arms has at least three degrees of freedom.

5. The robotic device of claim 1, wherein the first and second operational components are each chosen from a group consisting of a scalpel, a biopsy tool, a cauterizer, a forceps, a dissector, clippers, a stapler, and an ultrasound probe.

6. A robotic device, comprising:
   (a) a device body configured to be disposed within a patient, the device body comprising a first joint and a second joint;
   (b) an attachment component operably coupled with the device body;
   (c) a tether operably coupled with the device body;
   (d) an external power source operably coupled to the tether;
   (e) a first operational arm comprising:
      (i) a first inner arm segment operably coupled with the first joint;
      (ii) a first outer arm segment operably coupled with the first inner arm segment via a third joint; and
      (iii) a first operational component operably coupled with the first outer arm segment;
   (f) a second operational arm comprising:
      (i) a second inner arm segment operably coupled with the second joint;
      (ii) a second outer arm segment operably coupled with the second inner arm segment via a fourth joint; and
      (iii) a second operational component operably coupled with the second outer arm segment, wherein the first and second operational arms are configured such that the first and second operational arms are not positionable within an enclosure of the robotic device;
   (g) at least one actuator disposed within each arm, the at least one actuator operably coupled to the tether and the arm, wherein the actuator is configured to actuate movement of the arm; and
   (h) at least one imaging component operably coupled with the device body, wherein the at least one imaging component is positioned between the first and second operational arms such that the at least one imaging component is configured to provide a field of view comprising at least a portion of the first and second operational components.

7. The robotic device of claim 6, wherein each of the first and second operational arms has at least three degrees of freedom.

8. The robotic device of claim 6, wherein each of the first and second operational arms has at least four degrees of freedom.

9. The robotic device of claim 6, further comprising an external controller operably coupled to the tether, the external controller comprising:
(a) an image display component operably coupled to the at least one imaging component via the tether, the image display component configured to display images acquired by the at least one imaging component; and
(b) at least one joystick operably coupled to at least one of the first and second operational arms via the tether, the at least one joystick configured to control at least one of the first and second operational arms.

10. The robotic device of claim 6, wherein the first and second operational components are each chosen from a group consisting of a scalpel, a biopsy tool, a cauterizer, a forceps, a dissector, clippers, a stapler, and an ultrasound probe.

11. A method of surgery comprising:
making an incision in a patient, wherein the incision provides access to a target cavity in the patient;
inserting a robotic device through the incision and into the target cavity in the patient, the robotic device comprising:
(a) a device body configured to be disposed within a patient;
(b) an attachment component operably coupled with the device body;
(c) a connection component operably coupled with the device body, wherein the connection component comprises a tether;
(d) an external power source operably coupled to the tether;
(e) a first operational arm comprising:
(i) a first inner arm segment operably coupled with the device body via a first shoulder joint;
(ii) a first outer arm segment operably coupled with the first inner arm segment via a first elbow joint; and
(iii) a first operational component operably coupled with the first outer arm segment;
(f) a second operational arm comprising:
(i) a second inner arm segment operably coupled with the device body via a second shoulder joint;
(ii) a second outer arm segment operably coupled with the second inner arm segment via a second elbow joint; and
(iii) a second operational component operably coupled with the second outer arm segment, wherein the first and second operational arms are configured such that the first and second operational arms are not positionable within an enclosure of the robotic device;
(g) at least one actuator disposed within each arm, the at least one actuator operably coupled to the tether and the arm, wherein the actuator is configured to actuate movement of the arm; and
(h) at least one imaging component operably coupled with the device body, wherein the at least one imaging component is positioned between the first and second operational arms such that the first and second operational arms are viewable by a user via the at least one imaging component during operation of the first and second operational arms; and
performing a procedure in the target cavity of the patient using at least the robotic device.

12. The method of claim 11, wherein making the incision in the patient comprises making no more than two incisions in the patient.

13. The method of claim 11, wherein making the incision in the patient comprises making only a single incision in a patient.

14. The method of claim 11, further comprising positioning the robotic device against or near a wall within the target cavity using the attachment component prior to performing the procedure.

15. The method of claim 11, wherein performing the procedure further comprises performing the procedure using the robotic device and at least one additional device.

16. The method of claim 11, wherein performing the procedure further comprises operating an external controller operably coupled to the at least one actuator via the tether, wherein the external controller is configured to transmit instructions via the tether to the at least one actuator for actuating movement of the arms.

17. The method of claim 16, wherein the external controller comprises:
(a) an image display component operably coupled to the at least one imaging component via the tether, the image display component configured to display images acquired by the at least one imaging component; and
(b) at least one joystick operably coupled to at least one of the first and second operational arms via the tether, the at least one joystick configured to control at least one of the first and second operational arms.

18. The method of claim 11, wherein each of the first and second operational arms has at least three degrees of freedom.

19. The method of claim 11, wherein each of the first and second operational arms has at least four degrees of freedom.

20. The method of claim 11, wherein the first and second operational components are each chosen from a group consisting of a scalpel, a biopsy tool, a cauterizer, a forceps, a dissector, clippers, a stapler, and an ultrasound probe.

* * * * *